(12) United States Patent
Walter et al.

(10) Patent No.: US 9,321,813 B2
(45) Date of Patent: Apr. 26, 2016

(54) METHODS AND COMPOSITIONS FOR CYTOMEGALOVIRUS IL-10 PROTEIN

(75) Inventors: Mark R. Walter, Birmingham, AL (US); Peter A. Barry, Sacramento, CA (US)

(73) Assignees: UAB Research Foundation, Birmingham, AL (US); The Regents of the University of California, Oakland, CA (US)

( * ) Notice: Subject to any disclaimer, the term of this patent is extended or adjusted under 35 U.S.C. 154(b) by 0 days.

(21) Appl. No.: 14/008,484

(22) PCT Filed: Mar. 27, 2012

(86) PCT No.: PCT/US2012/030666
§ 371 (c)(1),
(2), (4) Date: Dec. 10, 2013

(87) PCT Pub. No.: WO2012/135177
PCT Pub. Date: Oct. 4, 2012

(65) Prior Publication Data
US 2014/0099299 A1 Apr. 10, 2014

Related U.S. Application Data

(60) Provisional application No. 61/468,945, filed on Mar. 29, 2011.

(51) Int. Cl.
| | |
|---|---|
| *C07K 14/005* | (2006.01) |
| *C07K 16/08* | (2006.01) |
| *A61K 39/245* | (2006.01) |
| *C07K 16/24* | (2006.01) |
| *A61K 39/12* | (2006.01) |
| *A61K 38/00* | (2006.01) |
| *A61K 39/00* | (2006.01) |

(52) U.S. Cl.
CPC .............. *C07K 14/005* (2013.01); *A61K 39/12* (2013.01); *A61K 39/245* (2013.01); *C07K 16/088* (2013.01); *C07K 16/244* (2013.01); *A61K 38/00* (2013.01); *A61K 2039/53* (2013.01); *A61K 2039/545* (2013.01); *A61K 2039/55566* (2013.01); *C07K 2317/76* (2013.01); *C07K 2319/02* (2013.01); *C07K 2319/21* (2013.01); *C12N 2710/16122* (2013.01); *C12N 2710/16133* (2013.01); *C12N 2710/16134* (2013.01); *C12N 2710/16162* (2013.01)

(58) Field of Classification Search
None
See application file for complete search history.

(56) References Cited

PUBLICATIONS

Pepperl-Klindworth et al (Viral Immunol. 2006 Spring;19(1):92-101).*
Bowie et al. (Science, 1990, 247:1306-1310).*
Burgess et al. (J. Cell Biol. 111:2129-2138, 1990).*
Lazar et al. (Mol. Cell. Biol., 8:1247-1252, 1988).*
Bork (Genome Research, 2000,10:398-400).*
Q0QIH2_HCMV (downloaded from http://www.uniprot.org/uniprot/Q0QIH2; last modified Sep. 5, 2006).*
Q0QIH2_HCMV alignment (downloaded from SCORE; last modified Sep. 5, 2006).*
Lin et al (Virus Research 131 (2008) 213-223.*
Garrigue et al (Journal of Clinical Virology 40 (2007) 120-128).*
GenBank Accession No. AAF200417 "Interleukin-10-like protein precursor (Macacine herpesvirus 3)" Mar. 26, 2000 (1 pg).
GenBank Accession No. AAF200740 "Interleukin-10-like protein precursor (Macacine herpesvirus 3)" Mar. 30, 2000 (1 pg).
GenBank Accession No. AAF202536 "Interleukin-10-like protein (human herpesvirus 5)" Apr. 12, 2000 (1 pg).
Jones et al. "Crystal structure of human cytomegalovirus IL-10 bound to soluble human IL-10R1" *PNAS* 99(14):9404-9409 (2002).
Oxford et al. "Open reading frames carried on UL/b' are implicated in shedding and horizontal transmission of rhesus cytomegalovirus in rhesus monkeys" *J. Virol.* 85(10):5205-5114 (2011).
Sequar et al. "Experimental coinfection of rhesus macaques with rhesus cytomegalovirus and simian immunodeficiency virus: pathogenesis" *Journal of Virology* 76(15):7661-7671 (2002).
Slobedman et al. "Virus-Encoded Homologs of Cellular Interleukin-10 and Their Control of Host Immune Function" *Journal of Virology* 83(19):9618-9629 (2009).
Spencer et al. "Potent Immunosuppressive Activities of Cytomegalovirus-Encoded Interleukin-10" *Journal of Virology* 73(3): 1285-1292 (2002).
Extended European Search Report Corresponding to European Patent Application No. 12764664.4; mailed Nov. 13, 2014 (6 pages).
Notification Concerning Transmittal of International Preliminary Report on Patentability in corresponding PCT Application No. PCT/US2012/030666, mailed Oct. 10, 2013 (7 pages).
International Search Report and Written Opinion issued in corresponding PCT Application No. PCT/US2012/030666, mailed Nov. 9, 2012 (12 pages).
Brodeur et al., "Antibodies to human IL-10 neutralize ebvIL-10-mediated cytokine suppression but have no effect on cmvIL-10 activity" *Virus Research* 153 (2010) pp. 265-268.

(Continued)

*Primary Examiner* — Brian J Gangle
*Assistant Examiner* — Andrea McCollum
(74) *Attorney, Agent, or Firm* — Myers Bigel & Sibley, P.A.

(57) ABSTRACT

The present invention provides methods and compositions for treating and/or preventing a cytomegalovirus infection in a subject, comprising administering to the subject an effective amount of a cytomegalovirus interleukin-10 (IL-10) protein modified to have reduced functional activity while retaining immunogenicity. The present invention further provides nucleic acid molecules encoding a cytomegalovirus IL-10 protein or fragment thereof of this invention as well as vectors comprising such nucleic acids. Also provided herein are neutralizing antibodies that specifically bind cmvIL-10.

5 Claims, 30 Drawing Sheets

(56) References Cited

PUBLICATIONS de Lemos Rieper et al., "Characterization of specific antibodies against cytomegalovirus (CMV)-encoded interleukin 10 produced by 28% of CMV-seropositive blood donors" *Journal of General Virology* (2011), 92, pp. 1508-1518.

Eberhardt et al., "Host Immune Responses to a Viral Immune Modulating Protein: Immunogenicity of Viral Interleukin-10 in Rhesus Cytomegalovirus-Infected Rhesus Macaques" *PLoS One*, May 2012, vol. 7(5), e37931, pp. 1-10.

Logsdon et al., "Design and Analysis of Rhesus Cytomegalovirus IL-10 Mutants as a Model for Novel Vaccines Against Human Cytomegalovirus" *PLoS One*, Nov. 2011, vol. 6(11), e28127, pp. 1-13.

Yue et al., "Immunogenicity and Protective Efficacy of DNA Vaccines Expressing Rhesus Cytomegalovirus Glycoprotein B, Phosphoprotein 65-2, and Viral Interleukin-10 in Rhesus Macaques" *Journal of Virology*, vol. 81(3), Nov. 15, 2006, pp. 1095-1099.

\* cited by examiner

```
              A  34↓  ↓38                B
RhCMV10   H----DHEHK--EVPPACDPVHGNLAGIFKELRATYASIREGLQKKDTVYYTSLFNDRVL
HuIL10    S----PGQGT--QSENSCTHFPGNLPNMLRDLRDAFSRVKTFFQMKDQLD-NLLLKESLL
RhIL-10   S----PGQGT--QSENSCTRFPGNLPHMLRDLRDAFSRVKTFFQMKDQLD-NILLKESLL
HuCMV10   SEEAKPATTTIKNTKPQC--RPEDYATRLQDLRVTFHRVKPTLQREDDY--SVWLDGTVV
              .   :    *      :  . :::**  ::   ::  :*  :*    .  :.  ::
                     C                    D
RhCMV10   HEMLSPMGCRVTNELMEHYLDGVLPRASHIDYDNSTLNGLHVFASSMQALYQHMLKCP-A
HuIL10    EDFKGYLGCQALSEMIQFYLEEVMPQAENQDPDIK--AHVNSLGENLKTLRLRLRRCHRFI
RhIL-10   EDFKGYLGCQALSEMIQFYLEEVMPQAENHDPDIK--EHVNSLGENLKTLRLRLRRCHRF
HuCMV10   ---KGCWGCSVMDWLLRRYLEIVFPAGDHVYPGIK--TELHSMRSTLESIYKDMRQCP-L
               **  . ..::. **: *:* ...: ..      ::  :  ..::::     :  :*

E          142↓  ↓144 F
RhCMV10   LACTGKTPAWMYFLEVEHKLNPWRGTAKAAAEADLLLNYLETFL---LQF
HuIL10    LPCENKSKAVEQVKNAFNKLQ-EKGIYKAMSEFDIFINYIEAYMTMKIRN
RhIL-10   LPCENKSKAVEQVKNAFSKLQ-EKGVYKAMSEFDIFINYIEAYMTMKIQN
HuCMV10   LGCGDKSVISRLSQEAERK-S-DNGTRKGLSELDTLFSRLEEYLH--SRK
          * *  .*:          :.   *   .*   *.  :* *  ::   :* ::      :
```

B.

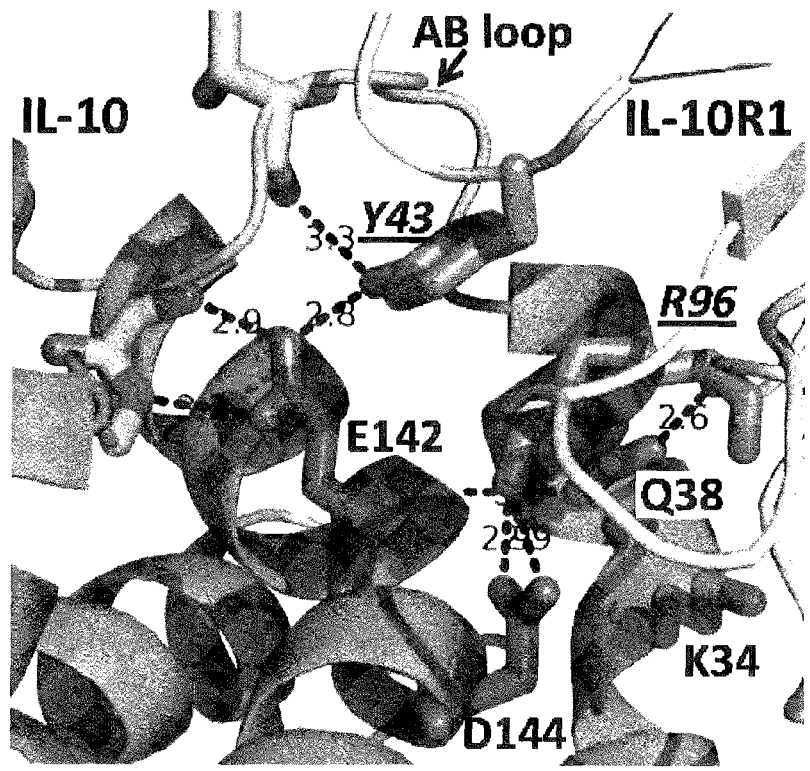

Fig. 4
A.
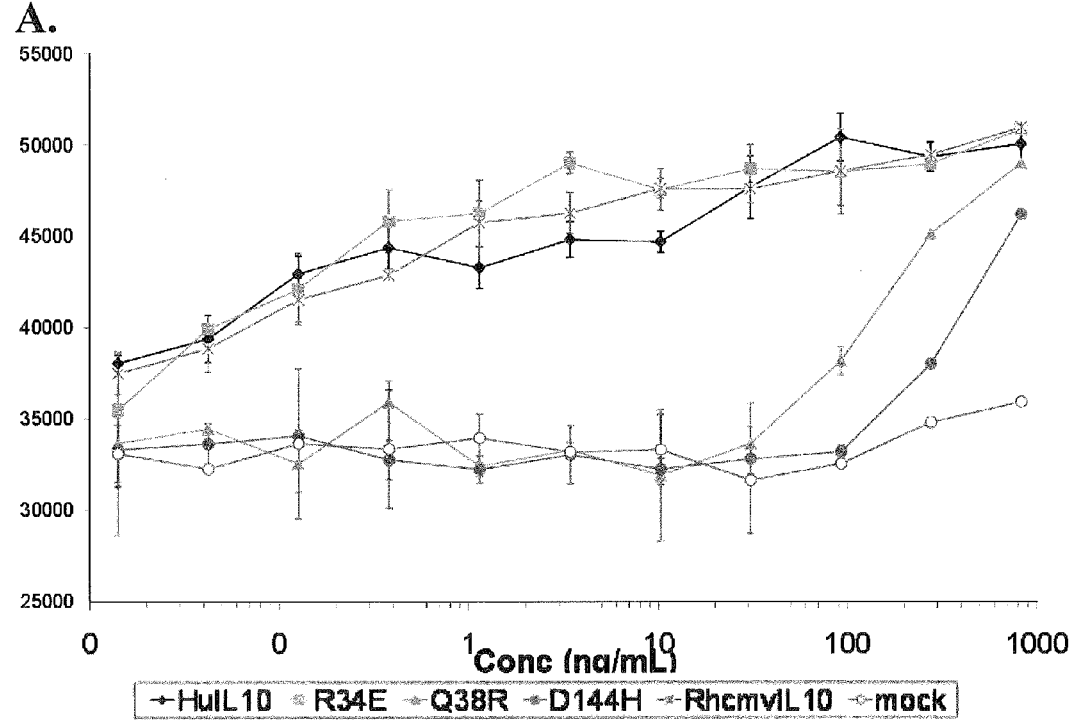
B.
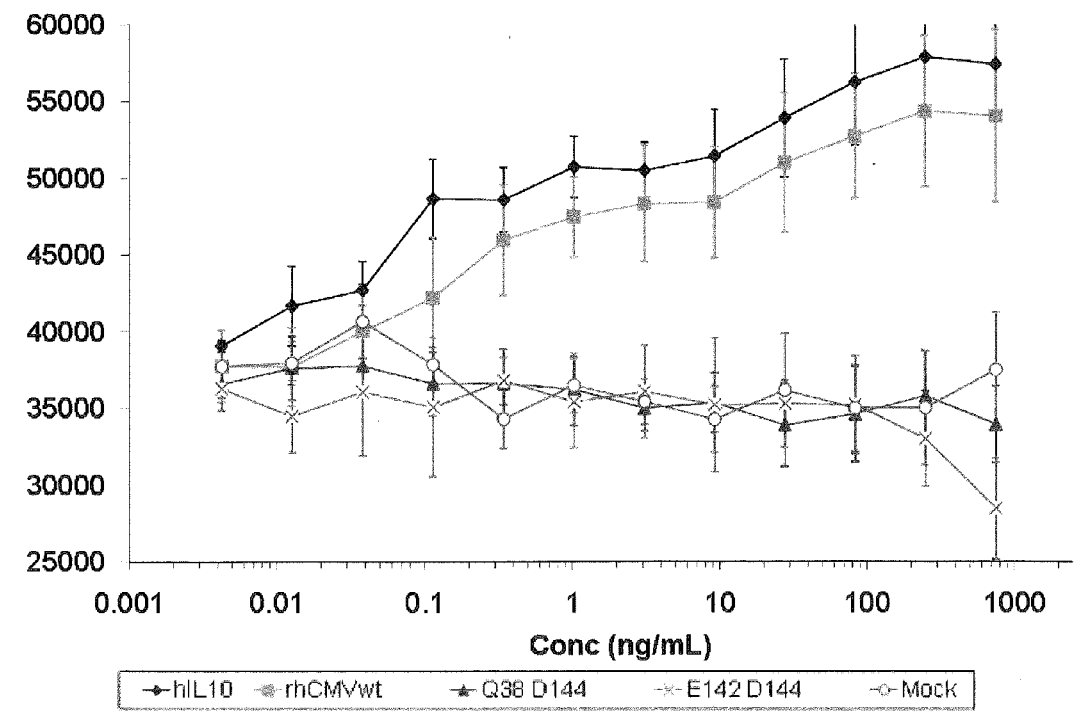

Fig. 8
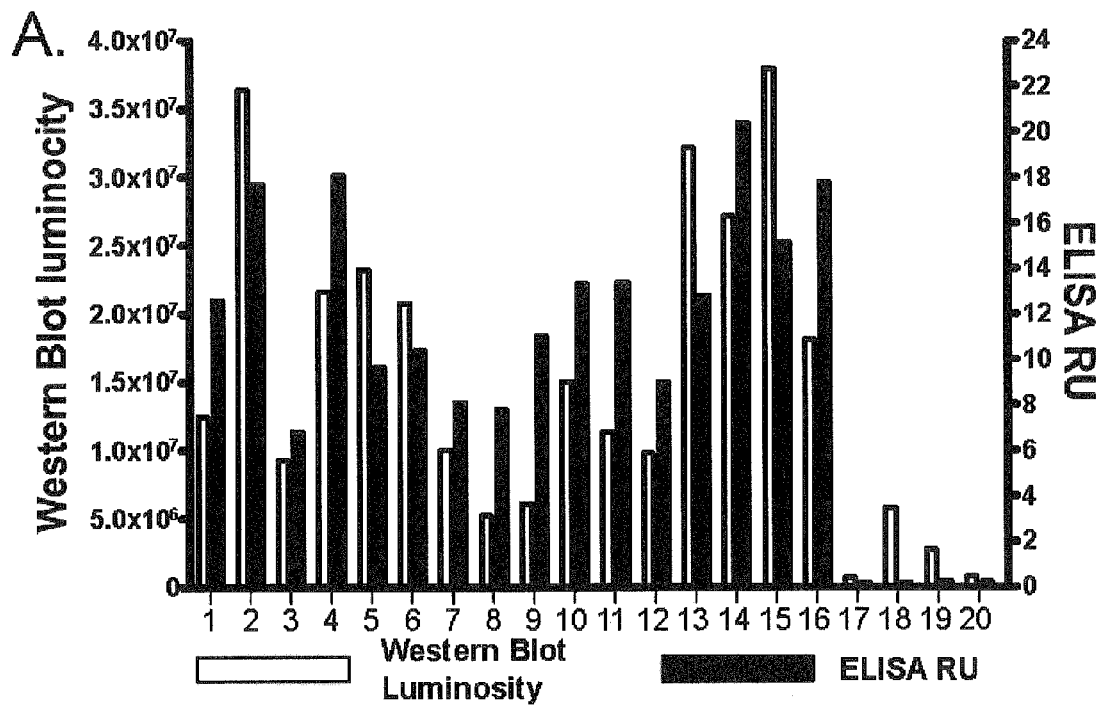
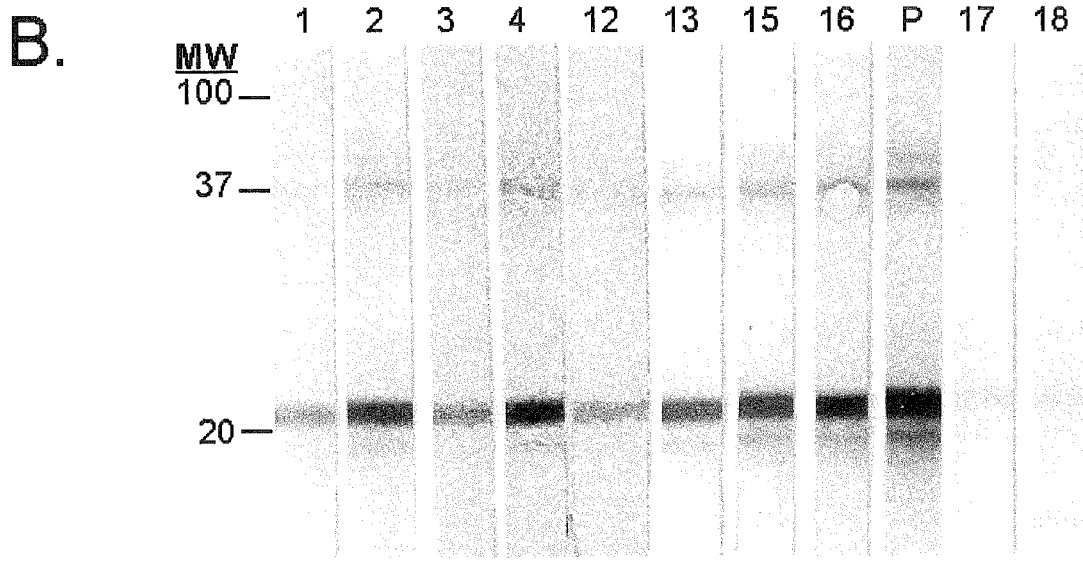

Fig. 9
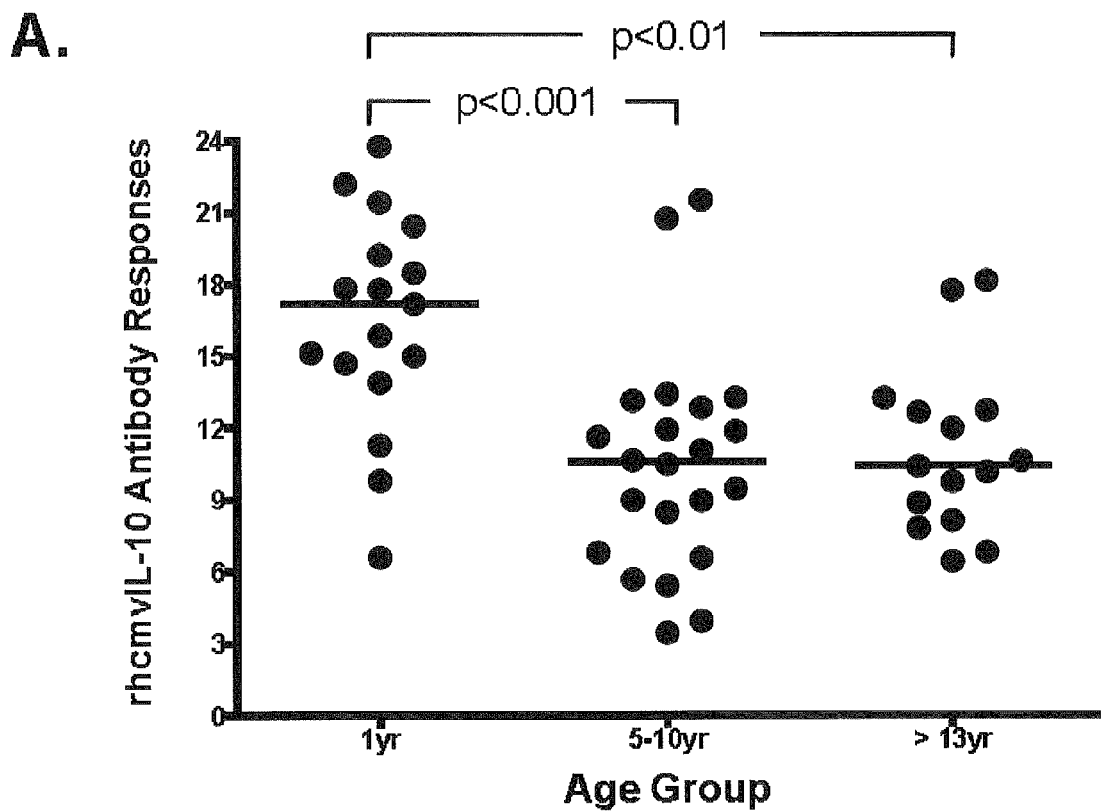
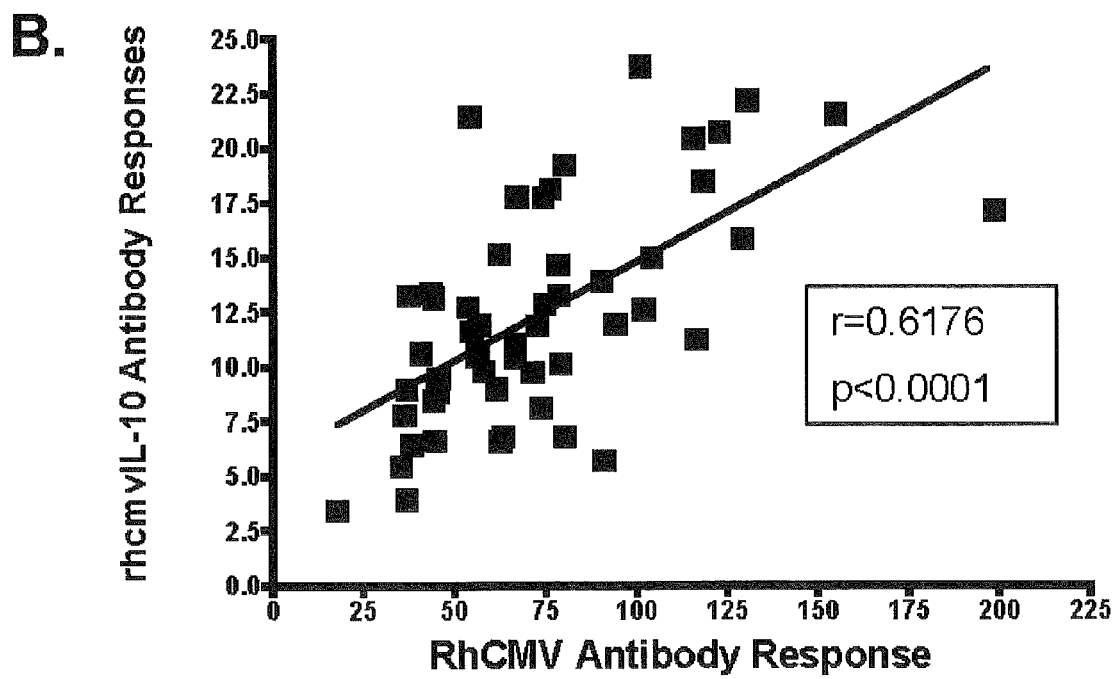

Fig. 12
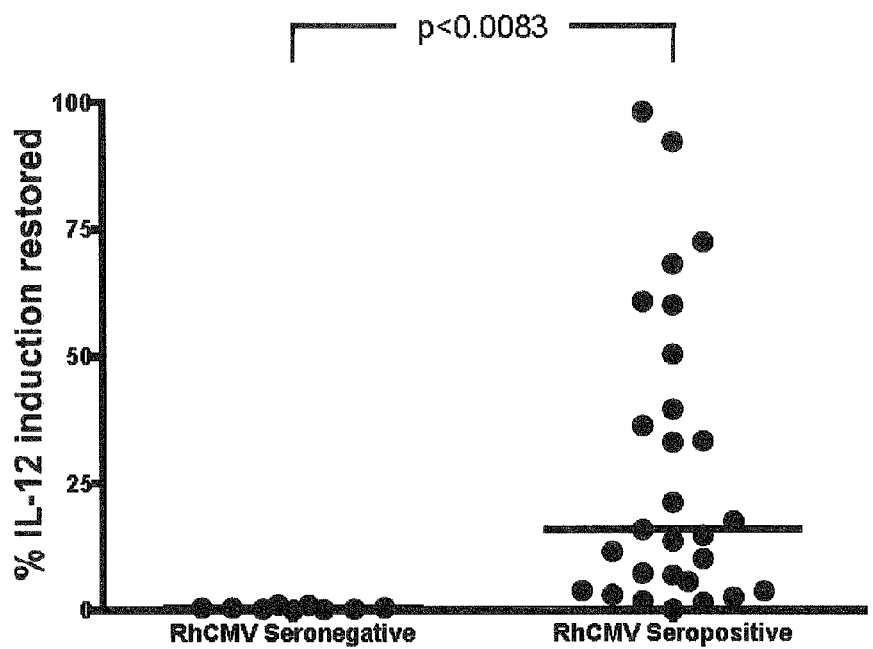
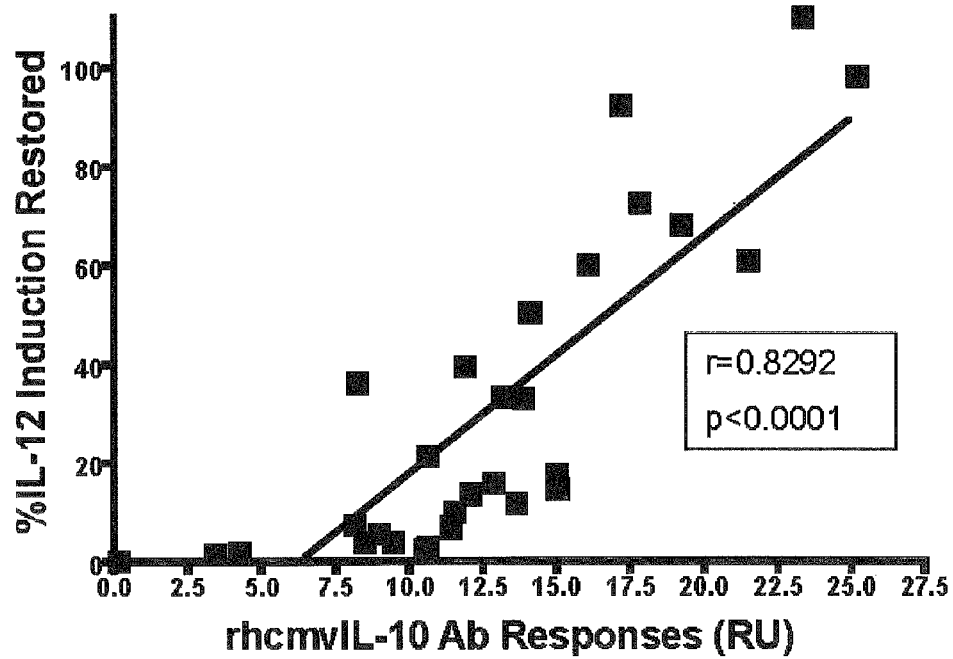

Fig. 13
A.
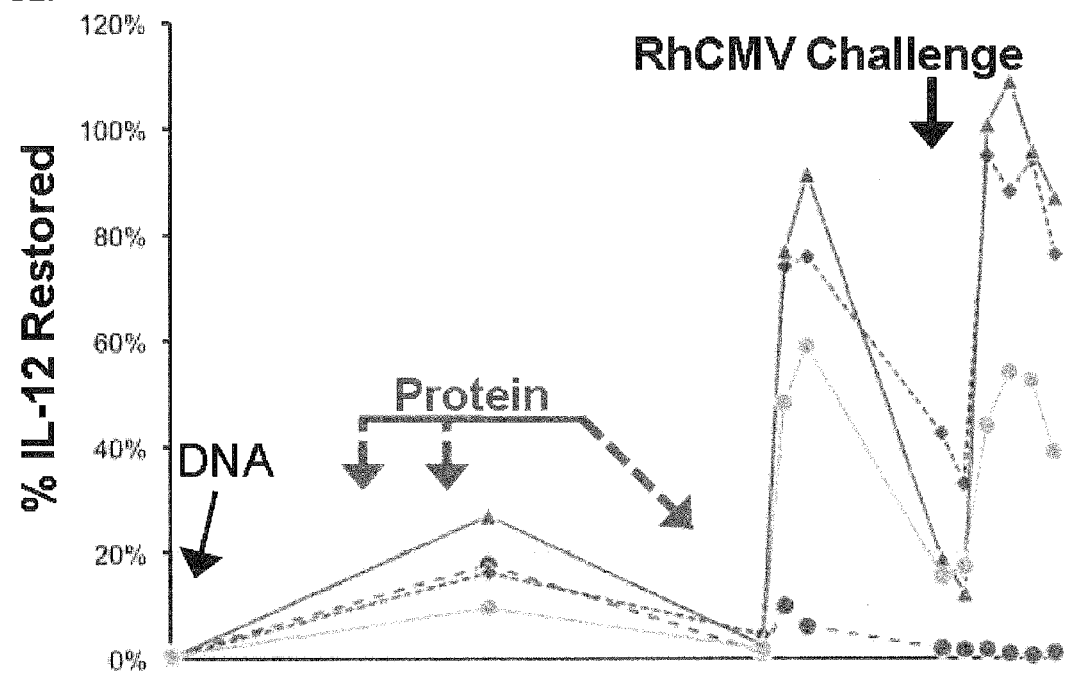
B.
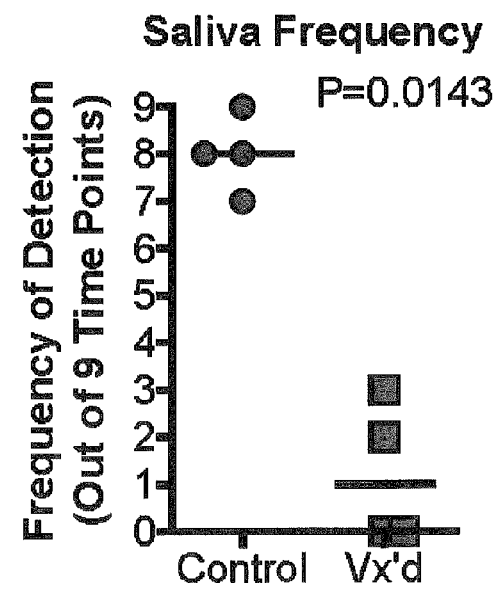
C.
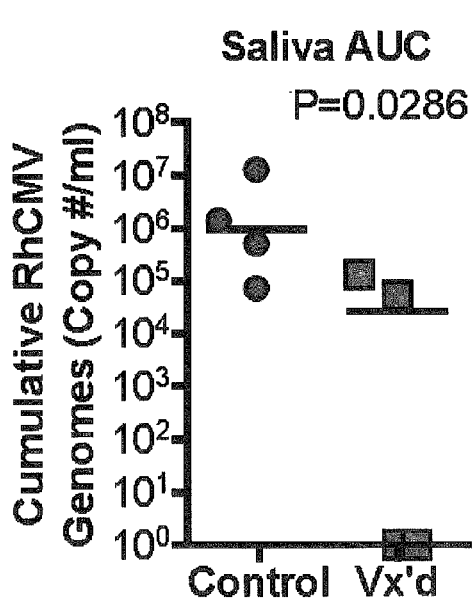

Fig. 14
A.
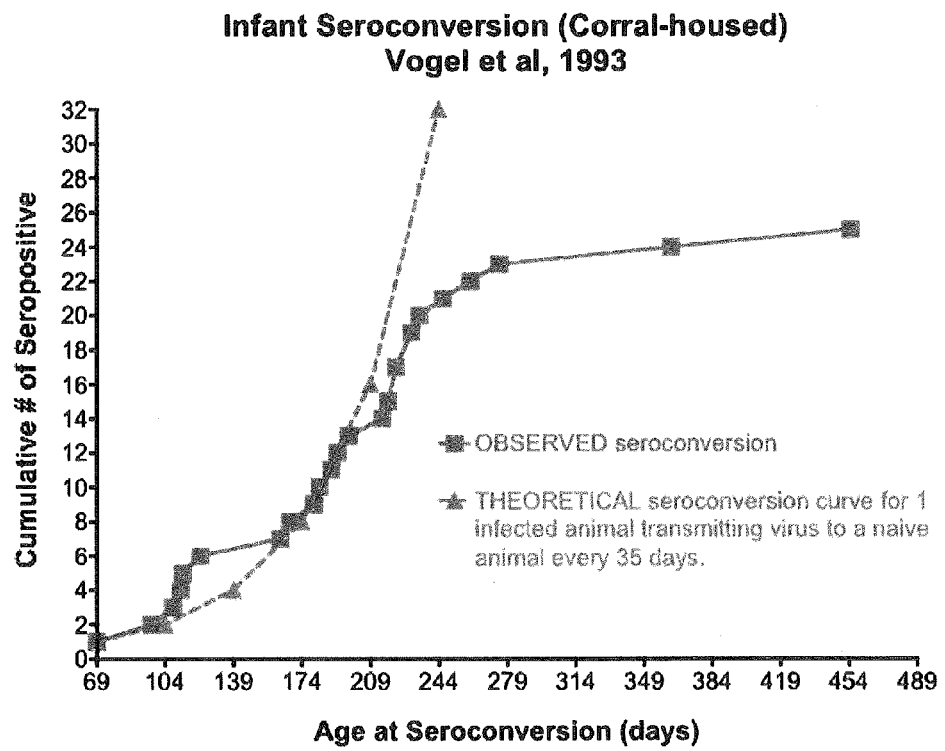
B.
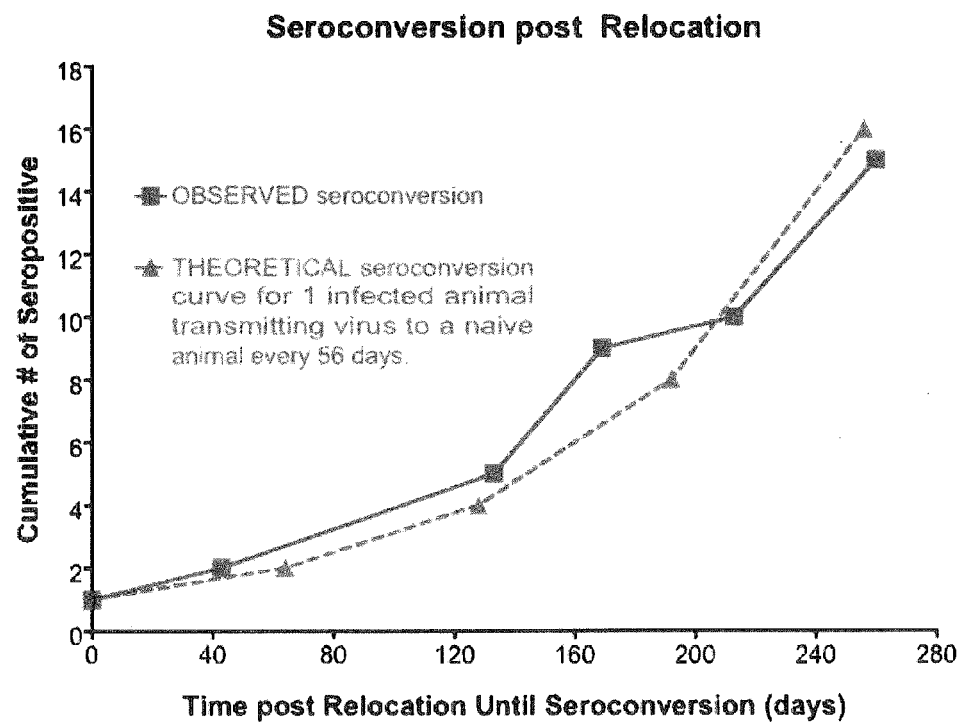

Fig. 15
A.
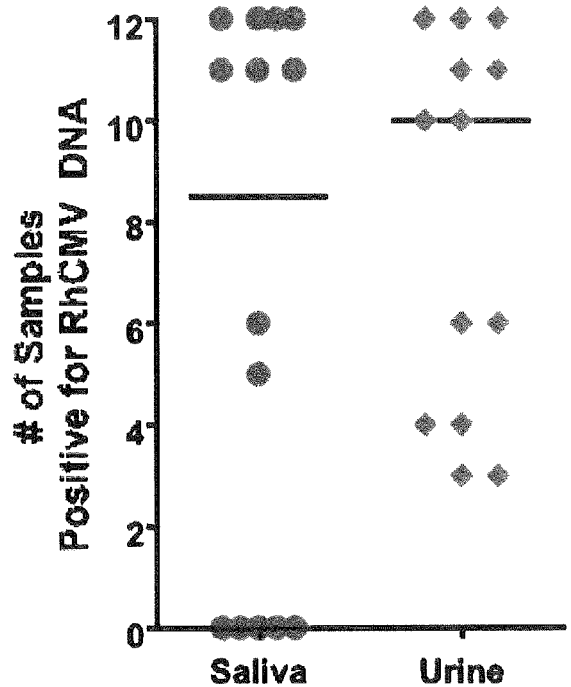
B.
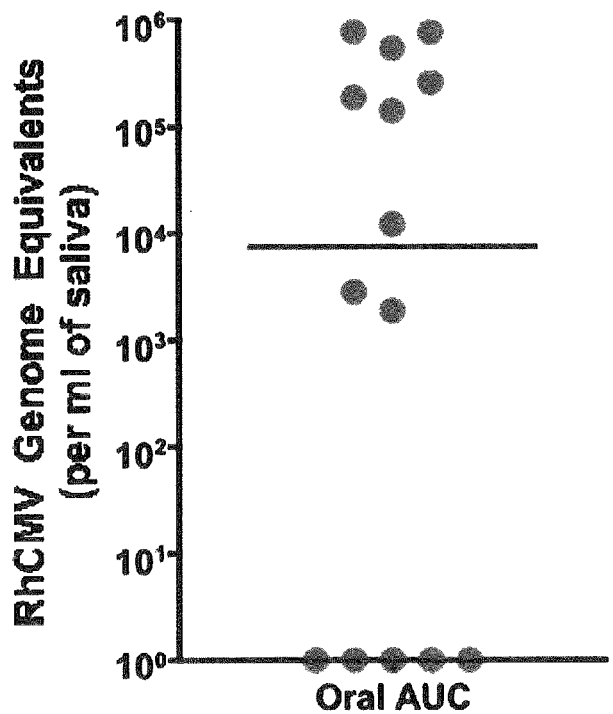

Urine
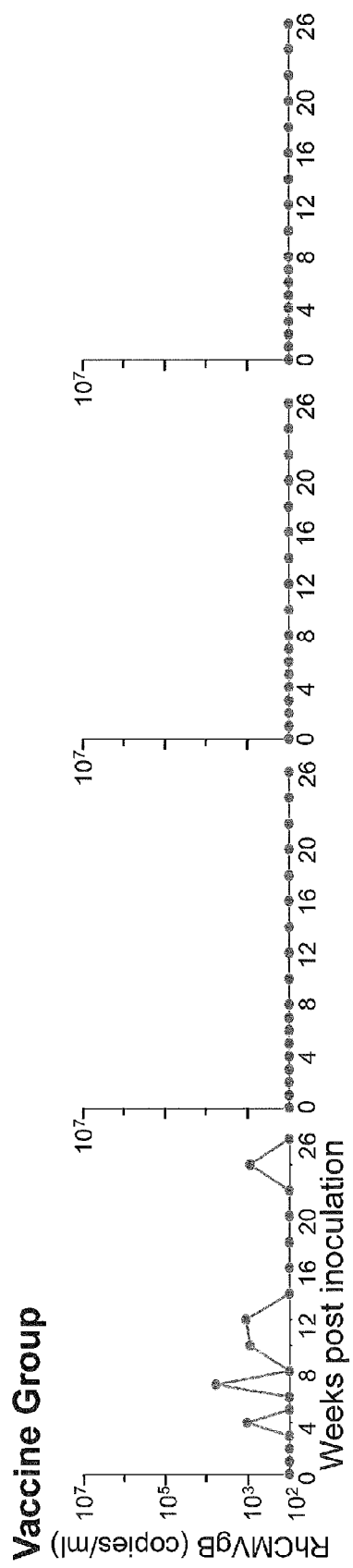
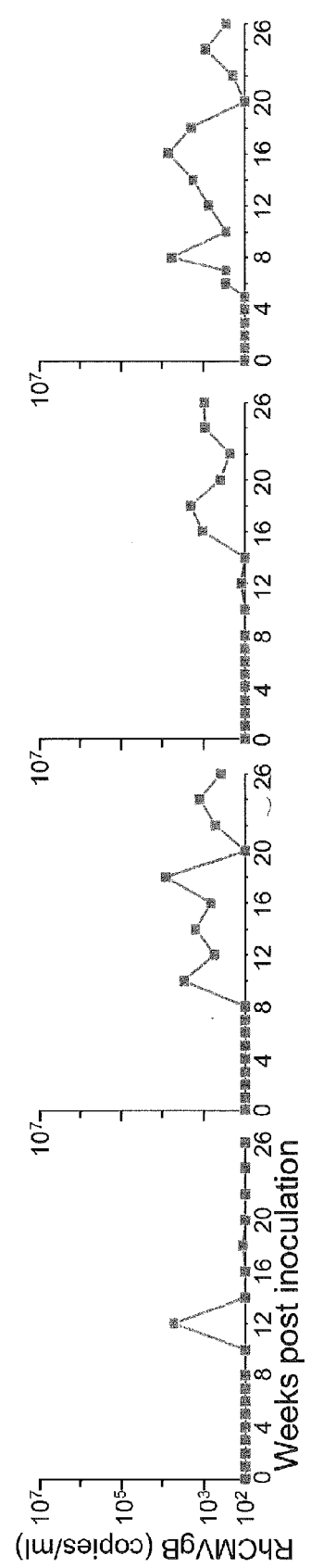
FIG 28

METHODS AND COMPOSITIONS FOR CYTOMEGALOVIRUS IL-10 PROTEIN

STATEMENT OF PRIORITY

This application is a 35 U.S.C. §371 national phase application of International Application Serial No. PCT/US2012/030666, filed Mar. 27, 2012, which claims the benefit, under 35 U.S.C. §119(e) of U.S. Provisional Application No. 61/468,945, filed Mar. 29, 2011, the entire contents of each of which are incorporated by reference herein.

STATEMENT OF GOVERNMENT SUPPORT

This invention was made with government support under Grant Nos. R01 AI49342 and R01 AI047300 awarded by the National Institutes of Health. The government has certain rights in the invention.

STATEMENT REGARDING ELECTRONIC FILING OF A SEQUENCE LISTING

A Sequence Listing in ASCII text format, submitted under 37 C.F.R. §1.821, entitled 5656-40TS_ST25.txt, 30,714 bytes in size, generated on Nov. 4, 2013 and filed via EFS-Web, is provided in lieu of a paper copy. This Sequence Listing is hereby incorporated by reference into the specification for its disclosures.

FIELD OF THE INVENTION

The present invention relates to cytomegalovirus IL-10 protein, antibodies thereto, and nucleic acids encoding the cytomegalovirus IL-10 protein, as well as their use in therapeutic methods.

BACKGROUND ART

Cytomegalovirus (CMV) has established persistent subclinical viral infections in the majority of the population. However, serious CMV-induced pathologies (blindness, hearing loss, mental retardation) occur in fetuses and newborns, as well as transplant recipients and acquired immunodeficiency syndrome (AIDS) patients (including retinitis and neuropathies), with immature or compromised immune systems. The ability of CMV to evade immune detection and elimination is facilitated by multiple proteins encoded in its genome that disrupt host processing and presentation of viral antigens, and interfere with chemokine and cytokine signaling.

The interleukin-10 (IL-10) signaling pathway is exploited by CMV, and many other viruses (e.g., human immunodeficiency virus (HIV), Hepatitis B and C) that establish persistent infections (Blackburn and Wherry, 2007; Rigopoulou et al., 2005). The main function of cellular IL-10 (cIL-10) is to protect the host from over-exuberant inflammatory responses by inhibiting the production of proinflammatory cytokines and chemokines, as well as major histocompatibility complex (MHC) and B7 on a variety of cell types (de Waal Malefyt et al., 1991a; de Waal Malefyt et al., 1991b). Human CMV (HCMV) and Rhesus CMV (RhCMV) encode functional IL-10 homologs (~26% amino acid sequence identity to that of the cIL-10 proteins encoded by their human and rhesus hosts, respectively) that exhibit the same immunosuppressive activities of cellular IL-10 (Chang et al., 2004; Kotenko et al., 2000; Lockridge et al., 2000). Functional studies with HCMVIL-10 (cmvIL-10) have demonstrated that it prevents effective T-cell priming by inhibiting dendritic cell (DC) maturation and trafficking, as well as inhibiting interleukin-12 (IL-12), MHC, and co-stimulatory molecule production (Chang et al., 2004). The functions of cmvIL-10 appear to be critical to the life cycle of the virus since it is highly conserved in sequence amongst numerous culture-adapted strains and clinical isolates.

For biological activity, cIL-10 and cmvIL-10 must bind to the IL-10R1 and IL-10R2 receptor chains (Moore et al., 2001). Binding studies demonstrate that HuIL-10 and cmvIL-10 form equivalent high affinity (~1 nM) interactions with the IL-10R1 chain and low affinity (~µM) contacts with the IL-10R2 chain (Yoon et al., 2006). As a result, the IL-10/IL-10R1 interaction occurs first, followed by the assembly of the IL-10/IL-10R1/IL-10R2 ternary complex, which activates intracellular kinases (Jak1 and Tyk2) and transcription factors (STAT3) leading to IL-10 cellular responses (Moore et al., 2001).

The present invention provides the discovery that the cytomegalovirus IL-10 protein can be modified to have reduced functional activity while retaining immunogenicity. Thus, the present invention overcomes previous shortcomings in the art by providing such a modified cytomegalovirus IL-10 protein and biologically active fragments thereof, as well as nucleic acids encoding this protein and its fragments. These proteins, fragments and nucleic acids are used, for example, in methods of treating and preventing infection by cytomegalovirus.

SUMMARY OF THE INVENTION

In one aspect, the present invention provides a cytomegalovirus IL-10 protein, wherein the protein comprises a mutation in one or more amino acids, wherein the mutation(s) result in a phenotype of reduced binding to an interleukin-10 (IL-10) receptor protein and reduced functional activity as compared to a cytomegalovirus IL-10 protein lacking said mutation(s).

In some aspects of the invention, the mutation in the cytomegalovirus of this invention can be in one or more amino acids located from position 39 through position 78 and/or from position 155 through position 176 in the amino acid sequence of SEQ ID NO:3. In further aspects, the mutation can be in one or more amino acids located from position 42 through position 85 and/or position 169 through position 189 in the amino acid sequence of SEQ ID NO:1 or 2.

Additional aspects of this invention include an isolated nucleic acid molecule comprising a nucleotide sequence encoding the cytomegalovirus IL-10 protein of this invention, as well as a vector comprising such a nucleic acid molecule.

Further aspects of this invention include a composition comprising the cytomegalovirus IL-10 protein of this invention, a nucleic acid molecule of this invention and/or a vector of this invention, in a pharmaceutically acceptable carrier.

Also provided herein is a method of eliciting an immune response to cytomegalovirus in a subject, comprising administering to the subject an effective amount of the cytomegalovirus IL-10 protein of this invention, a nucleic acid molecule of this invention, a vector of this invention and/or a composition of this invention, in any combination.

Furthermore, the present invention provides a method of treating a cytomegalovirus infection in a subject, comprising administering to the subject an effective amount of the cytomegalovirus IL-10 protein of this invention, a nucleic acid molecule of this invention, a vector of this invention and/or a composition of this invention, in any combination.

In additional aspects, the present invention provides a method of preventing or attenuating a primary cytomegalovirus infection in a subject, comprising administering an effective amount of the cytomegalovirus IL-10 protein of this invention, a nucleic acid molecule of this invention, a vector of this invention and/or a composition of this invention, in any combination.

The present invention further provides a method of reducing the risk of cytomegalovirus infection in a transplant recipient and/or in an immunocompromised or immunosuppressed subject, comprising administering to the transplant recipient or subject an effective amount of the cytomegalovirus IL-10 protein of this invention, a nucleic acid molecule of this invention, a vector of this invention and/or a composition of this invention, in any combination.

Other aspects of this invention include a method of preventing or attenuating a cytomegalovirus infection in a subject, reducing the risk of cytomegalovirus infection in a transplant recipient and/or reducing the risk of cytomegalovirus infection in an immunocompromised or immunosuppressed subject comprising administering to the subject an effective amount of an antibody specifically reactive against a cytomegalovirus IL-10 protein. In some embodiments, the antibody specifically blocks cytomegalovirus IL-10 functional activity. In particular embodiments, the subject or transplant recipient is a human and the antibody is a humanized monoclonal antibody.

Various other objectives and advantages of the present invention will become apparent from the following detailed description.

BRIEF DESCRIPTION OF THE DRAWINGS

FIGS. 2A-B. Sequence and structure model of rhcmvIL-10 binding residues. (A) Sequence alignment of cellular and viral human and rhesus IL-10 proteins (SEQ ID NOS:15-18). Human cIL-10 (HuIL-10, SEQ ID NO:16) helices are denoted on the alignment and labeled A-F. Residues chosen for mutagenesis are identified with arrows. (B) Structure model of the rhcmvIL-10/Rhesus IL-101R1 (RhIL-10R1) interface based on the crystal structure of the HuIL10/IL-10R1 complex (Protein Database Accession No. pdbid 1Y6K, Yoon et al., 2006). Residues chosen for mutagenesis that disrupt IL-10R1 binding are shown in black and K34, which exhibits essentially WT activity, is shown in dark grey.

FIGS. 4A-B. Ability of rhcmvIL-10 mutants to proliferate TF-1/HuIL-10R1 cells. (A) Cell supernatants containing rhcmvIL-10 single point mutants [Lys-34Glu (R34E), Gln-38Arg (Q38R), Asp-144His (D144H)] were evaluated for their ability to proliferate TF-1/HuIL-10R1 cells. (B) TF-1 cell proliferation assay of cell supernatants containing rhcmvIL-10WT and rhcmvIL-10 double mutants Gln-38Arg/Asp-144His (Q38D144) and Glu-142Gln/Asp-144 (E142D144).

FIGS. 8A-B. (A) Quantification of rhcmvIL-10 antibody titers by fluorescent luminosity (open columns, units on left Y-axis) versus rhcmvIL-10 ELISA (solid columns, right Y-axis) for 16 RhCMV-infected (#1-16) and 4 RhCMV-uninfected (#17-20) monkeys.

(B) Western blot detection of seroreactivity to rhcmvIL-10 in RhCMV-infected monkeys (#1-4, 12, 13, 15, and 16) and uninfected (#17 and 18) monkeys. A plasma sample from a hyperimmune monkey was included as a positive control (P, lane 9). All RhCMV seropositive samples were positive for antibodies to rhcmvIL-10 with the band of predicted size at ~20 kilodaltons (kDa) while the plasma samples from RhCMV-uninfected monkeys were negative. MW: Molecular Weight (in kDa).

FIGS. 9A-B. (A) An age comparison of rhcmvIL-10 responses in 53 macaques seropositive for RhCMV stratified into 3 age groups; infant (≤1 year), adult (5-10 years) and aged (>13 years). The infants had significantly higher antibody titers than the adults and aged ($p<0.001$, $p<0.01$, respectively). There was no significant difference between the adult and aged animal groups. (B) Linear regression analysis of RhCMV and rhcmvIL-10 antibody titers from 53 rhesus macaques. There was a significant correlation between total RhCMV and rhcmvIL-10 antibody titers with RhCMV antibody titers ($r=0.6176$, $p<0.0001$).

Figure 10:
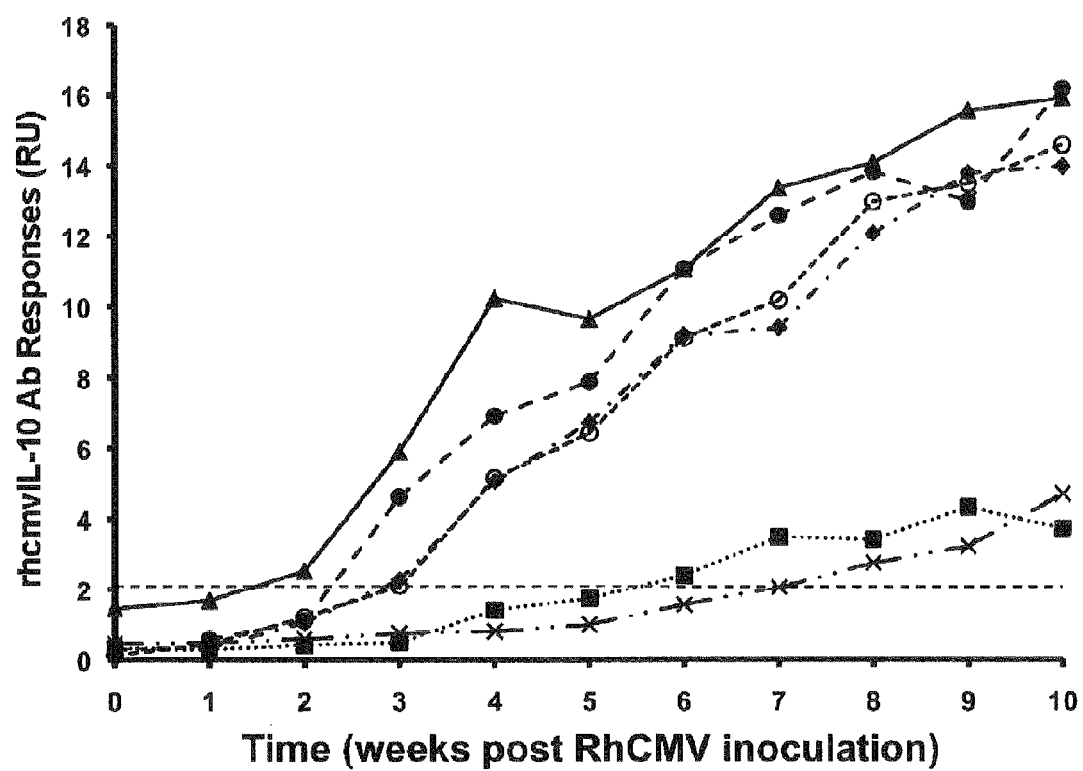

FIG. 10. rhcmvIL-10 binding antibody response during primary RhCMV infection. Six rhesus monkeys were experimentally inoculated with the 68-1 strain of RhCMV and prospectively analyzed for 10 weeks. rhcmvIL-10 antibodies were detected 2-3 weeks post RhCMV inoculation in 4 of the 6 animals while the remaining two developed a detectable response by 6-7 weeks. The cutoff threshold was set at 2 RU.

Figure 11:
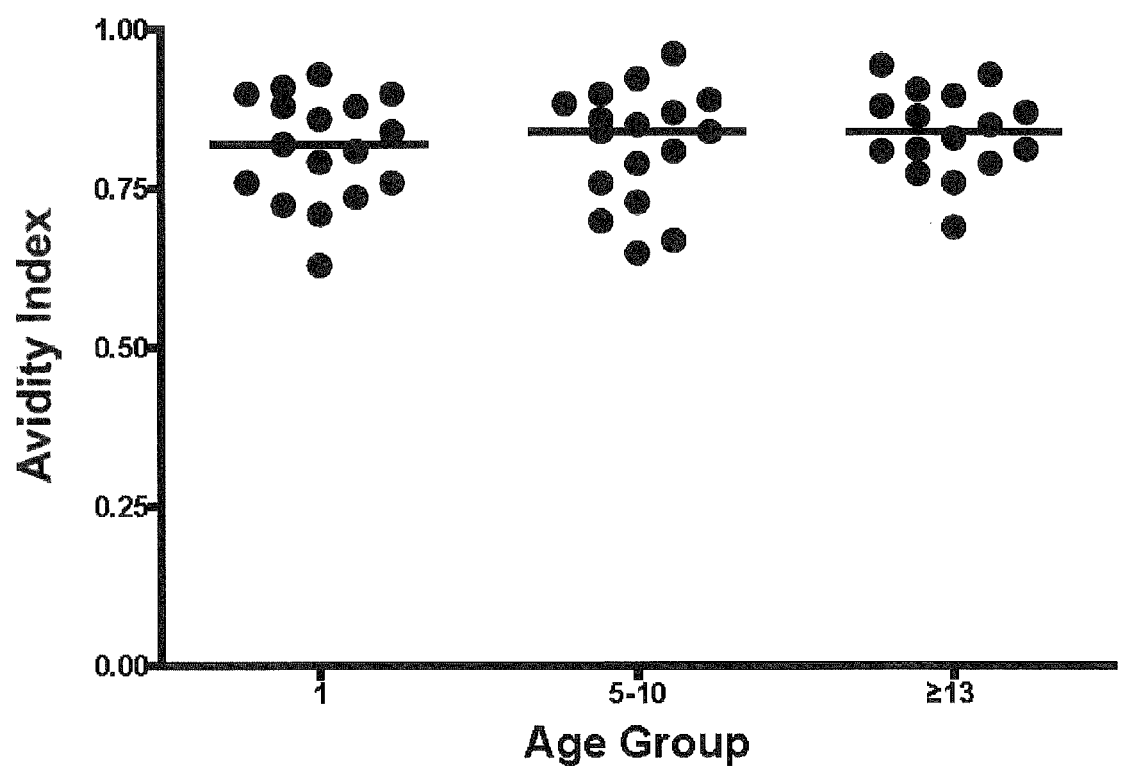

FIG. 11. The avidity of rhcmvIL-10 antibodies from 50 seropositive rhesus macaques was assayed by an avidity ELISA with a 6M urea wash. The average avidity ratio was 0.83 (standard deviation=0.076). There was no significant difference between age groups.

FIGS. 12A-B. rhcmvIL-10 neutralization was determined by incubating LPS-activated PBMC with either a pre-incubated mixture of rhcmvIL-10 and rhesus plasma, or plasma only. Neutralization was calculated as the inverse of the ratio of (IL-12 expressed in the presence of rhcmvIL-10/plasma)/ (IL-12 expressed in the presence of plasma only) and was expressed as the "percent (%) IL-12 induction restored." (A) rhcmvIL-10 neutralizing titers ranged from 0-100% IL-12 induction restored with a significant difference between the RhCMV seropositive and seronegative samples (p=0.0083). The median neutralization (% IL-12 induction restored) was 16% (indicated by the line). (B) % IL-12 induction restored was found to be directly correlated to rhcmvIL-10 antibody titers in RhCMV-seropositive monkeys (r=0.8292, p<0.0001).

FIGS. 13A-C. Immunization of naïve monkeys with rhcmvIL-10 and detection of RhCMV DNA in the saliva of control or rhcmvIL-10-vaccinated (Vx'd) monkeys challenged with subcutaneous inoculation of RhCMV. (A) Four naïve monkeys were immunized against rhcmvIL-10 M1 and M2 using a combined DNA prime (1×) and protein boost (3×) strategy. The restoration of IL-12 expression in LPS-activated PBMC measured the generation of NAb (see FIG. 5). (B) Frequency of detectable RhCMV DNA in oral swabs following the lag phase between the time of inoculation and the first positive sample in any of the control and Vx'd monkeys. (C) Cumulative RhCMV genomes in saliva (AUC) in control and Vx'd monkeys. Results were analyzed by Mann Whitney (one-tailed).

FIGS. 14A-B. The rate at which animals uninfected with RhCMV seroconvert to RhCMV antigens following birth in an outdoor breeding corral (A) or following co-relocation of 15 uninfected and 1 RhCMV-infected animals. The observed rates of seroconversion (solid line and squares) are plotted relative to the theoretical rates of seroconversion (dashed line and triangles) in which the number of seropositive animals doubles every 35 (A) or 56 (B) days.

FIGS. 15A-B. RhCMV shedding in RhCMV-infected monkeys. (A) The frequencies of detectable RhCMV DNA in saliva and urine samples collected over 12 consecutive weeks. (B) The cumulative magnitude of RhCMV shedding in saliva calculated as an Area Under the Curve (AUC). The lines represent the median values.

Figure 16:
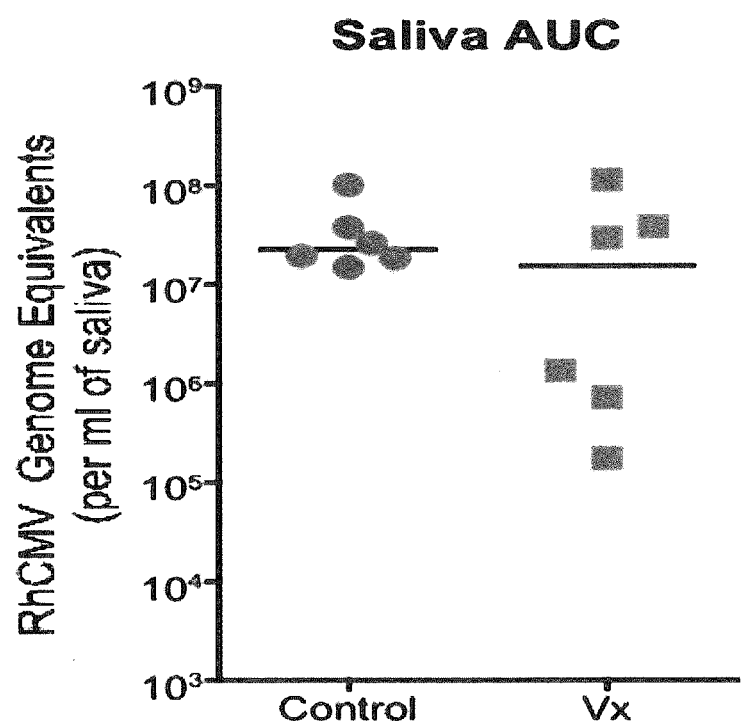

FIG. 16. RhCMV shedding in control and vaccinated (Vx) monkeys challenged with RhCMV. RhCMV-infected monkeys. The cumulative shedding of RhCMV in saliva showed significant reductions in shedding for a subset of vaccinated animals.

Figure 17A:
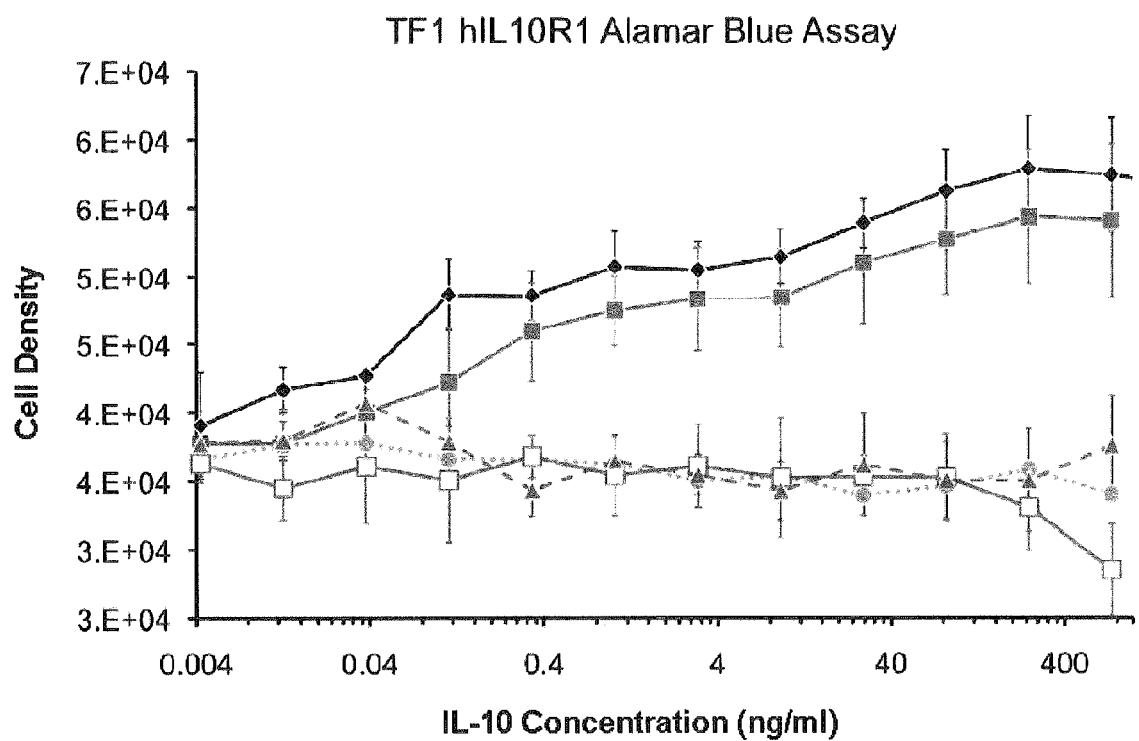
Figure 17B:
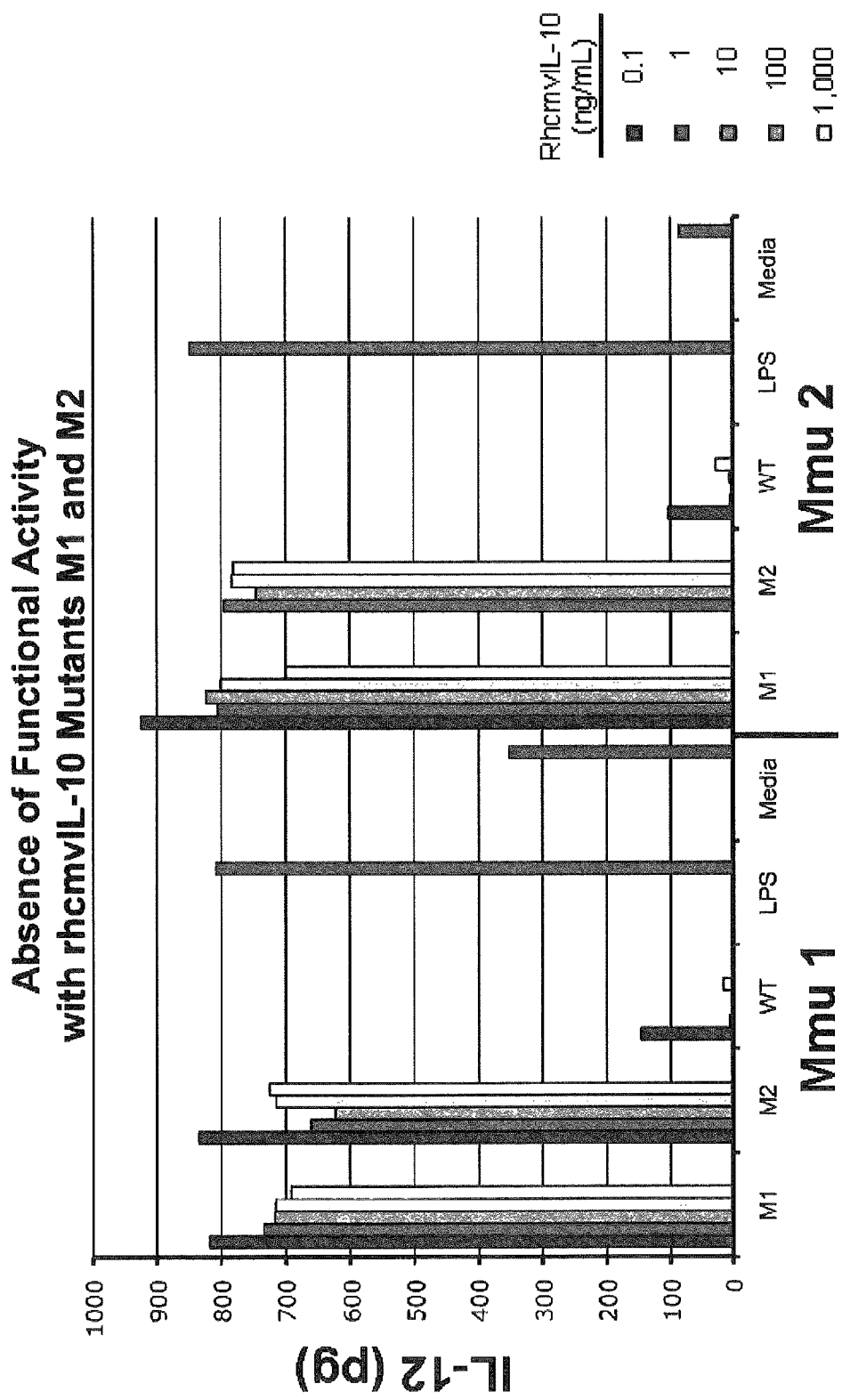

FIGS. 17A-B. Absence of functional activity with rhcmvIL-10 mutants M1 and M2. (A) TF1 cells expressing human IL-10R were assayed for proliferation in the presence of human cIL-10, wild-type rhcmvIL-10 (WT), rhcmvIL-10 M1 and M2, or media alone. (B) IL-12 production was assayed in the supernatant of rhesus PBMC activated with LPS alone or LPS plus increasing concentrations of either rhcmvIL-10 WT, M1, or M2 (0.1 ng; 1 ng; 10 ng; 100 ng; or 1,000 ng), or media alone. Results for PMBCs from 2 monkeys (Mmu 1 and 2) are shown.

Figure 18:
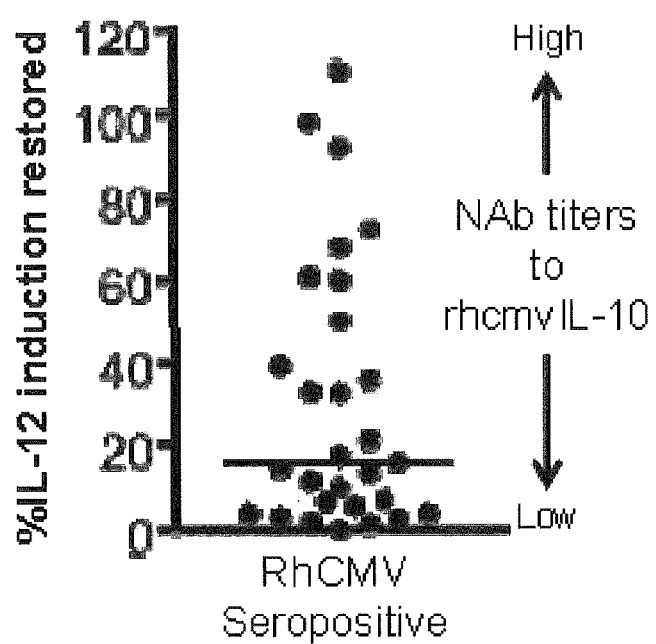

FIG. 18. Detection of NAb to rhcmvIL-10 in RhCMV-infected monkeys. Plasma samples were assayed for the ability to neutralize the immunosuppressive effects of rhcmvIL-10 on LPS-activated PBMC. Plasma samples with higher NAb titers are noted for higher IL-12 production following incubation of PBMC with rhcmvIL-10 WT and plasma. Results are expressed as the percent IL-12 induction restored compared to incubation of PBMC with LPS and medium.

Figure 5:
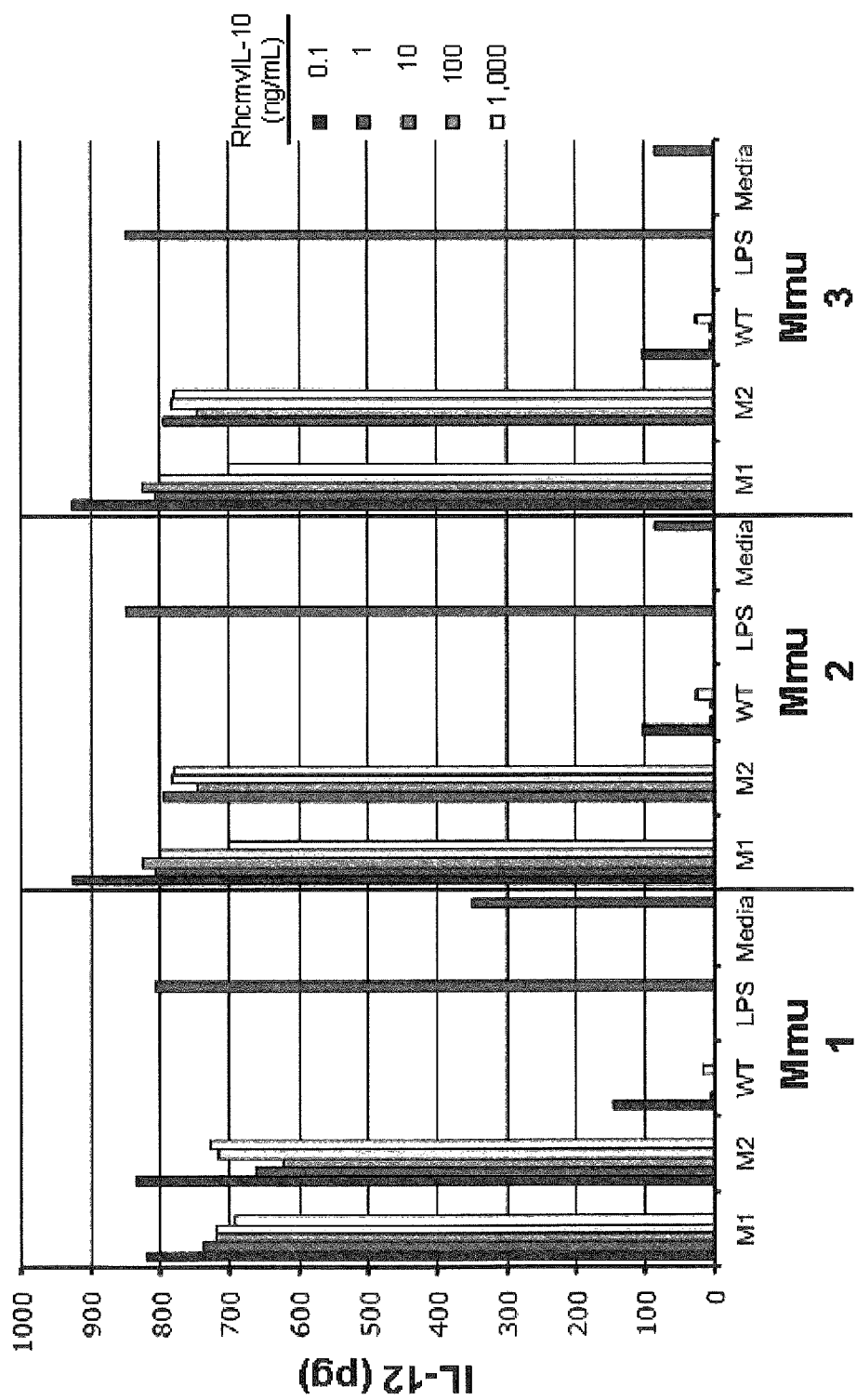
FIG. 5. Absence of functional activity with rhcmvIL-10 mutants M1 and M2. IL-12 production was assayed in the supernatant of rhesus PBMC from three monkeys (Mmu 1, Mmu 2, Mmu 3) activated with LPS alone, or LPS plus increasing concentrations of either rhcmvIL-10 WT, M1, or M2 over a concentration range of 0.1-1,000 ng/mL. Results of rhesus PBMC incubated with media alone are represented in right hand column. Only rhcmvIL-10 WT suppressed LPS-stimulated production of IL-12.
Figure 19:
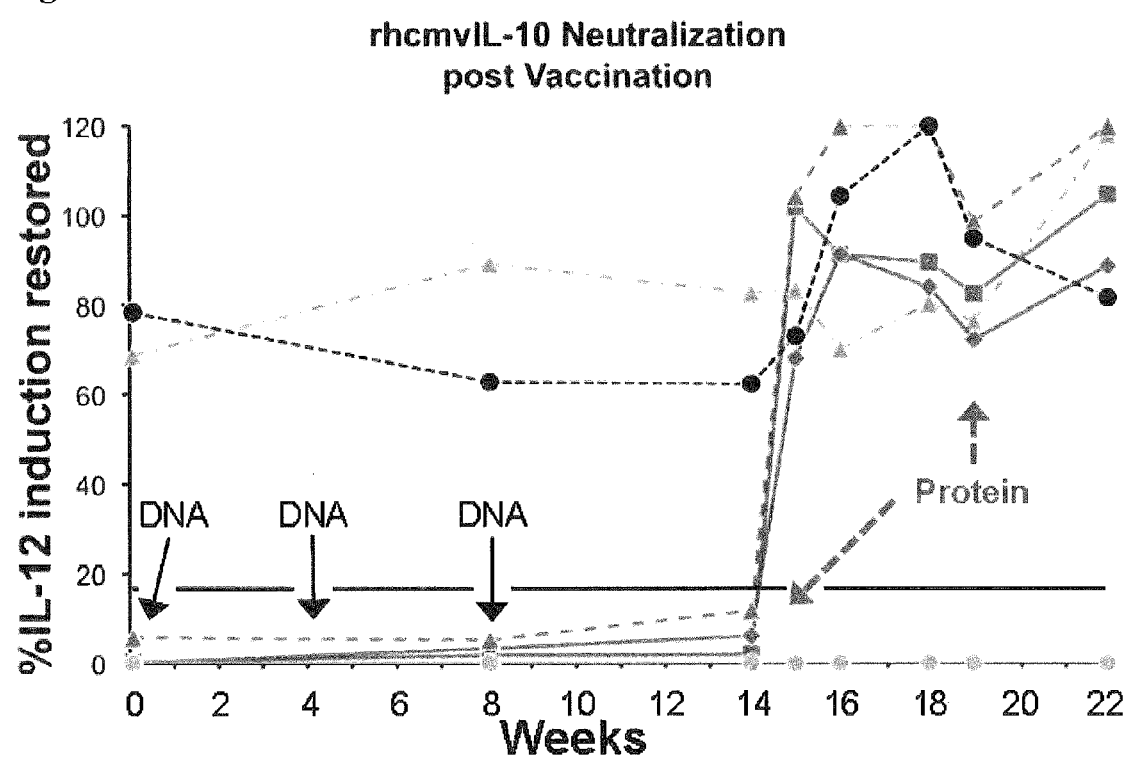

FIG. 19. Six RhCMV-infected monkeys were immunized three times with plasmid expression vectors for M1 and M2 (black solid arrows) and two times with recombinant protein adjuvanted in MONTANIDE® ISA 720. All six animals demonstrated increased binding Ab responses (not shown), and five animals demonstrated increased NAb responses after the protein immunizations, based on the IL-12-based assay described in FIG. 5. The solid line at ~16% IL-12 restored represents the median NAb response in naturally infected monkeys (FIG. 5).

Figure 20:
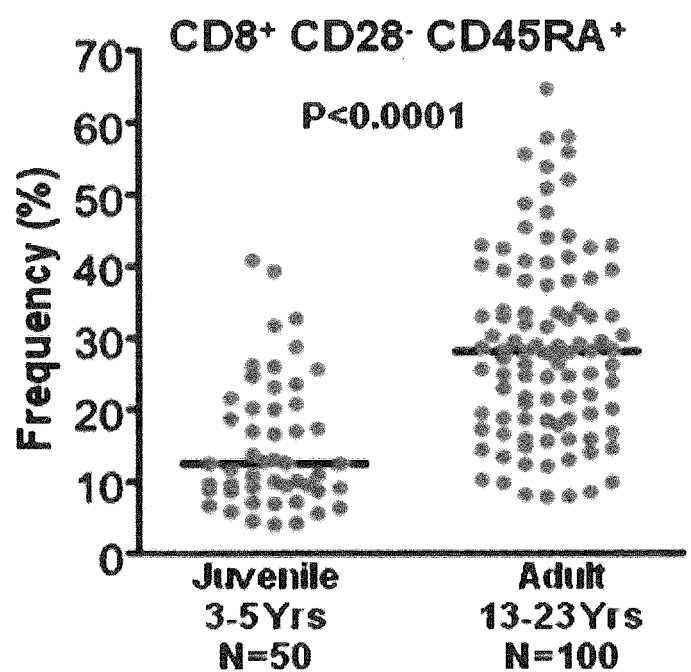

FIG. 20. Frequency of $CD8^{Pos}$ $CD28^{Neg}$ $CD45RA^{Pos}$ cells in juvenile (3-5 years) and aged adults (13-23 years).

Figure 21:
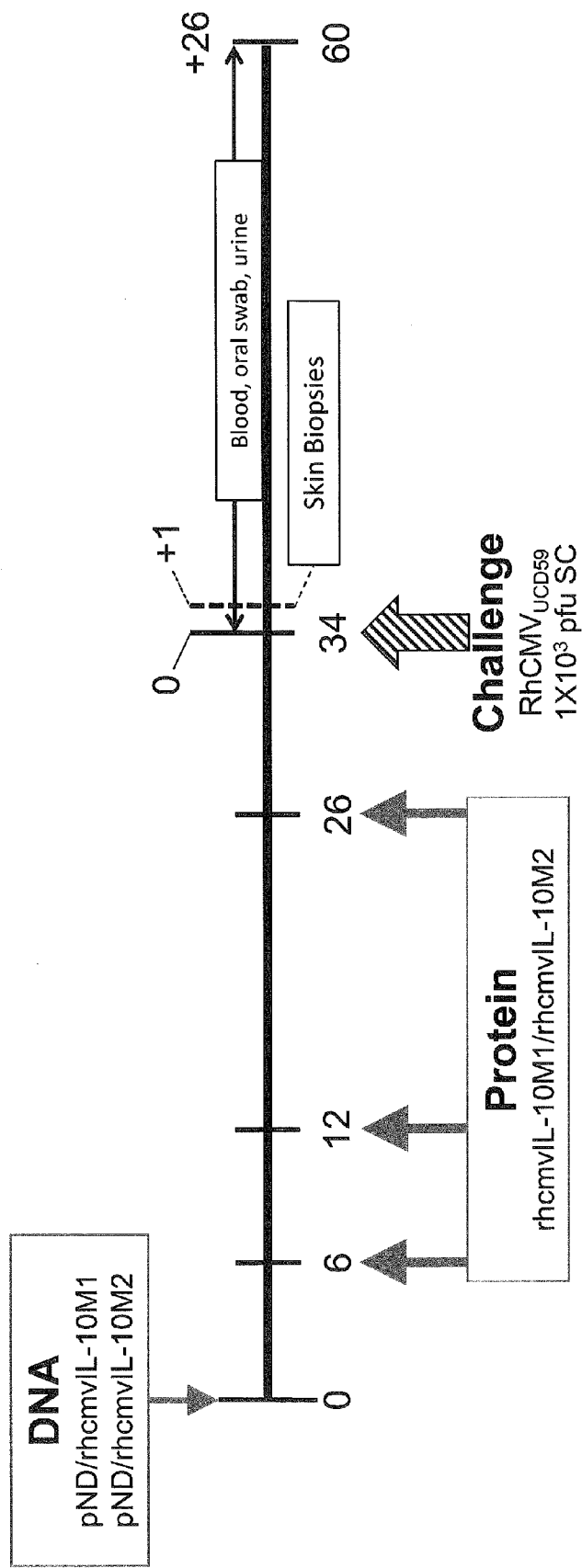

FIG. 21. DNA and protein vaccination and RhCMV challenge schedule. A group of 4 RhCMV-uninfected juvenile macaques was immunized over the course of 26 weeks with a mixture of two different non-functional forms of rhcmvIL-10, M1 and M2, by a heterologous DNA prime (50 ug ID and 100 ug IM) and 3 proteins boosts (50 ug ID and 100 ug IM). All animals were challenged with 1000 p.f.u. of $RhCMV_{UCD59}$ at 34 weeks. Skin biopsies were taken at 1 week post challenge (p.c.). Blood, oral swab and urine samples were taken weekly through week 8, and then bi-weekly through week 26.

Figure 22:
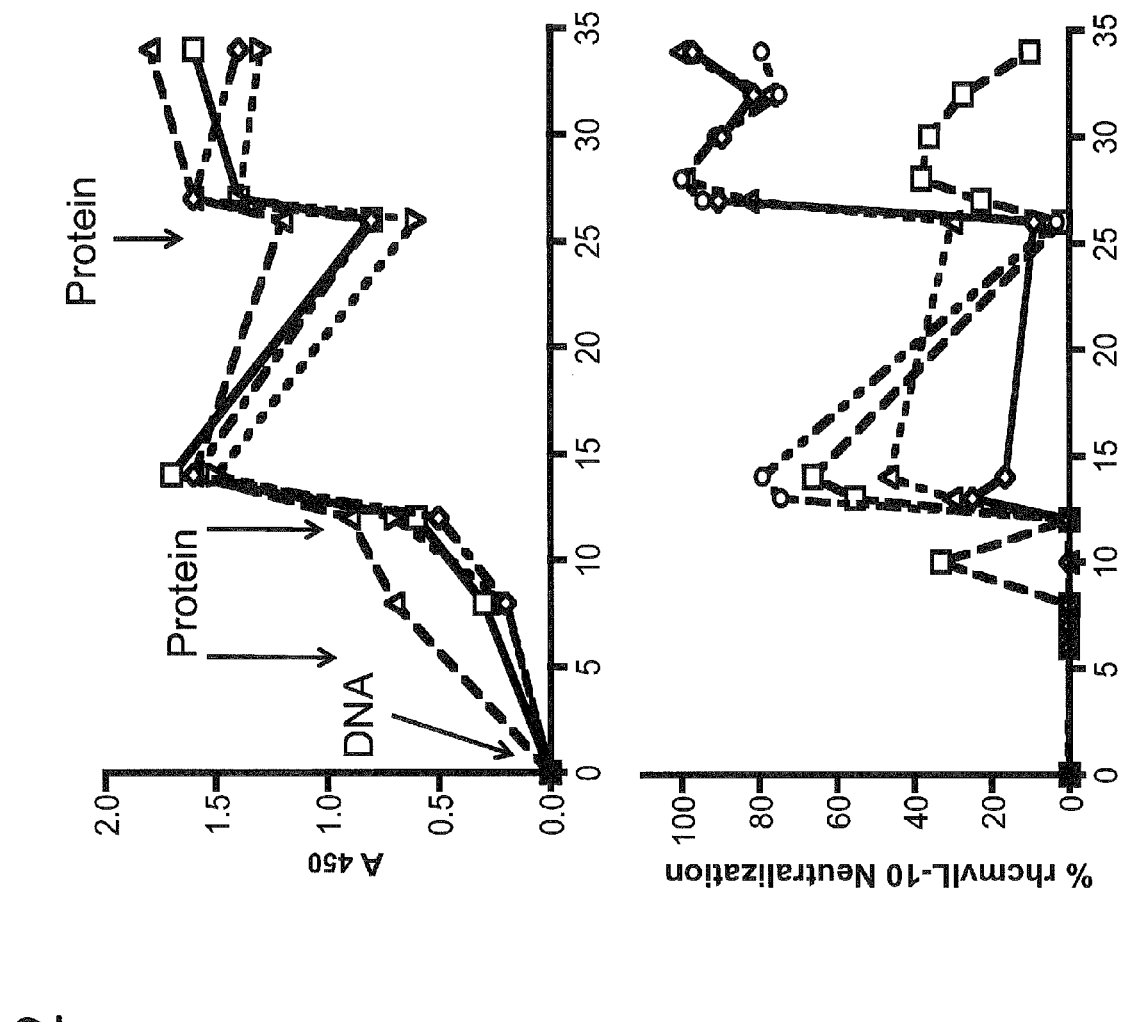

FIGS. 22A-B. Vaccination with rhcmvIL-10M1/M2 stimulates high binding and neutralizing antibody titers. (A) rhcmvIL-10 binding antibodies were found in the plasma of all 4 vaccinees as measured by rhcmvIL-10 ELISA. (B) High rhcmvIL-10 neutralizing antibody (NAb) titers were observed in 3 of the 4 vaccinated animals. Moderate NAb levels were observed in the fourth animal with peak titers reached 2-3 weeks after the third protein boost.

Figure 23:
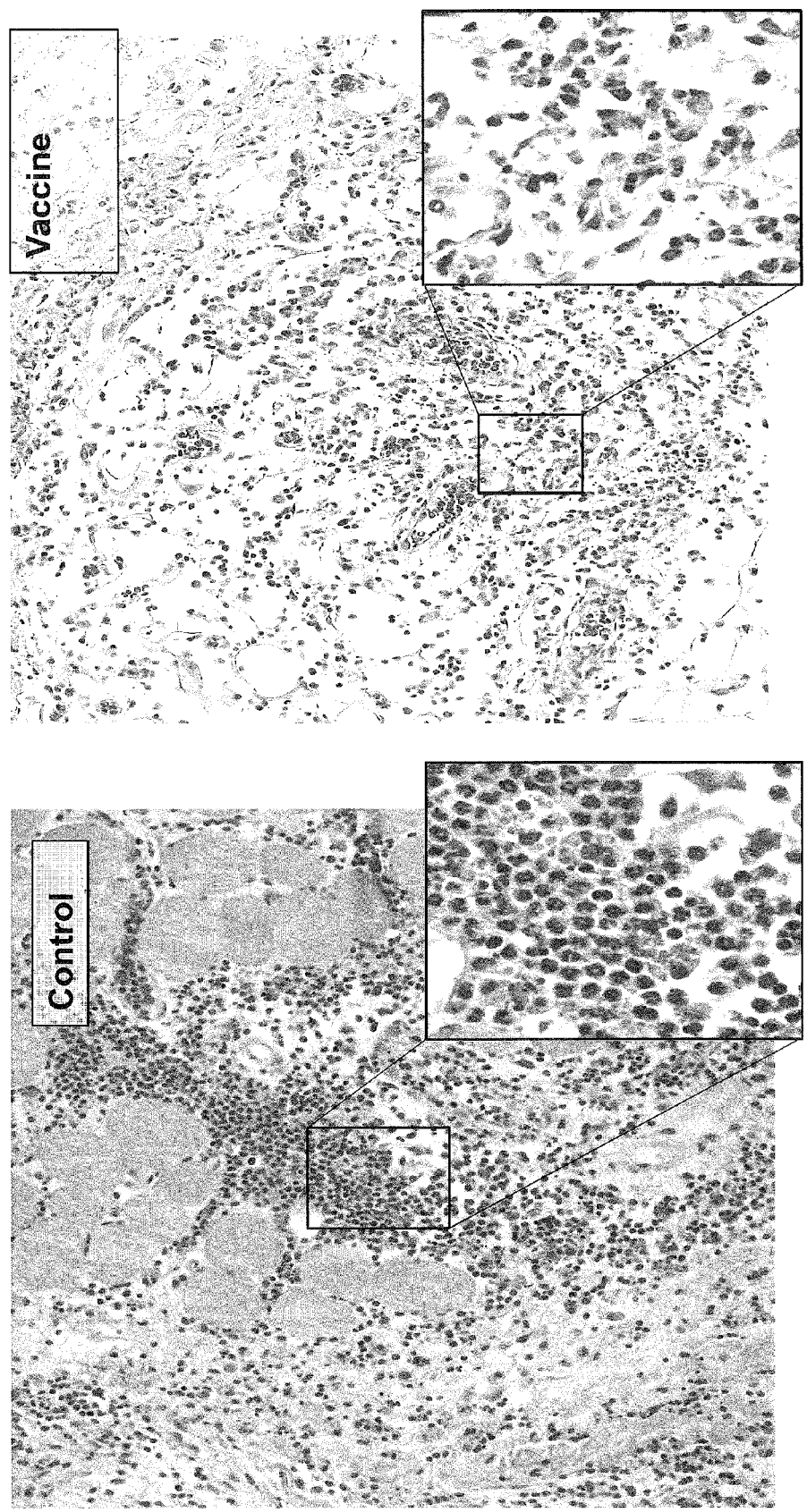

FIG. 23. Altered RhCMV replication and host inflammation at the inoculation site. Representative images from biopsies obtained from the site of inoculation 7 days post-challenge. Serial sections of tissue were stained with hematoxylin and eosin (H&E). Vaccinees showed a decrease in the inflammatory infiltrate with a specific decrease in polymorphonuclear (PMN) cell infiltrate. Vaccinated animals had fewer infected cells, observed by the presence of cytomegalic cells, as seen in the H & E stain.

Figure 24:
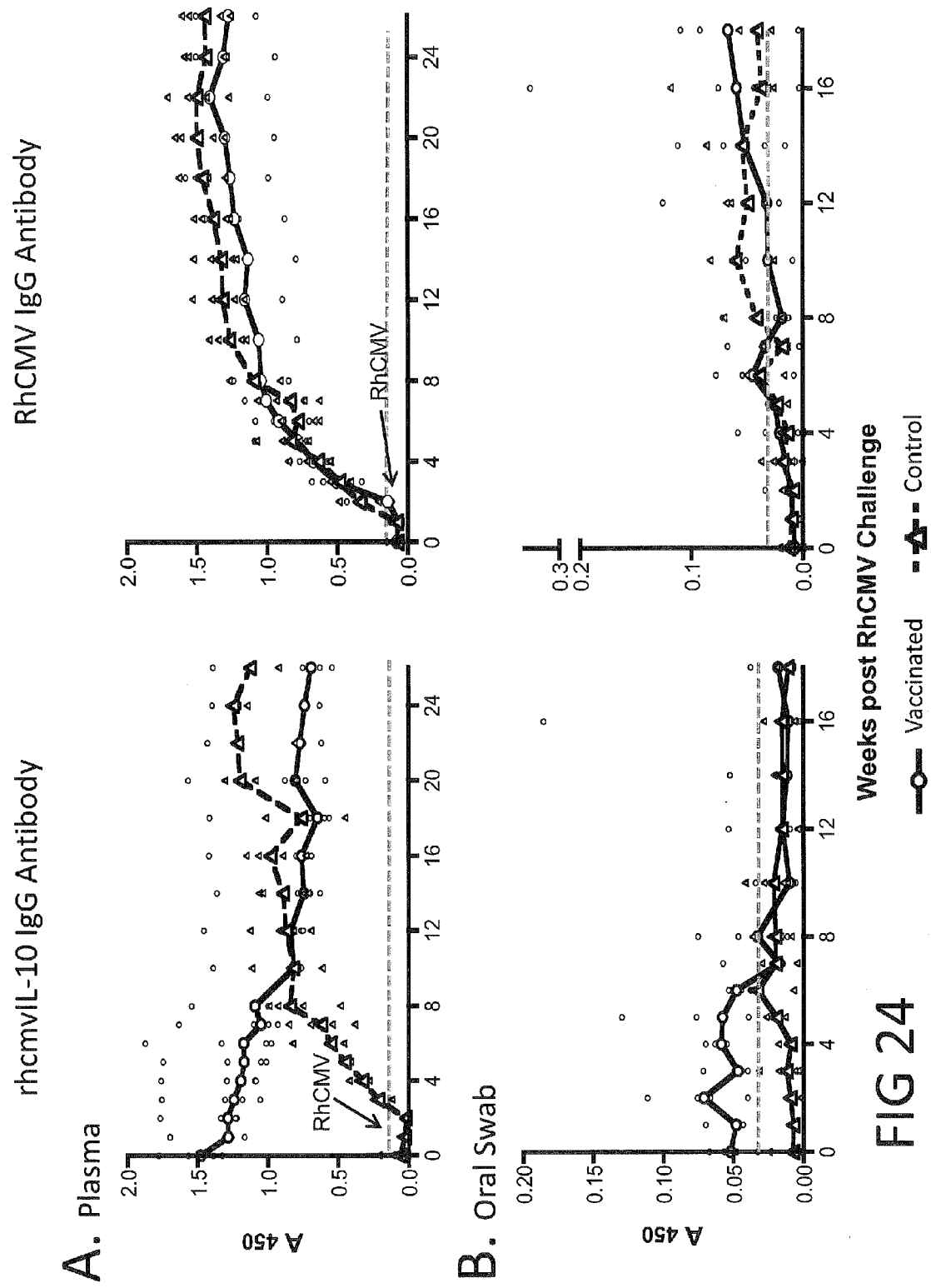

FIGS. 24A-B. Generation of rhcmvIL-10 and RhCMV binding antibodies in rhcmvIL-10 vaccinated (o) and un-vaccinated (Δ) control animals Antibody titers were analyzed by antigen-specific ELISA. Absorbance units ($A_{450}$) were measured at 450 nm. Plasma samples (A) were diluted at 1:100 and oral swab samples (B) were diluted 1:10. Week 0 indicates time of RhCMV challenge. Lines indicate the average of the vaccinated and unvaccinated groups, respectively. The horizontal dashed lines indicate the threshold for a positive antibody response. Average at wk 0=0.052

Figure 25:
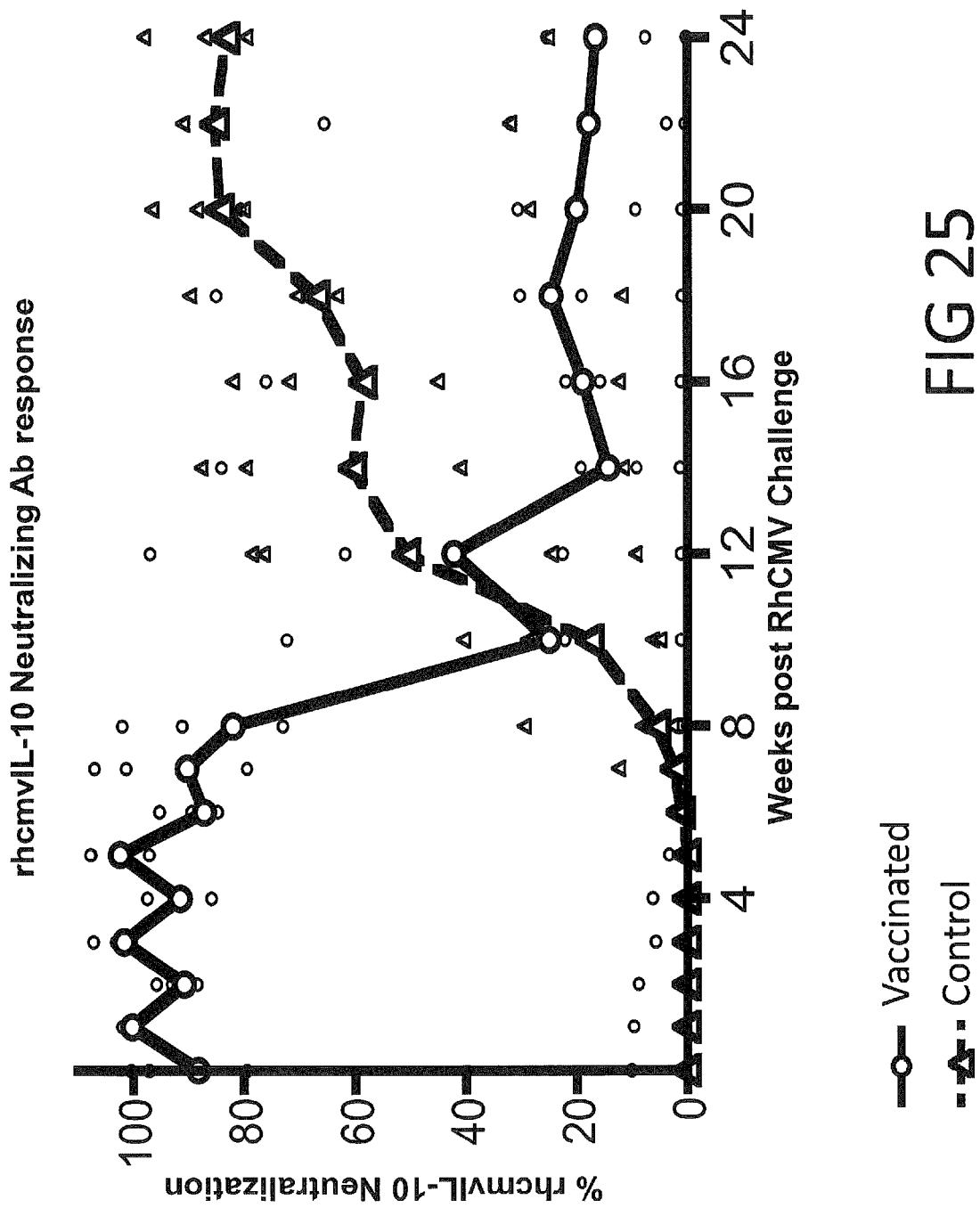

FIG. 25. Generation of rhcmvIL-10 neutralizing antibodies post-challenge. The 4 vaccinated animals (o) and 4 control animals (Δ) were tested for development of neutralizing antibodies in plasma. Plasma samples were diluted 1:1000 and tested weekly through week 8 and then bi-weekly until week 26. Lines indicate the average of the vaccinated and unvaccinated groups respectively.

Figure 26:
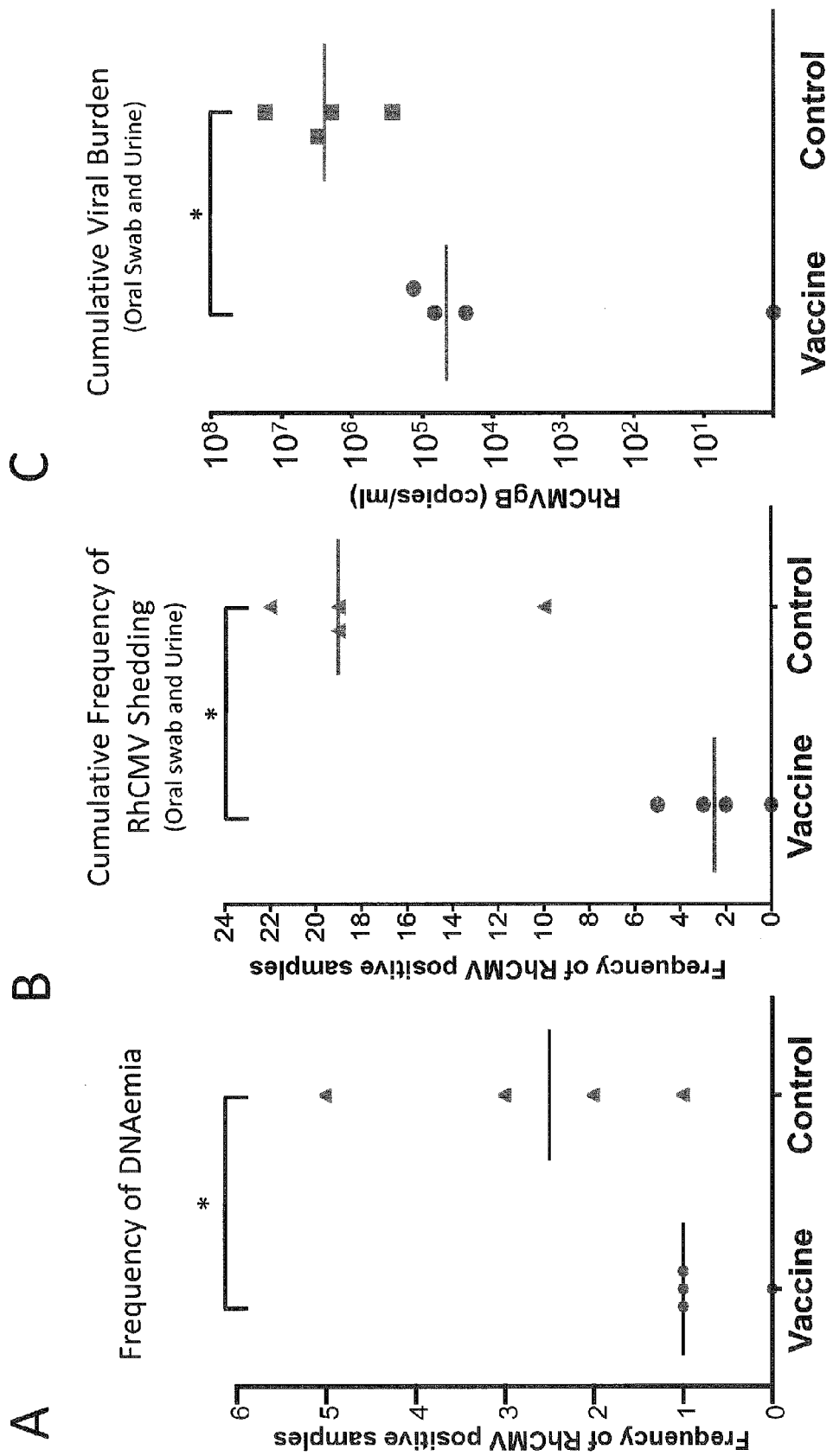

FIGS. 26A-C. Frequency of viral RhCMV DNA and frequency and cumulative viral burden in bodily fluids. Plasma, oral swabs and urine were collected weekly and bi-weekly and tested for RhCMV DNA (gB) by qPCR. (A) Plasma from the vaccine group was found to have a significantly lower frequency of samples with RhCMV DNA in the blood than the controls (p=0.0286 one-tailed Mann-Whitney). (B) The frequency of viral shedding in bodily fluids (oral swab and urine combined) was found to be significantly less in the vaccine group than the controls (p=0.014 one-tailed Mann-Whitney). Data represent a summary of FIGS. 27 and 28. Overall viral loads (C) in bodily fluids, derived by combining gB DNA levels from all time points, were also lower in vaccinated animals (p=0.014 one-tailed Mann-Whitney).

Figure 27:
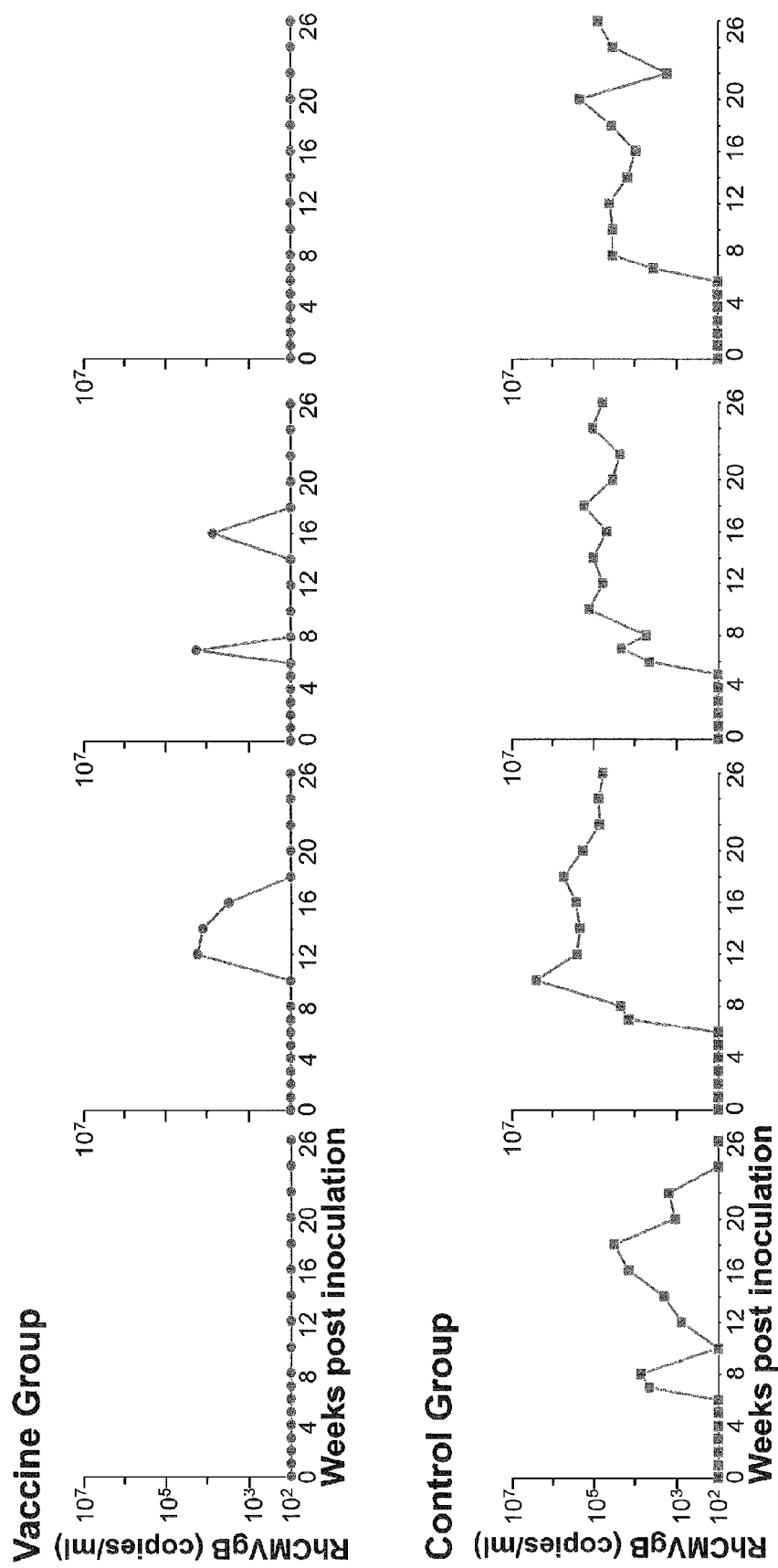

FIG. 27. RhCMV shedding in the saliva of vaccinated and control animals. Genomic RhCMV loads (gB qPCR) in oral swabs were measured by qPCR and shown as copies/mL. The limit of detection was 1,000 copies/ml, but for consistency with the urine qPCR results, the Y-axis starts at 100.

FIG. 28. RhCMV shedding in the urine of vaccinated and control animals. Genomic RhCMV loads (gB qPCR) in urine were measured by qPCR and shown as copies/mL. The limit of detection was 100 copies/ml.

Figure 29:
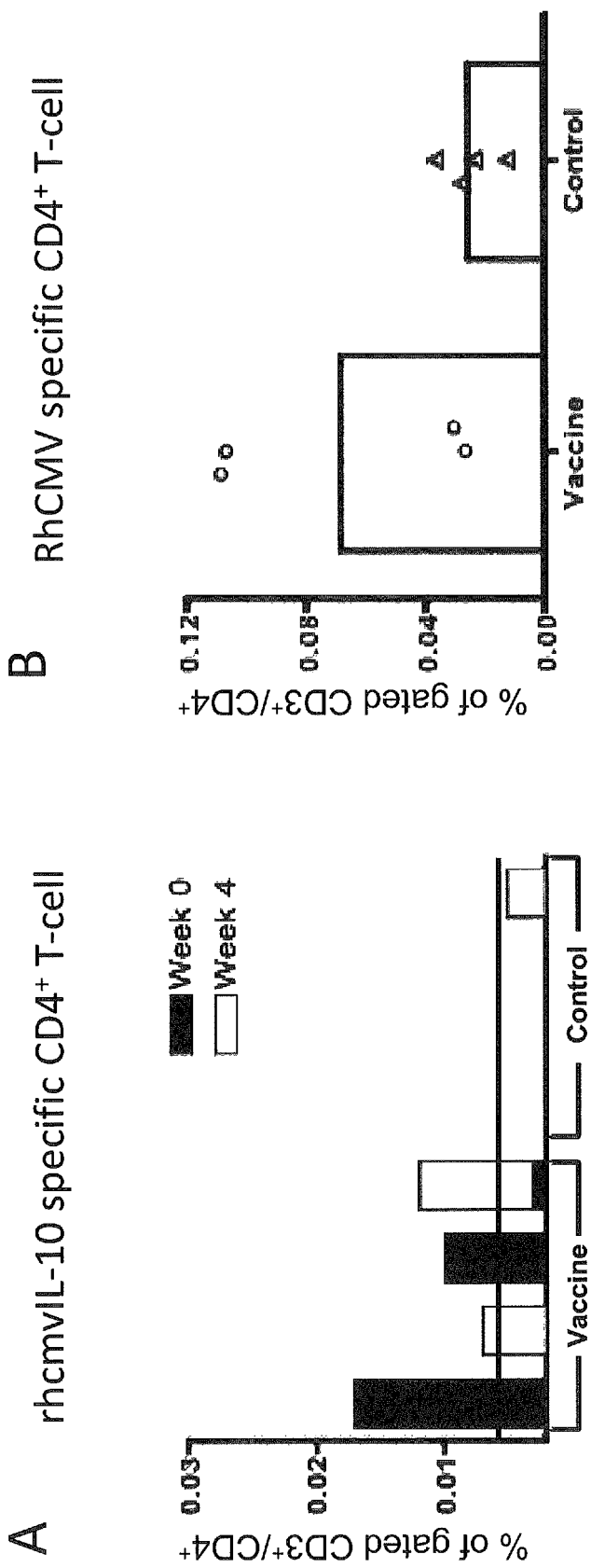

FIGS. 29A-B. FACS analysis of IFN-γ+/CD4+ T-cell specific response to rhcmvIL-10 and RhCMV. (A) All animals in the vaccine group show positive levels of CD3+/CD4+/IFN-γ+ T-cell specific response at week 0 (black) or week 4 (white). The percentage of cells represent those gated on total live CD3+/CD4+ cells. The black line represents positive cutoff at 0.005%. (B) Vaccinated animals show a trend of increased CD4+ T-cell response, specific to RhCMV compared to controls at week 4 p.c.

DETAILED DESCRIPTION OF THE INVENTION

The present invention is based on the unexpected discovery that the IL-10 protein of cytomegalovirus can be modified to have reduced binding to an interleukin-10 (IL-10) receptor and reduced functional activity while retaining immunogenicity. Thus, in one embodiment, the present invention provides a cytomegalovirus IL-10 protein, wherein the protein comprises a mutation in one or more amino acids, wherein the mutation(s) result in a phenotype of reduced binding to an interleukin-10 (IL-10) receptor protein and reduced functional activity as compared to a cytomegalovirus IL-10 protein lacking said mutation(s). In additional embodiments, the cytomegalovirus IL-10 protein of this invention can further comprise a phenotype of retained immunogenicity as compared to a cytomegalovirus IL-10 protein lacking said mutation(s).

In particular embodiments, the cytomegalovirus IL-10 protein of this invention can comprise a mutation in one or more amino acids located from position 39 through position 78 and/or from position 155 through position 176 in the amino acid sequence of SEQ ID NO:3, which is the amino acid sequence of human CMV IL-10. In some embodiments, the cytomegalovirus IL-10 protein can comprise a mutation at K58, Q62, E160 and/or D162 of SEQ ID NO:3, in any combination.

In other embodiments, the cytomegalovirus IL-10 protein of this invention can comprise a mutation in one or more amino acids located from position 42 through position 85 and/or position 169 through position 189 in the amino acid sequence of SEQ ID NO:1 or 2, which is the amino acid sequence of rhesus CMV IL-10. In some embodiments, the cytomegalovirus IL-10 protein can comprise a mutation at R63, Q67, E174 and/or D176 of SEQ ID NO:1 or 2, in any combination. In particular embodiments, the cytomegalovirus IL-10 protein can comprise a Q67R mutation, an R63E mutation, an E174Q mutation and/or a D176H mutation, in any combination.

Additional embodiments of this invention include rhesus CMV IL-10 protein comprising a Q67R mutation and a D176H mutation, referred to in the Examples section here in as M1. In further embodiment, a cytomegalovirus IL-10 protein is provided, comprising an E174Q mutation and a D176H mutation, referred to in the Examples section herein as M2.

The particular mutations described herein (e.g., Q67R, R63E, E174Q, D176H) are examples of mutations of this invention and it is to be understood that the present invention encompasses the substitution of any naturally occurring and/or non-naturally occurring amino acid residue for any of the amino acid residues described herein. It would be well within the skill of the ordinary artisan to produce any such mutants and test them for the phenotypic characteristics of the cytomegalovirus IL-10 protein of this invention.

It is to be understood that the mutations described herein are exemplary of mutations contemplated for this invention. Thus, the present invention includes mutations in any cytomegalovirus IL-10 protein at amino acid residues that correspond to the amino acid residues described herein. One of ordinary skill in the art would be able to determine which amino acid residues in a given CMV IL-10 sequence correspond to those identified herein according to methods well known in the art, such as alignment. For example, an alignment of various human cmvIL-10 amino acid sequences is provided in the SEQUENCE ALIGNMENT section provided herein, showing the amino acid residues that correspond to those described herein. These amino acid sequences have different lengths due to the varying number of threonines near the N terminus of this protein. Accordingly, the corresponding amino acid residue has a different number and these corresponding numbers are provided in the SEQUENCE ALIGNMENT provided below.

As used herein, "cytomegalovirus IL-10 protein" means the protein, and any sub-portion or fragment (e.g., 15-20 amino acids) of the full-length protein, encoded by the nucleic acid sequence of the UL111A open reading frame of the human cytomegalovirus genome (e.g., GENBANK® Database Accession Number AF202536. In some embodiments, the cytomegalovirus IL-10 protein can mean the protein, and any sub-portion of the full-length protein, encoded by the DNA sequence of the UL111A and UL111 open reading frames of the rhesus cytomegalovirus genome (e.g., GENBANK® Database Accession Numbers AF200417 and AF200740. It is also to be understood that the present invention is not limited to IL-10 protein of cytomegaloviruses; further encompassed within this invention is an IL-10 or IL-10 like protein identified in other viruses, including but not limited to Epstein Barr virus (EBV) and other herpes viruses, including equine herpesvirus 2, ovine herpesvirus 2, baboon cytomegalovirus, African green monkey cytomegalovirus, and rhesus lymphocryptovirus.

As used herein, "a phenotype of reduced binding to an IL-10 receptor protein and reduced functional activity" means impaired or reduced interaction(s) between the cytomegalovirus IL-10 protein and the cellular IL-10 receptor, and impaired or reduced ability to stimulate cellular responses resulting from activation of the IL-10R1/IL-10R2 complex signaling pathways relative to a control, as determined according to methods known in the art.

The reduction in binding and functional activity is relative to the binding and functional activity of a cytomegalovirus IL-10 protein lacking a mutation of this invention (e.g., a control, which can be, e.g., a wild type cytomegalovirus IL-10 protein). The reduction in binding activity can be about 5%, 10%, 15%, 20%, 25%, 30%, 35%, 40%, 45%, 50%, 55%, 60%, 65%, 70%, 75%, 80%, 85%, 90%, 95% or 100% relative to such a control cytomegalovirus IL-10 protein. Furthermore, the reduction in functional activity can be about 5%, 10%, 15%, 20%, 25%, 30%, 35%, 40%, 45%, 50%, 55%, 60%, 65%, 70%, 75%, 80%, 85%, 90%, 95% or 100% relative to such a control cytomegalovirus IL-10 protein. These reductions in binding and/or functional activity can also be, for example, one fold, two fold, three fold, four fold, or more relative to a control. Assays to determine binding activity and assays to determine functional activity of a cytomegalovirus IL-10 protein are well known in the art and as described in the Examples section provided herein.

As used herein, a phenotype of retained immunogenicity describes a CMV IL-10 protein of this invention that has immunogenicity (i.e., the ability to elicit an immune response) equivalent to or greater than the immunogenicity of a CMV-IL-10 protein lacking the mutation(s) described herein. Such retained immunogenicity of a CMV IL-10 protein of this invention can be determined according to methods well known in the art, whereby the immunogenicity of a CMV IL-10 protein of this invention is compared with that of a control (e.g., a wild type CMV IL-10 protein).

The present invention further provides an isolated nucleic acid molecule comprising a nucleotide sequence encoding a cmvIL-10 protein or fragment thereof of this invention. Also provided herein is a vector comprising a nucleic acid molecule encoding a cmvIL-10 protein and/or fragment thereof of this invention. The vector can be an expression vector which contains all of the genetic components required for expression of the nucleic acid in cells into which the vector has been introduced, as are well known in the art. The expression vector can be a commercial expression vector or it can be constructed in the laboratory according to standard molecular biology protocols. The expression vector can comprise viral nucleic acid including, but not limited to, poxvirus, vaccinia virus, adenovirus, retrovirus, alphavirus and/or adeno-associated virus nucleic acid. The nucleic acid or vector of this invention can also be in a liposome or a delivery vehicle, which can be taken up by a cell via receptor-mediated or other type of endocytosis.

The nucleic acid molecule of this invention can be in a cell, which can be a cell expressing the nucleic acid whereby acmvIL-10 protein and/or fragment thereof of this invention is produced in the cell (e.g., a host cell). In addition, the vector of this invention can be in a cell, which can be a cell expressing the nucleic acid of the vector whereby a cmvIL-10 protein and/or fragment thereof of this invention is produced in the cell. It is also contemplated that the nucleic acids and/or vectors of this invention can be present in a host organism (e.g., a transgenic organism), which expresses the nucleic acids of this invention and produces the cmvIL-10 protein and/or fragments of this invention.

In some embodiments, the nucleic acid molecules encoding the polypeptides and/or fragments of this invention can be part of a recombinant nucleic acid construct comprising any combination of restriction sites and/or functional elements as are well known in the art that facilitate molecular cloning and other recombinant nucleic acid manipulations. Thus, the present invention further provides a recombinant nucleic acid construct comprising a nucleic acid molecule encoding a polypeptide and/or fragment of this invention.

The nucleic acid molecule encoding the cmvIL-10 polypeptide and/or fragment of this invention can be any nucleic acid molecule that functionally encodes the polypeptides and/or fragments of this invention. To functionally encode the polypeptides and/or fragments (i.e., allow the nucleic acids to be expressed), the nucleic acid of this invention can include, for example, expression control sequences, such as an origin of replication, a promoter, an enhancer and necessary information processing sites, such as ribosome binding sites, RNA splice sites, polyadenylation sites and transcriptional terminator sequences.

Non-limiting examples of expression control sequences that can be present in a nucleic acid molecule of this invention include promoters derived from metallothionine genes, actin genes, immunoglobulin genes, CMV, SV40, adenovirus, bovine papilloma virus, etc. A nucleic acid molecule encoding a selected polypeptide and/or fragment can readily be determined based upon the genetic code for the amino acid sequence of the selected polypeptide and/or fragment and many nucleic acids will encode any selected polypeptide and/or fragment. Modifications in the nucleic acid sequence encoding the polypeptide and/or fragment are also contemplated. Modifications that can be useful are modifications to the sequences controlling expression of the polypeptide and/or fragment to make production of the polypeptide and/or fragment inducible or repressible as controlled by the appropriate inducer or repressor. Such methods are standard in the art. The nucleic acid molecule and/or vector of this invention can be generated by means standard in the art, such as by recombinant nucleic acid techniques and/or by synthetic nucleic acid synthesis or in vitro enzymatic synthesis.

The nucleic acids and/or vectors of this invention can be transferred into a host cell (e.g., a prokaryotic or eukaryotic cell) by well known methods, which vary depending on the type of cell host. For example, calcium chloride transfection is commonly used for prokaryotic cells, whereas calcium phosphate treatment, transduction, cationic lipid treatment and/or electroporation can be used for other cell hosts.

The terms "mutation," "mutant" and other grammatical variants encompass, at the amino acid sequence level of a cytomegalovirus IL-10 protein of this invention, any substitution with any naturally occurring amino acid residue (Table 1), any substitution with any non-naturally occurring amino acid residue (e.g., as listed in Table 2), any deletion, any insertion, and any combination thereof in a wild type amino acid sequence of a cytomegalovirus IL-10 protein. These terms are also intended to encompass the incorporation of additional glycosylation sites into the cytomegalovirus IL-10 protein of this invention, as well as modifications in the amino acid sequence of the cytomegalovirus IL-10 protein that result in an alteration of the framework of the protein.

These mutations can be introduced at the nucleic acid level by altering or modifying the nucleotide sequence encoding the cytomegalovirus IL-10 protein (e.g., to introduce into the nucleotide sequence a deletion, substitution, insertion, stop codon, missense mutation, nonsense mutation, etc.) according to well known methods to produce the desired mutation at the amino acid sequence level. The result of these mutations is the phenotype of reduced binding to an IL-10 receptor protein and reduced functional activity as defined herein. The production and testing of such mutants to identify those with the phenotype of this invention can be carried out according to methods well known in the art and as described herein.

The present invention further provides compositions. Thus, in one embodiment, provided herein is a composition comprising a cytomegalovirus IL-10 protein and/or fragment thereof of this invention and a pharmaceutically acceptable carrier. Also provided herein is a composition comprising an isolated nucleic acid molecule encoding a cytomegalovirus IL-10 protein or fragment thereof of this invention and a pharmaceutically acceptable carrier. Additionally provided herein is a composition comprising a vector comprising an isolated nucleic acid encoding a cytomegalovirus IL-10 protein or fragment thereof of this invention and a pharmaceutically acceptable carrier.

A "pharmaceutically acceptable" component such as a salt, carrier, excipient or diluent of a composition according to the present invention is a component that (i) is compatible with the other ingredients of the composition in that it can be combined with the compositions of the present invention without rendering the composition unsuitable for its intended purpose, and (ii) is suitable for use with subjects as provided herein without undue adverse side effects (such as toxicity, irritation, and allergic response). Side effects are "undue" when their risk outweighs the benefit provided by the composition. Non-limiting examples of pharmaceutically acceptable components (e.g., pharmaceutically acceptable carriers) include, without limitation, any of the standard pharmaceutical carriers such as phosphate buffered saline solutions, water, emulsions such as oil/water emulsion, microemulsions and various types of wetting agents. In particular, it is intended that a pharmaceutically acceptable carrier be a sterile carrier that is formulated for administration to or delivery into a subject of this invention.

The compositions of this invention can also comprise a pharmaceutically acceptable carrier and a suitable adjuvant. As used herein, "suitable adjuvant" describes an adjuvant capable of being combined with the polypeptide and/or fragment and/or nucleic acid molecule and/or vector of this invention to further elicit or enhance an immune response without deleterious effect on the subject or the cell of the subject. A suitable adjuvant can be, but is not limited to, MONTANIDE® ISA51 or ISA 720 (Seppic, Inc., Fairfield, N.J.), SYNTEX adjuvant formulation 1 (SAF-1), composed of 5 percent (wt/vol) squalene (DASF, Parsippany, N.J.), 2.5 percent PLURONIC®, L121 polymer (Aldrich Chemical, Milwaukee), and 0.2 percent polysorbate (Tween 80, Sigma) in phosphate-buffered saline. Other suitable adjuvants are well known in the art and include QS-21, Freund's adjuvant (complete and incomplete), alum, aluminum phosphate, aluminum hydroxide, N-acetyl-muramyl-L-threonyl-D-isoglutamine (thr-MDP), N-acetyl-nor-muramyl-L-alanyl-D-isoglutamine (CGP 11637, referred to as nor-MDP), N-acetylmuramyl-L-alanyl-D-isoglutaminyl-L-alanine-2-(1'-2'-dipalmitoyl-sn-glycero-3-hydroxyphosphoryloxy)-ethylamine (CGP 19835A, referred to as MTP-PE) and RIBI, which contains three components extracted from bacteria, monophosphoryl lipid A, trealosedimycolate and cell wall skeleton (MPL+ TDM+CWS) in 2% squalene/Tween 80 emulsion.

The compositions of the present invention can also include other medicinal agents, pharmaceutical agents, carriers, diluents, immunostimulatory cytokines, etc. Actual methods of preparing such dosage forms are known, or will be apparent, to those skilled in this art.

An "immunomodulatory molecule" of this invention can be, but is not limited to an immunostimulatory cytokine that can be, but is not limited to, GM/CSF, interleukin-2, interleukin-12, interferon-gamma, interleukin-4, tumor necrosis factor-alpha, interleukin-1, hematopoietic factor flt3L, CD40L, B7.1 co-stimulatory molecules and B7.2 co-stimulatory molecules.

Additional examples of an immunomodulatory molecule of this invention include the adjuvants of this invention, including, for example, SYNTEX adjuvant formulation 1 (SAF-1) composed of 5 percent (wt/vol) squalene (DASF, Parsippany, N.J.), 2.5 percent PLURONIC®, L121 polymer (Aldrich Chemical, Milwaukee), and 0.2 percent polysorbate (Tween 80, Sigma) in phosphate-buffered saline. Suitable adjuvants also include an aluminum salt such as aluminum hydroxide gel (alum), aluminum phosphate, or algannmulin, but may also be a salt of calcium, iron or zinc, or may be an insoluble suspension of acylated tyrosine, or acylated sugars, cationically or anionically derivatized polysaccharides, or polyphosphazenes.

Other adjuvants are well known in the art and include QS-21, Freund's adjuvant (complete and incomplete), aluminum hydroxide, N-acetyl-muramyl-L-threonyl-D-isoglutamine (thr-MDP), N-acetyl-normuramyl-L-alanyl-D-isoglutamine (CGP 11637, referred to as nor-MDP), N-acetylmuramyl-L-alanyl-D-isoglutaminyl-L-alanine-2-(1'-2'-dipalmitoyl-sn-glycero-3-hydroxyphosphoryloxy)-ethylamine (CGP 19835A, referred to as MTP-PE) and RIBI, which contains three components extracted from bacteria, monophosphoryl lipid A, trealosedimycolate and cell wall skeleton (MPL+ TDM+CWS) in 2% squalene/Tween 80 emulsion.

Additional adjuvants can include, for example, a combination of monophosphoryl lipid A, preferably 3-de-O-acylated monophosphoryl lipid A (3D-MPL) together with an aluminum salt. An enhanced adjuvant system involves the combination of a monophosphoryl lipid A and a saponin derivative, particularly the combination of QS21 and 3D-MPL as disclosed in PCT publication number WO 94/00153 (the entire contents of which are incorporated herein by reference), or a less reactogenic composition where the QS21 is quenched with cholesterol as disclosed in PCT publication number WO 96/33739 (the entire contents of which are incorporated herein by reference). A particularly potent adjuvant formulation involving QS21 3D-MPL & tocopherol in an oil in water emulsion is described in PCT publication number WO 95/17210 (the entire contents of which are incorporated herein by reference). In addition, the nucleic acid of this invention can include an adjuvant by comprising a nucleotide sequence encoding a A35R protein or active fragment thereof of this invention and a nucleotide sequence that provides an adjuvant function, such as CpG sequences. Such CpG sequences, or motifs, are well known in the art.

Further provided herein are various methods employing the cytomegalovirus IL-10 proteins or fragments thereof, nucleic acid molecules, vectors and compositions of this invention. Thus, in one embodiment, the present invention provides a method of eliciting an immune response to cytomegalovirus in a subject, comprising administering to the subject an effective amount of a cytomegalovirus IL-10 protein or fragment thereof, a nucleic acid molecule, a vector and/or a composition of this invention, in any combination.

Non-limiting examples of an immune response that can be elicited or enhanced by the methods of this invention include an antibody response (e.g., protective antibody response; neutralizing antibody response; antibody dependent cellular cytotoxicity), a cellular response (e.g., cytotoxic T cell response; T helper response; interleukin-2 (IL-2) production; regulatory T cell (Treg) response; T helper 1 (Th1) response; T helper 2 (Th2) response; T helper 17 (Th17) response), an innate response (e.g., dendritic cell, natural killer cell, macrophage, polymorphonuclear cell (neutrophil)), and any combination thereof.

Additionally, the present invention provides a method of treating a cytomegalovirus infection (e.g., a primary cytomegalovirus infection, a non-primary or secondary cytomegalovirus infection, a reactivated cytomegalovirus infection) in a subject in need thereof, comprising administering to the subject an effective amount of a cytomegalovirus IL-10 protein or fragment thereof, a nucleic acid molecule, a vector and/or a composition of this invention, in any combination.

As used herein, the term "primary cytomegalovirus infection" means the first or original cytomegalovirus infection in an individual without prior immunity to cytomegalovirus that may or may not be accompanied by clinically apparent signs and/or symptoms of infection.

As used herein, the term "non-primary or secondary cytomegalovirus infection" means a subsequent cytomegalovirus infection in an individual with prior immunity to cytomegalovirus that may or may not be accompanied by clinically apparent signs and/or symptoms of infection.

As used herein, the term "reactivated cytomegalovirus infection" means transcriptional reactivation of latent viral genomes and the production of infectious HCMV virions within a host previously infected with HCMV, usually during periods of compromise to the functional integrity of the immune system (e.g., iatrogenic immunosuppression for solid organ, bone marrow, or hematopoietic stem cell transplants; onset of AIDS in HIV-infected individuals; critically ill patients; cancer-related chemotherapies, etc.), or functional immaturity of the immune system (e.g., congenitally infected fetuses/neonates).

The terms "treat," "treating" or "treatment" include any type of action that imparts a modulating effect, which, for example, can be a beneficial effect, to a subject afflicted with a disorder, disease, condition or illness, including improvement in the disorder, disease, condition or illness of the subject (e.g., in one or more symptoms), delay in the progression of the disorder, disease, condition or illness, delay of the onset of the disorder, disease, condition or illness, and/or change in clinical parameters, disorder, disease, condition or illness status, etc., as would be well known in the art. These terms can also mean that the severity of the subject's condition is reduced, at least partially improved or stabilized and/or that some alleviation, mitigation, decrease or stabilization in at least one clinical symptom/sign is achieved.

Clinical signs of cytomegalovirus infection in immune competent individuals can include but are not limited to transient febrile mononucleosis (in the absence of Epstein-Barr virus infection) and mild hepatitis (in the absence of hepatitis viruses A, B, and C). In HIV infected individuals progressing to AIDS, HCMV-associated diseases can include but are not limited to retinitis, enterocolitis, gastritis, esophagitis, hepatitis, and/or encephalitis. In transplant recipients (e.g., solid organ, bone marrow, hematopoietic stem cell), HCMV-associated diseases can include fever, leukopenia, malaise, arthralgia, and/or mascular rash or tissue-invasive disease, which presents as hepatitis, pneumonitis, enterocolitis, encephalitis, chorioretinitis, nephritis, cystitis, myocarditis, and/or pancreatitis. In congenitally infected children, HCMV sequelae can include petechiae, jaundice, hepatosplenomegaly, intrauterine growth retardation (restriction), microcephaly, subtle to severe neurological and cognitive deficits, sensorineural hearing loss, and/or chorioretinitis. Clinical parameters of CMV infection that could be evaluated to determine efficacy of treatment include detection of host antiviral antibodies (IgM and IgG) in blood, phosphoprotein 65 (pp65) antigen testing, qualitative and/or quantitative polymerase chain reaction (PCR) analyses of HCMV in whole blood or its constituents (plasma, serum, peripheral blood mononuclear cells, granulocytes) and clinical specimens (e.g., saliva, urine), culture of HCMV from clinical specimens on susceptible cells, and/or cytopathology. Appropriate treatment can lead to a reduction in the severity of and/or elimination of one or more of these signs.

"Effective amount" or "treatment effective amount" as used herein refers to an amount of a protein, fragment, nucleic acid molecule, vector and/or composition of this invention that is sufficient to produce a desired effect, which can be a therapeutic effect and/or an improvement. Alternatively stated, a "treatment effective" or "effective" amount is an amount that will provide some alleviation, mitigation, decrease or stabilization in at least one clinical symptom/sign in the subject. Those skilled in the art will appreciate that the therapeutic effects need not be complete or curative, as long as some benefit is provided to the subject. The effective amount or treatment effective amount will vary with the age, general condition of the subject, the severity of the condition being treated, the particular compound, agent, substance or composition administered, the duration of the treatment, the nature of any concurrent treatment, the pharmaceutically acceptable carrier used if any, and like factors within the knowledge and expertise of those skilled in the art. As appropriate, an "effective amount" or "treatment effective amount" in any individual case can be determined by one of ordinary skill in the art by reference to the pertinent texts and literature and/or by using routine experimentation. (Remington, *The Science And Practice of Pharmacy* (20th ed. 2000)).

In further embodiments, the present invention provides a method of preventing or attenuating a primary cytomegalovirus infection in a subject, comprising administering to the subject an effective amount of a cytomegalovirus IL-10 protein or fragment thereof, a nucleic acid molecule, a vector and/or a composition of this invention, in any combination, thereby preventing or attenuating a primary cytomegalovirus infection in the subject.

Also provided herein is a method of preventing or attenuating a reactivated cytomegalovirus infection in a subject, comprising administering to the subject an effective amount of a cytomegalovirus IL-10 protein or fragment thereof, a nucleic acid molecule, a vector and/or a composition of this invention, in any combination, thereby preventing or attenuating a reactivated cytomegalovirus infection in the subject. The terms "prevent," "preventing," "attenuating," "prevention" (and grammatical variations thereof) refer to prevention and/or delay of the onset of a disease, disorder and/or a clinical signs and/or symptom(s) in a subject and/or a reduction or attenuation in the severity of the onset of the disease, disorder and/or clinical symptom(s) relative to what would occur in the absence of the methods of the invention. The prevention can be complete, e.g., the total absence of the disease, disorder and/or clinical signs and/or symptom(s). The prevention can also be partial, such that the occurrence of the disease, disorder and/or clinical signs and/or symptom(s) in the subject and/or the severity of onset is less than what would occur in the absence of the present invention (i.e., attenuated).

A "prevention effective" amount as used herein is an amount that is sufficient to prevent and/or delay the onset of a disease, disorder and/or clinical signs and/or symptoms in a subject and/or to reduce and/or delay the severity of the onset of a disease, disorder and/or clinical signs and/or symptoms in a subject relative to what would occur in the absence of the methods of the invention. Those skilled in the art will appreciate that the level of prevention need not be complete, as long as some benefit is provided to the subject.

The present invention also provides a method of reducing the risk of cytomegalovirus infection in a subject who is a transplant recipient, comprising administering to the subject an effective amount of a cytomegalovirus IL-10 protein or fragment thereof, a nucleic acid molecule, a vector and/or a composition of this invention, in any combination, thereby reducing the risk of cytomegalovirus infection in the subject. Such administration to the transplant recipient can be at any time relative to the transplantation (i.e., before, after and/or simultaneously, in any combination) and with any frequency necessary to deliver an effective amount as described herein.

Further provided herein is a method of reducing the risk of cytomegalovirus infection in an immunocompromised or immunosuppressed subject, comprising administering to the subject an effective amount of a cytomegalovirus IL-10 protein or fragment thereof, a nucleic acid molecule, a vector and/or a composition of this invention, in any combination, thereby reducing the risk of cytomegalovirus infection in the subject.

The present invention additionally provides a method of preventing or attenuating a primary cytomegalovirus infection or treating a reactivated cytomegalovirus infection in a subject who is a transplant recipient, an immunocompromised or immunosuppressed subject, comprising administering to the subject an effective amount of a cytomegalovirus IL-10 protein or fragment thereof, a nucleic acid molecule, a vector and/or a composition of this invention, in any combination, thereby preventing or attenuating a primary cytomegalovirus infection in the subject.

In the methods of reducing risk of cytomegalovirus infection described above, such a reduction in risk is identified by comparison with the level of risk of cytomegalovirus infection in a subject of this invention that has not been administered the CMV IL-10 protein, fragment thereof, nucleic acid molecule, vector and/or composition of this invention. The reduction in risk can be about 5%, 10%, 15%, 20%, 25%, 30%, 35%, 40%, 45%, 50%, 55%, 60%, 65%, 70%, 75%, 80%, 85%, 90%, 95% or 100% relative to such a control, as would be determined by protocols well known in the art.

A subject at risk of cytomegalovirus disease includes, but is not limited to a fetus who acquires HCMV from his/her mother following transplacental transmission, an immunosuppressed transplant recipient, an immunocompromised subject, a subject receiving chemotherapy, a critically ill subject, and/or a severely burned subject. These subjects at risk share a commonality of immature, impaired, or weakened ability to develop and/or maintain cellular and humoral immune responses to HCMV antigens that can protect against clinical outcomes associated with HCMV infection. The mechanisms by which the present invention could prevent congenital infection include, but are not limited to, stimulating the generation of antibodies that neutralize cmvIL-10 function in non-immune (i.e., HCMV seronegative) women following administering to the subject an effective amount of a cytomegalovirus IL-10 protein or fragment thereof, a nucleic acid molecule, a vector and/or a composition of this invention, in any combination; reductions in HCMV excretion (i.e., shedding) in close contacts (e.g., children, partners) of pregnant women following administering to the potentially HCMV-shedding subject an effective amount of a cytomegalovirus IL-10 protein or fragment thereof, a nucleic acid molecule, a vector and/or a composition of this invention, in any combination; and increasing the titers of antibodies that neutralize cmvIL-10 function in immune (i.e., HCMV seropositive) women following administering to the subject an effective amount of a cytomegalovirus IL-10 protein or fragment thereof, a nucleic acid molecule, a vector and/or a composition of this invention, in any combination.

The methods of treating or preventing infection caused by cytomegalovirus in a subject can be carried out, for example, by contacting an immune cell of the subject with any of the polypeptides, fragments, nucleic acids molecules and/or vectors of this invention.

Thus, in some embodiments, the methods of preventing infection caused by cytomegalovirus in a subject can be carried out, for example, by uptake of any of the polypeptides, fragments, nucleic acids molecules and/or vectors of this invention by a professional antigen presenting cell (i.e., a dendritic cell, macrophage, or B cell) to activate antigen-specific $CD4^+$ and $CD8^+$ T cells, and antigen-specific B cells, which express class I and class II MHC, and co-stimulatory molecules on the surface of the cell.

In some embodiments, the methods of treating infection caused by cytomegalovirus in a subject can be carried out, for example, by uptake of any of the polypeptides, fragments, nucleic acids molecules and/or vectors of this invention by cells to activate antigen-specific $CD4^+$ and $CD8^+$ T cells, and antigen-specific B cells. The cell can be, for example, a $CD8^+$ T cell which is contacted with the polypeptide and/or fragment of this invention in the presence of a class I MHC molecule, which can be a soluble molecule or it can be present on the surface of a cell which expresses class I MHC molecules. The cell can also be any cell that can take up and express exogenous nucleic acid and produce the polypeptides and/or fragments of this invention.

In some embodiments, the polypeptides and/or fragments of this invention can be produced by a cell that secretes them, whereby the polypeptide and/or fragment is produced and secreted and then taken up and subsequently processed by an antigen presenting cell or other class I MHC-expressing cell and presented to the immune system for induction of an immune response. In other embodiments, the nucleic acids and/or vectors of this invention can be directly introduced into an antigen presenting cell and/or other class I MHC-expressing cell in which the polypeptide and/or fragment is produced and processed directly and presented to the immune system on the cell surface.

As set forth above, it is contemplated that in the methods wherein the CMV IL-10 protein or fragment thereof, nucleic acid molecules, vectors and/or compositions of this invention are administered to a subject or to a cell of a subject, such methods can further comprise the step of administering a suitable adjuvant to the subject or to a cell of the subject. The adjuvant can be in the composition of this invention or the adjuvant can be in a separate composition comprising a suitable adjuvant and a pharmaceutically acceptable carrier. The adjuvant can be administered prior to, simultaneous with, and/or after administration of any of the polypeptides, fragments, nucleic acids and/or vectors of this invention. For example, QS-21, similar to alum, complete Freund's adjuvant, SAF, etc., can be administered within days/weeks/hours (before or after) of administration of the polypeptides, fragments, nucleic acids and/or vectors of this invention. The effectiveness of an adjuvant can be determined by measuring the immune response directed against the polypeptide and/or fragment of this invention with and without the adjuvant, using standard procedures, as described herein and as are well known in the art.

The subject of this invention can be any subject in need of the immune response of this invention and/or in need of treatment for or prevention from cytomegalovirus infection, as well as any subject in whom it is desirable to induce an immune response to cytomegalovirus. Such a subject can be any type of animal that is susceptible to infection by a cytomegalovirus, or another virus expressing a viral IL-10 protein, of this invention, as well as any animal to which the proteins, fragments thereof, nucleic acid molecules and/or vectors of this invention can be administered according to the methods of this invention. For example, an animal of this invention can include any mammal, such as a rhesus macaque, African green monkey, baboon, mouse, rabbit, goat, sheep, or horse. In certain embodiments, the subject of this invention is a human.

The compositions of this invention can be administered to a cell of a subject or to a subject either in vivo or ex vivo. For administration to a cell of the subject in vivo, as well as for administration to the subject, the compositions of this invention can be administered orally, parenterally (e.g., intravenously), by intramuscular injection, by intraperitoneal injection, subcutaneous injection, transdermally, transmucosally, intra-nasally, extracorporeally, topically or the like. Also, the compositions of this invention can be pulsed onto dendritic cells, which are isolated or grown from a subject's cells, according to methods well known in the art, or onto bulk peripheral blood mononuclear cells (PBMC) or various cell subfractions thereof from a subject.

The exact amount of the cytomegalovirus IL-10 protein or fragment thereof, nucleic acid molecule, vector and/or composition of this invention required will vary from subject to subject, depending on the species, age, weight and general condition of the subject, the particular cytomegalovirus IL-10 protein or fragment thereof, nucleic acid molecule, vector and/or composition used, its mode of administration and the like. Thus, it is not possible to specify an exact amount for every cytomegalovirus IL-10 protein or fragment thereof, nucleic acid molecule, vector and/or composition of this invention. However, an effective amount can be determined by one of ordinary skill in the art using only routine experimentation given the teachings herein.

As an example, to a subject in whom it is desirable to induce an immune response to cytomegalovirus, from about 0.1 μg/kg to about 10 μg/kg of a polypeptide and/or fragment of this invention can be administered by different routes, including but not limited to subcutaneous, intramuscular, intradermal, transcutaneous, intranasal, and/or transmucosal, and can optionally be in an adjuvant, at hourly, daily and/or weekly intervals until an evaluation of the subject's clinical parameters indicate that the subject demonstrates the desired immunological response. Alternatively, a polypeptide and/or fragment of this invention can be pulsed onto dendritic cells at a concentration of from about 0.1 ng to about 10 mg per $10^6$ dendritic cells, and the dendritic cells can be administered to the subject intradermally and/or subcutaneously at the same time intervals. The treatment can be continued or resumed if the subject's clinical parameters warrant and/or until the desired immunological response is achieved.

If ex vivo methods are employed, cells or tissues can be removed and maintained outside the subject's body according to standard protocols well known in the art. The polypeptides and/or fragments thereof and/or nucleic acid molecules of this invention can be introduced into the cells via known mechanisms for uptake of polypeptides into cells (e.g., phagocytosis, pulsing onto class I MHC-expressing cells, liposomes, etc.). The cells can then be infused (e.g., in a pharmaceutically acceptable carrier) or transplanted back into the subject per standard methods for the cell or tissue type. Standard methods are known for transplantation or infusion of various cells into a subject.

The pharmaceutical compositions of this invention include those suitable for oral, rectal, topical, inhalation (e.g., via an aerosol), buccal (e.g., sub-lingual), vaginal, parenteral (e.g., subcutaneous, intramuscular, intradermal, intraarticular, intrapleural, intraperitoneal, intracerebral, intraarterial, or intravenous), topical (i.e., both skin and mucosal surfaces, including airway surfaces) and transdermal administration, although the most suitable route in any given case will depend, as is well known in the art, on such factors as the species, age, gender and overall condition of the subject, the nature and severity of the condition being treated and/or on the nature of the particular composition (i.e., dosage, formulation) that is being administered.

Pharmaceutical compositions suitable for oral administration can be presented in discrete units, such as capsules, cachets, lozenges, or tables, each containing a predetermined amount of the composition of this invention; as a powder or granules; as a solution or a suspension in an aqueous or non-aqueous liquid; or as an oil-in-water or water-in-oil emulsion. Oral delivery can be performed by complexing a composition of the present invention to a carrier capable of withstanding degradation by digestive enzymes in the oral cavity and/or gut of an animal. Examples of such carriers include plastic capsules or tablets, as known in the art. Such formulations are prepared by any suitable method of pharmacy, which includes the step of bringing into association the composition and a suitable carrier (which may contain one or more accessory ingredients as noted above). In general, the pharmaceutical composition according to embodiments of the present invention are prepared by uniformly and intimately admixing the composition with a liquid or finely divided solid carrier, or both, and then, if necessary, shaping the resulting mixture. For example, a tablet can be prepared by compressing or molding a powder or granules containing the composition, optionally with one or more accessory ingredients. Compressed tablets are prepared by compressing, in a suitable machine, the composition in a free-flowing form, such as a powder or granules optionally mixed with a binder, lubricant, inert diluent, and/or surface active/dispersing agent(s). Molded tablets are made by molding, in a suitable machine, the powdered compound moistened with an inert liquid binder.

Pharmaceutical compositions suitable for buccal (sub-lingual) administration include lozenges comprising the composition of this invention in a flavored base, usually sucrose and acacia or tragacanth; and pastilles comprising the composition in an inert base such as gelatin and glycerin or sucrose and acacia.

Pharmaceutical compositions of this invention suitable for parenteral administration can comprise sterile aqueous and non-aqueous injection solutions of the composition of this invention, which preparations are preferably isotonic with the blood of the intended recipient. These preparations can contain anti-oxidants, buffers, bacteriostats and solutes, which render the composition isotonic with the blood of the intended recipient. Aqueous and non-aqueous sterile suspensions, solutions and emulsions can include suspending agents and thickening agents. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

The compositions can be presented in unit\dose or multi-dose containers, for example, in sealed ampoules and vials, and can be stored in a freeze-dried (lyophilized) condition requiring only the addition of the sterile liquid carrier, for example, saline or water-for-injection immediately prior to use.

Extemporaneous injection solutions and suspensions can be prepared from sterile powders, granules and tablets of the kind previously described. For example, an injectable, stable, sterile composition of this invention in a unit dosage form in a sealed container can be provided. The composition can be provided in the form of a lyophilizate, which can be reconstituted with a suitable pharmaceutically acceptable carrier to form a liquid composition suitable for injection into a subject. The unit dosage form can be from about 1 µg to about 1 gram of the composition of this invention. When the composition is substantially water-insoluble, a sufficient amount of emulsifying agent, which is physiologically acceptable, can be included in sufficient quantity to emulsify the composition in an aqueous carrier. One such useful emulsifying agent is phosphatidylcholine.

Pharmaceutical compositions suitable for rectal administration are preferably presented as unit dose suppositories. These can be prepared by admixing the composition with one or more conventional solid carriers, such as for example, cocoa butter, and then shaping the resulting mixture.

Pharmaceutical compositions of this invention suitable for topical application to the skin preferably take the form of an ointment, cream, lotion, paste, gel, spray, aerosol, or oil. Carriers that can be used include, but are not limited to, petroleum jelly, lanoline, polyethylene glycols, alcohols, transdermal enhancers, and combinations of two or more thereof. In some embodiments, for example, topical delivery can be performed by mixing a pharmaceutical composition of the present invention with a lipophilic reagent (e.g., DMSO) that is capable of passing into the skin.

Pharmaceutical compositions suitable for transdermal administration can be in the form of discrete patches adapted to remain in intimate contact with the epidermis of the subject for a prolonged period of time. Compositions suitable for transdermal administration can also be delivered by iontophoresis (see, for example, *Pharmaceutical Research* 3:318 (1986)) and typically take the form of an optionally buffered aqueous solution of the composition of this invention. Suitable formulations can comprise citrate or bis\tris buffer (pH 6) or ethanol/water. The present invention further provides a medicament and the preparation thereof for use in treating and/or preventing the disease and disorders described herein by employing the same steps as described in the methods disclosed herein. It is further contemplated that the methods, compositions and medicaments of this invention can be used for veterinary application as well as in applications involving humans.

Furthermore, the nucleic acid molecules and vectors of this invention can be administered orally, intranasally, parenterally (e.g., intravenously), by intramuscular injection, by intraperitoneal injection, transdermally, transmucosally, extracorporeally, topically or the like. In the methods described herein which include the administration and uptake of exogenous nucleic acid into the cells of a subject (i.e., gene transduction or transfection), the nucleic acid molecules of the present invention can be in the form of naked nucleic acid or the nucleic acid molecules can be in a vector for delivering the nucleic acid molecules to the cells for expression of the polypeptides and/or fragments of this invention. In some embodiments, the vector can be a commercially available preparation or can be constructed in the laboratory according to methods well known in the art. In further embodiments, the vector can be a viral vector, as is well known in the art.

Delivery of the nucleic acid molecule and/or vector of this invention to cells can be via a variety of mechanisms that are well known in the art. As one example, delivery can be via a liposome, using commercially available liposome preparations such as LIPOFECTIN®, LIPOFECTAMINE® (GIBCO-BRL, Inc., Gaithersburg, Md.), SUPERFECT® (Qiagen, Inc. Hilden, Germany) and TRANSFECTAM® (Promega Biotec, Inc., Madison, Wis.), as well as other liposomes developed according to procedures standard in the art. In addition, the nucleic acid molecule and/or vector of this invention can be delivered in vivo by electroporation, the technology for which is available from Genetronics, Inc. (San Diego, Calif.) as well as by means of a SONOPORATION® machine (ImaRx Pharmaceutical Corp., Tucson, Ariz.).

In particular embodiments as described herein, vector delivery can be via a viral system, such as a retroviral vector system, which can package a recombinant retroviral genome. The recombinant retrovirus can then be used to infect and thereby deliver to the infected cells nucleic acid molecules encoding the polypeptide and/or fragment of this invention. The exact method of introducing the exogenous nucleic acid into mammalian cells is, of course, not limited to the use of retroviral vectors. Other techniques are widely available for this procedure including the use of adenoviral vectors, alphaviral vectors, adeno-associated viral (AAV) vectors, lentiviral vectors, pseudo typed retroviral vectors and vaccinia viral vectors, as well as any other viral vectors now known or developed in the future. Physical transduction techniques can also be used, such as liposome delivery and receptor-mediated and other endocytosis mechanisms. This invention can be used in conjunction with any of these or other commonly used gene transfer methods.

As one nonlimiting example, the nucleic acid molecule of this invention can be delivered to the cells of a subject in a modified vaccinia Ankara (MVA) virus vector. The dosage for administration of MVA-based vectors to humans can typically range from about $10^7$ to about $5 \times 10^9$ plaqueforming units (pfu) per injection.

As another nonlimiting example, the nucleic acid molecule of this invention can be delivered to the cells of a subject in an adenovirus vector. The dosage for administration of adenovirus to humans can range from about $10^7$ to about $10^{11}$ pfu per injection.

In some embodiments, a subject will receive a single injection of a viral vector comprising a nucleic acid molecule of this invention. If additional injections are necessary, they can be repeated at daily/weekly/monthly intervals for an indefinite period and/or until the efficacy of the treatment has been established. As set forth herein, the efficacy of treatment can be determined by evaluating the symptoms and clinical parameters described herein and/or by detecting a desired immunological response.

The exact amount of the nucleic acid molecule and/or vector required will vary from subject to subject, depending on the species, age, weight and general condition of the subject, the particular nucleic acid molecule and/or vector used, its mode of administration and the like. Thus, it is not possible to specify an exact amount for every nucleic acid or vector. However, an appropriate amount can be determined by one of ordinary skill in the art using only routine experimentation given the teachings herein.

In the methods of the present invention, both nucleic acid molecules and/or vectors of this invention, as well as cytomegalovirus IL-10 proteins or fragments thereof of this invention can be administered to a subject. In one nonlimiting example, a vector comprising a nucleic acid molecule of this invention can be administered to the subject in a priming step and a cytomegalovirus IL-10 protein of this invention can be administered to the subject as a boosting step. The prime-boost strategy in humans can consist, e.g., of an initial nucleic acid priming immunization followed by one or more booster immunizations at intervals of about 4 to about 12 weeks apart. The booster immunizations can comprise nucleic acid molecules, proteins, fragments thereof, vectors and/or compositions of this invention in any combination. The exact timing of booster immunizations will vary from subject to subject, depending on the species, age, weight and general condition of the subject, the particular, protein, fragment thereof, nucleic acid molecule and/or vector used, its mode of administration and the like. In addition, the exact composition of the prime-boost immunization regimen will vary from subject to subject, depending on the species, age, weight and general condition of the subject, the particular protein, fragment thereof, nucleic acid molecule and/or vector used, its mode of administration and the like. Thus, it is not possible to specify an exact time for every booster immunization, and for the exact composition of the priming and booster immunizations. However, an appropriate schedule and composition of priming and booster immunizations can be determined by one of ordinary skill in the art using only routine experimentation given the teachings herein.

In certain embodiments, the polypeptides and/or fragments thereof of this invention can be fused with a "carrier" protein or peptide to produce a fusion protein. Such fusion can be carried out, for example, by linking a nucleic acid of this invention in frame with a nucleic acid encoding a carrier protein or fragment thereof of this invention and expressing the linked nucleotide sequence to produce the fusion protein. For example, the carrier protein or peptide can be fused to a polypeptide and/or fragment of this invention to increase the stability thereof (e.g., decrease the turnover rate) in the cell and/or subject. Exemplary carrier proteins include, but are not limited to, glutathione-S-transferase or maltose-binding protein. The carrier protein or peptide can alternatively be a reporter protein. For example, the fusion protein can comprise a polypeptide and/or fragment of this invention and a reporter protein or peptide (e.g., green fluorescence protein (GFP), β-glucoronidase, β-galactosidase, luciferase, and the like) for easy detection of transformed cells and transgene expression. Any suitable carrier protein and/or nucleic acid encoding the carrier protein, as is well known in the art can be used to produce a fusion protein of this invention.

The present invention further provides a cytomegalovirus IL-10 protein or fragment thereof of this invention as part of a conjugate, e.g., to improve or enhance physiological properties of the protein or fragment, such as solubility or half-life. The term "conjugate" (or interchangeably "conjugated polypeptide") is intended to indicate a heterogeneous (in the sense of composite or chimeric) molecule formed by the covalent attachment of one or more polypeptide(s) to one or more non-polypeptide moieties such as polymer molecules, lipophilic compounds, sugar moieties or organic derivatizing agents. Preferably, the conjugate is soluble at relevant concentrations and conditions, i.e., soluble in physiological fluids such as blood. Examples of conjugated polypeptides of the invention include glycosylated and/or PEGylated polypeptides.

The term "covalent attachment" means that the polypeptide and the non-polypeptide moiety are either directly covalently joined to one another, or else are indirectly covalently joined to one another through an intervening moiety or moieties, such as a bridge, spacer, or linkage moiety or moieties. The term "non-conjugated polypeptide" can be used to refer to the polypeptide part of the conjugate.

When used herein, the term "non-polypeptide moiety" means a molecule that is capable of conjugating to an attachment group of the polypeptide of the invention. Suitable examples of such molecules include polymer molecules, sugar moieties, lipophilic compounds, or organic derivatizing agents. When used in the context of a conjugate of the invention it will be understood that the non-polypeptide moiety is linked to the polypeptide part of the conjugate through an attachment group of the polypeptide. As explained above, the non-polypeptide moiety can be directly covalently joined to the attachment group or it can be indirectly covalently joined to the attachment group through an intervening moiety or moieties, such as a bridge, spacer, or linkage moiety or moieties.

The present invention further includes isolated polypeptides, peptides, proteins, fragments, domains and/or nucleic acid molecules that are substantially equivalent to those described for this invention. As used herein, "substantially equivalent" can refer both to nucleic acid and amino acid sequences, for example a mutant sequence, that varies from a reference sequence by one or more substitutions, deletions, or additions, the net effect of which does not result in an undesirable adverse functional dissimilarity between reference and subject sequences. In some embodiments, this invention can include substantially equivalent sequences that have an adverse functional dissimilarity. For purposes of the present invention, sequences having equivalent biological activity and equivalent expression characteristics are considered substantially equivalent.

The invention further provides homologs, as well as methods of obtaining homologs, of the polypeptides and/or fragments of this invention from other cytomegaloviruses as well as other herpesviruses. As used herein, an amino acid sequence or protein is defined as a homolog of a polypeptide or fragment of the present invention if it shares significant homology to one of the polypeptides and/or fragments of the present invention. Significant homology means at least 30%, 40%, 50%, 60%, 65%, 75%, 80%, 85%, 90%, 95%, 98% and/or 100% homology with another amino acid sequence. Specifically, by using the nucleic acids disclosed herein as a probe or as primers, and techniques such as PCR amplification and colony/plaque hybridization, one skilled in the art can identify homologs of the polypeptides and/or fragments of this invention in any other virus.

The present invention also provides a kit comprising the cmvIL-10 polypeptide, fragment thereof, nucleic acid molecule, vector and/or antibody of this invention, along with reagents, buffers, diluents, devices and/or instruments, etc., to facilitate use of the cmvIL-10 polypeptide, fragment thereof, nucleic acid molecule and/or vector of this invention in methods of this invention. It would be well understood by one of ordinary skill in the art that the kits of this invention can comprise one or more containers and/or receptacles to hold the reagents (e.g., antibodies, proteins, fragments, nucleic acids, vectors, etc.) of the kit, along with appropriate buffers and/or diluents and directions for using the kit, as would be well known in the art. Such kits can further comprise adjuvants and/or other immunostimulatory or immunomodulating agents, as are well known in the art.

A further embodiment of this invention is a method of preventing or attenuating a cytomegalovirus infection in a subject, comprising administering to the subject an effective amount of an antibody specifically reactive against a cytomegalovirus IL-10 protein.

Further provided herein is a method of reducing the risk of cytomegalovirus infection in a woman who is pregnant and is undergoing or at risk of undergoing a primary, non-primary, or reactivated CMV infection, as well as a method of preventing or attenuating a cytomegalovirus infection in such a subject, comprising administering to the subject an effective amount of an antibody specifically reactive against a cytomegalovirus IL-10 protein. In some embodiments, the antibody specifically blocks cytomegalovirus IL-10 functional activity.

Further provided herein is a method of reducing the risk of cytomegalovirus infection in a subject that is a transplant recipient, an immunocompromised subject, and/or an immunosuppressed subject, as well as a method of preventing or attenuating a cytomegalovirus infection in such a subject, comprising administering to the subject an effective amount of an antibody specifically reactive against a cytomegalovirus IL-10 protein. In some embodiments, the antibody specifically blocks cytomegalovirus IL-10 functional activity.

In certain embodiments of the methods of this invention employing an antibody, the subject can be a human and the antibody can be a humanized monoclonal antibody.

As used herein, the term "antibody" includes intact immunoglobulin molecules as well as fragments thereof that are capable of binding the epitopic determinant of an antigen (i.e., antigenic determinant). Antibodies that bind the polypeptides of this invention are prepared using intact polypeptides or fragments as the immunizing antigen. The polypeptide or fragment used to immunize an animal can be derived from enzymatic cleavage, recombinant expression, isolation from biological materials, synthesis, etc., and can be conjugated to a carrier protein, if desired. Commonly used carriers that are chemically coupled to peptides and proteins for the production of antibody include, but are not limited to, bovine serum albumin, thyroglobulin and keyhole limpet hemocyanin. The coupled peptide or protein is then used to immunize the animal (e.g., a mouse, rat, or rabbit). The polypeptide or peptide antigens can also be administered with an adjuvant, as described herein and as otherwise known in the art.

An antibody of this invention can be any type of immunoglobulin, including IgG, IgM, IgA, IgD, and/or IgE. The antibody can be monoclonal or polyclonal and can be of any species of origin, including, for example, mouse, rat, rabbit, horse, goat, sheep or human, or can be a chimeric or humanized antibody (e.g., Walker et al., *Molec. Immunol.* 26:403-11 (1989)). The antibodies can be recombinant monoclonal antibodies produced according to the methods disclosed in U.S. Pat. No. 4,474,893 or U.S. Pat. No. 4,816,567. The antibodies can also be chemically constructed according to methods disclosed in U.S. Pat. No. 4,676,980. The antibody can further be a single chain antibody (e.g., scFv) or bispecific antibody.

Antibody fragments included within the scope of the present invention include, for example, Fab, F(ab')2, and Fc fragments, and the corresponding fragments obtained from antibodies other than IgG. Such fragments can be produced by known techniques. For example, F(ab')2 fragments can be produced by pepsin digestion of the antibody molecule, and Fab fragments can be generated by reducing the disulfide bridges of the F(ab')2 fragments. Alternatively, Fab expression libraries can be constructed to allow rapid and easy identification of monoclonal Fab fragments with the desired specificity (Huse et al., (1989) *Science* 254:1275-1281). Antibodies can also be obtained by phage display techniques known in the art or by immunizing a heterologous host with a cell containing an epitope of interest.

The polypeptide, fragment or antigenic epitope that is used as an immunogen can be modified or administered in an adjuvant in order to increase antigenicity. Methods of increasing the antigenicity of a protein or peptide are well known in the art and include, but are not limited to, coupling the antigen with a heterologous protein (such as globulin or (3-galactosidase) or through the inclusion of an adjuvant during immunization.

For example, for the production of antibodies, various hosts including goats, rabbits, rats, mice, humans, and others, can be immunized by injection with the polypeptides and/or fragments of this invention, with or without a carrier protein. Additionally, various adjuvants may be used to increase the immunological response. Such adjuvants include, but are not limited to, Freund's complete and incomplete adjuvants, mineral gels such as aluminum hydroxide, and surface-active substances such as lysolecithin, pluronicpolyols, polyanions, peptides, oil emulsions, keyhole limpet hemocyanin, and dinitrophenol. Among adjuvants used in humans, BCG (bacilli Calmette-Guerin) and *Corynebacterium parvum* are especially preferable.

Monoclonal antibodies can be produced in a hybridoma cell line according to the technique of Kohler and Milstein (*Nature* 265:495-97 (1975)). Other techniques for the production of monoclonal antibodies include, but are not limited to, the human B-cell hybridoma technique, and the EBV-hybridoma technique (Kozbor et al. 1985. *J. Immunol. Methods* 81:31-42; Cote et al. 1983. *Proc. Natl. Acad. Sci.* 80:2026-2030; Cole et al. 1984. *Mol. Cell Biol.* 62:109-120), as well as phage display technologies (Bradbury et al. *Nat. Biotechnol* 29(3):245-254 (2011)).

For example, to produce monoclonal antibodies, a solution containing the appropriate antigen can be injected into a mouse and, after a sufficient time, the mouse sacrificed and spleen cells obtained. The spleen cells are then immortalized by fusing them with myeloma cells or with lymphoma cells, typically in the presence of polyethylene glycol, to produce hybridoma cells. The hybridoma cells are then grown in a suitable medium and the supernatant screened for monoclonal antibodies having the desired specificity. Monoclonal Fab fragments can be produced in a bacterial cell such as *E. coli* by recombinant techniques known to those skilled in the art (e.g., Huse. *Science* 246:1275-81 (1989)). Any one of a number of methods well known in the art can be used to identify the hybridoma cell, which produces an antibody with the desired characteristics. These include screening the hybridomas by ELISA assay, Western blot analysis, or radioimmunoassay. Hybridomas secreting the desired antibodies are cloned and the class and subclass are identified using standard procedures known in the art.

For polyclonal antibodies, antibody-containing serum is isolated from the immunized animal and is screened for the presence of antibodies with the desired specificity using any of the well known procedures as described herein.

In addition, techniques developed for the production of chimeric antibodies or humanized antibodies by splicing mouse antibody genes to human antibody genes to obtain a molecule with appropriate antigen specificity and biological activity can be used (Morrison et al. 1984 *Proc. Natl. Acad. Sci.* 81:6851-6855; Neuberger et al. 1984 *Nature* 312:604-608; Takeda et al. 1985 *Nature* 314:452-454). Alternatively, techniques described for the production of single chain antibodies can be adapted, using methods known in the art, to produce single chain antibodies specific for the polypeptides and fragments of this invention. Antibodies with related specificity, but of distinct idiotypic composition, can be generated by chain shuffling from random combinatorial immunoglobin libraries (Burton 1991. *Proc. Natl. Acad. Sci.* 88:11120-3).

In some embodiments, human monoclonal antibodies can be generated by reverse transcription-PCR amplification of the heavy and light chains of the variable genes of cmvIL-10-specific B cells from HCMV-infected humans. The amplicons are subsequently cloned in-frame into expression vectors that contain the HCMV immediate-early promoter/enhancer driving expression of (in order and in-frame) a murine immunoglobulin signal peptide sequence, appropriate cloning sites for the heavy and light chain variable genes, the human immunoglobulin constant regions containing translation stop codons, and a SV40 polyadenylation sequence downstream of the translation termination codon.

(Wrammert et al. 2011. *J. Exp. Med.* 208:181-93; Smith et al. 2009. *Nat. Protocol.* 4:372-84).

Various immunoassays can be used for screening to identify antibodies having the desired specificity for the proteins and peptides of this invention. Numerous protocols for competitive binding or immunoradiometric assays using either polyclonal or monoclonal antibodies with established specificity are well known in the art. Such immunoassays typically involve the measurement of complex formation between an antigen and its specific antibody (e.g., antigen/antibody complex formation). For example, a two-site, monoclonal-based immunoassay utilizing monoclonal antibodies reactive to two non-interfering epitopes on the proteins or peptides of this invention can be used, as well as a competitive binding assay.

DEFINITIONS

As used herein, "a" or "an" or "the" can mean one or more than one. For example, "a" cell can mean one cell or a plurality of cells.

Also as used herein, "and/or" refers to and encompasses any and all possible combinations of one or more of the associated listed items, as well as the lack of combinations when interpreted in the alternative ("or").

Furthermore, the term "about" as used herein when referring to a measurable value such as an amount of a compound or agent of this invention, dose, time, temperature, and the like, is meant to encompass variations of ±20%, ±10%, ±5%, ±1%, ±0.5%, or even ±0.1% of the specified amount.

A cytomegalovirus of this invention includes but is not limited to human cytomegalovirus (Human herpesvirus 5), rhesus cytomegalovirus (Macacine herpesvirus 3), African green monkey cytomegalovirus (also commonly referred to as simian cytomegalovirus, vervet cytomegalovirus, stealth virus 1; Cercopithecine herpesvirus 5), baboon herpesvirus, and any other cytomegalovirus, either now known or later identified.

The cytomegalovirus IL-10 protein of this invention is an IL-10 protein or its ortholog from a cytomegalovirus of this invention. The human cytomegalovirus IL-10 gene encodes a 176 amino acid protein (e.g., GENBANK® Database Accession No. AAF63437; Towne strain) (SEQ ID NO:3). The rhesus cytomegalovirus IL-10 gene encodes a 189 amino acid protein [e.g., GENBANK® Database Accession No. AAF59907 (Strain 68-2) (SEQ ID NO:1); GENBANK® Database Accession No. AAF61204 (Strain MMU28684) (SEQ ID NO:2)].

This invention further encompasses an IL-10 protein produced by viruses other than cytomegaloviruses, including but not limited to Epstein-Barr virus (Human herpesvirus 4), ovine herpesvirus 2, equine herpesvirus 2 (Equid herpesvirus 2), rhesus lymphocryptovirus (Macacine herpesvirus 4), as well as any other virus now known or later identified to produce an IL-10 or IL-10-like protein.

As used herein, "modulate," "modulates" or "modulation" refers to enhancement (e.g., an increase) or inhibition (e.g., diminished, reduced or suppressed) of the specified activity.

The term "enhancement," "enhance," "enhances," or "enhancing" refers to an increase in the specified parameter (e.g., at least about a 1.1-fold, 1.25-fold, 1.5-fold, 2-fold, 3-fold, 4-fold, 5-fold, 6-fold, 8-fold, 10-fold, twelve-fold, or even fifteen-fold or more increase) and/or an increase in the specified activity of at least about 5%, 10%, 25%, 35%, 40%, 50%, 60%, 75%, 80%, 90%, 95%, 97%, 98%, 99% or 100%.

The term "inhibit," "diminish," "reduce" or "suppress" refers to a decrease in the specified parameter (e.g., at least about a 1.1-fold, 1.25-fold, 1.5-fold, 2-fold, 3-fold, 4-fold, 5-fold, 6-fold, 8-fold, 10-fold, twelve-fold, or even fifteen-fold or more increase) and/or a decrease or reduction in the specified activity of at least about 5%, 10%, 25%, 35%, 40%, 50%, 60%, 75%, 80%, 90%, 95%, 97%, 98%, 99% or 100%. In particular embodiments, the inhibition or reduction results in little or essentially no detectable activity (at most, an insignificant amount, e.g., less than about 10% or about 5%).

As used herein, the transitional phrase "consisting essentially of" means that the scope of a claim is to be interpreted to encompass the specified materials or steps recited in the claim, "and those that do not materially affect the basic and novel characteristic(s)" of the claimed invention. See, In re Herz, 537 F.2d 549, 551-52, 190 USPQ 461, 463 (CCPA 1976) (emphasis in the original); see also MPEP §2111.03. Thus, the term "consisting essentially of" when used in a claim of this invention is not intended to be interpreted to be equivalent to "comprising."

"Isolated" as used herein means the nucleic acid or protein or protein fragment of this invention is sufficiently free of contaminants or cell components with which nucleic acids or proteins normally occur. "Isolated" does not mean that the preparation is technically pure (homogeneous), but it is sufficiently pure to provide the nucleic acid or protein or protein fragment in a form in which it can be used therapeutically.

"Epitope" or "antigenic epitope" or "antigenic peptide" as used herein means a specific amino acid sequence which, when present in the proper conformation, provides a reactive site for an antibody or T cell receptor. The identification of epitopes on antigens can be carried out by immunology protocols that are well known in the art. Typically, an epitope or antigenic peptide can be 4, 5, 6, 7, 8, 9, 10, 12, 14, 16, 18, 20, 25, 30, 35, 40, 45 or 50 amino acids in length.

As used herein, the term "polypeptide" or "protein" is used to describe a chain of amino acids that correspond to those encoded by a nucleic acid. A polypeptide of this invention can be a peptide, which usually describes a chain of amino acids of from two to about 30 amino acids. The term polypeptide as used herein also describes a chain of amino acids having more than 30 amino acids and can be a fragment or domain of a protein or a full length protein. Furthermore, as used herein, the term polypeptide can refer to a linear chain of amino acids or it can refer to a chain of amino acids that has been processed and folded into a functional protein. It is understood, however, that 30 is an arbitrary number with regard to distinguishing peptides and polypeptides and the terms can be used interchangeably for a chain of amino acids. The polypeptides of the present invention are obtained by isolation and purification of the polypeptides from cells where they are produced naturally, by enzymatic (e.g., proteolytic) cleavage, and/or recombinantly by expression of nucleic acid encoding the polypeptides or fragments of this invention. The polypeptides and/or fragments of this invention can also be obtained by chemical synthesis or other known protocols for producing polypeptides and fragments.

The amino acid sequences disclosed herein are presented in the amino to carboxy direction, from left to right. Nucleotide sequences are presented herein in the 5' to 3' direction, from left to right. It is intended that the nucleic acids of this invention can be either single or double stranded (i.e., including the complementary nucleic acid). A nucleic acid of this invention can be the complement of a nucleic acid described herein.

A "fragment" as used herein includes a polypeptide of this invention that comprises a sufficient number of amino acids to have one or more of the biological activities of the polypeptides of this invention. Such biological activities can include, but are not limited to immunogenic activity, as well as any other activity now known or later identified for the polypeptides and/or fragments of this invention. A fragment of a polypeptide of this invention can be produced by methods well known and routine in the art. Fragments of this invention can be produced, for example, by enzymatic or other cleavage of naturally occurring peptides or polypeptides or by synthetic protocols that are well known. Such fragments can be tested for one or more of the biological activities of this invention according to the methods described herein, which are routine methods for testing activities of polypeptides, and/or according to any art-known and routine methods for identifying such activities. Such production and testing to identify fragments of the polypeptides described herein would be well within the scope of one of ordinary skill in the art and would be routine.

Fragments of the polypeptides of this invention are preferably at least about ten amino acids in length and retain the immunological activities of the CMV IL-10 protein. Examples of the fragments of this invention include, but are not intended to be limited to, the following fragments identified by the amino acid number as shown for the respective amino acid sequences of SEQ ID NOs: 1, 2 and 3: Amino acids 1-10, 10-20, 20-30, 30-40, 40-50, 50-60, 60-70, 70-80, 80-90, 90-100, 110-120, 120-130, 130-140, 140-150, 150-160, 160-170, 165-176, 1-25, 1-50, 1-67, 1-75, 1-100, 1-125, 1-135, 1-145, 1-150, 1-160, 1-170, 1-180, etc.

It is understood that this list is exemplary only and that a fragment of this invention can be any amino acid sequence containing any combination of contiguous amino acids that are numbered in the Sequence Listing as amino acids 1 through 176 (SEQ ID NO:3) or amino acids 1 through 189 (SEQ ID NO:1 or 2) even if that combination is not specifically recited as an example herein. It is also understood that these fragments can be combined in any order or amount. For example, fragment 1-10 can be combined with fragment 10-20 to produce a fragment of amino acids 1-20. As another example, fragment 1-20 can be combined with fragment 50-60 to produce a single fragment of this invention having 31 amino acids (AA 1-20 and AA 50-60). Also fragments can be present in multiple numbers and in any combination in a fragment of this invention. Thus, for example, fragment 1-150 can be combined with a second fragment 1-150 and/or combined with fragment 135-170 to produce a fragment of this invention.

The terms "homology," "identity" and "complementarity" as used herein refer to a degree of similarity between two or more sequences. There may be partial homology or complete homology (i.e., identity). A partially complementary sequence that at least partially inhibits an identical sequence from hybridizing to a target nucleic acid is referred to as "substantially homologous." The inhibition of hybridization of the completely complementary sequence to the target sequence can be examined using a hybridization assay (Southern or Northern blot, solution hybridization and the like) under conditions of low stringency. A substantially homologous sequence or hybridization probe will compete for and inhibit the binding of a completely homologous sequence to the target sequence under conditions of low stringency, as this term is known in the art. This is not to say that conditions of low stringency are such that non-specific binding is permitted; low stringency conditions require that the binding of two sequences to one another be a specific (i.e., selective) interaction. The absence of non-specific binding can be tested by the use of a second target sequence that lacks even a partial degree of complementarity (e.g., less than about 30% identity). In the absence of non-specific binding, the probe will not hybridize to the second non-complementary target sequence.

The term "hybridization" as used herein refers to any process by which a first strand of nucleic acid binds with a second strand of nucleic acid through base pairing. Nucleic acids encoding the polypeptides and/or fragments of this invention can be detected by DNA-DNA, DNA-RNA, or RNA-RNA hybridization and/or amplification using probes, primers and/or fragments of polynucleotides encoding the polypeptides and/or fragments of this invention and/or designed to detect and/or amplify the nucleic acids of this invention.

The term "hybridization complex" as used herein refers to a complex formed between two nucleic acid sequences by virtue of the formation of hydrogen bonds between complementary G and C bases and between complementary A and T bases; these hydrogen bonds may be further stabilized by base stacking interactions. The two complementary nucleic acid sequences hydrogen bond in an antiparallel configuration. A hybridization complex may be formed in solution (e.g., $C_0 t$ or $R_0 t$ analysis) or between one nucleic acid sequence present in solution and another nucleic acid sequence immobilized on a solid support (e.g., paper, membranes, filters, chips, pins or glass slides, or any other appropriate substrate to which cells and/or nucleic acids have been fixed).

The term "nucleotide sequence" refers to a heteropolymer of nucleotides or the sequence of these nucleotides. The terms "nucleic acid," "nucleic acid molecule," nucleotide sequence," "oligonucleotide" and "polynucleotide" are also used interchangeably herein to refer to a heteropolymer of nucleotides. Generally, nucleic acid segments provided by this invention may be assembled from fragments of the genome and short oligonucleotide linkers, or from a series of oligonucleotides, or from individual nucleotides, to provide a synthetic nucleic acid which is capable of being expressed in a recombinant transcriptional unit comprising regulatory elements derived from a microbial or viral operon, or a eukaryotic gene. Nucleic acids of this invention can comprise a nucleotide sequence that can be identical in sequence to the sequence which is naturally occurring or, due to the well-characterized degeneracy of the nucleic acid code, can include alternative codons that encode the same amino acid as that which is found in the naturally occurring sequence. Furthermore, nucleic acids of this invention can comprise nucleotide sequences that can include codons which represent conservative substitutions of amino acids as are well known in the art, such that the biological activity of the resulting polypeptide and/or fragment is retained.

The term "probe" or "primer" includes naturally occurring and/or recombinant and/or chemically synthesized single-and/or double-stranded nucleic acids. They can be labeled for detection by nick translation, Klenow fill-in reaction, PCR and/or other methods well known in the art. Probes and primers of the present invention, their preparation and/or labeling are described in Sambrook et al. 1989. *Molecular Cloning: A Laboratory Manual*, Cold Spring Harbor Laboratory, NY and Ausubel et al. 1989. *Current Protocols in Molecular Biology*, John Wiley & Sons, New York N.Y., both of which are incorporated herein by reference in their entirety for these teachings.

The term "stringent" as used herein refers to hybridization conditions that are commonly understood in the art to define the conditions of the hybridization procedure. Stringency conditions can be low, high or medium, as those terms are commonly know in the art and well recognized by one of ordinary skill. In various embodiments, stringent conditions can include, for example, highly stringent (i.e., high stringency) conditions (e.g., hybridization in 0.5 M NaHPO$_4$, 7% sodium dodecyl sulfate (SDS), 1 mM EDTA at 65° C., and washing in 0.1×SSC/0.1% SDS at 68° C.), and/or moderately stringent (i.e., medium stringency) conditions (e.g., washing in 0.2×SSC/0.1% SDS at 42° C.).

"Amplification" as used herein includes the production of multiple copies of a nucleic acid molecule and is generally carried out using polymerase chain reaction (PCR) and/or any other amplification technologies as are well known in the art (Dieffenbach and Dveksler. 1995. *PCR Primer, a Laboratory Manual*, Cold Spring Harbor Press, Plainview, N.Y.).

The term "sample" as used herein is used in its broadest sense. A biological sample suspected of containing a polypeptide, fragment, antibody and/or nucleic acid of this invention can be any biological fluid, an extract from a cell, an extracellular matrix isolated from a cell, a cell (in solution or bound to a solid support), a tissue, a tissue print, and the like. A sample of this invention can also include a substance not obtained from the body of a subject of this invention. Examples of such a sample include but are not limited to, a water or fluid sample, a food or foodstuff sample, a plant or plant material sample, a soil or rock sample, an animal or animal material sample, an animal bedding sample, an animal cage sample, air sample a soil or dirt sample, a cloth, paper or other material used to swab, wipe, dust or clean a surface, an effluent sample, etc.

The present invention is more particularly described in the following examples, which are intended as illustrative only since numerous modifications and variations therein will be apparent to those skilled in the art.

EXAMPLES

Example 1

Design of Rhesus Cytomegalovirus IL-10 Mutants for Use in Vaccine Strategies

Abstract

Rhesus cytomegalovirus (RhCMV) produces a cellular interleukin-10 (IL-10) homolog (rhcmvIL-10) that blocks host immune responses and contributes to the establishment of persistent RhCMV infection. Neutralization of rhcmvIL-10 activity during infection might enhance the elimination of the virus. Based on its low sequence identity with cellular RhIL-10 (~26%), rhcmvIL-10 might be useful as an antigen in RhCMV vaccines. However, immunization with rhcmvIL-10 might be detrimental to the host because of its immunosuppressive biological activities. To overcome this problem, the present invention provides engineered rhcmvIL-10 mutants that cannot bind to the cell surface IL-10R1 receptor (IL-10R1) and fail to induce IL-10 biological activities. Immunization of rhesus macaques with the inactive rhcmvIL-10 mutants induces an immune response against the native rhcmvIL-10 molecule.

Cells

TF-1 cells, transfected with the human IL-10R1 gene (TF-1/cIL-10R1, (Liu et al., 1997)), were maintained in RPMI-1640 medium (Mediatech) supplemented with 10% fetal bovine serum (FBS, Biowhitaker), 2 mM L-glutamine, 100 U/ml penicillin, 100 μM streptomycin, 50 μM BME, 2 μg/ml puromycin (Sigma), and 2 ng/ml recombinant human GM-CSF (R&D systems). Rhesus PMBCs were maintained in RPMI medium.

Cloning, Expression, and Purification of rhCMVIL-10 and rhCMVIL-10 Mutants

The rhcmvIL-10 open reading frame (FIG. 2) (Lockridge et al., 2000) was amplified by polymerase chain reaction (PCR) and inserted into the pMTA-V5-His6 vector (Invitrogen) for expression in *Drosophila* S2 cells as previously described (Josephson et al., 2001b). rhcmvIL-10 was purified by affinity chromatography using human IL-10R1 beads (Jones et al., 2002). To purify rhcmvIL-10 mutants that could not bind IL-10R1, rhcmvIL-10 plasmids were constructed that encode N-terminal or C-terminal 6 histidine tags. Specifically, N-terminal histidine tagged rhcmvIL-10 mutants were expressed using a heterologous signal sequence from the human IFNγR2 chain, followed by an N-terminal 6 histidine-tag, followed by a factor Xa protease site (pAHF-rhcmvIL-10). C-terminal histidine tagged rhcmvIL-10 mutants were expressed using the IFNγR2 signal sequence and also contained a C-terminal factor Xa protease site followed by a 6 histidine tag (PMTA-rhcmvIL-10FXH). Sequences of these final protein constructs are shown herein in the Sequence Alignments.

Mutations were made using the QUIKCHANGE® site-directed mutagenesis kit (Stratagene) and confirmed by DNA sequencing. Large scale purification of rhcmvIL-10 mutants was performed using a 2-step nickel affinity purification protocol. Mutants from 1 liter of expression medium were dialyzed into bind buffer (20 mM Tris pH 8.0, 500 mM NaCl, and 5 mM imidazole) and bound to 5 mL of Ni-NTA his-bind resin (Novagen). Fractions eluted from the column using bind buffer+200 mM imidizole (~30 mL) were re-dialyzed into bind buffer and purified again over a 0.5 mL column of Ni-NTA resin.

Size Exclusion Chromatography

Size exclusion chromatography was performed by injecting protein samples onto a 24 mL SUPERDEX® 200 gel filtration column (GE Health Care).

Pull Down Assay

*Drosophila* medium (500 μL) containing transiently expressed rhcmvIL-10 proteins was incubated with 15 μL of human IL-10R1 coupled agarose beads (AFFIGEL® 10, Bio-Rad) for 1 hour at 4° C. The beads were recovered from the medium by spinning at 400×g and washed 3 times in 5004 of wash buffer consisting of 20 mM Tris-HCL, pH 8.0, 150 mM NaCl, 1% TWEEN®-20. Protein bound to 15 μL of the washed beads was added to sample buffer, boiled 5 minutes, and loaded onto a 12% SDS-PAGE gel. Protein was detected using Coomassie blue staining.

Western Blotting.

rhcmvIL-10 expression medium (10 μL) was run on a 12% SDS-PAGE gel. rhcmvIL-10 proteins were detected by western-blotting using a primary mouse anti-tetrahis antibody (Ab) (Qiagen), 1:2000 dilution in Tris-buffered saline with TWEEN®-20 (TBST) and 3% bovine serum albumin (BSA), followed by a mouse anti-horse radish peroxidase (HRP) secondary Ab, 1:5000 dilution, in TBST and 1% milk (Amersham) for ECL detection.

TF-1/HuIL-10R1 Cellular Proliferation Assay rhcmvIL-10 wild type or rhcmvIL-10 mutants were dispensed into 96-well microplates (Becton Dickinson) in duplicate wells and serially diluted three-fold across the plates. 5000 TF-1/HuIL-10R1 cells were added to each well and incubated for 2 days at 37° C. with 5% CO$_2$. Viable cells were assayed using Alamar Blue (Biosource International/Invitrogen). Fluorescence intensity was measured at room temperature using a POLAR star plate reader (BMG Lab Technologies) at wavelengths of 544 nm excitation and 590 nm emission.

IL-12 ELISA Assay 96-well microplates (IMMULON® 4 HBX, Dynex Technologies, Inc.) were coated with the IL-12 p40+p70 antibody pair and incubated over night at 4° C. The plates were then washed 6× with PBS-T and incubated with PBS/1% BSA blocking buffer for 1 hr at 37° C. The buffer was removed, 100 µL/well of PBMC supernatant was added, and the cell mixture was incubated at 4° C. overnight. The plates were then washed 6 times with PBS-T wash buffer, 100 µL/well of pAb anti-monkey ELISA detector antibody was added, and the cells were incubated 1 hr at 37° C. After washing, 100 µL/well of streptavidin-HR polymer (SPP) conjugate (U-Cytech) was added and the plates were incubated at 37° C. for 1 hr. After washing, TMB substrate (100 µL/well) was added per well, and the plates were incubated at 25° C. for 7-10 min. Color development was stopped by the addition of 0.5M sulfuric acid (50 µL/well). Following a 5-minute incubation at room temperature, the plates were read at a wavelength of 450 nm on a Model 680 microplate reader (BioRad). Concentrations of IL-12 were quantified using a 2-fold serially diluted recombinant IL-12 standard that was included on each plate.

Immunization Strategy

Seven RhCMV seropositive rhesus macaques were immunized with rhcmvIL-10. Immunization consisted of three intramuscular (IM; 150 µg) and intradermal (ID; 50 µg) injections of plasmid DNA encoding rhcmvIL-10 M1 (3 animals) or rhcmvIL-10M2 (3 animals) followed by two homologous protein boosts (50 µg IM adjuvanted in MONTANIDE® ISA 720), such that animals were immunized (DNA and protein) with either just M1 or M2. The second and third DNA injections were separated from the previous immunization by 28 and 21 days, respectively. The first protein boost was initiated 2 months following the third DNA injection and the second performed 1 month after the first. Plasma was collected weekly between DNA and protein injections. A seventh animal was only immunized with plasmid DNA.

Analysis of Rhesus Plasma for Neutralizing Anti-rhcmvIL-10 Antibodies

Plasma, collected between immunizations, was diluted 1:4000 in RPMI and incubated with 0.5 ng rhcmvIL-10 for 3 hours at 37° C. The plasma was mixed with 4×10⁵ rhesus PBMCs in a total volume of 200 µL for 30 minutes followed by addition of 1 µg of LPS and incubation for 24 hours. IL-12 levels were monitored by ELISA as described herein. IL-12 production is reported as the % increase by comparison of the IL-12 production in stimulated PBMC incubated with plasma versus stimulated PBMC incubated with rhcmvIL-10 and plasma.

Mass Spectrometry

Liquid chromatography mass spectrometry (LCMS) of rhcmvIL-10FXH was performed using an ABIsciex API 4000 LC/MS.

Figure 1:
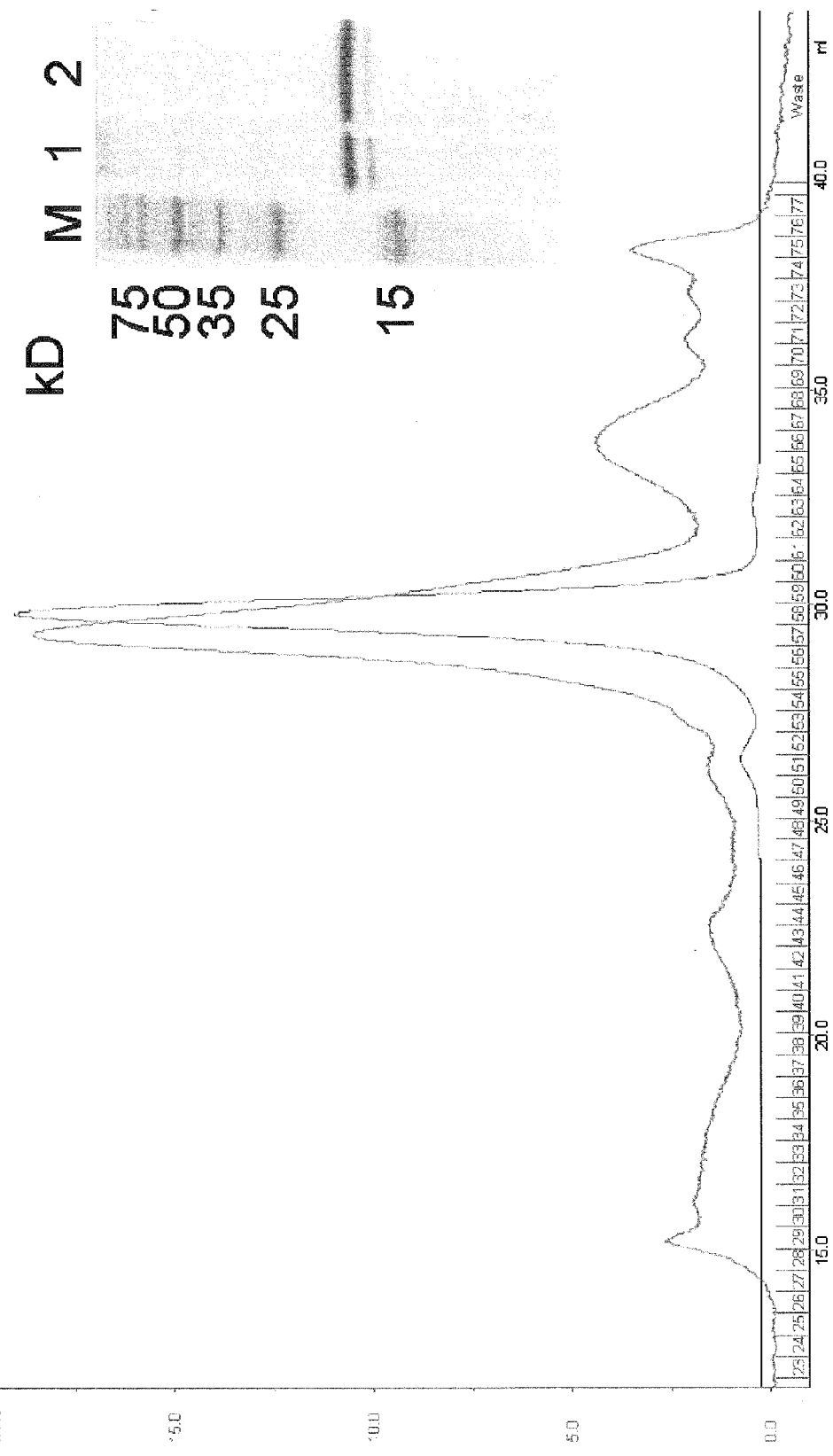
FIG. 1. Purification and quaternary structure of rhcmvIL-10. GF Chromatographs of HuIL-10 (grey) and rhcmvIL-10 (black). (Inset) SDS-PAGE gel of affinity purified rhCMVIL-10 (lane 1) and pooled fractions of the major gel filtration peak (lane 2).

Expression, Purification, and Characterization of rhcmvIL-10 rhcmvIL-10 was expressed in *Drosophila* Schneider S2 cells and purified by affinity chromatography using agarose beads coupled with the human IL-10R1 chain as previously described (Jones et al., 2002). Affinity purified rhcmvIL-10 ran as two bands on SDS-PAGE gels. The major band exhibited a molecular weight (MW) of ~19000, while a much less intense second band of ~18,000 was also observed (FIG. 1). The presence of two bands suggested rhcmvIL-10, expressed in insect cells, is predominantly glycosylated on its single N-linked glycosylation site, Asn-87 (FIG. 2). This was subsequently confirmed by mass spectrometry of rhcmvIL-10FHX in the presence and absence of PNGase F, which enzymatically removes N-linked glycans (Table 3). Affinity purified rhcmvIL-10 was injected onto a gel filtration (GF) column (FIG. 1). In the GF experiment, rhcmvIL-10 eluted from the column at essentially the same position as cellular human IL-10 (HuIL-10), which is a dimer (Walter and Nagabhushan, 1995; Windsor et al., 1993; Zdanov et al., 1995). The combined results of the SDS-PAGE and GF data confirm that rhcmvIL-10WT is a non-covalent homodimer, as previously determined for HuIL-10.

Design of rhcmvIL-10 Point Mutants Defective in IL-10R1 Binding

Sequence and structural analysis of rhcmvIL-10 were used to assist in the design of rhcmvIL-10 point mutants that could not bind to the IL-10R1 chain (FIG. 2). Mature HuIL-10 and RhIL-10 sequences share 94% sequence identity, while the viral IL-10s (rhcmvIL-10 and cmvIL-10) exhibit between 26-29% identity with each other and with the cellular IL-10s. Despite the divergent amino acid sequences, several residues that form extensive contacts with IL-10R1 in the HuIL-10/IL-10R1 and cmvIL-10/HuIL-10R1 binding interfaces (Jones et al., 2002; Josephson et al., 2001a) are conserved in rhcmvIL-10 (FIG. 2).

Using the structural information described herein (FIG. 2), 3 rhcmvIL-10 residues (Gln-38, Glu-142, and Asp-144, based on human IL-10 numbering) were identified that were expected to maximally disrupt rhcmvIL-10/RhIL-10R1 interactions and prevent or diminish rhcmvIL-10 biological activity. These residues were chosen based on the following criteria. 1) The residues were conserved among the human and viral IL-10 amino acid sequences, 2) the amino acids made extensive contacts with IL-10R1 in the HuIL-10/HuIL-10R1 complex, and 3) the residues were located in the center of the HuIL-10/HuIL-10R1 interface. This final criterion (#3) was required because rhcmvIL-10 mutations expected to disrupt IL-10R1 binding, but located on edge of the IL-10/IL-10R1 interface, could change their side chain conformations to maintain efficient IL-10R1 binding. To test this hypothesis, the Lys-34Glu mutant was made, which makes salt-bridge interactions with IL-10R1 residues Asp-100 and Glu-101 on the edge of the IL-10/IL-10R1 interface (FIG. 2B).

Characterization of rhcmvIL-10 Mutant Binding to IL-10R1

Figure 3:
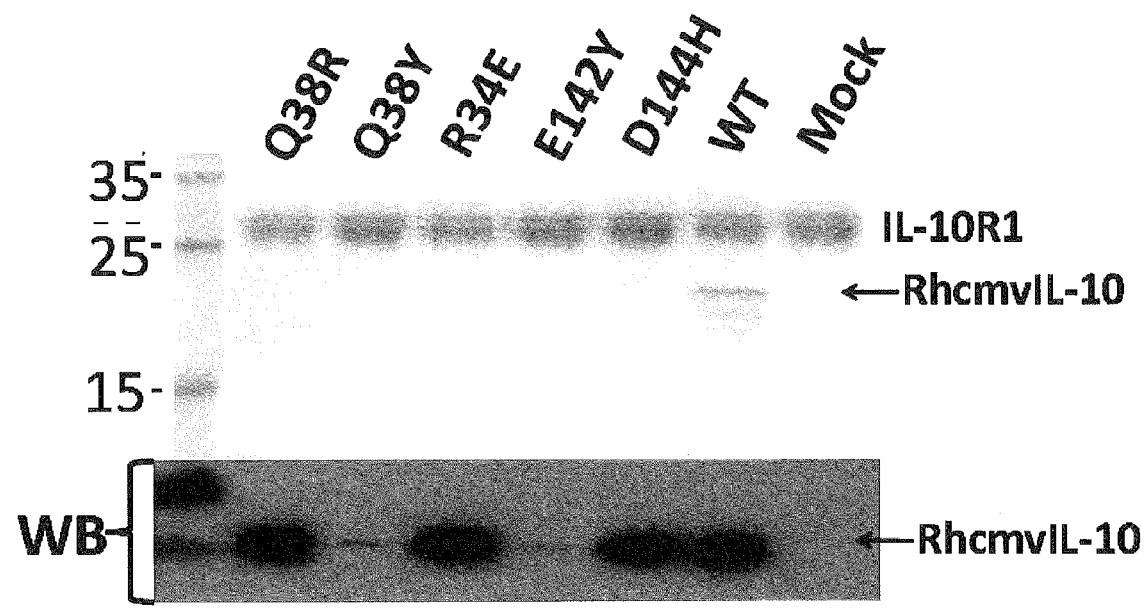
FIG. 3. Expression and IL-10R1 binding of rhcmvIL-10 point mutants. Expression of rhcmvIL-10 point mutants in Drosophila cell media was characterized by western-blotting (WB). Cell supernatants containing the point mutants were incubated with HuIL-10R1 coupled beads. After washing, the beads were loaded onto a 12% SDS-PAGE gel and subsequently stained with Coomassie blue dye.

Based on the analysis above, five rhcmvIL-10 point mutants (Gln-38Arg, Gln-38Tyr, Arg-34Glu, Glu-142Tyr, Asp-144His) were expressed in insect cells, and the supernatants tested for binding to the HuIL-10R1 chain (FIG. 3). To assist in purification, and provide a common epitope for detecting the RhCMVIL-10 mutants, a 6-residue histidine tag (H6) and a factor Xa protease site (Fxa) were added to the N-terminus of these rhcmvIL-10 mutants (H6FXa-rhcmvIL-10). Western blot analysis revealed that H6FXa-rhcmvIL-10 mutants Gln-38Tyr and Glu-142Tyr were not efficiently expressed (FIG. 3). The other 3 rhcmvIL-10 mutants (Arg-34Glu, Gln-38Arg, and Asp-144His) were expressed at comparable levels, but were unable to bind to HuIL-10R1 coupled beads (FIG. 3).

Analysis of rhcmvIL-10 Mutants in TF-1 Cell Proliferation Assays

To characterize the rhcmvIL-10 point mutants (Gln-38Arg, Arg-34Glu, and Asp-144His) in a more sensitive assay, the ability of each mutant to proliferate TF-1 cells, transfected with the human IL-10R1 chain (TF-1/HuIL-10R1) (Liu et al., 1997) was tested. The concentration of rhcmvIL-10, and rhcmvIL-10 point mutants, in *Drosophila* cell supernatants was estimated by SDS-PAGE. Serial dilutions of each rhcmvIL-10 and HuIL-10 proteins were added to TF-1/HuIL-10R1 cells and proliferation was measured after 2 days. As shown in FIG. 4, rhcmvIL-10 and HuIL-10 exhibit essentially equivalent biological activity in the assay. In addition, rhcmvIL-10 Arg-34Glu, presumably because of its location on the edge of the IL-10/IL-10R1 interface (FIG. 2), also exhibits essentially wild type biological activity. In contrast, rhcmvIL-10 Gln-38Arg and rhcmvIL-10 Asp-144His exhibited ~100 and ~300 fold reductions in activity compared to rhcmvIL-10 and HuIL-10 (FIG. 4).

Two rhcmvIL-10 double mutants were tested in the TF-1/HuIL-10R1 cell assay (FIG. 4B). rhcmvIL-10 mutant 1 (M1) contained Gln-38Arg and Asp-144His point mutations and rhcmvIL-10 mutant 2 (M2) contained Glu-142Gln and Asp-144His mutations. Because of the poor solubility of the H6FxarhcmvIL-10 proteins during initial purification studies, a C-terminal Fxa and H6 tag (rhcmvIL-10-FXaH6) was added to rhcmvIL-10 M1 and M2. Serial dilutions of M1 and M2, based on protein concentrations estimated from SDS-PAGE gels, were added to TF-1/HuIL-10R1 cells, which revealed rhcmvIL-10M1 and M2 did not exhibit biological activity at concentrations as high as ~1 µg/mL (FIG. 4B).

Analysis of rhcmvIL-10 Mutants' Ability to Suppress IL-12

Based on the results of the TF-1/HuIL-10R1 assays, rhcmvIL-10 double mutants, M1 and M2, were purified by nickel affinity chromatography. Purified M1 and M2 proteins were assayed for their ability to inhibit the production of IL-12 in Rh PMBCs stimulated with lipopolysaccharide (LPS) (FIG. 5). Five concentrations of rhcmvIL-10 M1 and M2, ranging from 0.1 ng/mL to 1 µg/mL, were tested in the assay. Comparison of IL-12 levels in PBMC cultures treated with LPS, LPS+M1, or LPS+M2 revealed that the rhcmvIL-10 double mutants are ~88-100% inactive in the assay (FIG. 5).

Immunization of Rhesus Macaques with rhcmvIL-10M1 and rhcmvIL-10M2.

Figure 6:
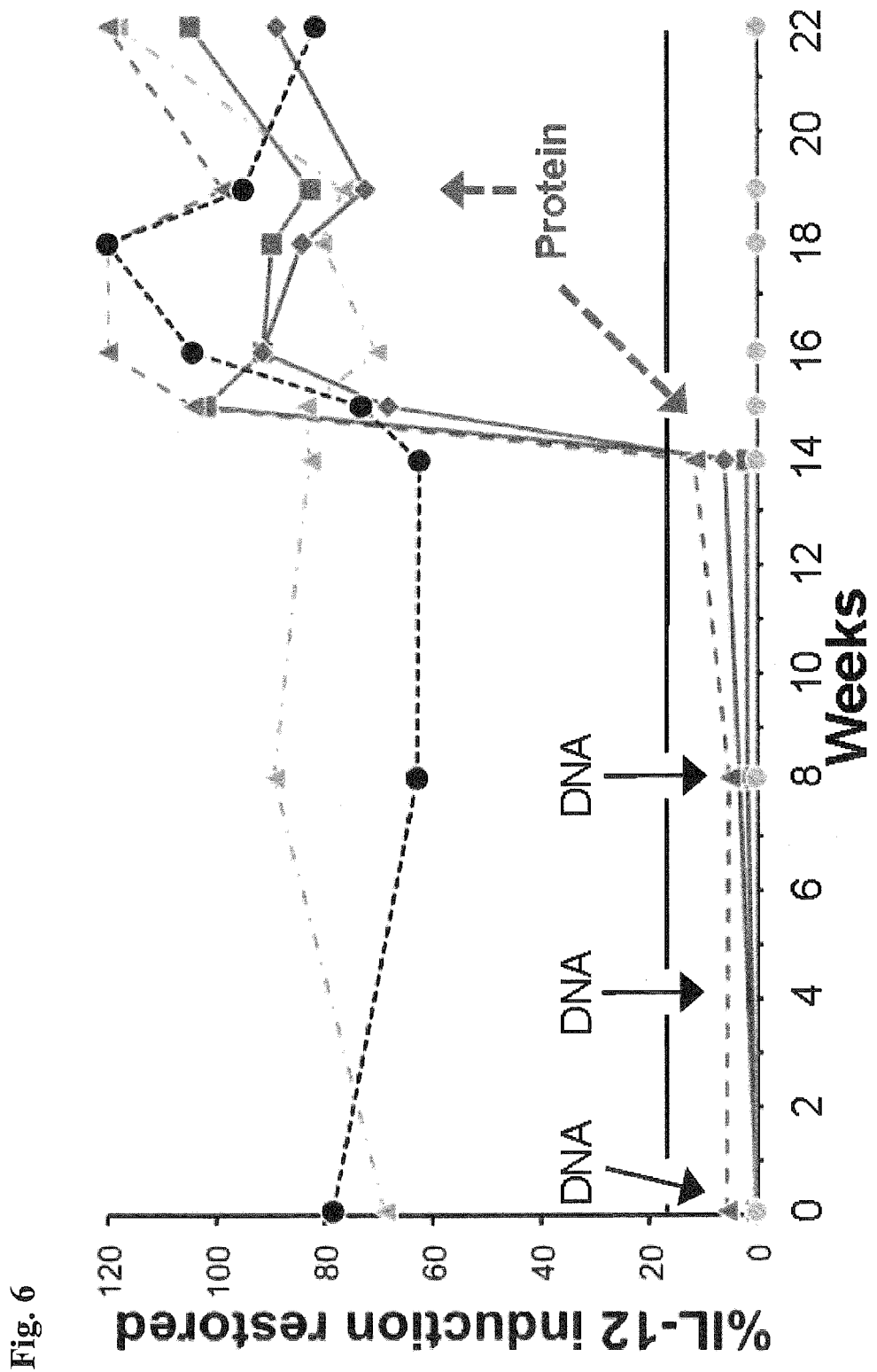
FIG. 6. Analysis of rhcmvIL-10 neutralizing antibodies (NAbs) upon vaccination. Six RhCMV-infected monkeys were immunized three times with plasmid expression vectors for M1 and M2 (black solid arrows) and two times with recombinant protein adjuvanted in MONTANIDE® ISA 720. All six animals demonstrated increased binding Ab responses (data not shown) and five animals demonstrated increased NAb responses after the protein immunizations, based on the IL-12 assay described in FIG. 5. The solid line at ~16% IL-12 restored represents the median NAb response in naturally infected monkeys (see FIG. 12A). The X-axis marks times of DNA and protein vaccinations (Vxs) as outlined in Table 4. The points on the graph denote blood draws following Vx, which were subsequently tested for the presence of rhcmvIL-10 NAb by IL-12 ELISA. Percent IL-12 induction denotes the increase in IL-12 production between LPS activated PBMCs incubated with plasma versus PBMCs incubated with plasma and rhcmvIL-10.

Based on the results of the cell-based assays, rhcmvIL-10 M1 and M2 were used to immunize seven RhCMV seropositive Rhesus macaques using the schedule outlined in Table 4. The production of rhcmvIL-10 neutralizing Abs (NAbs), during the immunization procedure, was monitored by testing the ability of plasma from immunized animals to block rhcmvIL-10 mediated inhibition of IL-12 in LPS stimulated PBMCs (FIG. 6). Using this assay, the presence of NAbs was evaluated 1 day prior to the initial DNA immunization, after the third DNA vaccination (Vx), and six times following the protein boosts (FIG. 6). Increased levels of NAbs were generated in 5 of 6 animals that received protein boosts. Two of the seven animals already had NAb titers (animals 35646 and 35735) that were increased, at least transiently, by the protein vaccinations. No increase in NAbs was observed for one animal that received the full immunization strategy (animal 35735) and one control animal that received only DNA vaccination (animal 35779). Both animals that failed to respond, 35735 and 35779, were vaccinated with the M2 protein. Despite this observation, both M1 and M2 induce NAbs in other animals. Thus, while M2 might be considered a poorer immunogen, the data indicate that the vaccination strategy and the immune status of an animal are the major contributors to achieving robust NAbs responses to rhcmvIL-10.

REFERENCES FOR EXAMPLE 1

1. Blackburn and Wherry (2007) IL-10, T cell exhaustion and viral persistence. *Trends Microbiol* 15:143-146
2. Chang et al. (2004) Human cytomegalovirus-encoded interleukin-10 homolog inhibits maturation of dendritic cells and alters their functionality. *J Virol* 78:8720-8731
3. de Waal Malefyt et al. (1991 a) Interleukin 10 (IL-10) inhibits cytokine synthesis by human monocytes: an autoregulatory role of IL-10 produced by monocytes. *J Exp Med* 174:1209-1220
4. de Waal Malefyt et al. (1991b) Interleukin 10 (IL-10) and viral IL-10 strongly reduce antigen-specific human T cell proliferation by diminishing the antigen-presenting capacity of monocytes via downregulation of class II major histocompatibility complex expression. *J Exp Med* 174: 915-924
5. Jones et al. (2002) Crystal structure of human cytomegalovirus IL-10 bound to soluble human IL-10R1. *Proc Natl Acad Sci USA* 99:9404-9409
6. Josephson et al. (2002) Non-competitive antibody neutralization of IL-10 revealed by protein engineering and X-ray crystallography. *Structure* 10:981-987
7. Josephson et al. (2001a). Crystal structure of the IL-10/IL-10R1 complex reveals a shared receptor binding site. *Immunity* 15:35-46
8. Josephson et al. (2001b) Purification, crystallization and preliminary X-ray diffraction of a complex between IL-10 and soluble IL-10R1. *Acta Crystallogr D Biol Crystallogr* 57:1908-1911
9. Kotenko et al. (2000) Human cytomegalovirus harbors its own unique IL-10 homolog (cmvIL-10) *Proc Natl Acad Sci USA* 97:1695-1700
10. Liu et al. (1997) The EBV IL-10 homologue is a selective agonist with impaired binding to the IL-10 receptor. *J Immunol* 158:604-613
11. Lockridge et al. (2000) Primate cytomegaloviruses encode and express an IL-10-like protein. *Virology* 268: 272-280
12. Moore et al. (2001) Interleukin-10 and the interleukin-10 receptor. *Annu Rev Immunol* 19:683-765
13. Rigopoulou et al. (2005) Blocking of interleukin-10 receptor—a novel approach to stimulate T-helper cell type 1 responses to hepatitis C virus. *Clin Immunol* 117:57-64
14. Spencer et al. (2002) Potent immunosuppressive activities of cytomegalovirus-encoded interleukin-10. *J Virol* 76:1285-1292
15. Walter and Nagabhushan (1995) Crystal structure of interleukin 10 reveals an interferon gamma-like fold. *Biochemistry* 34:12118-12125
16. Windsor et al. (1993) Disulfide bond assignments and secondary structure analysis of human and murine interleukin 10. *Biochemistry* 32:8807-8815
17. Yoon et al. (2006) Conformational changes mediate interleukin-10 receptor 2 (IL-10R2) binding to IL-10 and assembly of the signaling complex. *J Biol Chem* 281: 35088-35096
18. Zdanov et al. (1995) Crystal structure of interleukin-10 reveals the functional dimer with an unexpected topological similarity to interferon gamma. *Structure* 3:591-601

Example 2

Immunogenicity of Viral Interleukin-10 in Rhesus Cytomegalovirus-Infected Rhesus Macaques Abstract Human cytomegalovirus (HCMV) encodes a viral interleukin-10 protein (cmvIL-10) with comparable immune modulatory activity to that of cellular interleukin-10.

Little is known about the infected host's immune responses to cmvIL-10 and whether such immune responses offer a paradigm for vaccination against cmvIL-10 and other viral immune modulating proteins. In this study of rhesus macaques infected with rhesus cytomegalovirus (RhCMV), an ELISA-based format was used to determine the titer and avidity of antibodies to the rhCMV IL-10 protein (rhcmvIL-10), and neutralizing antibody titers were quantified by inhibition of rhcmvIL-10 functional activity in a bioassay of activated lymphoid cells. The results demonstrate that rhcmvIL-10 is generally a strong immunogen during primary infection, stimulating high plasma titers of high avidity neutralizing antibodies that persist for the life of the host. However, the results further suggest that the titer of rhcmvIL-10 antibodies in long-term infected animals may be insufficient to neutralize rhcmvIL-10 function at mucosal surfaces and in the underlying tissues. Extrapolating from these results, the absence of protective neutralizing titers in mucosal tissues may contribute to cmvIL-10-mediated immune modulation by HCMV, facilitating its ability to reinfect hosts with prior immunity. Immunization against cmvIL-10 represents a potential strategy for attenuating the virus' manipulation of the micro-immune environment of infected cells during both primary and secondary infection at a mucosal surface.

Human cytomegalovirus, a member of the Betaherpesviridae sub-family of the Order Herpesvirales (17), infects 50-100% of adults worldwide (4). Primary infection in immune competent individuals is generally subclinical, although clinically apparent outcomes, such as a mononucleosis-like syndrome, are observed in a minority of infections (2). In all cases, primary infection in an immune competent individual is followed by a lifelong viral persistence in which latently infected cells periodically reactivate to produce infectious virions in the absence of clinical signs of disease (8). While both the primary and persistent stages of HCMV infection are mostly asymptomatic in immune competent individuals, unrestricted HCMV replication is a cause of morbidity and mortality in immune compromised individuals, such as HIV-infected patients, immunosuppressed solid organ or bone marrow transplant recipients, and transplacentally infected fetuses/newborns. HCMV has long been recognized as a significant infectious threat to fetal development, sometimes manifesting as lifelong neurological deficits and sensorineural hearing loss in congenitally infected fetuses/neonates (21, 52). Efforts to develop a vaccine that confers protective efficacy against congenital transmission of HCMV have been ongoing for more than three decades (19, 21, 39, 49, 55). Recent progress has been made using recombinant glycoprotein B (gB) formulated in the MF59 adjuvant, which achieved 50% protective efficacy against seroconversion in seronegative pregnant women (37). The absence of complete protection with recombinant gB alone implies that inclusion of additional viral antigens could increase the level of protective efficacy. One class of antigens that has not been examined consists of those viral proteins that modulate host immune responses.

In vitro and comparative sequence data suggest that HCMV persistence is facilitated by the expression of multiple, virally-encoded, immune modulating proteins, which hinder the development of sufficient immune responses to clear long-term viral reservoirs. Subversion of the immune system to enable both dissemination from the primary site of infection and maintenance of a persistent infection is generally attributed to the virus' ability to disrupt cell signaling, activation, trafficking, and apoptosis (33, 35, 43). A substantial portion of the HCMV genome is devoted to viral immunomodulatory proteins. Roughly 70% of the entire HCMV genome can be removed with no impairment on viral replication in fibroblasts, leaving a majority of the genome dedicated towards encoding proteins that either modify the microenvironment of the infected cell or are required for specific cell tropisms (18, 56). Research on viral immune modulators has primarily focused on their interaction with and disruption of the immune system, leaving the immunogenicity of these proteins essentially unexplored. The considerable dedication of viral coding capacity to immunomodulatory proteins implies that they play vital roles in HCMV replication and dissemination in vivo.

Accordingly, vaccine-mediated immune responses directed towards this class of viral proteins could significantly impair HCMV parameters of growth following viral challenges.

The viral interleukin-10 protein encoded by the HCMV UL111a open reading frame (cmvIL-10) is secreted from infected cells and alters the functionality of multiple immune effector cells (12-14, 23, 24, 26, 28, 31, 43, 47, 48). As a first step towards evaluating whether vaccination against cmvIL-10 would confer a measure of immune protective efficacy, humoral responses to this viral protein were analyzed in rhesus macaques to investigate the ontogeny and biological relevance of antibody responses to rhcmvIL-10 following experimental inoculation or natural infection with RhCMV.

Expression and Purification of rhcmvIL-10

Restriction enzymes were purchased from New England Biolabs. The endogenous SacII site in the RhCMV IL-10 coding sequence (Genbank® Database Accession No. 59907) was removed by introducing a silent mutation using the QUIKCHANGE® site directed mutagenesis kit (Stratagene) with primer: 5'-GCACGGCAAAAGCAGCGGC-CGAGGCTG-3' (SEQ ID NO:19) and its reverse complement. The resulting cDNA was PCR amplified using PFU TURBO® polymerase (Stratagene) with forward primer: 5'-GCTCAGCCGCGGCCCATGACCATGAACACAAA GAAG-3' (SEQ ID NO:20) and reverse primer: 5'-CGTAT-CACCGGTGCGGCCCTCGATG CTGAACTGCAGCAG-CAGCAGGAACGTTTCC-3' SEQ ID NO:21). The 3' primer encoded an additional 13 amino acid residues (SIEGRTGH-HHHHH-stop, SEQ ID NO:14)) at the C-terminus of the protein. The PCR product was digested with SacII and AgeI followed by ligation into the pMT/V5-hisA expression vector (Invitrogen) containing a heterologous signal peptide to generate pMTA/rhcmvIL-10FXH. rhcmvIL-10 was expressed in Drosophila cells by calcium phosphate transfection of pMTA/rhcmvIL-10FXH as described by the manufacturer (Invitrogen). rhcmvIL-10 secreted into the media was purified by nickel affinity chromatography.

rhcmvIL-10 ELISA

Antibodies against rhcmvIL-10 were characterized by ELISA by modifying a previously published protocol(58). Briefly, 96-well microplates (IMMULON® 4 HBX, Dynex Technologies Inc.) were coated overnight at 4° C. with nickel affinity-purified rhcmvIL-10 (12.5 ng/well) in phosphate buffered saline (PBS) (Sigma)/0.375% sodium bicarbonate (GIBCO). Each plate was subsequently washed 6 times with PBS/0.05% TWEEN® 20 (Sigma) (PBS-T) and blocked with 300 µl/well PBS/1% bovine serum albumin (BSA) (Sigma) for 2 hours at 25° C. in a temperature-controlled incubator. After washing the plates 6 times with PBS-T, 100 µl of a 1:100 dilution of rhesus monkey plasma (in PBS-T/1% BSA) was added to each well and incubated at 25° C. for 2 hours. Plasma samples were from rhesus macaques serologically confirmed to be infected or uninfected with RhCMV. Each sample was assayed in triplicate. The plates were subsequently washed 6 times with PBS-T wash buffer and loaded with 100 µl/well of a 1:60,000 dilution of peroxidase-conjugated goat-anti-monkey IgG (Kirkegaard & Perry Laboratories, Inc—KPL) and incubated at 25° C. for 1 hour. The plates were then washed 6 times with PBS-T wash buffer and 100 µL/well of tetramethylbenzidine liquid substrate (TMB) (Sigma) was added and incubated for 30 min at 25° C. TMB color development was stopped by the addition of 50 µl/well of 0.5M sulfuric acid. After a 5-minute incubation at room temperature, color development was quantified spectrophotometrically at a wavelength of 450 nm on a Model 680 microplate reader (BioRad). Relative units (RU) were quantified using a standard curve of 10-fold serial dilutions of plasma from a rhesus macaque immunized with rhcmvIL-10. The threshold for a sample to be considered positive for a specific rhcmvIL-10 antibody response (RU=1) was set at 6 standard deviations above the control seronegative mean optical density derived from 30 seronegative samples.

Western Blot Detection of rhcmvIL-10

Antibody responses against rhcmvIL-10 protein were analyzed by SDS-PAGE gel electrophoresis and Western blot. rhcmvIL-10 protein (2.5 µg) was electrophoresed on a 12% denaturing acrylamide gel (Bio-Rad) and transferred to polyvinylidenedifluoride (PVDF)(50). The membrane was blocked overnight in 5% milk/PBS/0.1% TWEEN® 20 with shaking at room temperature. Individual strips of the membrane were then incubated for 2 hours at room temperature with 1 ml of rhesus macaque plasma diluted 1:100 dilution in 5% milk/PBS/0.1% TWEEN® 20. The strips were than washed three times (5 minutes per wash) with PBS/0.1% TWEEN® 20 and then incubated with 2 ml of a peroxidase conjugated anti-monkey IgG (KPL) (diluted 1:5,000 in 5% milk/PBS/0.1% TWEEN® 20) at room temperature for 1 hour. The membrane was washed again, and antibody binding was detected using the ECL Plus Western Blot Detection Kit (GE Healthcare). Fluorescence was detected using the Typhoon 9410 variable mode imager (GE Healthcare), and band intensity was quantified with the Image Quant software (GE Healthcare). Additionally, seroreactivity to rhcmvIL-10 was detected by Western blot using 3,3'-Diaminobenzidine (DAB) (Vector Laboratories) as a colorimetric detection reagent. In this case, the concentration of rhcmvIL-10 protein was increased to 5 ug, the primary incubation time was increased to an overnight incubation, and the secondary antibody (peroxidase conjugated anti-monkey IgG) was used at a concentration of 1:200. After the last wash (PBS/0.1% TWEEN®), the membrane was incubated at room temperature with DAB until bands were clearly visible.

Avidity Assay of Antibodies to rhcmvIL-10

Avidity binding of rhcmvIL-10 antibodies was assayed similarly to the ELISA protocol, except that after the primary 2-hour incubation with diluted plasma, the wells were incubated in freshly prepared 6M urea for five minutes at room temperature, and then washed extensively with PBS-T. Secondary goat anti-monkey antibody was then added for 1 hour, and the plates were washed and processed for colorimetric development according to the ELISA protocol. The Avidity Index (AI) was calculated by dividing the mean optical density of a sample treated with 6M urea by the mean optical density of the sample not treated with 6M urea.

Neutralization of rhcmvIL-10 Function In Vitro

Plasma samples from RhCMV seropositive and seronegative macaques were diluted (1:4,000) in RPMI/10% fetal bovine serum (600 µL final volume) in the presence or absence of recombinant rhcmvIL-10 (0.5 ng/mL) for 3 hours at 37° C. This dilution of plasma was necessary due to the presence in plasma of endogenous inhibitory factors in less dilute plasma that inhibited IL-12 production by activated PBMC. 200 µL of the plasma+/−rhcmvIL-10 mixtures were then incubated (each in duplicate) with $4 \times 10^5$ Ficoll-purified PBMC/well in a 96 well U-bottom plate (Falcon) for 30 minutes in a humidified 37° C. incubator (5% $CO_2$). LPS (from E. coli O127:B8; Sigma) was then added to the cells (5 ug/mL final concentration), and the cells were then incubated 24 hours at 37° C. (5% $CO_2$). The supernatant was collected the following day and stored at −80° C. until assayed for IL-12 production. IL-12 secretion by LPS-activated PBMC was measured by ELISA (U-Cytech, Netherlands), according to the manufacturer's protocol with slight variations. Briefly, 96-well microplates (IMMULON® 4 HBX) were coated with the supplied IL-12 antibody pair (p40+p70) and incubated overnight at 4° C. The plates were then washed 6× with PBS-T and incubated with PBS/1% BSA blocking buffer for 60 minutes at 37° C. The buffer was removed, 100 µL/well of PBMC supernatant was added, and the cell mixture was incubated at 4° C. overnight. The plates were then washed 6 times with PBS-T wash buffer, 100 µL/well of anti-monkey ELISA detector antibody was added, and the cells were incubated 1 hr at 37° C. After washing, 100 µL/well of streptavidin-HR polymer (SPP) conjugate (U-Cytech) was added and incubated at 37° C. for 1 hr. After washing, TMB substrate (100 µL/well) was added, and the plates were incubated at 25° C. for 11 min. Color development was stopped by the addition of 0.5M sulfuric acid (50 µL/well). Following a 5-minute incubation (25° C.), the plates were read at a wavelength of 450 nm on a Model 680 microplate reader (BioRad). Concentrations of IL-12 were quantified using a 2-fold serially diluted recombinant IL-12 standard (U-Cytech) that was included on each plate. Neutralization was calculated as the inverse of the ratio of (IL-12 concentration+rhcmvIL-10+plasma)/(IL-12 concentration+plasma only) and was expressed as the "percent (%) IL-12 induction restored."

Statistics

All ELISA based OD results were converted into IgG relative units using a log-log regression model equation. The statistical analysis program Prism 4 was used for all statistical analyses. All corral surveys for the presence of RhCMV and rhcmvIL-10 antibodies were analyzed using the student's t-test ($\alpha=0.05$). All significant correlations were determined using Pearson's correlation coefficient analysis. One-way ANOVA and Tukey-Kramer multiple comparison test ($\alpha=0.05$) were used for all age-matched analyses.

Serosurvey of rhcmvIL-10 Antibodies in RhCMV-Infected Monkeys

Figure 7:
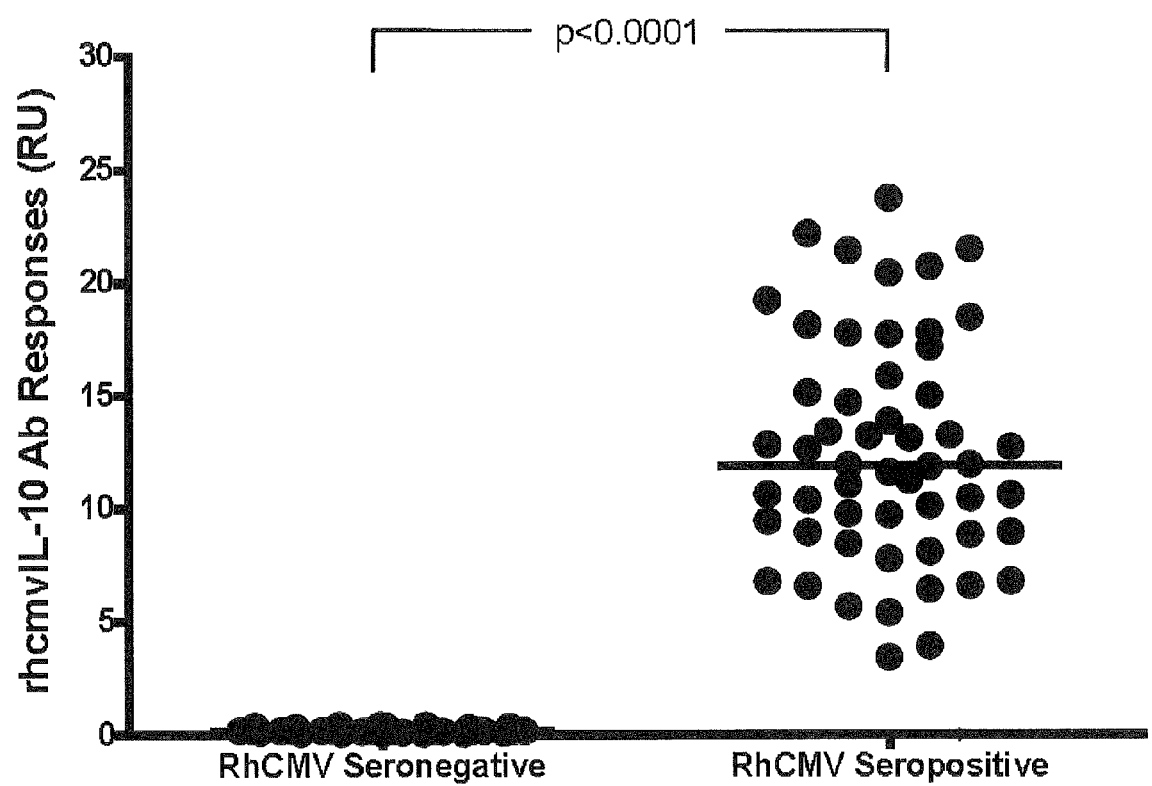
FIG. 7. rhcmvIL-10 antibody seroprevalence in rhesus macaques. Plasma samples from macaques confirmed negative (N=35) or positive (N=53) for RhCMV were screened for the presence of rhcmvIL-10 antibodies by a rhcmvIL-10 ELISA. RhCMV seropositive samples had significantly higher rhcmvIL-10 antibody titers than seronegative samples ($p<0.0001$) with a range of 3 to 24 Relative Units (RU). The median value is represented by the line.

A rhcmvIL-10 ELISA was developed to characterize the kinetics and magnitude of rhcmvIL-10-specific antibodies in RhCMV-infected macaques. Pilot assays were performed to optimize the amount of coating antigen and secondary antibody concentration necessary to give a broad linear range of reactivity and to maximize the distinction between plasma samples from RhCMV-infected and uninfected animals. Based on these assays, wells were coated with 12.5 ng/well of recombinant rhcmvIL-10, and a 1:60,000 dilution of goat anti-monkey IgG was used as the secondary antibody concentration. Plasma samples from outdoor-housed rhesus macaques, which were confirmed to be either RhCMV seropositive or seronegative by an ELISA using RhCMV-infected cell extract as antigen (53 RhCMV positive and 35 RhCMV negative) (58), were randomly chosen and screened by ELISA for the presence of rhcmvIL-10 antibodies. All RhCMV antibody-positive macaques were positive for rhcmvIL-10-binding antibodies, while all RhCMV antibody-negative samples were also negative for rhcmvIL-10 antibodies (p<0.0001) (FIG. 7). rhcmvIL-10-binding antibody titers in the RhCMV antibody-positive population ranged from 3-24 relative units (RU, described herein) with a median of 11.9 RU.

To verify the specificity of the rhcmvIL-10 ELISA, plasma samples from 16 RhCMV seropositive and 4 RhCMV seronegative animals that were screened by the rhcmvIL-10 ELISA were randomly chosen and assayed by Western blot using the same recombinant rhcmvIL-10 as the antigen. All RhCMV seropositive animals but two (#8 and 9) had detectable levels of fluorescent Western blot reactivity to a ~20 kDa protein, consistent with the predicted size, whereas no immune reactivity was detected in RhCMV seronegative macaques (#17-20) (Left Y-axis, FIG. 8A). Quantitative analysis of the Western blot reactivity generally confirmed the relative ELISA titers (Right Y-axis, FIG. 8A), although some minor discrepancies were noted. There was no detectable Western blot reactivity for animals #8 and 9, whereas the rhcmvIL-10 ELISA titers for both (8 and 11 RUs, respectively) were comparable to age-matched animals. However, increasing the sensitivity of the Western blot using DAB as the colorimetric detection reagent, allowed detection of a reactive 20 kDa bands in all RhCMV positive samples (FIG. 8B), including monkeys #8 and 9.

When rhcmvIL-10 antibody titers were stratified by the age of the animal, ($\leq 1$, 5-10, and >13 years, corresponding to infant, adult, and aged animals, respectively), significantly higher rhcmvIL-10-specific titers were detected in the infants, compared to the adult and aged groups ($p<0.001$, $p<0.01$ respectively) (FIG. 9A). The rhcmvIL-10 titers in the adult and aged animals were indistinguishable. Previous seroepidemiological studies have demonstrated that in outdoor, group-housed macaques, similar to those included in this study, there is 50% seroconversion to RhCMV infection by 6 months of age and complete seroconversion around 1 year (50). Thus, the adult and aged animals had, most probably, been infected long-term (>4->12 years) with RhCMV. The relative increased antibody responses to vIL-10 in the juveniles did not appear to be specific to this particular viral protein. A similar age-related pattern of seroreactivity was observed when an antigen preparation, consisting of a total protein lysate of RhCMV-infected cells, was used instead. There was a strong correlation between rhcmvIL-10 titers and RhCMV antibody titers (Pearson, $r=0.6176$, $P<0.0001$) (FIG. 9B), indicating that the magnitude of rhcmvIL-10 antibody titers reflected the magnitude of antibody titers to total RhCMV antigens.

Kinetics of De novo rhcmvIL-10 Antibodies Following RhCMV Infection

Detection of antiviral IgG antibodies in an experimental RhCMV infection generally occurs two to three weeks post inoculation (1, 30, 57). To determine the temporal kinetics of rhcmvIL-10-specific antibody development in relation to RhCMV-binding antibodies, 6 animals, experimentally inoculated with $5 \times 10^4$ Plaque Forming Units of RhCMV variant 68-1 by a combination of intravenous and subcutaneous injection, were prospectively analyzed by ELISA for development of RhCMV-binding and rhcmvIL-10-binding IgG antibodies. Four animals exhibited detectable rhcmvIL-10 antibodies (>2 RU) 2-3 weeks post inoculation while the remaining two animals became seroreactive to rhcmvIL-10 at 6-7 weeks post inoculation. The detection of rhcmvIL-10 antibody was approximately coincident with the development of the total RhCMV antibody response. Subsequent to the initial positive response, rhcmvIL-10 antibody levels increased to 14-16 RUs in 4 of the 6 animals and increased only to ~4-5 RUs in the remaining two animals by the cessation of the study at 10 weeks (FIG. 10).

Avidity of rhcmvIL-10 Antibodies

The binding strength of antibodies was evaluated for 50 RhCMV-positive macaques using an ELISA avidity assay with a 6M urea wash. All animals had a relatively high avidity index, ranging from 0.63 to 0.96 with an average of 0.83 (standard deviation=0.076) (FIG. 11). These results were consistent with what has previously been found in overall RhCMV antibody avidity (30). No differences in avidity were detected between the age groups.

Neutralizing Titers of rhcmvIL-10 Antibodies

Neutralizing antibody responses were detected by an in vitro assay in which plasma samples from RhCMV-immune animals were evaluated for the ability to neutralize rhcmvIL-10-mediated responses in activated peripheral blood mononuclear cells (PBMC). In brief, the assay compared the level of IL-12 synthesized by lipopolysaccharide (LPS)-activated PBMC following incubation with either rhcmvIL-10 diluted in rhesus plasma or plasma alone. Preliminary assays verified that LPS-stimulated PBMC secreted high amounts of IL-12 (an average of 1.5 ng/$2\times10^5$ cells), which was abrogated when the cells were pre-treated with rhcmvIL-10. Since rhcmvIL-10 inhibits the production of IL-12 in LPS-treated PBMC, antibody-mediated neutralization would be measured by greater levels of IL-12 production following incubation of LPS-activated PBMC with rhcmvIL-10. If a plasma sample did not have rhcmvIL-10 neutralizing antibodies, IL-12 expression would not be restored. Based on these results, IL-12 induction was used to quantify the ability of rhcmvIL-10 antibodies to bind to and neutralize rhcmvIL-10 activity. Plasma samples from 26 seropositive and 9 seronegative rhesus macaques were selected from the pool of those previously assayed by the vIL-10 binding ELISA and assessed for the ability to neutralize rhcmvIL-10 activity. RhCMV seropositive animals exhibited a wide range of neutralizing activity (0-100% IL-12 induction restored) with a median at 15.9% IL-12 induction restored (FIG. 12A). No neutralizing of rhcmvIL-10 was detected using plasma from RhCMV-uninfected monkeys. rhcmvIL-10 neutralizing titers exhibited a positive correlation with rhcmvIL-10 antibody titers (FIG. 12B; $r=6176$, $p<0.0001$). Juveniles showed slightly higher rhcmvIL-10 neutralizing titers than adults, consistent with the higher rhcmvIL-10 antibody titers observed in this age group (FIG. 9B).

The IL-10 protein of HCMV alters the in vitro functionality of multiple cell types comparable to the phenotype of cIL-10, despite the considerable sequence divergence between the two proteins (28, 31). Exposure of cultured cells to cmvIL-10 reduces: (i) proliferation of mitogen-stimulated PBMC and synthesis of proinflammatory cytokine production in activated PBMC and monocytes (48); (ii) maturation, and expression of proinflammatory cytokines and the CD80 and CD86 co-stimulatory molecules in monocyte-derived dendritic cells (MoDC) (14, 40); (iii) cell survival of activated MoDC (13); (iv) activation of IFN-$\alpha/\beta$ genes in plasmacytoid dendritic cells (12); and (v) endothelial cell and cytotrophoblast migration and invasion (54). In addition, cmvIL-10 stimulates B cell proliferation (47) and increases expression of cIL-10 (14). Based on the demonstrated functional properties of rhcmvIL-10 in vitro, this HCMV immune modulator is likely to manifest pleiotropic effects on both innate and adaptive immune effector cells in vivo. Therefore, it is reasonable to consider that neutralization of cmvIL-10 function through vaccination would augment the level of protective efficacy generated with other viral antigens, such as gB.

This study demonstrates that RhCMV infection stimulates the development of high avidity rhcmvIL-10-specific antibodies in all infected animals. There is a wide range in rhcmvIL-10 antibody titers between monkeys, and because neutralizing antibody titers strongly correlate with rhcmvIL-10-binding antibody titers, there is a correspondingly wide range of titers that neutralize rhcmvIL-10 function in vitro. The median level of rhcmvIL-10 neutralization measured in the IL-12-based assay is 16%, suggesting that the majority of infected animals do not develop titers of antibody commensurate with effective blocking of the rhcmvIL-10 ligand with its cellular IL-10 receptor. An important consideration of this interpretation is whether the in vitro results are relevant to the context of virus-host interactions in vivo. A previous study from this lab characterizing the immunosuppressive effects of the cmvIL-10 on MoDC showed that the concentration of cmvIL-10 secreted from HCMV-infected cells was in the range of 0.8-4 ng/ml (14). Based on this finding, the concentration of rhcmvIL-10 used for the neutralization assay in this report (0.5 ng/ml) is virologically appropriate.

The plasma samples were diluted 1:4,000 for the neutralization assay, and the results indicate that rhcmvIL-10 protein in blood would have little to no biological function in long-term infected hosts. Since it is well documented that HCMV can be transmitted across a mucosal surface and re-infect a host with prior seroimmunity (5, 6, 16, 36, 42, 53), the potential contribution of rhcmvIL-10-specific antibodies to protective immunity would primarily be a function of the local titer at mucosal surfaces across which HCMV can be transmitted. The concentration of IgG in mucosal fluids, such as saliva, is ≤0.1% of that found in plasma (3, 7, 10, 41, 51). Accordingly, the dilution of plasma used for the neutralization assays is a reasonable approximation of the anti-rhcmvIL-10 antibody titers that might be found in the tissues underlying mucosal surfaces in seroimmune individuals.

Taken together, the results in this study indicate that rhcmvIL-10 antibodies in the vast majority of immune monkeys would not contribute significantly to effective neutralization of rhcmvIL-10 function in the microenvironment of infected cells at a mucosal surface. Based on the exceedingly high affinity of cmvIL-10 for the human IL-10 receptor (27), it may not take many molecules of rhcmvIL-10 to initiate IL-10 receptor-mediated signaling cascades. One important implication of the absence of robust neutralizing titers within the mucosa is that a reinfecting virus might be able to suppress innate and memory immune responses via rhcmvIL-10, potentially enabling the systemic dissemination of a non-primary infection beyond the site of infection within an immune host.

In vitro studies of cmvIL-10 demonstrate that it similarly suppresses CD4$^+$ effector functions in an experimental model of latency and persistence. Infection of purified CD34$^+$ myeloid progenitor cells with a cmvIL-10-deleted variant of HCMV increases (i) cell surface expression of MHC class II molecules in infected cells, (ii) proliferation and (iii) interferon-γ expression by either co-cultivated autologous or allogeneic CD4$^+$ T cells, compared to infection with the parental cmvIL-10-expressing variant (15). A unifying theme linking the MCMV and in vitro HCMV studies is viral exploitation of cIL-10- or cmvIL-10-mediated attenuation of immune clearance, respectively, and the potential advantages of increasing cmvIL-10 neutralization at mucosal surfaces and sites of long-term persistence.

In vitro studies addressing cmvIL-10 alteration of myeloid and plasmacytoid dendritic cell functions lead to a model whereby cmvIL-10 plays a prominent role in the skewing of the immune system during primary infection, allowing the establishment of a persistent infection, and that subsequent reinfections are enabled by cmvIL-10 suppressive activity at the mucosa. A vaccine that includes cmvIL-10 as an antigen may prevent altered immune response during primary and subsequent infections, allowing the host to develop greater protective immune responses.

REFERENCES FOR EXAMPLE 2

1. Abel et al. 2008 A heterologous DNA prime/protein boost immunization strategy for rhesus cytomegalovirus. *Vaccine* 26: 6013-25
2. Alford and Britt. 1993 Cytomegalovirus, p. 227-255. In B. Roizman, R. J. Whitley, and C. Lopez (ed.), *The Human Herpesviruses* Raven Press, Ltd., New York
3. Bergquist et al. 1997 Intranasal vaccination of humans with recombinant cholera toxin B subunit induces systemic and local antibody responses in the upper respiratory tract and the vagina. *Infect Immun* 65:2676-84
4. Boppana and Fowler 2007 Persistence in the population: epidemiology and transmission, p. 795-813. In A. Arvin, G. Campadielli, P. Moore, E. Mocarski, B. Roizman, R. Whitley, and K. Yamanishi (ed.), *Human Herpesviruses: Biology, Therapy and Immunoprophylaxis* Cambridge University Press, Cambridge
5. Boppana et al. 1999 Symptomatic congenital cytomegalovirus infection in infants born to mothers with preexisting immunity to cytomegalovirus. *Pediatrics* 104:55-60
6. Boppana et al. 2001 Intrauterine transmission of cytomegalovirus to infants of women with preconceptional immunity. *N Engl J Med* 344:1366-71
7. Bouvet et al. 1994 Immunoglobulin G antibodies in human vaginal secretions after parenteral vaccination. *Infect Immun* 62:3957-61
8. Britt, W. 2008 Manifestations of human cytomegalovirus infection: proposed mechanisms of acute and chronic disease. *Curr Top Microbiol Immunol* 325:417-70
9. Campbell et al. 2008 The salivary glands as a privileged site of cytomegalovirus immune evasion and persistence. *Med Microbiol Immunol* 197:205-13
10. Cartry et al. 1997 Quantification of IgA and IgG and specificities of antibodies to viral proteins in parotid saliva at different stages of HIV-1 infection. *Clin Exp Immunol* 109:47-53
11. Cavanaugh et al. 2003 Vigorous innate and virus-specific cytotoxic T-lymphocyte responses to murine cytomegalovirus in the submaxillary salivary gland. *J Virol* 77:1703-17
12. Chang et al. 2009 Human cytomegalovirus suppresses type I interferon secretion by plasmacytoid dendritic cells through its interleukin 10 homolog. *Virology* 390:330-7
13. Chang et al. 2007 Exposure of myeloid dendritic cells to exogenous or endogenous IL-10 during maturation determines their longevity. *J Immunol* 178:7794-804
14. Chang et al. 2004 Human cytomegalovirus-encoded interleukin-10 homolog inhibits maturation of dendritic cells and alters their functionality. *J Virol* 78:8720-31
15. Cheung et al. 2009 The role of the human cytomegalovirus UL111A gene in down-regulating CD4+ T-cell recognition of latently infected cells: implications for virus elimination during latency. *Blood* 114:4128-37
16. Dar et al. 2008 Congenital cytomegalovirus infection in a highly seropositive semi-urban population in India. *Pediatr Infect Dis J* 27:841-3
17. Davison et al. 2009 The order Herpesvirales. *Arch Virol* 154:171-7
18. Dunn et al. 2003 Functional profiling of a human cytomegalovirus genome. *Proc Natl Acad Sci USA* 100:14223-8
19. Elek and Stern. 1974 Development of a vaccine against mental retardation caused by cytomegalovirus infection in utero. *Lancet* 1:1-5.
20. Gruber et al. 2008 Differential signaling of cmvIL-10 through common variants of the IL-10 receptor 1. *Eur J Immunol* 38:3365-75.

21. Hanshaw, J. B. 1971 Congenital cytomegalovirus infection: a fifteen year perspective. *J Infect Dis* 123:555-61
22. Humphreys et al. 2007 Cytomegalovirus exploits IL-10-mediated immune regulation in the salivary glands. *J Exp Med* 204:1217-25
23. Jaworowski et al. 2009 Enhanced monocyte Fc phagocytosis by a homologue of interleukin-10 encoded by human cytomegalovirus. *Virology* 391:20-4
24. Jenkins et al. 2004 A novel viral transcript with homology to human interleukin-10 is expressed during latent human cytomegalovirus infection. *J Virol* 78:1440-7
25. Jenkins et al. 2008 Expression of a human cytomegalovirus latency-associated homolog of interleukin-10 during the productive phase of infection. *Virology* 370:285-94
26. Jenkins et al. 2008 Immunomodulatory properties of a viral homolog of human interleukin-10 expressed by human cytomegalovirus during the latent phase of infection. *J Virol* 82:3736-50
27. Jones et al. 2002 Crystal structure of human cytomegalovirus IL-10 bound to soluble human IL-10R1. *Proc Natl Acad Sci USA* 99:9404-9
28. Kotenko et al. 2000 Human cytomegalovirus harbors its own unique IL-10 homolog (cmvIL-10). *Proc Natl Acad Sci* 97:1695-700
29. Kotenko et al. 2000 Human cytomegalovirus harbors its own unique IL-10 homolog (cmvIL-10). *Proc Natl Acad Sci USA* 97:1695-700
30. Lockridge et al. 1999 Pathogenesis of experimental rhesus cytomegalovirus infection. *J Virol* 73:9576-9583
31. Lockridge et al. 2000 Primate cytomegaloviruses encode and express an IL-10-like protein. *Virology* 268:272-80
32. Lu et al. 2006 Murine cytomegalovirus interference with antigen presentation contributes to the inability of CD8 T cells to control virus in the salivary gland. *J Virol* 80:4200-2
33. Miller-Kittrell et al. 2007 Functional characterization of chimpanzee cytomegalovirus chemokine, vCXCL-1 (CCMV). *Virology* 364:454-65
34. Mitchell et al. 1996 Murine cytomegalovirus DNA in peripheral blood of latently infected mice is detectable only in monocytes and polymorphonuclear leukocytes. *Virology* 223:198-207
35. Mocarski, E. S., Jr. 2002 Immunomodulation by cytomegaloviruses: manipulative strategies beyond evasion. *Trends Microbiol* 10:332-9
36. Mussi-Pinhata et al. 2009 Birth prevalence and natural history of congenital cytomegalovirus infection in a highly seroimmune population. *Clin Infect Dis* 49:522-8
37. Pass et al. 2009 Vaccine prevention of maternal cytomegalovirus infection. *N Engl J Med* 360:1191-9
38. Pilgrim et al. 2007 A focused salivary gland infection with attenuated MCMV: an animal model with prevention of pathology associated with systemic MCMV infection. *Exp Mol Pathol* 82:269-79
39. Plotkin, S. A. 1994 Vaccines for varicella-zoster virus and cytomegalovirus: recent progress. *Science* 265:1383-5
40. Raftery et al. 2004 Shaping phenotype, function, and survival of dendritic cells by cytomegalovirus-encoded IL-10. *J Immunol* 173:3383-91
41. Raux et al. 2000 IgG subclass distribution in serum and various mucosal fluids of HIV type 1-infected subjects. *AIDS Res Hum Retroviruses* 16:583-94
42. Ross et al. 2010 Cytomegalovirus reinfections in healthy seroimmune women. *J Infect Dis* 201:386-9
43. Slobedman et al. 2009 Virus-encoded homologs of cellular interleukin-10 and their control of host immune function. *J Virol* 83:9618-29
44. Slobedman et al. 2002 Latent cytomegalovirus down-regulates major histocompatibility complex class II expression on myeloid progenitors. *Blood* 100:2867-73
45. Soderberg et al. 1993 Identification of blood mononuclear cells permissive of cytomegalovirus infection in vitro. *Transplant Proc* 25:1416-8
46. Spencer, J. V. 2007 The cytomegalovirus homolog of interleukin-10 requires phosphatidylinositol 3-kinase activity for inhibition of cytokine synthesis in monocytes. *J Virol* 81:2083-6
47. Spencer et al. 2008 Stimulation of B lymphocytes by cmvIL-10 but not LAcmvIL-10. *Virology* 374:164-9
48. Spencer et al. 2002 Potent immunosuppressive activities of cytomegalovirus-encoded interleukin-10. *J Virol* 76:1285-92
49. Stratton et al. 2000 *Vaccines for the 21st Century: A Tool for Decision Making*, National Academy Press, Washington, D.C.
50. Vogel et al. 1994 Seroepidemiologic studies of cytomegalovirus infection in a breeding population of rhesus macaques. *Lab Anim Sci* 44:25-30
51. Wang et al. 1996 Mucosal antibodies to human cytomegalovirus glycoprotein B occur following both natural infection and immunization with human cytomegalovirus vaccines. *J Infect Dis* 174:387-92
52. Weller, T. H. 1971 The cytomegaloviruses: ubiquitous agents with protean clinical manifestations (second of two parts). *NE J Med* 285:267-274
53. Yamamoto et al. 2010 Human cytomegalovirus reinfection is associated with intrauterine transmission in a highly cytomegalovirus-immune maternal population. *Am J Obstet Gynecol* 202:297 e1-8
54. Yamamoto-Tabata et al. 2004 Human cytomegalovirus interleukin-10 downregulates metalloproteinase activity and impairs endothelial cell migration and placental cytotrophoblast invasiveness in vitro. *J Virol* 78:2831-40
55. Yow, M. D. 1989 Congenital cytomegalovirus disease: a now problem. *J. Infect. Dis.* 159:163-167
56. Yu et al. 2003 Functional map of human cytomegalovirus AD169 defined by global mutational analysis. *Proc Natl Acad Sci USA* 100:12396-401
57. Yue et al. 2007 Immunogenicity and protective efficacy of DNA vaccines expressing rhesus cytomegalovirus glycoprotein B, phosphoprotein 65-2, and viral interleukin-10 in rhesus macaques. *J Virol* 81:1095-109
58. Yue et al. 2003 Antibody responses to rhesus cytomegalovirus glycoprotein B in naturally infected rhesus macaques. *J Gen Virol* 84:3371-9

Example 3

Prime/Boost Vaccination of Rhesus Macaques with Functionally Inactive rhcmvIL-10

Site-directed mutations were introduced into the viral gene for interleukin-10 (rhcmvIL-10) of rhesus cytomegalovirus (RhCMV) using structure-based methods to create two non-functional versions of rhcmvIL-10 that would (a) not bind to the cellular receptor for rhcmvIL-10 (IL-10R), and (b) exhibit no immunosuppressive activity on rhesus lymphoid cells. Four rhesus macaques that were uninfected with RhCMV were genetically immunized at Week 0 with two separate plasmid expression vectors for the two mutated versions of rhcmvIL-10 (M1 and M2) followed by three protein booster immunizations at weeks 6, 12, and 26 using 50 µg of each of purified M1 and M2 adjuvanted in MONTANIDE® ISA 720. Longitudinal blood samples were collected, and the antirhcmvIL-10 antibodies were analyzed for neutralizing antibody (NAb) titers. The vaccinated animals were challenged at week 34 with a subcutaneous (S.C.) inoculation with $1\times10^3$ plaque forming units (PFU) of RhCMV strain UCD59. Four unimmunized macaques that were uninfected with RhCMV were used as controls by inoculating each S.C. with $1\times10^3$ PFU of RhCMV UCD59. Longitudinal plasma, saliva, and urine samples were collected post challenge to evaluate the viral and immune parameters of challenge virus infection.

NAbs to wild-type (i.e., functional) rhcmvIL-10 protein were quantified by the level (percent) of rhcmvIL-10 activity after the addition of plasma from post-vaccinated and post-RhCMV challenged animals. All four of the immunized animals developed NAb to rhcmvIL-10 after the second protein immunization. The titers all declined to background levels by the time of the third protein immunization at week 26. Three of the four animals developed prominent NAb titers that were indistinguishable from the NAb titers observed in macaques naturally infected with RhCMV. The NAb titers detected in the fourth animal following the third and final protein booster immunization were at the lower end of the normative range of NAb titers in RhCMV-infected macaques (FIG. 13).

The three animals with detectable NAb at the time of challenge (week 34) developed memory NAb responses within 2-3 weeks post RhCMV challenge. The remaining animal did not develop detectable increases in rhcmvIL-10 NAb titers post RhCMV inoculation.

DNA was purified from oral swabs and urine to quantify the number of RhCMV genomes per milliliter of body fluid by real-time PCR (Table 5). All four control monkeys became positive for RhCMV DNA in oral swabs by 41 weeks (7 weeks post RhCMV challenge at week 34), and all were positive for RhCMV DNA in urine by week 46. In contrast, only two of the vaccinated animals were positive for RhCMV DNA at single times (week 41 and week 46), whereas the other two vaccinees have remained negative for RhCMV detection in oral swabs. Similarly, only 1 of the vaccinees has been RhCMV DNA-positive at multiple times. All of the other vaccinees have remained negative. To better assess the infectious burden posed by shedding of RhCMV in either saliva or urine, an Area Under the Curve (AUC) was calculated to sum the total RhCMV shed in these two sites of HCMV shedding. The cumulative level of RhCMV shedding has been profoundly and significantly reduced by prior immunization with non-functional versions of rhcmvIL-10.

This study demonstrates that immunization of rhesus macaques with mutated versions of rhcmvIL-10 can (A) stimulate the generation of antibodies that neutralize the functional activity of wild-type rhcmvIL-10, and (B) dramatically alter the course of RhCMV infection, compared to unvaccinated control monkeys. Together, these data show that the immune evasion proteins of HCMV may be especially susceptible to vaccine-mediated inhibition.

Example 4

Targeting the IL-10 Signalling Pathway as a Vaccine Strategy for HCMV

Many evolutionarily disparate pathogens share a commonality of their natural histories: exploitation of the signaling pathways mediated by the high affinity receptor for IL-10 (IL-10R) and subversion of protective immunity. Pathogen strategies involve either the anti-inflammatory properties of the host cellular IL-10 (cIL-10) or a pathogen-encoded IL-10 protein to enable immune privilege, tolerance, and/or immune suppression. HCMV encodes a viral IL-10 (cmvIL-10) that has undergone extensive genetic drift from cIL-10, yet cmvIL-10 exhibits almost identical functional activities as cIL-10 on lymphoid cells. Based on the in vitro properties of cmvIL-10, it is likely that cmvIL-10 modulates host immune responses to both innate and adaptive immune responses to facilitate dissemination of progeny virions and a long-term infected state within an immune host. To test this hypothesis, rhesus macaques, uninfected with rhesus CMV (RhCMV), were immunized using a strategy that effectively blocked engagement of IL-10R by the RhCMV ortholog of cmvIL-10 (rhcmvIL-10). Immunized animals were subsequently challenged with 1,000 PFU of a strain of RhCMV (UCD59) that is noted for (i) recruitment of polymorphonuclear leukocytes to the subcutaneous site of inoculation, and (ii) sustained shedding of high titers of virus in saliva and urine. Immunized/challenged animals demonstrated prominent reductions in both local and systemic levels of challenge virus replication. Vaccinees were characterized by (i) fewer infected cells and fewer infiltrating PMN at the inoculation site, and (ii) large reductions in both the frequency and magnitude of detectable RhCMV in saliva and urine, compared to mock-immunized control monkeys. These data demonstrate that blocking the IL-10 signaling pathway elicits a dramatic level of protective immunity against challenge RhCMV infection, and offer novel vaccine strategies against HCMV.

Example 5

Vaccine-Mediated Targeting of Viral IL-10- to Control HCMV Shedding and Reinfection Immune responses to human cytomegalovirus (HCMV) infection in those with functional immunity present paradoxes with potentially devastating clinical ramifications for those without immune competency. The nearly four-decade quest for a licensed vaccine that confers protective immunity against HCMV has been impeded by multiple factors, including two apparent contradictions about HCMV natural history. (1) HCMV is generally considered to be a virus with low pathogenic potential in immune competent hosts. Yet, the virus is exceedingly efficient at maintaining a lifelong persistence in the presence of those very same immune responses that effectively limit clinical outcomes. Like all herpesviruses, a hallmark of HCMV persistence is the reactivation of latent viral genomes and the production of infectious virions that can be shed in bodily fluids far beyond resolution of primary infection. Horizontal transmission of HCMV represents an infectious threat to those most at-risk for primary HCMV infection, particularly the fetuses borne by mothers without preconceptional immunity to HCMV. An accumulating body of evidence also highlights another ambiguity about HCMV immunity. (2) The robust neutralizing and cytotoxic responses to HCMV antigens generated during primary and long-term infection, which generally protect against viral sequelae, are incompletely protective against reinfection with horizontally transmitted virions. An accumulating body of evidence now exists that women with prior immunity can be subclinically reinfected with antigenically distinct variants of HCMV that can then be vertically transmitted to their fetuses. As with primary infection during pregnancy in non-immune women, reinfection in immune women can also lead to permanent neurological deficits in the congenitally infected individual. Given the recognized clinical needs for an HCMV vaccine, a better understanding of these particular complexities of HCMV-host interactions is imperative for development of such a vaccine. This invention demonstrates that there is a key nexus linking virus-host interactions, persistence, and reinfection that is susceptible to vaccine-mediated intervention.

Specifically, HCMV modulation of host immune responses, especially those that occur at the earliest stage of infection through the functionality of the HCMV-encoded interleukin-10 protein (cmvIL10), enables both the establishment of a state of chronic viral reactivation after primary infection and systemic dissemination of progeny virions beyond mucosal sites of reinfection. The present invention develops the concept that post-exposure augmentation of neutralizing antibody (NAb) responses to cmvIL10 in HCMV-infected individuals will significantly (1) reduce viral shedding in bodily fluids and (2) increase immune-mediated resistance to reinfection with antigenically variant strains of HCMV.

This concept builds upon previous studies assessing the in vitro functionality of cmvIL10 and characterization of the in vivo modulation of host immune responses by the rhesus CMV (RhCMV)-encoded IL-10 protein (rhcmvIL10). Studies are carried out in the rhesus macaque model of HCMV persistence and pathogenesis to separately determine whether vaccine-mediated targeting of rhcmvIL-10 reduces RhCMV shedding in bodily fluids and/or the potential for reinfection in monkeys previously infected with RhCMV. These studies also provide a mechanistic basis for rhcmvIL-10-mediated attenuation of host antiviral immune responses, enabling optimization of vaccine design.

One impetus for developing an HCMV vaccine has been the protection of fetuses from the devastating consequences of intrauterine HCMV. The principle target population of vaccination consists of seronegative women of childbearing age who are at high risk for primary HCMV infection and transplacental transmission of HCMV. Since the rate of congenital infection is ~0.7%, the overwhelming preponderance of primary infections results from horizontal transmission of HCMV in bodily fluids. Accordingly, vaccine-mediated reductions in HCMV shedding would have immense clinical benefits by reducing the frequency by which women without preconceptional immunity acquire primary infections during pregnancy. Recent studies have documented congenital infection in populations with near universal seroprevalence to HCMV at young ages, demonstrating that prior immunity to HCMV does not sufficiently protect against reinfection. While the reasons for this remain to be resolved, augmenting immune responses in these women to prevent reinfection would also greatly reduce the personal and societal costs associated with permanent clinical outcomes resulting from congenital infection. The goal of this invention is to markedly shift the long-term virus-host balance to one which is decidedly in favor of the host by neutralizing the ability of cmvIL10 to attenuate both innate and effector/memory immune responses.

Many evolutionarily disparate, mammalian pathogens share a commonality of their natural histories: exploitation of the signaling pathways mediated by the high affinity receptor for IL-10 (IL-10R) and subversion of protective immunity. Multiple viruses (e.g. CMV (1-3), Lymphocytic Choriomeningitis Virus—LCMV (4-6), Dengue (7,8), HIV (9,10), human papillomavirus (11,12), Hepatitis B and C viruses (13-17)), bacteria (e.g., *M tuberculosis* (18,19), *C. trachomatis* (20), and *L. monocytogenes* (21,22)), protozoa (e.g., *Leishmania* (23,24), *Plasmodium* sp. (25)), and fungi (e.g., *Paracoccidioides brasiliensis* (26,27)) have coopted activation of IL-10R to facilitate the establishment and maintenance of a persistent infection, often in conjunction with pathogenic outcomes in the infected host (28). While strategies may vary between organisms, they involve the anti-inflammatory properties of either the host cellular IL-10 (cIL-10) or a pathogen-encoded IL-10 protein to enable micro environments of immune privilege, tolerance, and/or immune suppression, similar to those observed with some non-infectious disease ontogenies (28-34).

IL-10 is a central immune regulator during CMV infection, involving up-regulation of cIL-10 and/or expression of cmvIL-10. Both HCMV and RhCMV encode a viral ortholog of cIL-10 each of which exhibits extensive genetic drift from the cIL-10 of their host[41,42]. Despite the sequence variation, cmvIL-10 retains the immunosuppressive properties of cIL-10 on multiple cell types in vitro, especially dendritic cells (DC), which link innate and adaptive immunity (2,43-48).

There are compelling clinical needs that support the rationale of post-exposure alteration of the HCMV-host balance. The greatest infectious risk to a fetus, in terms of both the potential for and the severity of congenital infection, occurs in the context of primary HCMV infection in a woman lacking preconceptional immunity. Justifiably, HCMV vaccine efforts have been directed against protecting pregnant women from primary HCMV infection. However, reinfection of seroimmune women with antigenic variants of HCMV also constitutes a significant source of congenital infection and sequelae (49-57). The probability of infection in pregnant women, and by extension the probability of fetal infection, is related to the frequency of mucosal exposure to infectious bodily fluids from an infected individual (56,58-63). HCMV can be excreted in bodily fluids long after resolution of primary infection, increasing the odds of horizontal transmission (64-73). Therapies that reduce the frequency and/or the magnitude of HCMV shedding would correspondingly reduce the risk of transmission to pregnant women irrespective of whether they have or do not have preconceptional immunity to HCMV.

By extension, blocking engagement of IL-10R by cmvIL-10 could also increase resistance to HCMV reinfection. The annual rate of HCMV reinfection (~10%) is close to that of primary infection, despite an extraordinary devotion of the immune repertoire to HCMV antigens. In healthy long-term HCMV carriers, ~10% of memory T cells are HCMV-specific, and NAb are generated against multiple viral glycoproteins (74-79). One explanation for the high rate of reinfection is based on antigenic variation in critical epitopes of the incoming virus compared to the existing immune specificities of the infected host. Given the breadth of HCMV immunity, it doesn't appear that antigenic variation alone can explain HCMV reinfection in an immune host. Rather, it suggests that there is partial immune paralysis of effector/memory functions against conserved epitopes encoded by the reinfecting virus, enabling dissemination of progeny virions beyond the mucosal site of reinfection. Expression of viral IL-10 by the "challenge" virus is consistent with such a scenario, based on the in vitro and in vivo functionalities of cmvIL-10 and rhcmvIL-10 (2,34,43-47,80,81). Boosting the protective efficacy of anti-HCMV immune responses in infected women through targeted augmentation of preexisting immunity would also protect the fetus from congenital infection following reinfection of the mother. The long-stated goal of an HCMV vaccine that protects against primary infection has been inordinately difficult to achieve (82). Evaluating whether reducing the frequency of reinfection or the magnitude of HCMV shedding can prevent congenital infection has remained strictly conjectural. In this invention, a primate host is used to determine whether cmvIL-10 represents an especially vulnerable component of the HCMV proteome that can be targeted by vaccination to reduce the potential for both shedding and reinfection.

This experimental approach in rhesus monkeys takes advantage of an intriguing result of the protracted co-evolutionary relationship between primate CMV and their particular hosts. There has been extensive genetic drift of both cmvIL-10 and rhcmvIL-10 from human and monkey cIL-10, respectively. Herpesviridae, including CMV, are ancient viruses that evolved from a progenitor more the 200M years ago (83). More than half of the open reading frames (ORF) of the HCMV genome can be deleted without impairing replication in fibroblasts (84,85). As might be expected for a virus with ancient origins, a large portion of the HCMV ORF that is dispensable for replication in vitro encodes functions that modulate host innate and adaptive immune responses. These include viral proteins that disrupt antigen presentation and alter cell trafficking, signaling, activation and viability. Following the evolutionary divergence of primates and rodents, a primate CMV progenitor transduced the cIL-10 gene of its progenitor primate host. The viral IL-10 gene is still extant within HCMV, RhCMV, and other monkey CMVs (42), although it was apparently deleted during the evolution of chimp CMV41. As each primate CMV co-speciated with its host, the viral IL-10 genes underwent extreme genetic drift from the cIL-10 gene of their host such that the viral IL-10 proteins share only 25-27% identity with their host's cIL-10 (42). The extent of genetic drift in the viral orthologs is highlighted by the facts that (i) primate cIL-10 proteins share >95% identity, and (ii) the viral IL-10 orthologs are as divergent from each other as they are from the cIL-10 of their host. While sharing only 31% amino acid identity, both cmvIL-10 and rhcmvIL-10 are highly stable in sequence (>98% identity) amongst different strains of HCMV and RhCMV, respectively (86,87). The functionalities of cmvIL-10 are almost identical to those of cIL-10 (2,34,43-47,80,81). There is no evidence that cmvIL-10 has evolved new IL-10R-mediated signaling responses. Inter-specific drift of viral IL-10 proteins was likely driven as a compensatory selection to some aspect of its host's evolution. Since the binding affinity of cmvIL-10/IL-10R has been shown to exceed that of cIL-10/IL-10R (48), maintaining the higher binding affinity to the host IL-10R was probably critical in shaping the particular viral IL-10 sequence. As a result, the original transduced cIL-10 has drifted from what was once a 'self' protein, expressed in the context of viral infection, to one that is now highly recognizable by the host immune system.

Studies employed for this invention demonstrate the following points. (1) Rhesus monkeys either naturally exposed to wild-type RhCMV or experimentally inoculated with different strains of RhCMV develop rhcmvIL-10-binding and NAb responses coincident with development of Ab responses to other viral antigens. (2) While high NAb titers to rhcmvIL-10 are detected in plasma of infected animals, mucosal IgG titers are likely to be insufficient to neutralize rhcmvIL-10 secreted from infected cells in the mucosa and submucosa. (3) Site-directed mutations have been introduced into rhcmvIL-10, and the resultant recombinant proteins exhibit no binding to IL-10R, and no functional activity on rhesus lymphoid cells. (3) NAb titers can be increased >10-100-fold in RhCMV-infected monkeys boosted with mutated rhcmvIL-10 protein. (4) NAb titers can be stimulated in naïve monkeys immunized with non-functional rhcmvIL-10. (5) Naïve monkeys immunized with non-functional rhcmvIL-10 and subsequently challenged with wild-type RhCMV exhibit profoundly reduced parameters of RhCMV infection both at the site of inoculation and sites of virus excretion. (6) There is no evidence that generation of Ab to rhcmvIL-10 stimulates cross-reactive antibodies to rhesus cIL-10. These studies are the first to characterize the immunogenicity of a CMV immune evasion protein, and they demonstrate the feasibility of novel vaccine strategies that specifically target this class of CMV proteins. The present invention also establishes new paradigms for reducing congenital infection by focusing on shedding of virus and increasing immune-mediated resistance to reinfection in infected hosts. The results of these studies are important for other aspects of congenital infection. Maternal reactivation of latent viral genomes is another source of progeny virions that cross the maternal-fetal interface (88). Vaccine-stimulated reductions in shedding in the oral cavity and urogenital tract should be operative at those sites of reactivation that give rise to transplacentally transmitted virus. In addition, if rhcmvIL-10 expression is critical for reinfection of an individual with prior immunity, it is likely irrelevant whether prior immunity is generated from prior infection or prior vaccination. These findings indicate that cmvIL-10 should be included in any HCMV vaccine cocktail to enhance protective efficacy generated by the other antigens within the vaccine.

This invention also takes advantage of understanding RhCMV infection in mixed cohorts of infected and uninfected monkeys. The monkey cohorts recapitulate the challenges facing HCMV vaccine trials in humans, including repeated mucosal exposure to antigenically variant RhCMV strains that lead to highly efficient spread of virus to naïve cohorts and the presence of multiple genetic variants within one infected host (86, 89-91).

Quantification of Changes in RhCMV Shedding in Saliva and Urine in Long-Term, RhCMV-Infected Monkeys Following Immunization with Functionally Inactive Forms of rhcmvIL10

The goal of these studies is to demonstrate that altering the IL-10 signaling pathway in RhCMV-infected monkeys significantly attenuates a hallmark of persistent infection of both RhCMV and HCMV. These studies will show that blocking the engagement of IL-10R by rhcmvIL-10 in healthy, long-term infected animals elicits a biologically relevant reduction in RhCMV shedding in bodily fluids. The experimental design involves the quantification of both the frequency and magnitude of RhCMV shedding (saliva and urine) in RhCMV-infected monkeys during 12 weeks each of baseline observation, immunization with either non-functional versions of rhcmvIL-10 or control antigen, and post-vaccination observation. Key components required for these studies include the following technologies: (i) rigorous interrogation of longitudinal RhCMV shedding; (ii) detection of NAb to rhcmvIL-10; (iii) boosting of NAb to rhcmvIL-10 without inducing cross-reactive NAb to cIL-10; and (iv) quantification of mucosal Ab titers to RhCMV antigens, including rhcmvIL-10.

RhCMV natural history Like HCMV infection in humans, particularly in children, RhCMV is shed in saliva and urine for months to years after primary natural infection or experimental inoculation. The importance of viral shedding in RhCMV natural history is highlighted by the high rate of horizontal RhCMV transmission to naïve cohorts in mixed populations of infected and uninfected animals (FIG. 14). In corral-housed breeding cohorts of ~100 animals ranging in age up to 20 years, almost 100% of newborn animals (N=25) became seropositive for RhCMV IgG Ab within 1 year of age (FIG. 14A) (91). The seroconversion rate showed a doubling of newly seropositive animals every 5-6 weeks. In another study in which 15 1-year old uninfected juveniles were housed with a single RhCMV-infected adult, the number of seropositive animals doubled every 7-8 weeks (FIG. 14B). The primary factors for horizontal spread of RhCMV in these cohorts are the high rate of shedding of RhCMV in saliva and urine and the interactive social structure of rhesus monkeys. A cross-sectional survey of corral-housed, 3-5 year old monkeys (100% RhCMV infected) showed that ~75% of monkeys (N=50) have RhCMV DNA in saliva, indicating that the overwhelming majority of animals still shed RhCMV ≥2-4 years after primary exposure to virus. A prospective analysis of RhCMV shedding, involving quantification of RhCMV DNA in saliva and urine every week for 12 weeks, showed that a hallmark of long-term RhCMV infection is persistent shedding of virus (FIG. 15). Most animals had detectable RhCMV DNA in saliva on at least half of the weekly time points. All animals had detectable RhCMV in urine on at least 3 of the 12 time points. The infectious burden of RhCMV in saliva over 12 weeks, calculated as an Area Under the Curve, ranged from an absence of RhCMV DNA in 5 animals to >$10^3$-$10^6$ genomes in 9 animals.

Together, these results emphasize that the rhesus monkey model is an appropriate surrogate for HCMV infection to assess intervention strategies that focus on interruption of viral shedding as a means to impede horizontal spread of virus in populations of both infected and uninfected animals. HCMV-infected children excreting virus, including in saliva, pose a high risk for horizontal transmission to pregnant women and subsequent congenital infection (61,63,92-102). Importantly, these methods for evaluating longitudinal shedding profiles in infected animals enable the proposed studies to determine whether boosting NAb titers to rhcmvIL-10 reduces long-term shedding.

Immunization of naïve monkeys against RhCMV phosphoprotein 65 (pp65), glycoprotein B (gB), and immediate-early 1 (IE1) elicited significant reductions in oral shedding over 20-weeks of post challenge observation in a subset of vaccinated animals compared to unimmunized controls (FIG. 16)(103). These results indicate that vaccination against relevant RhCMV immunogens, such as pp65, gB, and IE1, can confer a partial level of protective immunity, as measured by reductions in oral excretion of RhCMV. However, expression of rhcmvIL-10 by the challenge virus attenuates the protection conferred by these vaccine antigens. Parallel approaches will be used to analyze this. In separate studies, uninfected monkeys will be immunized with a combination of antigens to determine whether inclusion of rhcmvIL-10 M1/M2 augments protective efficacy generated by the other antigens. This invention addresses an issue with relevance to all HCMV vaccine studies, i.e., whether rhcmvIL-10 must be a component of any HCMV vaccine to abrogate viral-IL-10-mediated modulation of vaccine-stimulated immune responses.

Expression of and Immunization with rhcmvIL-10

In order to immunize monkeys with rhcmvIL-10, the coding sequence was genetically engineered to formulate non-functional versions of the protein, thus avoiding vaccination with the immunosuppressive, wild-type form of the protein. Structure-based methods were used to introduce minimal site-specific mutations within rhcmvIL-10 such that the mutated variants would exhibit the dual phenotype of failure to (1) bind to IL-10R and (2) suppress lymphoid effector functions. Two mutants, M1 and M2, contain two altered amino acids each (M1: positions 38 and 144; M2: positions 142 and 144, based on human IL-10 numbering of amino acids). The goal was to minimize binding to IL-10R while retaining maximum immunogenicity. Two assays were used to demonstrate the absence of wild-type functionality: proliferation of human erythroleukemic TF-1 cells transfected with the human IL-10R1 chain (111); and inhibition of IL-12 production in LPS-activated rhesus lymphoid cells.

Proliferation of TF1 hIL10R1 cells is IL-10-dependent, and only human cIL-10 and wild-type rhcmvIL-10 (WT) induced TF1 proliferation across a broad concentration of cytokine (FIG. 17A). In contrast, the phenotypes of the two mutated versions of rhcmvIL-10 (M1 and M2) were identical to mock-treated cells; there was a complete absence of TF1 proliferation at concentrations ranging from $4 \times 10^{-3}$-750 ng/ml. A second assay was performed to test the ability of M1 and M2 to suppress the production of IL-12 in lipopolysaccharide (LPS)-stimulated rhesus peripheral blood mononuclear cells (PBMC). Whereas rhcmvIL-10 WT potently inhibited IL-12 expression in LPS-treated PBMC, M1 and M2 failed to inhibit IL-12 expression using PBMC from macaques (two animals are shown, FIG. 17B).

Alternate vaccine strategies in monkeys were used to show that rhcmvIL-10 M1 and M2 were immunogenic. In the first, RhCMV-infected monkeys were immunized with M1 and M2 using a combined DNA priming and protein boosting. ELISA shows that 100% of RhCMV infected monkeys increased binding Ab to rhcmvIL-10. A neutralization assay was developed in which IL-12 production was quantified in LPS-activated rhesus PBMC incubated with rhcmvIL-10 WT and plasma from infected monkeys. RhCMV-infected monkeys display a wide range in plasma NAb titers to rhcmvIL-10 (FIG. 18), despite nearly comparable binding Ab titers. rhcmvIL-10 NAb responses were evaluated in 6 RhCMV-infected monkeys that were immunized with plasmid expression vectors for M1 and M2 followed by two boosts with purified recombinant M1 and M2 proteins (FIG. 19). Increases in rhcmvIL-10-binding Ab titers were found in all 6 animals post vaccination, and increases in NAb were observed in 5 of 6 vaccinees. NAb were stimulated in 3 animals from almost undetectable (pre-immunization) to levels that were ≥100-fold higher, and far above the median NAb responses observed in naturally infected monkeys (FIG. 18). Similarly, two animals with high rhcmvIL-10 NAb responses pre-immunization were boosted to higher levels.

Four RhCMV-uninfected rhesus monkeys were also immunized with the heterologous DNA prime (one immunization) and protein boost (three immunizations) and then challenged with RhCMV to determine whether immunization against this sole viral evasion protein could alter the course of RhCMV challenge (FIG. 13A). All four of the animals developed robust rhcmvIL-10 binding Ab. Three of the animals also developed strong NAb responses to rhcmvIL-10, whereas one animal developed transient NAb responses that were just above the level of detection at the time of viral challenge.

The monkeys were challenged with a variant of RhCMV (UCD59; 1,000 PFU) by a subcutaneous (S.C.) route of infection (113). UCD59 is noted for persistent shedding of virus in saliva and urine after a variable lag phase after S.C. inoculation (113). All control animals were uniformly positive for RhCMV DNA in saliva by 6-7 weeks after challenge. Once shedding started, the control animals were positive for RhCMV in saliva 6-9 times each for the 9 time points analyzed (FIG. 13B). In marked contrast, RhCMV DNA has been undetectable in 2 vaccinated monkeys through 20 weeks post challenge. In the other two vaccinees, RhCMV DNA has been detected only 2 and 3 times out of the 9 time points. In addition to a significant reduction in the frequency of shedding in the vaccinated animals, the magnitude of shedding was also significantly reduced (Saliva AUC, FIG. 13C). This study is the first to show that immunization against a viral immune evasion protein can elicit biologically relevant changes in challenge viral infection, particularly in relation to reducing the potential for horizontal transmission of virions in bodily fluids.

An important focus of these studies is on mucosal antibody responses. Tissue titers of rhcmvIL-10 NAb should be the most relevant for immune-mediated control of shedding. Both rhcmvIL-10 and cmvIL-10 are secreted proteins (43, 114), and results from the HCMV proteome indicate that cmvIL-10 is not present in the HCMV virion (115). Saliva IgG will be evaluated to provide a surrogate measure of tissue levels of rhcmvIL-10 NAb either secreted by plasma cells in the submucosa or transudated from plasma. Like IgG responses to HCMV (112), IgG titers to RhCMV in saliva are ~0.13% of those in plasma. Based on the NAb responses in plasma (FIG. 18), there should be little neutralization of rhcmvIL-10 in the submucosa. A key element of these studies is to demonstrate that immunization with rhcmvIL-10 boosts the NAb titers in saliva as a surrogate measure of increased tissue titers.

Animals and Sample Collection

Genetically outbred, RhCMV-seropositive animals (~2 years old) co-housed outdoors at the CNPRC will be used for this study. Blood, urine, and oral swabs will be collected weekly from 20 animals over the course of 36 weeks, which will be divided into three phases. Samples collected during the initial 12-week period of observation (weeks 1-12) will determine baselines of immune and viral parameters of RhCMV infection (Table 6), according to known protocols (103,113,116). Beginning at week 12, one-half of the animals will be immunized with a mixture of the recombinant rhcmvIL-10 M1 and M2 proteins. The remaining animals will be immunized with a non-specific protein (influenza) to control for any changes in shedding related to non-specific immune effects. The basis for assignment to both treatment groups is described below. Animals will be boosted at weeks 18 and 24, during which blood, urine, and oral swabs will be collected weekly. Samples will be collected weekly during a final phase (weeks 25-36) to determine if there are permanent changes in shedding. Blood will be processed for PBMC and plasma, the latter of which will be used for DNA and immune assays. Saliva will be processed for both real-time PCR and immune assays. The specific assays that will be performed with the different fluid samples are listed in Table 6. The number proposed for each study group (N=10) is based on rhcmvIL-10 immunization studies in both immune and naïve monkeys (FIGS. 19 and 13A). Out of a total of 10 immunized animals, 2 (20%) did not develop increased NAb responses, although both developed increased binding Ab titers. An initial group size of 10 animals includes the potential for ~2 (20%) not to develop increased NAb titers post immunization. This would leave a total of 8 animals that are expected to be responsive, which is the minimum number required to enable statistically significant and scientifically relevant differences between the different treatment groups. Based on a 1-tailed power analysis of the total infectious burden in saliva over 21 weeks in a previous study (103), group sizes of N=8 provide an 88% power to detect a 1-log difference between groups (alpha=5%) for the cumulative shedding of virus following immunization.

Assignment of Animals to Treatment Groups

Animals will be assigned to either treatment group at week 12 based on a hierarchical stratification of results collected during weeks 1-12. The overall goal is to equalize distribution of animals to each group based on anti-rhcmvIL-10 and anti-RhCMV immune responses. The primary basis for assigning animals to either group will be predicated on rhcmvIL-10 NAb responses in saliva. Based on the analysis of plasma NAb to rhcmvIL-10 (FIG. 18), it is anticipated that there will be a similar distribution of NAb responses in saliva. Animals will be assigned to the groups so that there is an equal distribution of NAb responses in both groups. The NAb responses in saliva will be ranked by calculating the cumulative NAb during weeks 1-12 using an Area Under the Curve (AUC) approach similar to that used to determine vaccine-mediated reductions in shedding following primary RhCMV challenge (103) (FIG. 16). Each animal at the CNPRC is routinely typed by microsatellite mapping for parentage and MHC class I haplotype (Mamu A*01, B*01, and B*17). The distribution of animals to either group will also include a goal of equalizing genetic diversity between both groups. If rhcmvIL-10 NAb are undetectable in saliva, plasma NAb to rhcmvIL-10 will be used as a basis for assignment. Following distribution based on rhcmvIL-10 NAb, a secondary criterion will be applied, if necessary, using neutralizing titers to RhCMV infectivity.

Immunization rhcmvIL-10 M1, M2, and WT will be expressed in *Drosophila* Schneider S2 cells and purified by affinity chromatography using agarose beads coupled with the human IL-10R1 chain, according to known protocols (48). Proteins will be confirmed for purity (western blot) and the absence of endotoxin. Animals will be immunized by an intramuscular (IM) route with 200 µg of rhcmvIL-10 M1 and M2 (100 µg each) in MONTANIDE® ISA 720 (117,118), according to known protocols (103,116). Control animals will be immunized with the current high-dose FLUZONE® vaccine (0.5 ml/180 µg of influenza A and B antigens; IM in adjuvant) (Sanofi Pasteur). DNA immunization (FIGS. 19 and 13A) will not be used for this proposal.

Antiviral Immune Responses

Multiple assays will be used to characterize immune responses during the three phases of this study. ELISA will be used to quantify the titer and avidity of anti-rhcmvIL-10 binding Ab using rhcmvIL-10 WT as antigen (2,103,116,119-122). Control monkeys plasma will be evaluated by ELISA for influenza-specific Ab responses using influenza proteins as antigen, and whole egg proteins as negative controls. Since rhcmvIL-10 is likely not incorporated into the virion envelope, IgA Ab to rhcmvIL-10 should not protect against infection. The primary focus will be on IgG, although IgA responses will be interrogated, as needed. NAb to rhcmvIL-10 will be quantified. Diluted saliva and plasma samples will be incubated in the presence or absence of rhcmvIL-10 WT for 3 hours, and then incubated (in duplicate) with rhesus PBMC. LPS (*E. coli* 0127:B8; Sigma) will then added to the cells (5 µg/mL) for 24 hours. The supernatant will be assayed for IL-12 by ELISA (U-Cytech). Neutralization is calculated as the inverse of the ratio of (IL-12 concentration+rhcmvIL-10+plasma)/(IL-12 concentration+plasma only) and is expressed as the "percent IL-12 induction restored." Humoral responses will be prospectively assayed for each weekly sample. NAb titers will be stratified by calculating the AUC for weeks 1-12, 12-24, and 25-36 according to known protocols (103). Briefly, the AUC between two successive time points is calculated as the area of the trapezoid formed by the NAb at those two time points, and the sum of individual AUC values represents the cumulative NAb for that animal during a particular phase of the study.

Cellular responses to RhCMV will be assayed using inactivated RhCMV virions as antigen and cryopreserved PBMC, as described (103,116). Cellular responses to rhcmvIL-10 will be similarly measured using a mixture of rhcmvIL-10 M1 and M2 as antigens.

Real-Time PCR

DNA will be purified from plasma, saliva, and urine, and quantified for RhCMV genome copy numbers by real-time PCR (2,103,113,116,120-123). Based on seroepidemiological studies, the age of the animals for this study (~2 years) is consistent with the animals having been infected with RhCMV for 1-1.5 years. It is estimated that >90% of the animals will still be persistently shedding RhCMV in saliva and urine. Animals will be confirmed to be shedding RhCMV at three consecutive time points prior to the study. The shedding profile of each animal, determined by AUC (103), will be stratified by the frequency and magnitude of RhCMV detection during the three 12-week phases of the study.

Outcome Criteria and Statistical Analysis

There are multiple outcome criteria that will be evaluated as part of this study (Table 7). Five important aspects of RhCMV natural history will be characterized during the pre-vaccination phase (weeks 1-12) to determine whether there are correlates between shedding and any anti-RhCMV immune responses in naturally infected animals (#1-5, Table 7). Shedding will include both the frequency and magnitude of RhCMV (AUC). Immune parameters that will be analyzed include peripheral responses (NAb and CMI) to both rhcmvIL-10 and RhCMV antigens, and saliva NAb titers to rhcmvIL-10. Another important aspect of this study will be to determine if saliva NAb titers to rhcmvIL-10 are reflective of those in plasma, or whether IgG responses detected in saliva are independent of those in plasma. This has implications for optimization of vaccine-mediated mucosal immunity to RhCMV as a model for similar approaches in human studies. Immune and viral parameters will be compared during the three phases of the study to determine if rhcmvIL-10 immunization leads to biologically relevant decreases in shedding, and if changes in RhCMV viral loads correlate with increased NAb and/or CMI responses. Statistical analyses using appropriate primary and post hoc tests will be similar to those used in studies evaluating vaccine-related changes in viral parameters after RhCMV challenge (103).

These studies will allow a determination of whether RhCMV shedding in bodily fluids of infected animals can be reduced by post-exposure boosting of rhcmvIL-10-specific immune responses. This approach serves as a surrogate measure of changes of viral persistence in the host and horizontal spread in the population. The focus is on rhcmvIL-10 NAb, but this approach also enables correlative analysis of whether peripheral CMI also contributes to reductions in shedding.

Based on preliminary data (FIGS. 4-7), these analyses allow for the translation of mouse studies to a primate host that strongly reflects the human condition. It is important to emphasize that the studies in mice focused on T cell effector functions in specific tissues related to sites of MCMV persistence, such as the salivary gland. Similarly, the present studies are focused on the role of rhcmvIL-10 in facilitating persistence in two sites especially relevant for RhCMV shedding, the salivary glands and the genitourinary tract. Peripheral responses to RhCMV and HCMV are noted for vigorous NAb and T cells responses, consistent with an absence of RhCMV and HCMV viremia in long-term infected hosts. This model is built upon the scenario that all CMV manipulate the microenvironments in those tissues critical for release of progeny virions to facilitate spread to susceptible secondary hosts. These studies take into consideration a key element of the studies in LCMV-infected mice: clearance of infected cells through either therapeutic manipulation of IL-10/IL-10R signaling or by "continuous instruction from the antigenic environment" may have a temporal association. The longer the mice had been infected, the less restoration of a functional status to effector cells (36). However, the authors of one LCMV study conclude that, "components of CD4+ and CD8+ T cell function remain intact and can be restored throughout persistent infection" (36). This study is designed to look at a relatively early stage of RhCMV infection prior to the accumulation of a subset of terminally differentiated CD8$^+$ T cells. In a large study of 100% RhCMV-infected juvenile (N=50) and aging adult (N=100) monkeys, it was found that there is a very prominent increase in CD8$^{pos}$/CD28$^{neg}$/CD45RA$^{pos}$ T cells (FIG. 20), a phenotype indicative of effector cells. The age-related change in this cell population, and other T cell sub-populations, is likely a combination of an age-related expansion of effector T cells and the decline in naïve T cells (CD28$^{pos}$) during aging. The results (FIG. 20) suggest that there could be differential responses to rhcmvIL-10 immunization in young versus older macaques, based on differences in the frequencies of T cell subsets.

Comparison of RhCMV Reinfection in RhCMV-Immune Monkeys that Differ in the Magnitude of their NAb Titers to rhcmvIL10

The number of annual congenital HCMV infections in a population is directly related to the frequency of maternal HCMV infection prior to conception (63,124). Thus, while the rate of transplacental transmission is higher during maternal primary infection than the frequency of congenital infections in women with preconceptional immunity, the latter gives rise to a greater number of congenital infections (57, 125). The demonstration that 10% of seropositive women who give birth to a congenitally infected infant acquired new antigenic reactivity to HCMV antigens between pregnancies is indisputable evidence that prior immunity is incompletely protective against reinfection with antigenic HCMV variants (54). While such cases of congenital infections in seropositive women were once ascribed to cases of maternal reactivation, evidence of new antigenic specificities is most compatible with de novo exposure to and transplacental transmission of a non-endemic virus. Assuming that such congenital infections resulted from maternal reactivation of a minor antigenic variant already resident within the mother, the fact that congenital infection still occurred indicates the spread of a variant within a mother possessing broad antiviral immunity from the site(s) of reactivation to the maternal-fetal interface. Irrespective of whether congenital infections in immune women result from reinfection and/or reactivation, the central question remains the same. How can HCMV spread systemically within an individual who has broad and robust specificities to neutralizing and cellular immunogens? Undoubtedly, HCMV has evolved redundant, overlapping, and independent functionalities within its proteome to enable its highly efficient spread to both nave and immune hosts. During reinfection, resident effector T cells, which are enriched at mucosal surfaces, should rapidly respond to viral antigens and clear virally infected cells. However, accumulating evidence demonstrates that there is a conspiracy of viral proteins that subjugates CD4$^+$ and CD8$^+$ effector/memory T cells and resident dendritic cells (DC).

Studies of both HCMV and MCMV demonstrate that signaling through IL-10R via either cmvIL-10 or murine cIL-10, respectively, disrupts CD4$^+$ recognition of infected cells (HCMV) and CD4$^+$ effector T cell differentiation (MCMV) (3,126). A study using a recombinant RhCMV deleted of viral genes coding for proteins that disrupt MHC class I antigen presentation showed that, whereas these proteins were dispensable for establishing a primary infection, they were essential for reinfection of an immune host(127). cmvIL-10 immune suppression of resident DC should inhibit activation of HCMV-specific memory T cells (43). In short, HCMV has evolved the capacity to attenuate almost the entire innate and adaptive immune repertoire, which would account for HCMV's high efficiency at spreading through immune and non-immune populations. These studies examine the contributions of rhcmvIL-10 to the ability of RhCMV to reinfect an immune host by analyzing the efficiency of reinfection in hosts that differ in their NAb titers to rhcmvIL-10. Using antigenically tagged variants of RhCMV, RhCMV-infected monkeys can be inoculated S.C. with as little as 100 PFU and develop T cell responses to the SIV antigens expressed in the context of RhCMV expression (127). These studies measured development of de novo immune responses to successive inoculations with different RhCMV variants expressing different SIV antigens and showed that recombinant viruses could be detected in the urine of the super-infected animals. These studies were based on an RhCMV strain (68-1), which does not encode the complex of viral proteins essential for epithelial tropism (UL128/UL130/UL131A), and three alpha chemokine-like open reading frames (ORF) (128). RhCMV 68-1 does express rhcmvIL-10. The UL128 complex and/or the α-chemokine-like ORF are essential for high levels of persistent shedding in inoculated animals (113). The presence of RhCMV 68-1 DNA in bodily fluids is profoundly attenuated compared to wild-type-like strains of RhCMV (UCD59).

RhCMV-uninfected monkeys will be inoculated (400 PFU) with a variant of RhCMV 68-1 in which the rhcmvIL-10 gene (UL111A) has been deleted (RhCMVΔUL111A) (114). Inoculation of naïve monkeys with this low titer of RhCMVΔUL111A results in 100% infection as measured by generation of persistent antiviral immune responses. Like the parental RhCMV 68-1, RhCMVΔUL111A exhibits severely attenuated shedding. The animals inoculated with RhCMVΔUL111A will be stratified by NAb titers to RhCMV at 12 weeks post inoculation to generate two groups with comparable ranges in RhCMV NAb titers. One-half of the animals will be immunized with rhcmvIL-10 M1/M2 at 12, 18, and 24 weeks, and the other half of the animals will be immunized with control protein. Animals will then be inoculated orally (PO) with the minimal titer of RhCMV UCD59 that results in 100% shedding after reinfection in RhCMVΔUL111A-inoculated animals (described below). The oral route of challenge with RhCMV UCD59 will be used since it best reflects the trans-mucosal mode of acquisition of horizontally transmitted HCMV by pregnant women. Uninfected monkeys can be infected orally with RhCMV 68-1 (119). The frequency and magnitude of shedding will be compared with animals immunized with control protein to determine if immunization against rhcmvIL-10 confers increased resistance to reinfection.

Animals and rhcmvIL-10 Immunization

Twenty macaques (~1 year old) repeatedly confirmed to be seronegative for RhCMV infection will be used for this study (Years 4 and 5). Animals will be inoculated with RhCMV ΔUL111A (400 PFU, subcutaneous) (114). Blood, saliva, and urine will be prospectively analyzed through 26 weeks post inoculation. Animals will be stratified for RhCMV NAb at week 10 so that there is an equal distribution to the vaccine (rhcmvIL-10) and control (influenza) groups. One-half of the animals will be immunized at week 12 with rhcmvIL-10 M1/M2, as described in Aim 1, and boosted at weeks 18 and 24. The other animals will be immunized against influenza antigens, as described in Aim 1.

RhCMV UCD59 Reinfection

Animals will be challenged PO at week 26 with RhCMV UCD59. The titer of virus will be determined by a study in which animals inoculated first with RhCMVΔUL111A are reinfected with serial 10-fold increases in titer of UCD59. Briefly, seronegative macaques (N=12) will be inoculated with ΔUL111A as described above. Beginning at week 18 when antiviral immune responses have mostly stabilized, groups of animals will then be inoculated PO with UCD59 at titers ranging from $10^3$-$10^6$ (N=3 per 10-fold increase in titer) (119). Animals will be prospectively evaluated for shedding of UCD59 in saliva and urine. Based on the previous study, only UCD59 should be detected in bodily fluids by PCR-based assays, which will be confirmed by differential PCR (113). The minimum titer that results in 100% shedding will be used to reinfect the animals immunized against rhcmvIL-10 or influenza. Samples will be collected, and the immunologic and virologic parameters of UCD59 reinfection will be analyzed as described herein. The primary criterion that will be evaluated is whether prior immunization with rhcmvIL-10 M1/M2 stimulates a biologically relevant reduction in UCD59 shedding, although the contributions of independent variables will be statistically analyzed.

A central tenet of this approach is that immunizing against rhcmvIL-10 will boost NAb in the mucosa and submucosa to achieve the maximum protective efficacy against challenge virus reinfection. Uninfected animals immunized against rhcmvIL-10 M1/M2 (FIG. 13) were positive for rhcmvIL-10 IgG in the saliva on the day of challenge, demonstrating that systemic immunization achieves a measure of protective immunity at the mucosal surface. In addition, a biopsy of one of the sites of S.C. challenge inoculation showed demonstrable differences from the biopsies from control animals. Whereas inoculation of naïve animals with UCD59 stimulates a mixed lymphocytic infiltrate consisting of mononuclear cells and neutrophils at 7 days post inoculation, the biopsies from immunized animals were notable for a reduction in neutrophils and a predominance of mononuclear cells. The interpretation is immunization stimulated effector immune responses that could be rapidly localized to the site of viral antigens, leading to significant reductions in shedding in saliva (FIG. 13). Based on these results following S.C. inoculation, it is highly probable that effector cells will similarly home to the oral mucosa following oral challenge with RhCMV.

Characterization of rhcmvIL-10-Induced Alterations to Host Anti-RhCMV Immunity

Immunization of naive macaques with rhcmvIL-10 M1/M2 (i) stimulates antibodies that neutralize rhcmvIL-10 WT functionality, and (ii) decreases the frequency of detection and level of replication of RhCMV in animals challenged with RhCMV (FIG. 13). These findings imply that antibodies against rhcmvIL-10 alone sufficiently alter the host response to RhCMV during primary infection resulting in greater control of challenge virus replication and spread within the host. There are non-exclusive corollaries to this postulate with important clinical ramifications for preventative and therapeutic vaccines. One corollary is that, in the vaccine-mediated absence of functional rhcmvIL-10, there is greater potential to develop de novo antiviral host responses to other viral antigens following primary challenge that will more efficiently limit virus excretion. The basis for this derives from a study comparing antiviral immune responses in unimmunized animals inoculated with either RhCMV 68-1 (expressing rhcmvIL-10) or with a variant in which the rhcmvIL-10 gene (UL111A) has been deleted (ΔUL111A) (114). Monkeys inoculated with ΔUL111A develop higher IgG titers to RhCMV antigens, greater antibody avidity, and enhanced T cell responses than those inoculated with the 68-1 parent (not shown). A second corollary is that rhcmvIL-10 immunization in persistently infected animals may augment the breadth and magnitude of existing immune specificities. Studies of LCMV infection in mice show that, "dysfunctional T cells can be functionally reactivated during persistent infection" (36). In addition, there is a notable skewing of cellular immune responses to HCMV antigens, implying that generation of responses to additional antigens is possible. HCMV-specific T cells are directed primarily to viral structural, tegument, and immediate-early proteins with almost no reactivity to the proteins involved in DNA metabolism and replication (74). If cmvIL-10 immunization, either in the context of preventing primary infection or modifying an existing infection, increases protective immunity to other viral antigens, relevant outcomes should include the limitation of both horizontal spread to cohorts and vertical spread to the fetus.

These studies are directed to defining differential changes in kinetics, magnitude, and specificity of antibody responses to other RhCMV antigens that modify the pattern of viral replication in immunized monkeys. Specific issues include quantification of (i) virus NAb plasma and saliva, (ii) the frequency of antiviral Ab-secreting plasmablasts; and characterization of (iii) the specific reactivity of anti-envelope Ab, and (iv) affinity maturation of RhCMV-specific antibodies. cmvIL-10, like cIL-10, is functionally pleiotropic towards multiple cell types bearing IL-10R, including T cells. Abrogation of rhcmvIL-10 engagement of IL-10R by immunization could have important effects on T cell function and regulation. Cellular immune responses will be analyzed in the different treatment groups to determine if there are changes in the specificity and magnitude of RhCMV-specific responses. In addition, changes in regulatory T cells (Treg) will be characterized since these cells are critical for maintaining a homeostatic balance between inflammation and T cell effector function, potentially "impairing pathogen clearance" (129). Studies have shown that exposure of monocyte-derived DC to IL-10 and TGF-β generates a tolerogenic phenotype in these cells which in turn induces a state of anergy in antigen-specific T cells and development of a regulatory T cell phenotype (130). HCMV infection of epithelial cells has been shown to stimulate expression of TGF-β1 (131), suggesting a synergistic basis by which cmvIL-10 and TGF-β1 could induce dysfunctional T cells. The dramatic reduction in viral shedding following rhcmvIL-10 immunization and RhCMV challenge (FIG. 13) demonstrates that this is a viable vaccine strategy. However, the absence of increased rhcmvIL-10 NAb titers in 20% of immunized animals indicates that further optimization of the rhcmvIL-10 immunogen is warranted. Towards that end, the epitope specificity of rhcmvIL-10 Nab will be defined to optimize antigen design. The outcomes have broad clinical potential in maximizing the utility of appropriate immunogens to stimulate NAb against different HCMV strains, and also in exploring the use of engineered monoclonal antibodies (MAb) as clinical therapeutics for congenital infections and transplant recipients.

Quantification of NAb Responses to RhCMV

Virus NAb titers will be titered in the different treatment groups by microneutralization for the 50% reduction in input virus infectivity in both rhesus fibroblasts and epithelial cells using RhCMV strains 68-1/EGFP and UCD59, respectively (113,123). The temporal kinetics of de novo NAb responses following primary RhCMV challenge in naive animals either immunized with rhcmvIL-10 M1/M2 or controls (FIG. 13) will also be analyzed. Plasma NAb are postulated to limit systemic RhCMV dissemination (103). Antiviral Ab present in mucosal fluids, such as saliva, are thought to limit local viral replication by limiting spread in the mucosa and submucosa and secondarily limiting excretion of virus in saliva. Mucosal Ab are derived primarily by transudation of serum IgG, although evidence consistent with local IgG synthesis in the oral cavity has been presented (133,134). Plasma NAb titers will likely reflect those in saliva, although salivary NAb will be quantified in the different treatment groups.

Quantification of Plasma Blast Responses

To further quantify the modulation of the antibody response to RhCMV in rhcmvIL-10 immunized animals, the frequency of RhCMV plasmablasts in different treatment groups will be determined using a modified ELISPOT assay. Briefly, wells of a 96-well plate are coated with anti-rhesus IgG or purified RhCMV, to quantify total IgG and RhCMV-specific IgG, respectively, similar to that described by Wrammert, et al (135). IgG-secreting and RhCMV-secreting cells will be detected with biotinylated anti-rhesus IgG followed by avidin-AEC and quantified as the number of antibody secreting cells per $10^6$ PBMC. Quantification of plasmablasts will be coordinated with the cellular assays measuring T cell responses.

Characterization of Specific Reactivity of Anti-Envelope Ab

Based on studies in HCMV, MCMV, guinea pig CMV, and RhCMV, virus NAb are directed at viral envelope proteins (75,79,136-144). The reactivity of RhCMV antibodies against known RhCMV envelope proteins including gB, gH, gL, and the UL128/131a/130 complex will be determined. These assays will take advantage of modified vaccinia Ankara (MVA) constructs individually expressing these ORF. BHK cells infected with antigen-expressing or control MVA will be used as source of antigen for use in binding assays of antibodies in plasma from the different treatment groups, similar to studies of HCMV Ab reactivity (139). In addition, the possibility that immunization with rhcmvIL-10 leads to an increased breadth of Ab responses, including those to envelope proteins that may be unrecognized targets of antiviral Ab, will be investigated. Two sources of labeled RhCMV envelope derived from gradient purified virions will be used. The initial approach will utilize biotinylated envelope proteins, precipitation with avidin beads, followed by SDS-PAGE and immunoblotting with rhesus serum. Alternatively, $^{125}$I-labeled RhCMV virions will be immune precipitated with IgG antibodies in plasma and resolved by SDS-PAGE (141,145). In either approach, proteins will be identified by molecular weight. If new antibody reactivities are defined to proteins other than known envelope proteins utilized in the binding assays described above, proteins will be isolated from SDS-PAGE gels, or appropriate membranes, and analyzed by mass spectroscopy.

Determination of Affinity Maturation of RhCMV Specific Ab

In initial studies, gradient purified RhCMV virions will be used in a solid phase binding assay to determine the affinity maturation of IgG anti-envelope antibodies in rhcmvIL-10 immunized and control animals using methodologies similar to studies in HCMV (146). This assay will determine if rhcmvIL-10 immunized animals accelerate development of high affinity antibodies, compared to control animals. The affinity of salivary IgG antibodies present in rhcmvIL-10 immunized and control animals will also be assayed (FIG. 20). Finally, a modification of this assay will be used to investigate the affinity maturation of plasma antibodies reactive with selected individual envelope proteins (146). The results of this series of experiments will allow for the identification of differences in affinity maturation in anti-envelope antibodies generated by rhcmvIL-10 immunized and control animals Alterations in CMI Cellular immune responses to rhcmvIL-10 and RhCMV antigens will be examined in PBMC of animals in the different treatment groups (FIG. 13) by multiparameter intracellular cytokine staining (ICS) (103,116). Phenotypic and functional analyses will determine the frequencies of naïve ($CD28^+CD45RA^+$), central ($CD28^+CCR7^+$), transitional effector ($CD28^+CCR7^-$), and effector memory ($CD28^-CCR7^-$) T cells (CD4 and CD8), and their ability to produce cytokines (IFN-γ, TNF-α, and IL-2) and the degranulation marker CD107a upon antigen stimulation. RhCMV antigens for ICS assays will include RhCMV lysate, rhcmvIL-10 M1/M2, and overlapping peptide pools for the RhCMV pp65-2 and pp28 proteins. While pp65 is immunogenic in RhCMV-infected monkeys (147), reactivity to pp28 is minimally immunogenic. Thus, pp28 will serve as a marker for de novo acquisition of immune reactivity in the absence of functional rhcmvIL-10. Relative Treg frequencies in peripheral blood will be assayed by flow cytometry using $CD\ 127^{Low}$ $CD25^{Hi}$ and intracellular Foxp3 as markers Immune activation will be assayed for the frequencies of CD4 and CD8 T cells expressing CCR5, CXCR3, CD69, and Ki67. All studies will use MAb that cross-react with rhesus epitopes (NIH Nonhuman Primate Reagent Resource).

Identification of Neutralizing Epitopes in rhcmvIL-10

The generation of macaque MAb to rhcmvIL-10 will follow procedures established for other antigens, including HCMV, SIV, and influenza (135,148-151). Plasmablasts will be sorted from live cells by gating initially on $CD19^+/CD20^{lo/-}/CD3^-$, followed by gating on $IgG^+/CD38^{high}/CD27^{high}$. Single cells are sorted into each well of a 96-well plate for RNA isolation. PBMC from a subset of the different treatment groups and immunized animals (FIG. 13) will be used, based primarily on the magnitude of rhcmvIL-10 NAb. Immunized animals that developed binding but not NAb responses to rhcmvIL-10 will also be included. RNA will be isolated from each well and used for reverse transcription-PCR to amplify the genes for the Heavy (H) and Light (L) (κ and λ) chain variable regions using rhesus-specific primer pairs described by Kuwata et al. (149). VDJ (H) and VJ (L) amplicons will be verified by sequencing, and appropriate clones will be re-amplified with primers containing restriction sites for cloning into expression vectors containing the constant regions for human IgG1, Igκ, and Igλ (152). HEK293 cells will be transfected with both H and L chain vectors. The recombinant Ab in the transfected cell supernatants will be purified by protein A sepharose and analyzed for reactivity to rhcmvIL-10, and RhCMV antigens, by ELISA.

To optimize immunogen design, the characteristics of an effective and ineffective immune response to current rhcmvIL-10 antigens must be defined at the molecular level. Approximately 25 Abs, each obtained from animals exhibiting high NAb titers (immunized and naturally infected) versus those producing Abs that bind rhcmvIL-10, but do not neutralize bioactivity will be characterized. Sequence analysis will provide an initial estimation of the diversity of Abs generated during immunization and infection. The H and L chains of the Abs will be co-expressed in a single dual promoter expression vector in HEK293 cells to increase Ab yields for biophysical characterization. The affinity of the Abs for rhcmvIL10 will be determined using surface plasmon resonance (SPR). Ab affinity for rhcmvIL-10 is expected to be related to the effectiveness of the immune response. Second, the Ab binding epitopes will be mapped using SPR. These experiments will allow the Abs to be grouped into classes that recognize similar regions of rhcmvIL-10. The function of each Ab will then be characterized in an in vitro rhcmvIL-10 neutralization assay. Finally, the detailed contacts of the groups of epitopes will be determined by X-ray crystallography. This will be accomplished by preparing Fabs of each Ab and crystallizing them with rhcmvIL-10 as previously performed with cmvIL-10 (48). Understanding these contacts, along with the other parameters outlined above, will allow a determination of what specific epitopes are most effective in neutralizing rhcmvIL-10. These data will enable rational optimization of rhcmvIL-10 mutant immunogens to stimulate higher titers of NAb to rhcmvIL-10.

Isolation of rhcmvIL-10-specific MAb is dependent on the presence of sufficient number of circulating plasmablasts to facilitate efficient isolation of specific H and L chain clones[150]. B cells will be isolated at peak times of the vaccine-mediated Ab response to maximize the potential for isolating rhcmvIL-10-specific clones. If necessary, immortalization of B cells with EBV will be used (153), if rhcmvIL-10-specific clones are not readily isolated by the proposed methodology. The overall approach of these studies enables novel insights into HCMV's modulation of host immune responses and a rationale basis for a broad expansion of current HCMV vaccine target populations.

REFERENCES FOR EXAMPLE 5

1. Campbell, A. E., Cavanaugh, V. J. & Slater, J. S. The salivary glands as a privileged site of cytomegalovirus immune evasion and persistence. Med Microbiol Immunol 197, 205-213 (2008).
2. Chang, W. & Barry, P. Attenuation of innate immunity by cytomegalovirus IL-10 establishes a long-term deficit of adaptive antiviral immunity. Proceedings of the National Academy of Sciences (USA) in press (2011).
3. Humphreys, I. R., de Trez, C., Kinkade, A., Benedict, C. A., Croft, M. & Ware, C. F. Cytomegalovirus exploits IL-10-mediated immune regulation in the salivary glands. The Journal of experimental medicine 204, 1217-1225 (2007).
4. Brooks, D. G., Trifilo, M. J., Edelmann, K. H., Teyton, L., McGavern, D. B. & Oldstone, M. B. Interleukin-10 determines viral clearance or persistence in vivo. Nature medicine 12, 1301-1309 (2006).
5. Brooks, D. G., Walsh, K. B., Elsaesser, H. & Oldstone, M. B. IL-10 directly suppresses CD4 but not CD8 T cell effector and memory responses following acute viral infection. Proceedings of the National Academy of Sciences of the United States of America 107, 3018-3023 (2010).
6. Brooks, D. G., Lee, A. M., Elsaesser, H., McGavern, D. B. & Oldstone, M. B. IL-10 blockade facilitates DNA vaccine-induced T cell responses and enhances clearance of persistent virus infection. The Journal of experimental medicine 205, 533-541 (2008).
7. Sierra, B., Perez, A. B., Vogt, K., Garcia, G., Schmolke, K., Aguirre, E., Alvarez, M., Kern, F., Kouri, G., Volk, H. D. & Guzman, M. G. Secondary heterologous dengue infection risk: Disequilibrium between immune regulation and inflammation? Cell Immunol 262, 134-140 (2010).
8. Ubol, S., Phuklia, W., Kalayanarooj, S. & Modhiran, N. Mechanisms of immune evasion induced by a complex of dengue virus and preexisting enhancing antibodies. J. Infect. Dis. 201, 923-935 (2010).
9. Alter, G., Kavanagh, D., Rihn, S., Luteijn, R., Brooks, D., Oldstone, M., van Lunzen, J. & Altfeld, M. IL-10 induces aberrant deletion of dendritic cells by natural killer cells in the context of HIV infection. The Journal of clinical investigation 120, 1905-1913 (2010).

10. Song, W., Li, Y., Wilson, C. & Tang, J. Identification of Three Immunologic Correlates for HIV Type 1 Pathogenesis in Youth. AIDS research and human retroviruses in press (2010).
11. Bolpetti, A., Silva, J. S., Villa, L. L. & Lepique, A. P. Interleukin-10 production by tumor infiltrating macrophages plays a role in Human Papillomavirus 16 tumor growth. BMC Immunol 11, 27 (2010).
12. Welters, M. J., Kenter, G. G., de Vos van Steenwijk, P. J., Lowik, M. J., Berends-van der Meer, D. M., Essahsah, F., Stynenbosch, L. F., Vloon, A. P., Ramwadhdoebe, T. H., Piersma, S. J., van der Hulst, J. M., Valentijn, A. R., Fathers, L. M., Drijfhout, J. W., Franken, K. L., Oostendorp, J., Fleuren, G. J., Melief, C. J. & van der Burg, S. H. Success or failure of vaccination for HPV 16-positive vulvar lesions correlates with kinetics and phenotype of induced T-cell responses. Proceedings of the National Academy of Sciences of the United States of America 107, 11895-11899.
13. Barboza, L., Salmen, S., Peterson, D. L., Montes, H., Colmenares, M., Hernandez, M., Berrueta-Carrillo, L. E. & Berrueta, L. Altered T cell costimulation during chronic hepatitis B infection. Cell Immunol 257, 61-68 (2009).
14. Flynn, J. K., Dore, G. J., Hellard, M., Yeung, B., Rawlinson, W. D., White, P. A., Kaldor, J. M., Lloyd, A. R. & Ffrench, R. A. Early IL-10 predominant responses are associated with progression to chronic hepatitis C virus infection in injecting drug users. J Viral Hepat in press (2010).
15. Kaplan, D. E., Ikeda, F., Li, Y., Nakamoto, N., Ganesan, S., Valiga, M. E., Nunes, F. A., Rajender Reddy, K. & Chang, K. M. Peripheral virus-specific T-cell interleukin-10 responses develop early in acute hepatitis C infection and become dominant in chronic hepatitis. J Hepatol 48, 903-913 (2008).
16. Langhans, B., Braunschweiger, I., Arndt, S., Schulte, W., Satoguina, J., Layland, L. E., Vidovic, N., Hoerauf, A., Oldenburg, J., Sauerbruch, T. & Spengler, U. Core-specific adaptive regulatory T-cells in different outcomes of hepatitis C. Clin Sci (Lond) 119, 97-109 (2010).
17. Li, J., Wu, W., Peng, G., Chen, F., Bai, M., Zheng, M. & Chen, Z. HBcAg induces interleukin-10 production, inhibiting HBcAg-specific Th17 responses in chronic hepatitis B patients. Immunol Cell Biol in press (2010).
18. de la Barrera, S., Aleman, M., Musella, R., Schierloh, P., Pasquinelli, V., Garcia, V., Abbate, E. & Sasiain Mdel, C. IL-10 down-regulates costimulatory molecules on *Mycobacterium tuberculosis*-pulsed macrophages and impairs the lytic activity of CD4 and CD8 CTL in tuberculosis patients. Clin Exp Immunol 138, 128-138 (2004).
19. Ho, J. L. & Lapa e Silva, J. R. Promotion of a down-modulated lung immune state may be a strategy by *M. tuberculosis* to foster active disease and persistence. Discov Med 9, 34-41 (2010).
20. Marks, E., Tam, M. A. & Lycke, N. Y. The Female Lower Genital Tract Is a Privileged Compartment with IL-10 Producing Dendritic Cells and Poor Th1 Immunity following *Chlamydia trachomatis* Infection. PLoS pathogens 6, e1001179 (2010).
21. Bahjat, K. S., Meyer-Morse, N., Lemmens, E. E., Shugart, J. A., Dubensky, T. W., Brockstedt, D. G. & Portnoy, D. A. Suppression of cell-mediated immunity following recognition of phagosome-confined bacteria. PLoS pathogens 5, e1000568 (2009).
22. Biswas, P. S., Pedicord, V., Ploss, A., Menet, E., Leiner, I. & Pamer, E. G. Pathogen-specific CD8 T cell responses are directly inhibited by IL-10. J. Immunol. 179, 4520-4528 (2007).
23. Peters, N. & Sacks, D. Immune privilege in sites of chronic infection: *Leishmania* and regulatory T cells. Immunol Rev 213, 159-179 (2006).
24. Silverman, J. M., Clos, J., Horakova, E., Wang, A. Y., Wiesgigl, M., Kelly, I., Lynn, M. A., McMaster, W. R., Foster, L. J., Levings, M. K. & Reiner, N. E. *Leishmania* exosomes modulate innate and adaptive immune responses through effects on monocytes and dendritic cells. J. Immunol. 185, 5011-5022 (2010).
25. Bueno, L. L., Morais, C. G., Araujo, F. F., Gomes, J. A., Correa-Oliveira, R., Soares, I. S., Lacerda, M. V., Fujiwara, R. T. & Braga, E. M. *Plasmodium vivax*: induction of CD4+CD25+FoxP3+ regulatory T cells during infection are directly associated with level of circulating parasites. PLoS ONE 5, e9623 (2010).
26. Ferreira, M. C., de Oliveira, R. T., da Silva, R. M., Blotta, M. H. & Mamoni, R. L. Involvement of regulatory T cells in the immunosuppression characteristic of patients with paracoccidioidomycosis. Infect Immun 78, 4392-4401 (2010).
27. Moreira, A. P., Dias-Melicio, L. A. & Soares, A. M. Interleukin-10 but not Transforming Growth Factor beta inhibits murine activated macrophages *Paracoccidioides brasiliensis* killing: effect on H2O2 and NO production. Cell Immunol 263, 196-203 (2010).
28. Wilson, E. B. & Brooks, D. G. The Role of IL-10 in Regulating Immunity to Persistent Viral Infections. Curr. Top. Microbiol. Immunol. in press (2010).
29. D'Orazio, T. J. & Niederkorn, J. Y. A novel role for TGF-beta and IL-10 in the induction of immune privilege. J. Immunol. 160, 2089-2098 (1998).
30. Skelsey, M. E., Mayhew, E. & Niederkorn, J. Y. CD25+, interleukin-10-producing CD4+ T cells are required for suppressor cell production and immune privilege in the anterior chamber of the eye. Immunology 110, 18-29 (2003).
31. Szajnik, M., Czystowska, M., Szczepanski, M. J., Mandapathil, M. & Whiteside, T. L. Tumor-derived microvesicles induce, expand and up-regulate biological activities of human regulatory T cells (Treg). PLoS ONE 5, e11469 (2010).
32. Wilczynski, J. R., Radwan, M. & Kalinka, J. The characterization and role of regulatory T cells in immune reactions. Front Biosci 13, 2266-2274 (2008).
33. Suter, T., Biollaz, G., Gatto, D., Bernasconi, L., Herren, T., Reith, W. & Fontana, A. The brain as an immune privileged site: dendritic cells of the central nervous system inhibit T cell activation. Eur J Immunol 33, 2998-3006 (2003).
34. Slobedman, B., Barry, P. A., Spencer, J. V., Avdic, S. & Abendroth, A. Virus-encoded homologs of cellular interleukin-10 and their control of host immune function. J. Virol. 83, 9618-9629 (2009).
35. Ha, S. J., West, E. E., Araki, K., Smith, K. A. & Ahmed, R. Manipulating both the inhibitory and stimulatory immune system towards the success of therapeutic vaccination against chronic viral infections. Immunol Rev 223, 317-333 (2008).
36. Brooks, D. G., McGavern, D. B. & Oldstone, M. B. Reprogramming of antiviral T cells prevents inactivation and restores T cell activity during persistent viral infection. The Journal of clinical investigation 116, 1675-1685 (2006).

37. Redpath, S., Angulo, A., Gascoigne, N. R. & Ghazal, P. Murine cytomegalovirus infection down-regulates MHC class II expression on macrophages by induction of IL-10. J. Immunol. 162, 6701-6707 (1999).
38. Cheeran, M. C., Hu, S., Palmquist, J. M., Bakken, T., Gekker, G. & Lokensgard, J. R. Dysregulated interferon-gamma responses during lethal cytomegalovirus brain infection of IL-10-deficient mice. Virus Res 130, 96-102 (2007).
39. Oakley, O. R., Garvy, B. A., Humphreys, S., Qureshi, M. H. & Pomeroy, C. Increased weight loss with reduced viral replication in interleukin-10 knock-out mice infected with murine cytomegalovirus. Clin Exp Immunol 151, 155-164 (2008).
40. Jones, M., Ladell, K., Wynn, K. K., Stacey, M. A., Quigley, M. F., Gostick, E., Price, D. A. & Humphreys, I. R. IL-10 restricts memory T cell inflation during cytomegalovirus infection. J. Immunol. 185, 3583-3592 (2010).
41. Davison, A. J., Dolan, A., Akter, P., Addison, C., Dargan, D. J., Alcendor, D. J., McGeoch, D. J. & Hayward, G. S. The human cytomegalovirus genome revisited: comparison with the chimpanzee cytomegalovirus genome. J Gen Virol 84, 17-28 (2003).
42. Lockridge, K. M., Zhou, S. S., Kravitz, R. H., Johnson, J. L., Sawai, E. T., Blewett, E. L. & Barry, P. A. Primate cytomegaloviruses encode and express an IL-10-like protein. Virol 268, 272-280 (2000).
43. Chang, W. L., Baumgarth, N., Eberhardt, M. K., Lee, C. Y., Baron, C. A., Gregg, J. P. & Barry, P. A. Exposure of myeloid dendritic cells to exogenous or endogenous IL-10 during maturation determines their longevity. J. Immunol 178, 7794-7804 (2007).
44. Chang, W. L., Baumgarth, N., Yu, D. & Barry, P. A. Human cytomegalovirus-encoded interleukin-10 homolog inhibits maturation of dendritic cells and alters their functionality. J. Virol. 78, 8720-8731 (2004).
45. Raftery, M. J., Wieland, D., Gronewald, S., Kraus, A. A., Giese, T. & Schonrich, G. Shaping phenotype, function, and survival of dendritic cells by cytomegalovirus-encoded IL-10 J Immunol. 173, 3383-3391 (2004).
46. Spencer, J. V., Cadaoas, J., Castillo, P. R., Saini, V. & Slobedman, B. Stimulation of B lymphocytes by cmvIL-10 but not LAcmvIL-10. Virol 374, 164-169 (2008).
47. Spencer, J. V., Lockridge, K. M., Barry, P. A., Lin, G., Tsang, M., Penfold, M. E. & Schall, T. J. Potent immunosuppressive activities of cytomegalovirus-encoded interleukin-10. J. Virol. 76, 1285-1292. (2002).
48. Jones, B. C., Logsdon, N. J., Josephson, K., Cook, J., Barry, P. A. & Walter, M. R. Crystal structure of human cytomegalovirus IL-10 bound to soluble human IL-10R1. Proceedings of the National Academy of Sciences of the United States of America 99, 9404-9409 (2002).
49. Sohn, Y. M., Park, K. I., Lee, C., Han, D. G. & Lee, W. Y. Congenital cytomegalovirus infection in Korean population with very high prevalence of maternal immunity. J Korean Med Sci 7, 47-51 (1992).
50. Boppana, S. B., Rivera, L. B., Fowler, K. B., Mach, M. & Britt, W. J. Intrauterine transmission of cytomegalovirus to infants of women with preconceptional immunity. The New England journal of medicine 344, 1366-1371 (2001).
51. Gaytant, M. A., Rours, G. I., Steegers, E. A., Galama, J. M. & Semmekrot, B. A. Congenital cytomegalovirus infection after recurrent infection: case reports and review of the literature. Eur J Pediatr 162, 248-253 (2003).
52. Gaytant, M. A., Steegers, E. A., Semmekrot, B. A., Merkus, H. M. & Galama, J. M. Congenital cytomegalovirus infection: review of the epidemiology and outcome. Obstet Gynecol Surv 57, 245-256 (2002).
53. Gandhoke, I., Aggarwal, R., Lal, S. & Khare, S. Congenital CMV infection in symptomatic infants in Delhi and surrounding areas. Indian J Pediatr 73, 1095-1097 (2006).
54. Ross, S. A., Arora, N., Novak, Z., Fowler, K. B., Britt, W. J. & Boppana, S. B. Cytomegalovirus reinfections in healthy seroimmune women. J. Infect. Dis. 201, 386-389 (2010).
55. Yamamoto, A. Y., Mussi-Pinhata, M. M., Boppana, S. B., Novak, Z., Wagatsuma, V. M., Oliveira Pde, F., Duarte, G. & Britt, W. J. Human cytomegalovirus reinfection is associated with intrauterine transmission in a highly cytomegalovirus-immune maternal population. Am J Obstet Gynecol 202, 297 e291-298 (2010).
56. Ross, S. A., Fowler, K. B., Ashrith, G., Stagno, S., Britt, W. J., Pass, R. F. & Boppana, S. B. Hearing loss in children with congenital cytomegalovirus infection born to mothers with preexisting immunity. J Pediatr 148, 332-336 (2006).
57. Wang, C., Zhang, X., Bialek, S. & Cannon, M. J. Attribution of congenital cytomegalovirus infection to primary versus non-primary maternal infection. Clin Infect Dis 52, ell-13 (2011).
58. Colugnati, F. A., Staras, S. A., Dollard, S. C. & Cannon, M. J. Incidence of cytomegalovirus infection among the general population and pregnant women in the United States. BMC Infect Dis 7, 71 (2007).
59. Fowler, K. B. & Pass, R. F. Risk factors for congenital cytomegalovirus infection in the offspring of young women: exposure to young children and recent onset of sexual activity. Pediatrics 118, e286-292 (2006).
60. Marshall, B. C. & Adler, S. P. The frequency of pregnancy and exposure to cytomegalovirus infections among women with a young child in day care. Am J Obstet Gynecol (2008).
61. Noyola, D. E., Valdez-Lopez, B. H., Hernandez-Salinas, A. E., Santos-Diaz, M. A., Noyola-Frias, M. A., Reyes-Macias, J. F. & Martinez-Martinez, L. G. Cytomegalovirus excretion in children attending day-care centers. Arch Med Res 36, 590-593 (2005).
62. Staras, S. A., Flanders, W. D., Dollard, S. C., Pass, R. F., McGowan, J. E., Jr. & Cannon, M. J. Cytomegalovirus seroprevalence and childhood sources of infection: A population-based study among pre-adolescents in the United States. J Clin Virol 43, 266-271 (2008).
63. Hyde, T. B., Schmid, D. S. & Cannon, M. J. Cytomegalovirus seroconversion rates and risk factors: implications for congenital CMV. Rev Med Virol 20, 311-326 (2010).
64. Hamprecht, K., Vochem, M., Baumeister, A., Boniek, M., Speer, C. P. & Jahn, G. Detection of cytomegaloviral DNA in human milk cells and cell free milk whey by nested PCR. Virol Meth 70, 167-176 (1998).
65. Schleiss, M. R. Role of breast milk in acquisition of cytomegalovirus infection: recent advances. Current opinion in pediatrics 18, 48-52 (2006).
66. Britt, W. Manifestations of human cytomegalovirus infection: proposed mechanisms of acute and chronic disease. Curr. Top. Microbiol. Immunol. 325, 417-470 (2008).
67. Dworsky, M., Yow, M., Stagno, S., Pass, R. F. & Alford, C. Cytomegalovirus infection of breast milk and transmission in infancy. Pediatrics 72, 295-299 (1983).
68. Gautheret-Dejean, A., Aubin, J. T., Poirel, L., Huraux, J. M., Nicolas, J. C., Rozenbaum, W. & Agut, H. Detection of human Betaherpesvirinae in saliva and urine from immunocompromised and immunocompetent subjects. J Clin Microbiol 35, 1600-1603. (1997).

69. Howard, M. R., Whitby, D., Bahadur, G., Suggett, F., Boshoff, C., Tenant-Flowers, M., Schulz, T. F., Kirk, S., Matthews, S., Weller, I. V., Tedder, R. S. & Weiss, R. A. Detection of human herpesvirus 8 DNA in semen from HIV-infected individuals but not healthy semen donors. AIDS (London, England) 11, F15-19. (1997).
70. Kashiwagi, Y., Nemoto, S., Hisashi, Kawashima, Takekuma, K., Matsuno, T., Hoshika, A. & Nozaki-Renard, J. Cytomegalovirus DNA among children attending two daycare centers in Tokyo. Pediatr Int 43, 493-495. (2001).
71. Mansat, A., Mengelle, C., Chalet, M., Boumzebra, A., Mieusset, R., Puel, J., Prouheze, C. & Segondy, M. Cytomegalovirus detection in cryopreserved semen samples collected for therapeutic donor insemination. Hum Reprod 12, 1663-1666. (1997).
72. Stagno, S., Reynolds, D., Tsiantos, A., Fuccillo, D. A., Smith, R., Tiller, M. & Alford, C. A., Jr. Cervical cytomegalovirus excretion in pregnant and nonpregnant women: suppression in early gestation. J. Infect. Dis. 131, 522-527. (1975).
73. Arora, N., Novak, Z., Fowler, K. B., Boppana, S. B. & Ross, S. A. Cytomegalovirus Viruria and DNAemia in Healthy Seropositive Women. J. Infect. Dis. in press (2010).
74. Sylwester, A. W., Mitchell, B. L., Edgar, J. B., Taormina, C., Pelte, C., Ruchti, F., Sleath, P. R., Grabstein, K. H., Hosken, N. A., Kern, F., Nelson, J. A. & Picker, L. J. Broadly targeted human cytomegalovirus-specific CD4+ and CD8+ T cells dominate the memory compartments of exposed subjects. The Journal of experimental medicine 202, 673-685 (2005).
75. Britt, W. J. & Mach, M. Human cytomegalovirus glycoproteins. Intervirology 39, 401-412 (1996).
76. Revello, M. G. & Gerna, G. Human cytomegalovirus tropism for endothelial/epithelial cells: scientific background and clinical implications. Rev Med Virol 20, 136-155 (2010).
77. Cui, X., Meza, B. P., Adler, S. P. & McVoy, M. A. Cytomegalovirus vaccines fail to induce epithelial entry neutralizing antibodies comparable to natural infection. Vaccine 26, 5760-5766 (2008).
78. Macagno, A., Bernasconi, N. L., Vanzetta, F., Dander, E., Sarasini, A., Revello, M. G., Gerna, G., Sallusto, F. & Lanzavecchia, A. Isolation of human monoclonal antibodies that potently neutralize human cytomegalovirus infection by targeting different epitopes on the gH/gL/UL128-131A complex. J. Virol. 84, 1005-1013 (2009).
79. Britt, W. J. Neutralizing antibodies detect a disulfide-linked glycoprotein complex within the envelope of human cytomegalovirus. Virol 135, 369-378 (1984).
80. Chang, W. L., Barry, P. A., Szubin, R., Wang, D. & Baumgarth, N. Human cytomegalovirus suppresses type I interferon secretion by plasmacytoid dendritic cells through its interleukin 10 homolog. Virol 390, 330-337 (2009).
81. Kotenko, S. V., Saccani, S., Izotova, L. S., Mirochnitchenko, O. V. & Pestka, S. Human cytomegalovirus harbors its own unique IL-10 homolog (cmvIL-10). Proc Natl Acad Sci 97, 1695-1700 (2000).
82. Pass, R. F., Zhang, C., Evans, A., Simpson, T., Andrews, W., Huang, M. L., Corey, L., Hill, J., Davis, E., Flanigan, C. & Cloud, G. Vaccine prevention of maternal cytomegalovirus infection. NE J Medicine 360, 1191-1199 (2009).
83. McGeoch, D. J., Cook, S., Dolan, A., Jamieson, F. E. & Telford, E. A. Molecular phylogeny and evolutionary timescale for the family of mammalian herpesviruses. J. Molec. Biol. 247, 443-458 (1995).
84. Dunn, W., Chou, C., Li, H., Hai, R., Patterson, D., Stole, V., Zhu, H. & Liu, F. Functional profiling of a human cytomegalovirus genome. Proceedings of the National Academy of Sciences of the United States of America 100, 14223-14228 (2003).
85. Yu, D., Silva, M. C. & Shenk, T. Functional map of human cytomegalovirus AD169 defined by global mutational analysis. Proceedings of the National Academy of Sciences of the United States of America 100, 12396-12401 (2003).
86. Barry, P. A. & Chang, W.-L. W. Primate Betaherpesviruses, in Human Herpesviruses: Biology, Therapy and Immunoprophylaxis. (eds. A. Arvin, G. Campadielli, P. Moore, E. Mocarski, B. Roizman, R. Whitley & K. Yamanishi) 1051-1075 (Cambridge University Press, Cambridge; 2007).
87. Cunningham, C., Gatherer, D., Hilfrich, B., Baluchova, K., Dargan, D. J., Thomson, M., Griffiths, P. D., Wilkinson, G. W., Schulz, T. F. & Davison, A. J. Sequences of complete human cytomegalovirus genomes from infected cell cultures and clinical specimens. J Gen Virol 91, 605-615 (2010).
88. Alford, C. A., Stagno, S. & Pass, R. F. Natural history of perinatal cytomegaloviral infection. Ciba Found Symp, 125-147 (1979).
89. Barry, P., Marthas, M., Lerche, N., McChesney, M. & Miller, C. Virology Research, in The Laboratory Primate: Handbook of Experimental Animals. (ed. S. Wolfe-Coote) 561-578 (Elsevier Academic Press, Burlington; 2005).
90. Barry, P. A. & Strelow, L. Development of Breeding Populations of Rhesus Macaques That Are Specific Pathogen Free for Rhesus Cytomegalovirus. Comparative Medicine 58, 43-46 (2008).
91. Vogel, P., Weigler, B. J., Kerr, H., Hendrickx, A. & Barry, P. A. Seroepidemiologic studies of cytomegalovirus infection in a breeding population of rhesus macaques. Lab Anim Sci 44, 25-30 (1994).
92. Adler, S. P. The molecular epidemiology of cytomegalovirus transmission among children attending a day care center. J. Infect. Dis. 152, 760-768 (1985).
93. Adler, S. P. Molecular epidemiology of cytomegalovirus: evidence for viral transmission to parents from children infected at a day care center. Pediatr Infect Dis 5, 315-318 (1986).
94. Adler, S. P. Cytomegalovirus infection in parents of children at day-care centers. The New England journal of medicine 315, 1164-1165 (1986).
95. Adler, S. P. Molecular epidemiology of cytomegalovirus: viral transmission among children attending a day care center, their parents, and caretakers. J Pediatr 112, 366-372 (1988).
96. Adler, S. P. Cytomegalovirus and child day care: risk factors for maternal infection. Pediatr Infect Dis J 10, 590-594 (1991).
97. Marshall, B. C. & Adler, S. P. The frequency of pregnancy and exposure to cytomegalovirus infections among women with a young child in day care. Am J Obstet Gynecol 200, 163e161-165 (2009).
98. Revello, M. G., Campanini, G., Piralla, A., Furione, M., Percivalle, E., Zavattoni, M. & Gema, G. Molecular epidemiology of primary human cytomegalovirus infection in pregnant women and their families. J. Med. Virol. 80, 1415-1425 (2008).
99. Butler, L. M., Neilands, T. B., Mosam, A., Mzolo, S. & Martin, J. N. A population-based study of how children are exposed to saliva in KwaZulu-Natal Province, South 99. Africa: implications for the spread of saliva-borne pathogens to children. Trop Med Int Health 15, 442-453 (2010).
100. Hendrie, C. A. & Brewer, G. Kissing as an evolutionary adaptation to protect against Human Cytomegalovirus-like teratogenesis. Med Hypotheses 74, 222-224 (2010).
101. Grosjean, J., Hantz, S., Cotin, S., Baclet, M. C., Mengelle, C., Trapes, L., Virey, B., Undreiner, F., Brosset, P., Pasquier, C., Denis, F. & Alain, S. Direct genotyping of cytomegalovirus envelope glycoproteins from toddler's saliva samples. J Clin Virol 46 Suppl 4, S43-48 (2009).
102. Rosenthal, L. S., Fowler, K. B., Boppana, S. B., Britt, W. J., Pass, R. F., Schmid, S. D., Stagno, S. & Cannon, M. J. Cytomegalovirus shedding and delayed sensorineural hearing loss: results from longitudinal follow-up of children with congenital infection. Pediatr Infect Dis J 28, 515-520 (2009).
103. Abel, K., Martinez, J., Yue, Y., Lacey, S. F., Wang, Z., Strelow, L., Dasgupta, A., Li, Z., Schmidt, K. A., Oxford, K. L., Assaf, B., Longmate, J. A., Diamond, D. J. & Barry, P. A. Vaccine-induced Control of Viral Shedding Following Rhesus Cytomegalovirus Challenge in Rhesus Macaques. J. Virol. in press (2011).
104. Donnelly, R. P., Sheikh, F., Dickensheets, H., Savan, R., Young, H. A. & Walter, M. R. Interleukin-26: an IL-10-related cytokine produced by Th17 cells. Cytokine Growth Factor Rev 21, 393-401 (2010).
105. Josephson, K., Jones, B. C., Walter, L. J., DiGiacomo, R., Indelicato, S. R. & Walter, M. R. Noncompetitive antibody neutralization of IL-10 revealed by protein engineering and x-ray crystallography. Structure (Camb) 10, 981-987 (2002).
106. Josephson, K., Logsdon, N. J. & Walter, M. R. Crystal structure of the IL-10/IL-10R1 complex reveals a shared receptor binding site. Immunity 15, 35-46 (2001).
107. Schreiber, G. & Walter, M. R. Cytokine-receptor interactions as drug targets. Curr Opin Chem Biol 14, 511-519 (2010).
108. Yoon, S. I., Jones, B. C., Logsdon, N. J., Harris, B. D., Deshpande, A., Radaeva, S., Halloran, B. A., Gao, B. & Walter, M. R. Structure and mechanism of receptor sharing by the IL-10R2 common chain. Structure 18, 638-648 (2010).
109. Yoon, S. I., Jones, B. C., Logsdon, N. J. & Walter, M. R. Same structure, different function crystal structure of the Epstein-Barr virus IL-10 bound to the soluble IL-10R1 chain. Structure 13, 551-564 (2005).
110. Yoon, S. I., Logsdon, N. J., Sheikh, F., Donnelly, R. P. & Walter, M. R. Conformational changes mediate interleukin-10 receptor 2 (IL-10R2) binding to IL-10 and assembly of the signaling complex. J. Biol. Chem. 281, 35088-35096 (2006).
111. Liu, Y., Malefyt, R.d.W., Briere, F., Parhan, C., Bridon, J.-M., Banchereau, J., Moore, K. W. & Xu, J. The EBV IL-10 homologue is a selective agonist with impaired binding to the IL-10 receptor. J Immunol 158, 604-613 (1997).
112. Wang, J. B., Adler, S. P., Hempfling, S., Burke, R. L., Duliege, A. M., Starr, S. E. & Plotkin, S. A. Mucosal antibodies to human cytomegalovirus glycoprotein B occur following both natural infection and immunization with human cytomegalovirus vaccines. J. Infect. Dis. 174, 387-392. (1996).
113. Oxford, K. L., Strelow, L., Yue, Y., Chang, W.-L. W., Schmidt, K. A., Diamond, D. J. & Barry, P. A. UL/b'-Encoded Open Reading Frames Are Essential for Shedding and Horizontal Transmission of Rhesus Cytomegalovirus in Rhesus Monkeys. submitted (2011).
114. Chang, W. & Barry, P. Attenuation of innate immunity by cytomegalovirus IL-10 establishes a long-term deficit of adaptive antiviral immunity. Proceedings of the National Academy of Sciences (USA) 107, 22647-22652 (2010).
115. Varnum, S. M., Streblow, D. N., Monroe, M. E., Smith, P., Auberry, K. J., Pasa-Tolic, L., Wang, D., Camp, D. G., 2nd, Rodland, K., Wiley, S., Britt, W., Shenk, T., Smith, R. D. & Nelson, J. A. Identification of proteins in human cytomegalovirus (HCMV) particles: the HCMV proteome. J. Virol. 78, 10960-10966 (2004).
116. Abel, K., Strelow, L., Yue, Y., Eberhardt, M. K., Schmidt, K. A. & Barry, P. A. A heterologous DNA prime/protein boost immunization strategy for rhesus cytomegalovirus. Vaccine 26, 6013-6025 (2008).
117. Aucouturier, J., Dupuis, L., Deville, S., Ascarateil, S. & Ganne, V. Montanide ISA 720 and 51: a new generation of water in oil emulsions as adjuvants for human vaccines. Expert review of vaccines 1, 111-118 (2002).
118. Aucouturier, J., Ganne, V. & Laval, A. Efficacy and safety of new adjuvants. Annals of the New York Academy of Sciences 916, 600-604 (2000).
119. Lockridge, K. M., Sequar, G., Zhou, S. S., Yue, Y., Mandell, C. M. & Barry, P. A. Pathogenesis of experimental rhesus cytomegalovirus infection. J. Virol. 73, 9576-9583 (1999).
120. Sequar, G., Britt, W. J., Lakeman, F. D., Lockridge, K. M., Tarara, R. P., Canfield, D. R., Zhou, S. S., Gardner, M. B. & Barry, P. A. Experimental coinfection of rhesus macaques with rhesus cytomegalovirus and simian immunodeficiency virus: pathogenesis. J. Virol. 76, 7661-7671. (2002).
121. Yue, Y., Kaur, A., Eberhardt, M. K., Kassis, N., Zhou, S. S., Tarantal, A. F. & Barry, P. A. Immunogenicity and protective efficacy of DNA vaccines expressing rhesus cytomegalovirus glycoprotein B, phosphoprotein 65-2, and viral interleukin-10 in rhesus macaques. J. Virol. 81, 1095-1109 (2007).
122. Yue, Y., Wang, Z., Abel, K., Li, J., Strelow, L., Mandarino, A., Eberhardt, M. K., Schmidt, K. A., Diamond, D. J. & Barry, P. A. Evaluation of Recombinant Modified Vaccinia Ankara Virus-Based Rhesus Cytomegalovirus Vaccines in Rhesus Macaques. Med Microbiol Immunol 197, 117-123 (2008).
123. Chang, W. L., Tarantal, A. F., Zhou, S. S., Borowsky, A. D. & Barry, P. A. A recombinant rhesus cytomegalovirus expressing enhanced green fluorescent protein retains the wild-type phenotype and pathogenicity in fetal macaques. J. Virol. 76, 9493-9504 (2002).
124. Read, J. S., Cannon, M. J., Stanberry, L. R. & Schuval, S. Prevention of mother-to-child transmission of viral infections. Curr Probl Pediatr Adolesc Health Care 38, 274-297 (2008).
125. Kenneson, A. & Cannon, M. J. Review and meta-analysis of the epidemiology of congenital cytomegalovirus (CMV) infection. Rev Med Virol 17, 253-276 (2007).
126. Cheung, A. K., Gottlieb, D. J., Plachter, B., Pepperl-Klindworth, S., Avdic, S., Cunningham, A. L., Abendroth, A. & Slobedman, B. The role of the human cytomegalovirus UL111A gene in down-regulating CD4+ T-cell recognition of latently infected cells: implications for virus elimination during latency. Blood 114, 4128-4137 (2009).
127. Hansen, S. G., Powers, C. J., Richards, R., Ventura, A. B., Ford, J. C., Siess, D., Axthelm, M. K., Nelson, J. A., Jarvis, M. A., Picker, L. J. & Fruh, K. Evasion of CD8+ T cells is critical for superinfection by cytomegalovirus. Science (New York, N.Y 328, 102-106 (2010).

128. Oxford, K. L., Eberhardt, M. K., Yang, K. W., Strelow, L., Kelly, S., Zhou, S. S. & Barry, P. A. Protein coding content of the U(L)b' region of wild-type rhesus cytomegalovirus. Virol 373, 181-188 (2008).
129. Joosten, S. A. & Ottenhoff, T. H. Human CD4 and CD8 regulatory T cells in infectious diseases and vaccination. Human Immunol. 69, 760-770 (2008).
130. Torres-Aguilar, H., Aguilar-Ruiz, S. R., Gonzalez-Perez, G., Munguia, R., Bajana, S., Meraz-Rios, M. A. & Sanchez-Torres, C. Tolerogenic dendritic cells generated with different immunosuppressive cytokines induce antigen-specific anergy and regulatory properties in memory CD4+ T cells. J. Immunol. 184, 1765-1775.
131. Shimamura, M., Murphy-Ullrich, J. E. & Britt, W. J. Human Cytomegalovirus Induces TGF-betaI Activation in Renal Tubular Epithelial Cells after Epithelial-to-Mesenchymal Transition. PLoS pathogens 6, e1001170 (2010).
132. Boppana, S. B., Smith, R. J., Stagno, S. & Britt, W. J. Evaluation of a microtiter plate fluorescent-antibody assay for rapid detection of human cytomegalovirus infection. J Clin Microbiol 30, 721-723 (1992).
133. Wu, X. & Jackson, S. Plasma and salivary IgG subclasses in HIV type 1 infection: evidence of both transudation and local synthesis of IgG in parotid saliva. AIDS research and human retroviruses 16, 1423-1431 (2000).
134. Robbins, J. B., Schneerson, R. & Szu, S. C. Perspective: hypothesis: serum IgG antibody is sufficient to confer protection against infectious diseases by inactivating the inoculum. J. Infect. Dis. 171, 1387-1398 (1995).
135. Wrammert, J., Koutsonanos, D., Li, G. M., Edupuganti, S., Sui, J., Morrissey, M., McCausland, M., Skountzou, I., Hornig, M., Lipkin, W. I., Mehta, A., Razavi, B., Del Rio, C., Zheng, N. Y., Lee, J. H., Huang, M., Ali, Z., Kaur, K., Andrews, S., *Amara*, R. R., Wang, Y., Das, S. R., O'Donnell, C. D., Yewdell, J. W., Subbarao, K., Marasco, W. A., Mulligan, M. J., Compans, R., Ahmed, R. & Wilson, P. C. Broadly cross-reactive antibodies dominate the human B cell response against 2009 pandemic H1N1 influenza virus infection. The Journal of experimental medicine 208, 181-193 (2011).
136. Britt, W. J. & Harrison, C. Identification of an abundant disulfide-linked complex of glycoproteins in the envelope of guinea pig cytomegalovirus. Virol 201, 294-302 (1994).
137. Britt, W. J. & Vugler, L. G. Oligomerization of the human cytomegalovirus major envelope glycoprotein complex gB (gp55-116). J. Virol. 66, 6747-6754 (1992).
138. Li, L., Coelingh, K. L. & Britt, W. J. Human cytomegalovirus neutralizing antibody-resistant phenotype is associated with reduced expression of glycoprotein H. J. Virol. 69, 6047-6053 (1995).
139. Shimamura, M., Mach, M. & Britt, W. J. Human cytomegalovirus infection elicits a glycoprotein M (gM)/gN-specific virus-neutralizing antibody response. J. Virol. 80, 4591-4600 (2006).
140. Urban, M., Klein, M., Britt, W. J., Hassfurther, E. & Mach, M. Glycoprotein H of human cytomegalovirus is a major antigen for the neutralizing humoral immune response. J Genl Virol 77, 1537-1547 (1996).
141. Li, L., Nelson, J. A. & Britt, W. J. Glycoprotein H-related complexes of human cytomegalovirus: identification of a third protein in the gCIII complex. J. Virol. 71, 3090-3097 (1997).
142. Kropff, B., Koedel, Y., Britt, W. & Mach, M. Optimal replication of human cytomegalovirus correlates with endocytosis of glycoprotein gpUL132. J. Virol. 84, 7039-7052 (2010).
143. Loh, L. C., Balachandran, N. & Britt, W. J. Characterization of a membrane-associated phosphoprotein of murine cytomegalovirus (pp50) and its immunological cross-reactivity with a human cytomegalovirus protein. Virol 183, 181-194 (1991).
144. Rapp, M., Messerle, M., Bühler, B., Tannheimer, M., Keil, G. M. & Koszinowski, U. H. Identification of the murine cytomegalovirus glycoprotein B gene and its expression by recombinant vaccinia virus. J. Virol. 66, 4399-4406 (1992).
145. Britt, W. J., Vugler, L., Butfiloski, E. J. & Stephens, E. B. Cell surface expression of human cytomegalovirus (HCMV) gp55-116 (gB): use of HCMV-vaccinia recombinant virus-infected cells in analysis of the human neutralizing response. J. Virol. 64, 1079-1085 (1990).
146. Boppana, S. B. & Britt, W. J. Antiviral antibody responses and intrauterine transmission after primary maternal cytomegalovirus infection. J. Infect. Dis. 171, 1115-1121 (1995).
147. Yue, Y., Kaur, A., Zhou, S. S. & Barry, P. A. Characterization and immunological analysis of the rhesus cytomegalovirus homologue (Rh112) of the human cytomegalovirus UL83 lower matrix phosphoprotein (pp65). J Genl Virol 87, 777-787 (2006).
148. Funaro, A., Gribaudo, G., Luganini, A., Ortolan, E., Lo Buono, N., Vicenzi, E., Cassetta, L., Landolfo, S., Buick, R., Falciola, L., Murphy, M., Garotta, G. & Malavasi, F. Generation of potent neutralizing human monoclonal antibodies against cytomegalovirus infection from immune B cells. BMC Biotechnol 8, 85 (2008).
149. Kuwata, T., Katsumata, Y., Takaki, K., Miura, T. & Igarashi, T. Isolation of Potent Neutralizing Monoclonal Antibodies from an SIV-Infected Rhesus Macaque by Phage Display. AIDS research and human retroviruses (2010).
150. Smith, K., Garman, L., Wrammert, J., Zheng, N. Y., Capra, J. D., Ahmed, R. & Wilson, P. C. Rapid generation of fully human monoclonal antibodies specific to a vaccinating antigen. Nat. Protoc. 4, 372-384 (2009).
151. Tiller, T., Busse, C. E. & Wardemann, H. Cloning and expression of murine Ig genes from single B cells. Journal of immunological methods 350, 183-193 (2009).
152. Tiller, T., Meffre, E., Yurasov, S., Tsuiji, M., Nussenzweig, M. C. & Wardemann, H. Efficient generation of monoclonal antibodies from single human B cells by single cell RT-PCR and expression vector cloning. Journal of immunological methods 329, 112-124 (2008).
153. Lanzavecchia, A., Corti, D. & Sallusto, F. Human monoclonal antibodies by immortalization of memory B cells. Curr Opin Biotechnol 18, 523-528 (2007).

Example 6

DNA/Protein Immunization and RhCMV Challenge of Rhesus Macaques

DNA recombinant expression constructs, pND/rhcmvIL-10M1 and pND/rhcmvIL-10M2 (1), were purified using an endotoxin-free plasmid purification kit (Qiagen) and concentration was determined spectrophotometrically. DNA was then diluted in PBS buffer at 1 mg/mL and stored at −80° C. rhcmvIL-10M1 and rhcmvIL-10M2 proteins were transfected using a pMT expression vector system in *Drosophila* S2 cells and were purified by nickel affinity purification protocol as previously described (1).

Four RhCMV negative rhesus macaques were immunized with a combination of rhcmvIL-10M1 and rhcmvIL-10M2 using a dual DNA/Protein strategy. Animals were immunized first with rhcmvIL-10M1/M2 plasmid DNA (150 μg intramuscular (IM); 50 μg intradermally (ID)) injection at week 0 and subsequently given three boost of rhcmvIL-10M1/M2 protein (50 μg each of M1 and M2 IM) at weeks 6, 12 and 26. The proteins were adjuvanted in MONTANIDE® ISA 720, as described (1). The four immunized macaques and 4 additional RhCMV seronegative rhesus macaque controls were then challenged subcutaneously with a UC Davis CNPRC RhCMV variant UCD59 (RhCMV$_{UCD59}$) at 1,000 pfu at four separate locations on the back of the animal.

DNA Extraction

Viral DNA was extracted from plasma, oral swab and urine using the QIASYMPHONY® kit (Qiagen). Samples were extracted following the manufacturer's protocols and stored for use at −80° C.

Quantitative Real-Time PCR

Real-time PCR quantifying RhCMV DNA in plasma, oral swabs and urine was performed according to previously published protocols (2). Primers and probes were designed for the RhCMV gB gene with TET placed on the 5' end of the probe as the reporter dye and the quencher dye, 6-carboxymethyl-rhodamine (TAMRA) placed on the 3' end (Applied Biosystems, Foster City, Ca). Total volume of each PCR was 12.5 μl using 1× TAQMAN® universal PCR master mixture (Applied Biosystems) with 17.5 pmol forward and reverse primers, 2.5 pmol probe and 5 μl DNA sample. qPCR was performed using the ABI prism 7900 sequence detection system. All samples were run in triplicate and quantified using a 10-fold serial dilution standard curve of RhCMV gB plasmid containing $10^6$ to $10^0$ copies per 5 μl.

ELISA to Detect rhcmvIL-10 Antibodies

Binding antibodies against rhcmvIL-10 were characterized by ELISA (1). Briefly, 96-well microplates (IMMULON® 4 HBX, Dynex Technologies Inc.) were coated overnight at 4° C. with nickel affinity-purified rhcmvIL-10 (12.5 ng/well) in coating buffer (phosphate buffered saline (PBS) (Sigma)/0.375% sodium bicarbonate (GIBCO)). Each plate was subsequently washed 6 times with PBS/0.05% TWEEN® 20 (Sigma) (PBS-T) and blocked with 300 μl/well PBS/1% bovine serum albumin (BSA) (Sigma) for 2 hours at 25° C. in a temperature-controlled incubator. After washing the plates 6 times with PBS-T, 100 μl of a 1:100 dilution of rhesus monkeys plasma (in PBS-T/1% BSA), or 100 μl of oral swab in PBS (1:10 final concentration) was added to each well and incubated at 25° C. for 2 hours. Each sample was assayed in triplicate. The plates were subsequently washed 6 times with PBS-T wash buffer and loaded with 100 μl/well of a 1:120,000 dilution of peroxidase-conjugated goat-anti-monkey IgG (Kirkegaard & Perry Laboratories, Inc—KPL) and incubated at 25° C. for 1 hour. The plates were then washed 6 times with PBS-T wash buffer and 100 μl/well of tetramethylbenzidine liquid substrate (TMB) (Sigma) was added and incubated for 30 min at 25° C. TMB color development was stopped by the addition of 50 μl/well of 0.5M sulfuric acid. After a 5 minute incubation at room temperature, color development was quantified spectrophotometrically at a wavelength of 450 nm on a Model 680 microplate reader (BioRad). The threshold for a sample to be considered positive for a specific rhcmvIL-10 antibody response was set at 3 standard deviations above the control seronegative mean optical density derived from 30 seronegative samples.

RhCMV ELISA

RhCMV ELISA was performed similar to rhcmvIL-10 ELISA with slight variations. 96-well microplates were coated with 0.25 RhCMV heat-inactivated virions in coating buffer and incubated overnight at 4° C. The plates were then washed with PBS/T and incubated 2 hours at room temperature (RT) with plasma or oral swab (1:100 or 1:10 dilutions in PBS/T, respectively). Plates were washed with PBS/T and then incubated 1 hour at RT with peroxidase conjugated goat anti-monkey IgG diluted in PBS/T at 1:190,000. Plates were then developed and quantified identically to the rhcmvIL-10 ELISA.

Avidity Assay of Antibodies to rhcmvIL-10

Avidity binding of rhcmvIL-10 antibodies was assayed similarly to the ELISA protocol, except that after the primary 2 hour incubation with diluted plasma, the wells were incubated in freshly prepared 6M urea for five minutes at room temperature and then washed extensively with PBS-T. Secondary goat anti-monkey antibody was then added for 1 hour and the plates were washed and processed for colorimetric development according to the ELISA protocol. The Avidity Index (AI) was calculated by dividing the mean optical density of a sample treated with 6M urea by the mean optical density of the sample not treated with 6M urea.

Neutralization of rhcmvIL-10 Function In Vitro

Antibodies in animal plasma directed against rhcmvIL-10 were characterized by a cellular based protein neutralization assay (1) with minor modifications. Briefly, plasma samples were diluted (1:1,000) in RPMI/10% fetal bovine serum/penicillin-streptomycin/L-glutamine (1 mL final volume) in the presence or absence of recombinant rhcmvIL-10 (1.0 ng/mL) for 3 hours at 37° C. 200 μL of plasma+/−rhcmvIL-10 mixtures were then incubated (each in triplicate) with $4×10^5$ Ficoll-purified PBMC/well in a 96 well U-bottom plate (Falcon) for 30 minutes in a humidified 37° C. incubator (5% $CO_2$). Lipopolysaccharide (LPS) (from *E. coli* 0127:B8; Sigma) was then added to the cells (5 μg/mL final concentration) and the cells were incubated 24 hours at 37° C. (5% $CO_2$). The supernatant was collected the following day and stored at −80° C. until assayed for IL-12 production. IL-12 secretion by LPS-activated PBMC was measured by ELISA (U-Cytech, Netherlands), according to the manufacturer's protocol with slight variations. Briefly, 96-well microplates (IMMULON® 4 HBX) were coated with the supplied IL-12 antibody pair (p40+p70) and incubated overnight at 4° C. The plates were then washed 6× with PBS-T and incubated with PBS/1% BSA blocking buffer for 60 minutes at 37° C. The buffer was removed, 100 μL/well of PBMC supernatant was added, and the cell mixture was incubated at 4° overnight. The plates were then washed 6 times with PBS-T wash buffer, 100 μL/well of anti-monkey ELISA detector antibody was added, and the cells were incubated 1 hr at 37° C. After washing, 100 μL/well of streptavidin-HR polymer (SPP) conjugate (U-Cytech) was added and incubated at 37° C. for 1 hr. After washing, TMB substrate (100 μL/well) was added, and the plates were incubated at 25° C. for 11 min. Color development was stopped by the addition of 0.5M sulfuric acid (50 μL/well). Following a 5 minute incubation (25° C.), the plates were read at a wavelength of 450 nm on a Model 680 microplate reader (BioRad). Concentrations of IL-12 were quantified using a 2-fold serially diluted recombinant IL-12 standard (U-Cytech) that was included on each plate. Neutralization was calculated as the inverse of the ratio of (IL-12 concentration+rhcmvIL-10+plasma)/(IL-12 concentration+plasma only) and was expressed as the "percent (%) IL-10 neutralized."

Intracellular Cytokine Staining (ICS)

To evaluate T-cell responses to rhcmvIL-10, cryogenically preserved Ficoll-gradient purified PBMC were thawed and rested overnight at 37° in complete RPMI medium containing 10% endotoxin-free FCS, 2 mM L-glutamine, 100 U/mL penicillin, 100 μg/mL streptomycin, 50 μM 2-mercaptoethanol, and 10 mM Hepes and stained (3) with slight modifications. Briefly, PBMC ($2.5\times10^6$ cells/mL in 48-well plates) were treated with either heat-inactivated RhCMV virion (10.0 µg/mL), nonfunctional rhcmvIL-10 proteins rhcmvIL-10M1 and rhcmvIL-10M2 (5.0 µg/mL), or media only in the presence of costimulatory monoclonal antibodies to CD28 (clone 28.2) and CD49d (clone 9F10) (5 ug/mL each; ebiosciences) for 6.5 hours with the addition of Golgistop and Golgiplug after the first 1.5 hours. Surface staining was done using directly conjugated monoclonal antibodies against human (rhesus-macaques cross-reactive) CD3 (clone SP34-2), CD4 (clone L200) and CD8 (Clone SK1) (BD Biosciences). Cells were then fixed and permeabilized using the Fixation/Permeabilization Kit (BD Biosciences) and cells were stained internally for IFN-γ (clone 4S.B3; BD Biosciences). A background baseline value was established for each animal by running a parallel sample without antigen stimulation. This value was subtracted from the corresponding antigen stimulated sample.

Flow Cytometry

Four-color flow cytometry was performed using the FACSCalibur with CellQuest software (BD Biosciences). Results were analyzed and displayed using FlowJo software (Tree Star).

Microscopy

Skin biopsies were fixed in paraformaldehyde, paraffin embedded, serially sectioned and processed for H&E staining and immunofluorescence labeling. All sections were deparafinized with 100% xylene (3 washes, 5 minutes each) and washed 3 times in 100% ethanol (EtOH). Endogenous peroxidase activity was inactivated by immersing sections in 3% $H_2O_2$ in methanol (MeOH) for 20 minutes followed by 2 additional 100% EtOH washes and one wash in 95% and 70% EtOH each. Sections were then washed for 10 minutes in deionized $H_2O$ and treated with Antigen DECLOAKER solution (Biocare Medical) for 4 hours at 97° C. and gradually brought down to room temperature (RT). After washing samples in PBS (2 times, 5 minutes each) samples were blocked in Dako Universal Blocker (Invitrogen) for 30 minutes. Sections were then stained with monoclonal antibodies cross-reactive to monkey CD68 (KP1) (Thermo Scientific) and rabbit anti-RhCMV IE-1 polyclonal antibodies. Sections were washed and then fluorescently stained with DyLight 488 and DyLight 595 (Vector Labs) and subsequently mounted with Prolong Gold antifade reagent with Dapi (Invitrogen). Images were taken using fluorescent light and a single pass filter (Omega Optical) with a digital camera (Axicam, Carl Zeiss, Germany) operated by AxioVision software. Images were processed with Adobe Photoshop (Adobe systems).

Statistical Analysis

All statistical analysis was performed using Prism 4 (GraphPad Software Inc.).

Antibody Responses in Immunized Rhesus Macaques

Four RhCMV-seronegative rhesus macaques were immunized with a combination of expression plasmids of rhcmvIL-10M1 and rhcmvIL-10M2 (rhcmvIL-10M1/M2) followed by 3 boosts of purified rhcmvIL-10M1/M2 protein according to FIG. 21. As previously described (1), rhcmvIL-10M1 and rhcmvIL-10M2 have two point mutations rendering them biologically nonfunctional. This allows the production of anti-rhcmvIL-10 antibody development upon immunization, in the absence of the immunosuppressive activity of the wild-type rhcmvIL-10 cytokine. The rhcmvIL-10M1/M2 vaccine stimulated high binding antibody titers with comparable kinetics between all four animals (FIG. 22A). While the initial DNA plasmid immunization elicited minimal antibody levels with only one animal measuring detectable levels, all animals were positive for rhcmvIL-10 specific Abs at week 8 post immunization (p.i.), two weeks after the first protein boost (administered at wk 6 p.i.). Subsequent protein boosts (at weeks 12 p.i. and 26 p.i.) elicited rapid binding antibody increases with an average absorbance ($A_{450}$) of 1.5 at time of challenge (week 34 p.i.). No rhcmvIL-10 specific antibodies were present before immunization.

In order to determine the efficacy of binding antibodies in blocking rhcmvIL-10 activity, a rhcmvIL-10 neutralization assay was performed. This assay measures IL-12 production in isolated PBMCs stimulated with LPS. IL-12 production is completely blocked by addition of recombinant rhcmvIL-10 to the assay. Thus, neutralizing antibodies (NAbs) present in animal plasma neutralize the recombinant rhcmvIL-10 biological activity resulting in an increase in IL-12 production, which is monitored by ELISA. As shown in FIG. 22B, 1 of the 4 vaccinated animals developed NAb titers 4 weeks after the initial protein boost (33% rhcmvIL-10 neutralization) while all animals exhibited NAbs against rhcmvIL-10 1 week after the second protein boost with an average of 46% rhcmvIL-10 activity neutralized (FIG. 22B). Three animals demonstrated an increase in NAbs following the third protein boost with peak levels (~100% rhcmvIL-10 neutralization) achieved at weeks 27-30 p.i. (1-4 weeks after the third protein boost). The third protein boost elicited only a moderate increase in neutralizing antibody levels (~38% rhcmvIL-10 neutralization) in the remaining animal. These findings demonstrate the vaccinated animals have developed antibody responses efficacious in blocking rhcmvIL-10 function.

Post-Challenge Immune Responses: The rhcmvIL-10M1/M2 Vaccine Alters the Milieu of Cells Recruited to Site of Infection.

Six weeks after the last protein boost, the four vaccinated macaques, and a control group of four un-vaccinated macaques, were inoculated subcutaneously with $10^3$ p.f.u. of $RhCMV_{UCD59}$ (FIG. 21) To observe the induction of local immune responses to viral challenge, skin biopsies were taken at the site of inoculation one week post challenge (p.c.). H&E stains revealed the immunized animals had demonstrable decreases in the overall inflammatory cell infiltrate at the site of inoculation with a specific decrease in polymorphonuclear (PMN) cell recruitment (FIG. 3). There was also evidence of increased cellular debris indicative of neutrophil death in the vaccinated animals. Additionally, while still showing some difference, the vaccinee previously found to have low rhcmvIL-10 NtAb titers (37% rhcmvIL-10 neutralization pre-challenge), had an immune response more phenotypically characteristic of the control unvaccinated animals with increased immune cell infiltrate and a higher frequency of PMN cells.

Skin biopsies also revealed a visible decrease of infected cells at the site of inoculation in the vaccine group compared to the controls. Specifically, a decrease in cytomegalic cells was observed in the H&E stain, and when sections were immunofluorescently stained for RhCMV IE-1 antigen (data not shown). There were no distinguishable differences in the frequency of macrophages at the site of infection as visualized using a monoclonal antibody to CD68.

Immune Responses to RhCMV and rhcmvIL-10

Post-challenge rhcmvIL-10 binding antibody responses were measured in vaccinated and control groups (FIG. 24A). The vaccinated animals exhibited peak binding antibody titers at the time of challenge. In contrast, rhcmvIL-10 binding antibody titers in control animals could not be detected until ~3 weeks after challenge. (FIG. 24A). Three vaccinated animals exhibited high levels of RhcmvIL10 NAbs that persisted for 8 weeks p.c. (FIG. 25). The remaining vaccinee maintained low levels of rhcmvIL-10 NAbs (~10% rhcmvIL-10 neutralization), subsequently declining to undetectable levels. In contrast to the vaccinated group, rhcmvIL-10 NAbs were not detected in the control group until 7-10 weeks p.c. and reached a median level of 85% rhcmvIL-10 neutralization by week 20 p.c. (FIG. 25).

Total RhCMV plasma antibody titers increased with essentially identical kinetics and reached similar levels between vaccine and control groups (FIG. 24A). Similar antibody kinetics and titers were seen in all animals with initial detection of antibodies starting at 2-4 weeks p.c., increasing to median levels of 1.3 $A_{450}$ in the vaccinated group and 1.4 $A_{450}$ in the controls by week 24 p.c. The apparent binding strength of the Abs was similar, as no significant differences were observed between the groups in the avidity assay.

Since differences in cell pathology were observed at the site of infection following viral challenge (FIG. 23), mucosal binding rhcmvIL-10 and RhCMV antibody levels were measured via oral swabs (FIG. 24B). These studies were performed to estimate antibody (Ab) levels present in the skin and other tissues at the time of challenge, and through the course of the infection. Binding antibody titers detected in saliva were lower than in plasma. However, similar to what was seen in plasma, RhCMV binding antibodies developed with essentially identical kinetics and to similar overall levels in the vaccine and control groups (FIG. 24B). Analysis of rhcmvIL-10 binding antibodies revealed low but significant levels of rhcmvIL-10 specific IgG antibodies present in the saliva of the vaccine group (median level=0.052 $A_{450}$), which persisted out to 6 weeks p.c. (FIG. 24B). In contrast, control animals never developed positive levels of rhcmvIL-10 specific antibodies for the entire course of the study.

Previous studies in RhCMV seropositive rhesus macaques have shown that antibody responses induced, or boosted, by rhcmvIL-10M1/M2 immunizations do not cross-react with cellular rhIL-10. To verify this is also true upon vaccination of RhCMV seronegative animals, serum antibodies from all vaccinated animals were tested and found to have no cross-reactivity with cellular rhIL-10.

rhcmvIL-10 Vaccine Reduced the Frequency and Magnitude of Plasma Viral Loads and Viral Shedding In order to assess whether the rhcmvIL-10M1/M2 vaccine would confer protection to RhCMV, plasma, oral swab and urine samples were also assessed for viral DNA loads using quantitative real-time PCR (qPCR) to measure RhCMV gB levels. The vaccine group had a significantly lower frequency of plasma samples positive for RhCMV DNA (FIG. 26A, p=0.0286). For the group of vaccinated animals, viral DNA was never detected, while the three remaining vaccinees were positive at a single time point, 1 week p.c. Control animal plasma samples were positive for viral DNA, 1 week p.c., and continued to display intermittent low levels of viral DNA in their plasma throughout the course of the study.

The vaccinated animals exhibit significantly lower frequencies, and magnitudes of RhCMV shedding, in bodily fluids, as monitored by the qPCR assay for RhCMV gB (FIGS. 27 and 28, p=0.014). Two vaccinated animals evidenced a complete absence of viral shedding in saliva with the remaining 2 vaccinees testing positive at 2 and 3 time points (weeks 7 and 16 p.c., and weeks 12, 14 and 16 p.c. respectively; FIG. 27). By contrast all control animals began shedding 6-7 weeks p.c. and continued shedding significantly higher loads of virus for the length of the study. Urine samples from the vaccine group exhibited an extremely low frequency of shedding with no virus being found at any time point in 3 of the animals, while the remaining animal displayed low levels of intermittent shedding (FIG. 28). All control animals showed intermittent shedding in urine throughout the course of the study. Interestingly, the three vaccinated animals that shed virus in saliva had no virus present in the urine while conversely, the animal that lacked shedding in the saliva was the only urine viral shedder in the vaccine group. Additionally, there was a single vaccinee that completely lacked any evidence of viral gB DNA in plasma, and did not shed virus in either saliva or urine for the entire course of the study.

In association with the decreases in viral shedding, vaccinated animals were found to have specific T cell responses to rhcmvIL-10 at either 0 or 4 weeks p.c. (FIG. 29A). Responses were monitored by IFN-γ expression, which ranged from 0.005%-0.02% of CD3+/CD4+ cells following stimulation with rhcmIL-10 M1/M2 (FIG. 29A). Control animals never developed rhcmvIL-10-specific responses. Additionally, at week 4, 50% of the vaccine animals were found to have ~4 times the frequency of RhCMV-specific CD4+ T cell activation by IFN-γ+ expression, compared to the mean frequency of the controls (0.12% vs. 0.025% IFN-γ+ CD4+ T-cells of gated CD3+CD4+ T-cells) (FIG. 29B). While not reaching significance due to the small sample size, the results follow the trend of increased immune defense exhibited by decreased viral DNA and frequency of shedding in the vaccine group.

REFERENCES FOR EXAMPLE 6

1. Logsdon et al. Design and Analysis of Rhesus Cytomegalovirus IL-10 Mutants as a Model for Novel Vaccines against Human Cytomegalovirus *PloS one,* 2011. 6(11)
2. Sequar et al. Experimental coinfection of rhesus macaques with rhesus cytomegalovirus and simian immunodeficiency virus: pathogenesis. *J Virol* 2002. 76(15):7661-71.
3. Oxford et al. Open reading frames carried on UL/b' are implicated in shedding and horizontal transmission of rhesus cytomegalovirus in rhesus monkeys. *J Virol* 2011. 85(10):5105-14.

Although the present process has been described with reference to specific details of certain embodiments thereof, it is not intended that such details should be regarded as limitations upon the scope of the invention except as and to the extent that they are included in the accompanying claims.

Throughout this application, various patents, patent publications and non-patent publications are referenced. The disclosures of these patents and publications in their entireties are hereby incorporated by reference into this application in order to more fully describe the state of the art to which this invention pertains.

SEQUENCES

RhCMV Strain 68-1

```
DNA: GenBank ® Database Accession No. AF200417 (SEQ ID NO: 5)
   1 gcttattagatacctgttgttaaggaaggtgcaggctnagttttttgcaaggtaagcctt
  61 cttctaccccctacacatgcggacttgttcttgagttaagtgtttgttntttttttctta
 121 atagttatcgtttncaagtctggcttgattgttcaggggggttgcatcttttagtgag
```

-continued

| SEQUENCES |
|---|

```
 181 tgtgataccacgacgtagggtgtggtaaccgtacaataatatctgttggttaggagaact
 241 taaatgtgtattaggtattattctcttatgctgctaacagaattgcttctccgtaactat
 301 tatcgtcttacagatagattgcgtttgttttttttttttcaagttccccagcaaaaacagg
 361 gagtctgtggcttttttggttcgtgtacatccgtgttcgcgtatcgaatttgatcttcctg
 421 cgatgatgtagggtccttgatgtaggatttcgaatatcggtatttttctttttagcaaag
 481 tgagggttcgtgtaagtttctatacaaacttatgtgaagtttatgacgttcgtttgttat
 541 ctcgagagcggctcgaaccttcttctgtagagctttatttagtgcaacttttacggggtgt
 601 agaagctaaatgaatctctgaaggtgctactcatttcacttcgaagaaacatccagttc
 661 gtgaaaaaaacaagtgtcttcgaaatcatgtttccactattttttgcaattacatctgtga
 721 aagtaggcagtagataccagattctnttttannttttgtntgtctcttatacaatggacta
 781 cgatgtttctcgagagtatgtcgtaagcttgtcgtggtgtanatngagttgctattgtt
 841 atttccttttgcacacacagttgttttcaattagatgtttgaccgtgattttgcccacccg
 901 gcccgggagacaaggcaaggagatntgttttntgcgtttgccatttatcatcgttattta
 961 ctattagtggtgacaatgacctgtcagattgttgattacttttttgggctacagactataa
1021 atcttcaaggatcgaggaaaagcaaacaaataggaaaggaaaaaagggaccaccttacct
1081 gtggcgtctcattctctgttgcagcggcggtcggtgctgttgtttagcctggagaaggag
1141 acgagaacgacgaatcggcggttacaatgcggaggaggaggaggtcttcggcatcatcg
1201 tcgccggcgctatcggaacactactcatgatggcggtggtcgtgctttcagcccatgacc
1261 atgaacacaaagaagtaccaccggcctgtgaccccgttcacggtaacttggcaggcatct
1321 tcaaggagttgcgggcgacctacgcttccattagagaaggtttggtatgttaggcaacgc
1381 agttctcggatgtcagtccgaatcggaggagtcacagtctgtcatgtgatgatatattgc
1441 ttaatttttgttttgcagcaaaagaaggacacggtgtactacacatcgctgttcaatgac
1501 cgcgtgctccatgaaatgctgagtcctatgggctgtcgcgtgaccaatgaactcatggaa
1561 cattatttagatgtgttctgcctcgagcaagtcatttagactacgataatagcactctg
1621 aatggcttacatgtgtttgcttcatccatgcaggcgctgtatcagcacatgttaaagtgt
1681 gtaagtgtttcaggttcgataaccccgcgatatgacacgtaaatagcgatatcgtggcac
1741 cagacgtcagtcacagtcttccccggtcgagacgcatcttatatcgcgatatatcgcgga
1801 ttatcgcagtatgtagccgatatatcgtgtcaaagcactccgaacgacattctgatgacg
1861 gctatcgccttatgtcgcggtatatcgcggaatatcgcagtatatcgcggttatgtcgcg
1921 acataaccgtcatgtcgcgactatcgccgcatatcgccactatcgcgacttggcaccgtg
1981 ccaacgatagtcgaccttagggtggtcgtgtggtggtgggggggctgcttgcggtttgcaa
2041 accggagaggtagcacacgctgattgtcggtttgaagcgttgtttacacatgtcttttgtc
2101 ttggcagcccgcgttggcatgtactggcaaaacgccagcttggatgtacttcttggaagt
2161 ggaacacaaggtcagttaaggttgccaggtaggttaaaacgcagaaaccattgttctacc
2221 ggtttcctaaaacgccgttcaacgtgttttgcagctcaaccctggaggggcacggcaaa
2281 agccgcggccgaggctgacctttttgctgaactacttggaaacgttcctgctgcagttctg
2341 agccagctgtcaatcaaggcagccaaaagcagcgttctccggtttacaattctcggatcg
2401 tttcgctagttaagctctaataaacgtactgtttaaccacc
```

Protein: GenBank® Database Accession No. AAF59907 (SEQ ID NO: 1)
MRRRRRSFGI IVAGAIGTLL MMAVVVLSAH DHEHKEVPPA CDPVHGNLAG IFKELRATYA
SIREGLQKKD TVYYTSLFND RVLHEMLSPM GCRVTNELME HYLDGVLPRA SHLDYDNSTL
NGLHVFASSM QALYQHMLKC PALACTGKTP AWMYFLEVEH KLNPWRGTAK AAAEADLLLN
YLETFLLQF RhCMV Strain MMU28684

DNA: GenBank® Database Accession No. AF200740 (SEQ ID NO: 6)
```
    1 gcagtagataccagattcttttttagtttgtctcttatacaatggactacgatgtttctc
   61 gagagtatgtcgtaagcttgtccgtggtgtagatcgagttgctactgttatttccttttg
  121 cacacacagttgtttcaattagatgtttgaccgtgattttgcccaccccggcccgggagac
  181 aaggcaaggagatttgtttttttgcgtttgccatttatcatcgctatttactattagtggt
  241 gacaatgacctgtcagattgttgattatttttttgggctacagactataaatcttcaagga
  301 tcaaggaaaagcaaacaaataggaaaggaaaaaagggaccaccttacctgtggcgtctca
  361 ttctctgttgcagcggcggtcggtgctgttgtttagcccggagaaggagacgggaacgac
  421 gaatcggcggttacaatgcggaggaggaggggtcttttcgacatcatcgtcgccggcgct
  481 atcggaacactactcatgatggcggtggtcgtgctttcagcccatgccatgaacacaaa
  541 gaagtaccaccggcctgtgaccccgttcacggtaacttggcaggcatcttcaaggagttg
  601 cgggcgacctacgcttccattagagaaggtttggtatgttaggcaacgcagttctcggat
  661 gtcagtccggatcggaggagtcacagtctgtcatgtgatgatatattgcttcattttttgt
  721 tttgtagcaaaagaaggacacggtgtactacacatcgctgttcaatgagcgcgtgctcca
  781 tgaaatgctgagtcctatgggctgtcgcgtgaccaacgaactcatggaacattatttaga
  841 tggtgttctgcctcgagcaagtcatttagactacgataatagcactctgaatggcttaca
  901 tgtgtttgcttcatccatgcaggcgctgtatcagcacatgttaaagtgtgtaagtgtttc
  961 aggttcgataaccccgcgatatgacacgtaaatagcgatatcgtggcaccagacgtcagt
 1021 cacagtcttccccggtcgagacgcatcttatatcgcgatatatcgcggattatcgcagta
 1081 tgttgcgatatatcgtgtcagaacactccgaacgacattctaatgacgatcatcgcctta
 1141 tgtcgcggtatatcgcggaatatcgcagtatgtcgcggttatgtcgcgacataaccgtca
 1201 tgtcgcgactatcgccgcatatcgccactatcgcgacttggcacggtgccaacaatagtt
 1261 gcctctagggtggtcgtgtggtggtaggggggctgcttgcggtttgcaaaccggagaggta
 1321 gcacacgctgattgtcggtttggaaacgttgtttacgcatgtctttgtcttggcagcccg
 1381 cgttggcatgtactggcaaaacgccagcttggatgtacttcttggaggtggaacacaagg
 1441 tcagttaaggttgccaggtaggttaaaacgcagaaaccattgttctaccggtttcctaaa
 1501 acgccgttcaacgtgttttgcagctcaaccctggaggggcacggcaaaagccgcggccg
 1561 aggctgaccttttgctgaactacttggaaacgttcctgctgcagttctgagccagctgtc
 1621 aatcaaggcagccaaaagcagcgttctccggtttacaattctcggatcgtttcgctagtt
 1681 aagctctaataaacgtactgtttaaccac
```

SEQUENCES

Protein: GenBank ® Database Accession No. AAF61204 (SEQ ID NO: 2)
MRRRRGSFDI IVAGAIGTLL MMAVVVLSAH DHEHKEVPPA CDPVHGNLAG IFKELRATYA
SIREGLQKKD TVYYTSLFNE RVLHEMLSPM GCRVTNELME HYLDGVLPRA SHLDYDNSTL
NGLHVFASSM QALYQHMLKC PALACTGKTP AWMYFLEVEH KLNPWRGTAK AAAEADLLLN
YLETFLLQF HCMV Strain Towne DNA: GenBank ® Database Accession No. AF202536 (SEQ ID NO: 7)
```
  1 atgctgtcggtgatggtctcttcctctctggtcctgatcgtcttttttctaggcgcttcc
 61 gaggaggcgaagccggcgacgacgacgataaagaatacaaagccgcagtgtcgtcca
121 gaggattacgcgaccagattgcaagatctccgcgtcacctttcatcgagtaaaacctacg
181 ttgcaacgtgaggacgactactccgtgtggctcgacggtacggtggtcaaaggctgttgg
241 ggatgcagcgtcatggactggttgttgaggcggtatctggagatcgtgttccccgcaggc
301 gaccacgtctatcccggactcaagacggaattgcatagtatgcgctcgacgctagaatcc
361 atctacaaagacatgcggcaatgccctctgttaggttgcggagataagtccgtgattagt
421 cggctgtctcaggaggcggaaaggaaatcggataacggcacgcggaaaggtctcagcgag
481 ttggacacgttgtttagccgtctcgaagagtatctgcactcgagaaagtagcgttgcgat
541 ttgcagtccgcttccggtgtcgttcacccagttacttaataaacgtactgtttaacc
```

Protein: GenBank ® Database Accession No. AAF63437 (SEQ ID NO: 3)
MLSVMVSSSL_VLIVFFLGAS_EEAKPATTTT_IKNTKPQCRP_EDYATRLQDL_RVTFHRVKPT
LQREDDYSVW_LDGTVVKGCW_GCSVMDWLLR_RYLEIVFPAG_DHVYPGLKTE_LHSMRSTLES
IYKDMRQCPL_LGCGDKSVIS_RLSQEAERKS_DNGTRKGLSE_LDTLFSRLEE_YLHSRK Human IL-10 amino acid sequence (GenBank ® Database Accession No.
P22301.1) (SEQ ID NO: 4). Numbering of amino acid residues that
are mutated as described herein is based on this amino acid
sequence, such that the S at amino acid position 19 (underlined
in the alignment below) is amino acid number 1.
MHSSALLCCL VLLTGVRASP GQGTQSENSC THFPGNLPNM LRDLRDAFSR VKTFFQMKDQ
LDNLLLKESL LEDFKGYLGC QALSEMIQFY LEEVMPQAEN QDPDIKAHVN SLGENLKTLR
LRLRRCHRFL PCENKSKAVE QVKNAFNKLQ EKGIYKAMSE FDIFINYIEA YMTMKIRN

SEQUENCE ALIGNMENTS

Two rhesus strains are 98% identical—1 amino acid change in the signal sequence.
Rhesus and human cmvIL-10 share 27% sequence identity.
Rhesus cmvIL-10 and human IL-10 are 17% identical
Human cmvIL-10 and human IL-10 are 26% identical rhcmvIL-10 residue segments 42-85, 169-189 are shaded; rhcmvIL-10 mutated residue positions R63(34), Q67(38), E174(142), D176(144) are numbered (bold numbers above the sequences) according to the mature human IL-10 sequence (SEQ ID NO:4) such that S19 (underlined in the alignment above) is residue 1.

hucmvIL-10 residue segments 39-78, 155-176 are shaded; human cmvIL-10 mutated residue positions K58(34), Q62 (38), E160(142), D162(144) are numbered (bold numbers above the sequences) according to the mature human IL-10 sequence such that S19 (underlined) is residue 1.

```
                (SEQ ID NO:)                                                            20|
RhCMV68-2         (1)      MRRRRRSFGIIVAG---AIGTLLMMAVVVLSAHDHEHKEVPPACDPVHGNLAGIFKELRA    57
RhCMVMMU28684     (2)      MRRRRGSFDIIVAG---AIGTLLMMAVVVLSAHDHEHKEVPPACDPVHGNLAGIFKELRA    57
huHCMV            (3)      ------MLSVMVSSSLVLIVFFLGASEEAKPATTTTIKNTKPQCRPED--YATRLQDLRV    52
huIL10P22301      (4)      -----------MHSSALLCCLVLLTGVRASPGQGTQSENS---CTHFPGNLPNMLRDLRD    46
                                          : .       *   .  . . ::   * .    . :::**

34|  38|
RhCMV68-2                  TYASIREGLQKKDTVYYTSLENDRVLHEMLSPMGCRVTNELMEHYLDGVLPRASHLDYDN   117
RhCMVMMU28684              TYASIREGLQKKDTVYYTSLFNERVLHEMLSPMGCRVTNELMEHYLDGVLPRASHLDYDN   117
huHCMV                     TFHRVKPTLQRED--DYSVWLDGTVVKGCWG---CSVMDWLLRRYLEIVEPAGDHVYPG-   106
huIL10P22301               AFSRVKTFFQMKD-QLDNLLLKESLLEDFKGYLGCQALSEMIQFYLEEVMPQAENQDPD-   104
                           :: :: :* :*    . :. ::.   . * . . ::. **: *:*  .

142|   |144
RhCMV68-2                  STLNGLHVFASSMQALYQHMLKCP-ALACTGKTPAWMYFLEVEHKLNPWRGTAKAAAEAD   176
RhCMVMMU28684              STLNGLHVFASSMQALYQHMLKCP-ALACTGKTPAWMYFLEVEHKLNPWRGTAKAAAEAD   176
huHCMV                     -LKTELHSMRSTLESIYKDMRQCP-LLGCGDKSVISRLSQEAERKSD--NGTRKGLSELD   162
huIL10P22301               -IKAHVNSLGENLKTLRLRLRRCHRFLPCENKSKAVEQVKNAFNKLQE-KGIYKAMSEFD   162
                           ::  :  ..::::    : :*    *   * .*:           :.  .* :  .* *

|145
RhCMV68-2                  LLLNYLETFLLQF---                                              189
RhCMVMMU28684              LLLNYLETFLLQF---                                              189
huHCMV                     TLFSRLEEYLHSRK--                                              176
huIL10P22301               IFINYIEAYMTMKIRN                                              178
                            ::. :* ::
```

Other desirable residue positions for mutations, in addition to the current ones, are residue 20 (mature human IL-10 sequence numbering), which is Ala49 in RhcmvIL-10, and Ala44 in human cmvIL-10 (mature human IL-10 sequence numbering).

Shown below are amino acid sequences of human cmvIL-10 proteins (identified by GENBANK® Database accession number) that have different lengths, with 3-7 threonines near the N terminus. These sequences are aligned with the amino acid sequence of SEQ ID NO:3 described herein (GENBANK® Database Accession No. AAF63437) and the amino acid regions and mutations that correspond to those described herein for the amino acid sequence of SEQ ID NO:3 are provided below.

|  | | muts hIL10 mature # | | | |
|---|---|---|---|---|---|
| | Range 1 | range 2 | 34 | 38 | 142 | 144 |
| gb\|ABD18476.1\| | 40-79 | 156-177 | 59 | 63 | 161 | 163 |
| SEQ ID NO: 3 | 39-78 | 155-176 | 58 | 62 | 160 | 162 |
| gb\|ACL27109.1\| | 43-82 | 159-180 | 62 | 66 | 164 | 166 |

```
                    (SEQ ID NO:)
gb|ABD18482.1|          (8)      MLSVMVSSSLVLIVFFLGASEEAKPAATTTTTTIKNTKPQCRPEDYATRLQDLRVTFHR   60
AF182315                (9)      MLSVMVSSSLVLIVFFLGASEEAKPA-----TTTIKNTKPQCRPEDYATRLQDLRVTFHR   55
gb|ABD18476.1|         (10)      MLSVMVSSSLVLIVFFLGASEEAKPAT---TTTIKNTKPQCRPEDYATRLQDLRVTFHR   57
SEQ ID NO: 3            (3)      MLSVMVSSSLVLIVFFLGASEEAKPAT----TTTIKNTKPQCRPEDYATRLQDLRVTFHR   56
gb|ACL27109.1|         (11)      MLSVMVSSSLVLIVFFLGASEEAKPA-----TTTTKNTKPQCRPEDYATRLQDLRVTFHR   55
                                 **********************     * ************************* gb|ABD18482.1|                   VKPTLQREDDYSVWLDGTVVKGCWGCSVMDWLLRRYLEIVFPAGDHVYPGLKTELHSMRS  120
AF182315                         VKPTLQREDDYSVWLDGTVVKGCWGCSVMDWLLRRYLEIVFPAGDHVYPGLKTELHSMRS  115
gb|ABD18476.1|                   VKPTLQREDDYSVWLDGTVVKGCWGCSVMDWLLRRYLEIVFPAGDHVYPGLKTELHSMRS  117
SEQ ID NO: 3                     VKPTLQREDDYSVWLDGTVVKGCWGCSVMDWLLRRYLEIVFPAGDHVYPGLKTELHSMRS  116
gb|ACL27109.1|                   VKPTLQREDDYSVWLDGTVVKGCWGCSVMDWLLRRYLEIVFPAGDHVYPGLKTELHSMRS  115
                                 ************************************************************ gb|ABD18482.1|                   TLESIYKDMRQCPLLGCGDKSVISRLSQEAERKSDNGTRKGLSELDTLFSRLEEYLHSRK  180
AF182315                         TLESIYKDMRQCPLLGCGDKSVISRLSQEAERKSDNGTRKGLSELDTLFSRLEEYLHSRK  175
gb|ABD18476.1|                   TLESIYKDMRQCPLLGCGDKSVISRLSQEAERKSDNGTRKGLSELDTLFSRLEEYLHSRK  177
SEQ ID NO: 3                     TLESIYKDMRQCPLLGCGDKSVISRLSQEAERKSDNGTRKGLSELDTLFSRLEEYLHSRK  176
gb|ACL27109.1|                   TLESIYKDMRQCPLLGCGDKSVISRLSQEAERKSDNGTRKGLSELDTLFSRLEEYLHSRK  175
                                 ************************************************************
```

|  | | muts hIL10 mature # | | | |
|---|---|---|---|---|---|
| | Range 1 | range 2 | 34 | 38 | 142 | 144 |
| gb\|ABD18482.1\| | 43-82 | 159-180 | 62 | 66 | 164 | 166 |
| AF182315 | 38-77 | 154-175 | 57 | 61 | 159 | 161 |

Shown below are the amino acid sequences of his-tagged rhcmvIL-10 proteins expressed in insect cells for initial characterization and immunization.

AF1 signal sequence underlined, FXa site=IEGR. Protease cuts to the right of the R Immunizations were performed with pMTA-rhcmvIL-10FXH with the appropriate mutations.

```
                    (SEQ ID NO:)
pAHF-rhcmvIL10         (12)      MRPTLLWSLLLLLGVFAAAAAAPPHHHHHHSDIEGRAHDHEHKEVPPACDPVHGNLAGIF   60
pMTA-rhcmvIL10FXH      (13)      MRPTLLWSLLLLLGVFAAAAAA---------------HDHEHKEVPPACDPVHGNLAGIF   45
rhcmvil10WT 68-2        (1)      MRRRRRSFGIIVAGAIGTLLMMAVVVLS--------AHDHEHKEVPPACDPVHGNLAGIF   52
                                 **        :::  *.::.                *********************** pAHF-rhcmvIL10                   KELRATYASIREGLQKKDTVYYTSLFNDRVLHEMLSPMGCRVTNELMEHYLDGVLPRASH  120
pMTA-rhcmvIL10FXH                KELRATYASIREGLQKKDTVYYTSLFNDRVLHEMLSPMGCRVTNELMEHYLDGVLPRASH  105
rhcmvil10WT 68-2                 KELRATYASIREGLQKKDIVYYTSLENDRVLHEMLSPMGCRVINELMEHYLDGVLPRASH  112
                                 **************** * *********** ***************** pAHF-rhcmvIL10                   LDYDNSTLNGLHVFASSMQALYQHMLKCPALACTGKTPAWMYFLEVEHKLNPWRGTAKAA  180
pMTA-rhcmvIL10FXH                LDYDNSTLNGLHVFASSMQALYQHMLKCPALACTGKTPAWMYFLEVEHKLNPWRGTAKAA  165
rhcmvil10WT 68-2                 LDYDNSTLNGLHVFASSMQALYQHMLKCPALACTGKTPAWMYFLEVEHKLNPWRGTAKAA  172
                                 ************************************************************ pAHF-rhcmvIL10                   AEADLLLNYLETFLLQF-------------                               197
pMTA-rhcmvIL10FXH                AEADLLLNYLETFLLQFSIEGRTGHHHHHH                               195
rhcmvil10WT 68-2                 AEADLLLNYLETFLLQF-------------                               189
                                 *****************
```

TABLE 1

| Amino Acid Residue | Abbreviation | |
|---|---|---|
| | Three-Letter Code | One-Letter Code |
| Alanine | Ala | A |
| Arginine | Arg | R |
| Asparagine | Asn | N |
| Aspartic acid (Aspartate) | Asp | D |
| Cysteine | Cys | C |
| Glutamine | Gln | Q |
| Glutamic acid (Glutamate) | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

TABLE 2

| Modified Amino Acid Residue | Abbreviation |
|---|---|
| Amino Acid Residue Derivatives | |
| 2-Aminoadipic acid | Aad |
| 3-Aminoadipic acid | bAad |
| beta-Alanine, beta-Aminoproprionic acid | bAla |
| 2-Aminobutyric acid | Abu |
| 4-Aminobutyric acid, Piperidinic acid | 4Abu |
| 6-Aminocaproic acid | Acp |
| 2-Aminoheptanoic acid | Ahe |
| 2-Aminoisobutyric acid | Aib |
| 3-Aminoisobutyric acid | bAib |
| 2-Aminopimelic acid | Apm |
| t-butylalanine | t-BuA |
| Citrulline | Cit |
| Cyclohexylalanine | Cha |
| 2,4-Diaminobutyric acid | Dbu |
| Desmosine | Des |
| 2,2'-Diaminopimelic acid | Dpm |
| 2,3-Diaminoproprionic acid | Dpr |
| N-Ethylglycine | EtGly |
| N-Ethylasparagine | EtAsn |
| Homoarginine | hArg |
| Homocysteine | hCys |
| Homoserine | hSer |
| Hydroxylysine | Hyl |
| Allo-Hydroxylysine | aHyl |
| 3-Hydroxyproline | 3Hyp |
| 4-Hydroxyproline | 4Hyp |
| Isodesmosine | Ide |
| allo-Isoleucine | aIle |
| Methionine sulfoxide | MSO |
| N-Methylglycine, sarcosine | MeGly |
| N-Methylisoleucine | MeIle |
| 6-N-Methyllysine | MeLys |
| N-Methylvaline | MeVal |
| 2-Naphthylalanine | 2-Nal |
| Norvaline | Nva |
| Norleucine | Nle |
| Ornithine | Orn |
| 4-Chlorophenylalanine | Phe(4-Cl) |
| 2-Fluorophenylalanine | Phe(2-F) |
| 3-Fluorophenylalanine | Phe(3-F) |
| 4-Fluorophenylalanine | Phe(4-F) |
| Phenylglycine | Phg |
| Beta-2-thienylalanine | Thi |

TABLE 3

Mass Spectrometry of Analysis of RhCMVIL-10

| Protein | Calculated Mass | Observed Mass | Difference |
|---|---|---|---|
| RnCMVIL–10FxaH6* | 20,755** | 20,762 | 7 |
| RhCMVIL–10FxaH6* + PNGase | 19,717 | 19,724 | 7 |

*C-terminal sequence = SIEGRTGHHHHHH (SEQ ID NO: 14),
**Protein mass + 1038 corresponding to 1N-linked glycan

TABLE 4 rhcmvIL-10 M1 and M2 Immunization Schedule

| WEEK | Immunogen | amount | route | | amount | Route | # animals | Mutant |
|---|---|---|---|---|---|---|---|---|
| 0 | DNA | 150 µg | IM | & | 50 µg | ID | 3 | M1 |
| " | " | " | " | & | " | " | 4 | M2 |
| 4 | DNA | 150 µg | IM | & | 50 µg | ID | 3 | M1 |
| " | " | " | " | & | " | " | 4 | M2 |
| 8 | DNA | 150 µg | IM | & | 50 µg | ID | 3 | M1 |
| " | " | " | " | & | " | " | 4 | M2 |
| 14 | Protein | 50 µg | IM | | | | 3 | M1 |
| " | " | " | " | | | | 3* | M2 |
| 19 | Protein | 50 µg | IM | | | | 3 | M1 |
| " | " | " | " | | | | 3* | M2 |

IM = Intramuscular, ID = Intradermal, * = 4$^{th}$ M2 animal DNA immunized only.

TABLE 5

Detection of RhCMV in oral swabs and urine post RhCMV inoculation at week 34

| | | Weeks post RhCMV Challenge | | | | | | | | | | Area Under |
|---|---|---|---|---|---|---|---|---|---|---|---|---|
| | | 34 | 35 | 36 | 37 | 48 | 59 | 40 | 41 | 42 | 44 | 46 | the Curve |
| | Oral Swabs | | | | | | | | | | | | |
| CONTROLS | Mmu 22 | 0 | 0 | 0 | 0 | 0 | 0 | 0 | 9,149 | 15,176 | 0 | 1,567 | 33,480 |
| | Mmu 61 | 0 | 0 | 0 | 0 | 0 | 0 | 0 | 29,709 | 45,609 | 5,151,941 | 526,527 | 10,928,532 |
| | Mmu 83 | 0 | 0 | 0 | 0 | 0 | 0 | 9,380 | 44,703 | 11,106 | 267,843 | 124,704 | 731,132 |
| | Mmu 09 | 0 | 0 | 0 | 0 | 0 | 0 | 0 | 7,311 | 69,950 | 70,532 | 84,309 | 337,509 |
| VACCINEES | Mmu 19 | 0 | 0 | 0 | 0 | 0 | 0 | 0 | 0 | 0 | 0 | 0 | 0 |
| | Mmu 81 | 0 | 0 | 0 | 0 | 0 | 0 | 0 | 0 | 0 | 0 | 35359 | 35,359 |
| | Mmu 66 | 0 | 0 | 0 | 0 | 0 | 0 | 37293 | 0 | 0 | 0 | 0 | 37,293 |
| | Mmu 86 | 0 | 0 | 0 | 0 | 0 | 0 | 0 | 0 | 0 | 0 | 0 | 0 |

TABLE 5-continued

Detection of RhCMV in oral swabs and urine post RhCMV inoculation at week 34

| | | Weeks post RhCMV Challenge | | | | | | | | | | | Area Under the Curve |
|---|---|---|---|---|---|---|---|---|---|---|---|---|---|
| | | 34 | 35 | 36 | 37 | 48 | 59 | 40 | 41 | 42 | 44 | 46 | |
| | Urine | | | | | | | | | | | | |
| CONTROLS | Mmu 22 | 0 | 0 | 0 | 0 | 0 | 0 | 0 | 0 | 0 | 0 | 11,383 | 11,383 |
| | Mmu 61 | 0 | 0 | 0 | 0 | 0 | 0 | 0 | 0 | 0 | 6,356 | 1,152 | 13,864 |
| | Mmu 83 | 0 | 0 | 0 | 0 | 0 | 0 | 0 | 0 | 0 | 0 | 184 | 184 |
| | Mmu 09 | 0 | 0 | 0 | 0 | 0 | 0 | 590 | 581 | 12,226 | 572 | 1,528 | 22,181 |
| VACCINEES | Mmu 19 | 0 | 0 | 0 | 0 | 2,127 | 0 | 0 | 12,100 | 0 | 1,798 | 2,301 | 20,125 |
| | Mmu 81 | 0 | 0 | 0 | 0 | 0 | 0 | 0 | 0 | 0 | 0 | 0 | 0 |
| | Mmu 66 | 0 | 0 | 0 | 0 | 0 | 0 | 0 | 0 | 0 | 0 | 0 | 0 |
| | Mmu 86 | 0 | 0 | 0 | 0 | 0 | 0 | 0 | 0 | 0 | 0 | 0 | 0 |

RhCMV Genome Copy#/ml of fluid

TABLE 6

| Saliva | RhCMV R-T PCR; rhcmvIL-10 NAb; RhCMV NAb |
| PBMC | RhCMV & rhcmvIL-10 CMI; B cell ELISPOT |
| Plasma | RhCMV R-T PCR; rhcmvIL-10 & RhCMV NAb; RhCMV ELISA |
| Urine | RhCMV R-T PCR |

R-T: real-time; CMI: cell-mediated immunity;

TABLE 7

Partial Listing of Outcome Criteria

1. Plasma rhcmvIL-10 NAb versus shedding pre-Vx
2. Saliva rhcmvIL-10 NAb versus shedding pre-Vx
3. Plasma RhCMV NAb versus shedding pre-Vx TABLE 7-continued Partial Listing of Outcome Criteria 4. Plasma versus saliva rhcmvIL-10 NAb
5. rhcmvIL-10 & RhCMV CMI versus shedding Pre-Vx
6. Pre-Vx, Peri-Vx, Post-Vx rhcmvIL-10 NAb
7. Pre-Vx, Peri-Vx, Post-Vx shedding
8. Pre-Vx, Peri-Vx, Post-Vx CMI Shedding: Frequency and AUC; Pre-Vx: weeks 1-12; Peri-Vx: weeks 13-24; Post-Vx: weeks 25-36

What is claimed is:

1. A cytomegalovirus IL-10 protein, wherein the protein comprises a substitution in one or more amino acids, wherein the substitution results in a phenotype of reduced binding to an interleukin-10 (IL-10) receptor protein and reduced functional activity as compared to a cytomegalovirus IL-10 protein lacking said substitution, and wherein the substitution is at K58, Q62, E160 and/or D162 in the amino acid sequence of SEQ ID NO:3, in any combination.

2. The cytomegalovirus IL-10 protein of claim 1, wherein the substitution further results in a phenotype of retained immunogenicity as compared to a cytomegalovirus IL-10 protein lacking said substitution.

3. The cytomegalovirus IL-10 protein of claim 1, wherein the substitution is K58E, Q62R, E160Q and/or D162H in the amino acid sequence of SEQ ID NO:3, in any combination.

4. The cytomegalovirus IL-10 protein of claim 1, wherein the substitution is D162H and either Q62R or E160Q in the amino acid sequence of SEQ ID NO:3.

5. A composition comprising the cytomegalovirus IL-10 protein of claim 1, in a pharmaceutically acceptable carrier.

* * * * *

SEQUENCE LISTING

```
<160> NUMBER OF SEQ ID NOS: 21

<210> SEQ ID NO 1
<211> LENGTH: 189
<212> TYPE: PRT
<213> ORGANISM: Macaca mulatta cytomegalovirus

<400> SEQUENCE: 1

Met Arg Arg Arg Arg Ser Phe Gly Ile Ile Val Ala Gly Ala Ile
1               5                   10                  15

Gly Thr Leu Leu Met Met Ala Val Val Val Leu Ser Ala His Asp His
            20                  25                  30

Glu His Lys Glu Val Pro Pro Ala Cys Asp Pro Val His Gly Asn Leu
        35                  40                  45

Ala Gly Ile Phe Lys Glu Leu Arg Ala Thr Tyr Ala Ser Ile Arg Glu
    50                  55                  60

Gly Leu Gln Lys Lys Asp Thr Val Tyr Tyr Thr Ser Leu Phe Asn Asp
65                  70                  75                  80

Arg Val Leu His Glu Met Leu Ser Pro Met Gly Cys Arg Val Thr Asn
                85                  90                  95

Glu Leu Met Glu His Tyr Leu Asp Gly Val Leu Pro Arg Ala Ser His
            100                 105                 110

Leu Asp Tyr Asp Asn Ser Thr Leu Asn Gly Leu His Val Phe Ala Ser
        115                 120                 125

Ser Met Gln Ala Leu Tyr Gln His Met Leu Lys Cys Pro Ala Leu Ala
    130                 135                 140
```

```
Cys Thr Gly Lys Thr Pro Ala Trp Met Tyr Phe Leu Glu Val Glu His
145                 150                 155                 160

Lys Leu Asn Pro Trp Arg Gly Thr Ala Lys Ala Ala Glu Ala Asp
                165                 170                 175

Leu Leu Leu Asn Tyr Leu Glu Thr Phe Leu Leu Gln Phe
            180                 185

<210> SEQ ID NO 2
<211> LENGTH: 189
<212> TYPE: PRT
<213> ORGANISM: Macaca mulatta cytomegalovirus

<400> SEQUENCE: 2

Met Arg Arg Arg Gly Ser Phe Asp Ile Ile Val Ala Gly Ala Ile
1               5                   10                  15

Gly Thr Leu Leu Met Met Ala Val Val Leu Ser Ala His Asp His
            20                  25                  30

Glu His Lys Glu Val Pro Pro Ala Cys Asp Pro Val His Gly Asn Leu
            35                  40                  45

Ala Gly Ile Phe Lys Glu Leu Arg Ala Thr Tyr Ala Ser Ile Arg Glu
        50                  55                  60

Gly Leu Gln Lys Lys Asp Thr Val Tyr Tyr Thr Ser Leu Phe Asn Glu
65                  70                  75                  80

Arg Val Leu His Glu Met Leu Ser Pro Met Gly Cys Arg Val Thr Asn
                85                  90                  95

Glu Leu Met Glu His Tyr Leu Asp Gly Val Leu Pro Arg Ala Ser His
            100                 105                 110

Leu Asp Tyr Asp Asn Ser Thr Leu Asn Gly Leu His Val Phe Ala Ser
        115                 120                 125

Ser Met Gln Ala Leu Tyr Gln His Met Leu Lys Cys Pro Ala Leu Ala
130                 135                 140

Cys Thr Gly Lys Thr Pro Ala Trp Met Tyr Phe Leu Glu Val Glu His
145                 150                 155                 160

Lys Leu Asn Pro Trp Arg Gly Thr Ala Lys Ala Ala Glu Ala Asp
                165                 170                 175

Leu Leu Leu Asn Tyr Leu Glu Thr Phe Leu Leu Gln Phe
            180                 185

<210> SEQ ID NO 3
<211> LENGTH: 176
<212> TYPE: PRT
<213> ORGANISM: Human herpesvirus 5

<400> SEQUENCE: 3

Met Leu Ser Val Met Val Ser Ser Leu Val Leu Ile Val Phe Phe
1               5                   10                  15

Leu Gly Ala Ser Glu Glu Ala Lys Pro Ala Thr Thr Thr Ile Lys
            20                  25                  30

Asn Thr Lys Pro Gln Cys Arg Pro Glu Asp Tyr Ala Thr Arg Leu Gln
        35                  40                  45

Asp Leu Arg Val Thr Phe His Arg Val Lys Pro Thr Leu Gln Arg Glu
        50                  55                  60

Asp Asp Tyr Ser Val Trp Leu Asp Gly Thr Val Val Lys Gly Cys Trp
65                  70                  75                  80

Gly Cys Ser Val Met Asp Trp Leu Leu Arg Arg Tyr Leu Glu Ile Val
                85                  90                  95
```

Phe Pro Ala Gly Asp His Val Tyr Pro Gly Leu Lys Thr Glu Leu His
                100                 105                 110

Ser Met Arg Ser Thr Leu Glu Ser Ile Tyr Lys Asp Met Arg Gln Cys
            115                 120                 125

Pro Leu Leu Gly Cys Gly Asp Lys Ser Val Ile Ser Arg Leu Ser Gln
        130                 135                 140

Glu Ala Glu Arg Lys Ser Asp Asn Gly Thr Arg Lys Gly Leu Ser Glu
145                 150                 155                 160

Leu Asp Thr Leu Phe Ser Arg Leu Glu Glu Tyr Leu His Ser Arg Lys
                165                 170                 175

<210> SEQ ID NO 4
<211> LENGTH: 178
<212> TYPE: PRT
<213> ORGANISM: Homo sapiens

<400> SEQUENCE: 4

Met His Ser Ser Ala Leu Leu Cys Cys Leu Val Leu Leu Thr Gly Val
1               5                   10                  15

Arg Ala Ser Pro Gly Gln Gly Thr Gln Ser Glu Asn Ser Cys Thr His
            20                  25                  30

Phe Pro Gly Asn Leu Pro Asn Met Leu Arg Asp Leu Arg Asp Ala Phe
        35                  40                  45

Ser Arg Val Lys Thr Phe Phe Gln Met Lys Asp Gln Leu Asp Asn Leu
    50                  55                  60

Leu Leu Lys Glu Ser Leu Leu Glu Asp Phe Lys Gly Tyr Leu Gly Cys
65                  70                  75                  80

Gln Ala Leu Ser Glu Met Ile Gln Phe Tyr Leu Glu Glu Val Met Pro
                85                  90                  95

Gln Ala Glu Asn Gln Asp Pro Asp Ile Lys Ala His Val Asn Ser Leu
            100                 105                 110

Gly Glu Asn Leu Lys Thr Leu Arg Leu Arg Leu Arg Arg Cys His Arg
        115                 120                 125

Phe Leu Pro Cys Glu Asn Lys Ser Lys Ala Val Glu Gln Val Lys Asn
    130                 135                 140

Ala Phe Asn Lys Leu Gln Glu Lys Gly Ile Tyr Lys Ala Met Ser Glu
145                 150                 155                 160

Phe Asp Ile Phe Ile Asn Tyr Ile Glu Ala Tyr Met Thr Met Lys Ile
                165                 170                 175

Arg Asn

<210> SEQ ID NO 5
<211> LENGTH: 2441
<212> TYPE: DNA
<213> ORGANISM: Macaca mulatta cytomegalovirus
<220> FEATURE:
<221> NAME/KEY: misc_feature
<222> LOCATION: (38)..(38)
<223> OTHER INFORMATION: n is a, c, g, or t
<220> FEATURE:
<221> NAME/KEY: misc_feature
<222> LOCATION: (109)..(109)
<223> OTHER INFORMATION: n is a, c, g, or t
<220> FEATURE:
<221> NAME/KEY: misc_feature
<222> LOCATION: (134)..(134)
<223> OTHER INFORMATION: n is a, c, g, or t
<220> FEATURE:
<221> NAME/KEY: misc_feature
<222> LOCATION: (746)..(746)
<223> OTHER INFORMATION: n is a, c, g, or t

```
<220> FEATURE:
<221> NAME/KEY: misc_feature
<222> LOCATION: (752)..(753)
<223> OTHER INFORMATION: n is a, c, g, or t
<220> FEATURE:
<221> NAME/KEY: misc_feature
<222> LOCATION: (759)..(759)
<223> OTHER INFORMATION: n is a, c, g, or t
<220> FEATURE:
<221> NAME/KEY: misc_feature
<222> LOCATION: (814)..(814)
<223> OTHER INFORMATION: n is a, c, g, or t
<220> FEATURE:
<221> NAME/KEY: misc_feature
<222> LOCATION: (823)..(823)
<223> OTHER INFORMATION: n is a, c, g, or t
<220> FEATURE:
<221> NAME/KEY: misc_feature
<222> LOCATION: (826)..(826)
<223> OTHER INFORMATION: n is a, c, g, or t
<220> FEATURE:
<221> NAME/KEY: misc_feature
<222> LOCATION: (925)..(925)
<223> OTHER INFORMATION: n is a, c, g, or t
<220> FEATURE:
<221> NAME/KEY: misc_feature
<222> LOCATION: (932)..(932)
<223> OTHER INFORMATION: n is a, c, g, or t
<220> FEATURE:
<221> NAME/KEY: misc_feature
<222> LOCATION: (1187)..(1187)
<223> OTHER INFORMATION: n is a, c, g, or t

<400> SEQUENCE: 5
```

| | | | | | |
|---|---|---|---|---|---|
| gcttattaga | tacctgttgt | taaggaaggt | gcaggctnag | tttttttgcaa | ggtaagcctt     60 |
| cttctacccc | ctacacatgc | ggacttgttc | ttgagttaag | tgtttgttnt | tttttttctta   120 |
| atagttatcg | tttncaagtc | tggcttgatt | gttcaggggg | ggttgcatct | ttttagtgag   180 |
| tgtgatacca | cgacgtaggg | tgtggtaacc | gtacaataat | atctgttggt | taggagaact   240 |
| taaatgtgta | ttaggtatta | ttctcttatg | ctgctaacag | aattgcttct | ccgtaactat   300 |
| tatcgtctta | cagatagatt | gcgtttgttt | tttttttttca | agttccccag | caaaaacagg   360 |
| gagtctgtgg | ctttttggtt | cgtgtacatc | cgtgttcgcg | tatcgaattt | gatcttcctg   420 |
| cgatgatgta | gggtccttga | tgtaggattt | cgaatatcgg | tattttttct | tttagcaaag   480 |
| tgagggttcg | tgtaagtttc | tatacaaact | tatgtgaagt | ttatgacgtt | cgtttgttat   540 |
| ctcgagagcg | gctcgaacct | tcttctgtag | agctttattt | agtgcaactt | tacggggtgt   600 |
| agaagctaaa | tgaatctctg | aaggtgctac | tcatttacac | ttcgaagaaa | catccagttc   660 |
| gtgaaaaaaa | caagtgtctt | cgaaatcatg | tttccactat | ttttgcaatt | acatctgtga   720 |
| aagtaggcag | tagataccag | attctnttt | annttttgtnt | gtctcttata | caatggacta   780 |
| cgatgtttct | cgagagtatg | tcgtaagctt | gtcngtggtg | tanatngagt | tgctattgtt   840 |
| atttcctttt | gcacacacag | ttgtttcaat | tagatgtttg | accgtgattt | tgcccacccg   900 |
| gcccgggaga | caaggcaagg | agatntgttt | tntgcgtttg | ccatttatca | tcgttattta   960 |
| ctattagtgg | tgacaatgac | ctgtcagatt | gttgattact | ttttgggcta | cagactataa  1020 |
| atcttcaagg | atcgaggaaa | agcaaacaaa | taggaaagga | aaaagggac | caccttacct  1080 |
| gtggcgtctc | attctctgtt | gcagcggcgg | tcggtgctgt | tgtttagcct | ggagaaggag  1140 |
| acgagaacga | cgaatcggcg | gttacaatgc | ggaggaggag | gaggtcnttc | ggcatcatcg  1200 |
| tcgccggcgc | tatcggaaca | ctactcatga | tggcggtggt | cgtgctttca | gcccatgacc  1260 |
| atgaacacaa | agaagtacca | ccggcctgtg | accccgttca | cggtaacttg | gcaggcatct  1320 |

```
tcaaggagtt gcgggcgacc tacgcttcca ttagagaagg tttggtatgt taggcaacgc    1380
agttctcgga tgtcagtccg aatcggagga gtcacagtct gtcatgtgat gatatattgc    1440
ttaattttg ttttgcagca aaagaaggac acggtgtact acacatcgct gttcaatgac     1500
cgcgtgctcc atgaaatgct gagtcctatg ggctgtcgcg tgaccaatga actcatggaa    1560
cattatttag atggtgttct gcctcgagca agtcatttag actacgataa tagcactctg    1620
aatggcttac atgtgtttgc ttcatccatg caggcgctgt atcagcacat gttaaagtgt    1680
gtaagtgttt caggttcgat aaccccgcga tatgacacgt aaatagcgat atcgtggcac    1740
cagacgtcag tcacagtctt ccccggtcga gacgcatctt atatcgcgat atatcgcgga    1800
ttatcgcagt atgtagccga tatatcgtgt caaagcactc cgaacgacat tctgatgacg    1860
gctatcgcct tatgtcgcgg tatatcgcgg aatatcgcag tatatcgcgg ttatgtcgcg    1920
acataaccgt catgtcgcga ctatcgccgc atatcgccac tatcgcgact tggcaccgtg    1980
ccaacgatag tcgaccttag ggtggtcgtg tggtggtggg gggctgcttg cggtttgcaa    2040
accggagagg tagcacacgc tgattgtcgg tttgaagcgt tgtttacaca tgtctttgtc    2100
ttggcagccc gcgttggcat gtactggcaa aacgccagct tggatgtact tcttggaggt    2160
ggaacacaag gtcagttaag gttgccaggt aggttaaaac gcagaaacca ttgttctacc    2220
ggtttcctaa aacgccgttc aacgtgtttt gcagctcaac ccctggaggg gcacggcaaa    2280
agccgcggcc gaggctgacc ttttgctgaa ctacttggaa acgttcctgc tgcagttctg    2340
agccagctgt caatcaaggc agccaaaagc agcgttctcc ggtttacaat tctcggatcg    2400
tttcgctagt taagctctaa taaacgtact gtttaaccac c                         2441

<210> SEQ ID NO 6
<211> LENGTH: 1709
<212> TYPE: DNA
<213> ORGANISM: Macaca mulatta cytomegalovirus

<400> SEQUENCE: 6
gcagtagata ccagattctt ttttagtttg tctcttatac aatggactac gatgtttctc      60
gagagtatgt cgtaagcttg tccgtggtgt agatcgagtt gctactgtta tttccttttg     120
cacacacagt tgtttcaatt agatgtttga ccgtgatttt gcccacccgg cccgggagac     180
aaggcaagga gatttgtttt ttgcgtttgc catttatcat cgctatttac tattagtggt     240
gacaatgacc tgtcagattg ttgattattt tttgggctac agactataaa tcttcaagga    300
tcaaggaaaa gcaaacaaat aggaaaggaa aaaagggacc accttacctg tggcgtctca    360
ttctctgttg cagcggcggt cggtgctgtt gtttagcccg gagaaggaga cgggaacgac    420
gaatcggcgg ttacaatgcg gaggaggagg gggtctttcg acatcatcgt cgccggcgct    480
atcggaacac tactcatgat ggcggtggtc gtgctttcag cccatgacca tgaacacaaa    540
gaagtaccac cggcctgtga ccccgttcac ggtaacttgg caggcatctt caaggagttg    600
cgggcgaccc tacgcttcca ttagagaagg tttggtatgt taggcaacgc agttctcgga    660
tgtcagtccg gatcggagga gtcacagtct gtcatgtgat gatatattgc tcattttgt     720
tttgtagcaa aagaaggaca cggtgtacta cacatcgctg ttcaatgagc gcgtgctcca    780
tgaaatgctg agtcctatgg gctgtcgcgt gaccaacgaa ctcatggaac attatttaga    840
tggtgttctg cctcgagcaa gtcatttaga ctacgataat agcactctga atggcttaca    900
tgtgtttgct tcatccatgc aggcgctgta tcagcacatg ttaaagtgtg taagtgtttc    960
aggttcgata accccgcgat atgacacgta aatagcgata tcgtggcacc agacgtcagt   1020
```

-continued

```
cacagtcttc cctggtggag acgcatctta tatcgcgata tatcgcggat tatcgcagta    1080
tgttgcgata tatcgtgtca gaacactccg aacgacattc taatgacgac tatcgcctta    1140
tgtcgcggta tatcgcggaa tatcgcagta tgtcgcggtt atgtcgcgac ataaccgtca    1200
tgtcgcgact atcgccgcat atcgccacta tcgcgacttg gcacggtgcc aacaatagtt    1260
gcctctaggg tggtcgtgtg gtggtagggg gctgcttgcg gtttgcaaac cggagaggta    1320
gcacacgctg attgtcggtt tggaaacgtt gtttacgcat gtctttgtct ggcagcccg     1380 cgttggcatg tactggcaaa acgccagctt ggatgtactt cttggaggtg aacacaagg     1440 tcagttaagg ttgccaggta ggttaaaacg cagaaaccat tgttctaccg gtttcctaaa    1500
acgccgttca acgtgttttg cagctcaacc cctggagggg cacggcaaaa gccgcggccg    1560
aggctgacct tttgctgaac tacttggaaa cgttcctgct gcagttctga gccagctgtc    1620
aatcaaggca gccaaaagca gcgttctccg gtttacaatt ctcggatcgt ttcgctagtt    1680
aagctctaat aaacgtactg tttaaccac                                      1709

<210> SEQ ID NO 7
<211> LENGTH: 598
<212> TYPE: DNA
<213> ORGANISM: Human herpesvirus 5

<400> SEQUENCE: 7
atgctgtcgg tgatggtctc ttcctctctg gtcctgatcg tcttttttct aggcgcttcc     60
gaggaggcga agccggcgac gacgacgacg ataaagaata caaagccgca gtgtcgtcca    120
gaggattacg cgaccagatt gcaagatctc cgcgtcacct tcatcgagt aaaacctacg     180 ttgcaacgtg aggacgacta ctccgtgtgg ctcgacggta cggtggtcaa aggctgttgg    240
ggatgcagcg tcatggactg gttgttgagg cggtatctgg agatcgtgtt ccccgcaggc    300
gaccacgtct atcccggact caagacggaa ttgcatagta tgcgctcgac gctagaatcc    360
atctacaaag acatgcggca atgccctctg ttaggttgcg gagataagtc cgtgattagt    420
cggctgtctc aggaggcgga aaggaaatcg gataacggca gcggaaagg tctcagcgag    480 ttggacacgt tgtttagccg tctcgaagag tatctgcact cgagaagta gcgttgcgat    540 ttgcagtccg cttccggtgt cgttcaccca gttactttaa taaacgtact gtttaacc    598

<210> SEQ ID NO 8
<211> LENGTH: 180
<212> TYPE: PRT
<213> ORGANISM: Human herpesvirus 5

<400> SEQUENCE: 8

Met Leu Ser Val Met Val Ser Ser Leu Val Leu Ile Val Phe Phe
1               5                   10                  15

Leu Gly Ala Ser Glu Glu Ala Lys Pro Ala Ala Thr Thr Thr Thr Thr
                20                  25                  30

Thr Thr Ile Lys Asn Thr Lys Pro Gln Cys Arg Pro Glu Asp Tyr Ala
            35                  40                  45

Thr Arg Leu Gln Asp Leu Arg Val Thr Phe His Arg Val Lys Pro Thr
        50                  55                  60

Leu Gln Arg Glu Asp Asp Tyr Ser Val Trp Leu Asp Gly Thr Val Val
65                  70                  75                  80

Lys Gly Cys Trp Gly Cys Ser Val Met Asp Trp Leu Leu Arg Arg Tyr
                85                  90                  95
```

```
Leu Glu Ile Val Phe Pro Ala Gly Asp His Val Tyr Pro Gly Leu Lys
                100                 105                 110

Thr Glu Leu His Ser Met Arg Ser Thr Leu Glu Ser Ile Tyr Lys Asp
            115                 120                 125

Met Arg Gln Cys Pro Leu Leu Gly Cys Gly Asp Lys Ser Val Ile Ser
        130                 135                 140

Arg Leu Ser Gln Glu Ala Glu Arg Lys Ser Asp Asn Gly Thr Arg Lys
145                 150                 155                 160

Gly Leu Ser Glu Leu Asp Thr Leu Phe Ser Arg Leu Glu Glu Tyr Leu
                165                 170                 175

His Ser Arg Lys
            180

<210> SEQ ID NO 9
<211> LENGTH: 175
<212> TYPE: PRT
<213> ORGANISM: Human herpesvirus 5

<400> SEQUENCE: 9

Met Leu Ser Val Met Val Ser Ser Leu Val Leu Ile Val Phe Phe
1               5                   10                  15

Leu Gly Ala Ser Glu Glu Ala Lys Pro Ala Thr Thr Ile Lys Asn
                20                  25                  30

Thr Lys Pro Gln Cys Arg Pro Glu Asp Tyr Ala Thr Arg Leu Gln Asp
            35                  40                  45

Leu Arg Val Thr Phe His Arg Val Lys Pro Thr Leu Gln Arg Glu Asp
        50                  55                  60

Asp Tyr Ser Val Trp Leu Asp Gly Thr Val Val Lys Gly Cys Trp Gly
65                  70                  75                  80

Cys Ser Val Met Asp Trp Leu Leu Arg Arg Tyr Leu Glu Ile Val Phe
                85                  90                  95

Pro Ala Gly Asp His Val Tyr Pro Gly Leu Lys Thr Glu Leu His Ser
                100                 105                 110

Met Arg Ser Thr Leu Glu Ser Ile Tyr Lys Asp Met Arg Gln Cys Pro
            115                 120                 125

Leu Leu Gly Cys Gly Asp Lys Ser Val Ile Ser Arg Leu Ser Gln Glu
        130                 135                 140

Ala Glu Arg Lys Ser Asp Asn Gly Thr Arg Lys Gly Leu Ser Glu Leu
145                 150                 155                 160

Asp Thr Leu Phe Ser Arg Leu Glu Glu Tyr Leu His Ser Arg Lys
                165                 170                 175

<210> SEQ ID NO 10
<211> LENGTH: 177
<212> TYPE: PRT
<213> ORGANISM: Human herpesvirus 5

<400> SEQUENCE: 10

Met Leu Ser Val Met Val Ser Ser Leu Val Leu Ile Val Phe Phe
1               5                   10                  15

Leu Gly Ala Ser Glu Glu Ala Lys Pro Ala Thr Thr Thr Thr Ile
                20                  25                  30

Lys Asn Thr Lys Pro Gln Cys Arg Pro Glu Asp Tyr Ala Thr Arg Leu
            35                  40                  45

Gln Asp Leu Arg Val Thr Phe His Arg Val Lys Pro Thr Leu Gln Arg
        50                  55                  60
```

```
Glu Asp Asp Tyr Ser Val Trp Leu Asp Gly Thr Val Val Lys Gly Cys
 65                  70                  75                  80

Trp Gly Cys Ser Val Met Asp Trp Leu Leu Arg Arg Tyr Leu Glu Ile
                 85                  90                  95

Val Phe Pro Ala Gly Asp His Val Tyr Pro Gly Leu Lys Thr Glu Leu
            100                 105                 110

His Ser Met Arg Ser Thr Leu Glu Ser Ile Tyr Lys Asp Met Arg Gln
        115                 120                 125

Cys Pro Leu Leu Gly Cys Gly Asp Lys Ser Val Ile Ser Arg Leu Ser
    130                 135                 140

Gln Glu Ala Glu Arg Lys Ser Asp Asn Gly Thr Arg Lys Gly Leu Ser
145                 150                 155                 160

Glu Leu Asp Thr Leu Phe Ser Arg Leu Glu Glu Tyr Leu His Ser Arg
                165                 170                 175

Lys

<210> SEQ ID NO 11
<211> LENGTH: 175
<212> TYPE: PRT
<213> ORGANISM: Human herpesvirus 5

<400> SEQUENCE: 11

Met Leu Ser Val Met Val Ser Ser Ser Leu Val Leu Ile Val Phe Phe
1               5                   10                  15

Leu Gly Ala Ser Glu Glu Ala Lys Pro Ala Thr Thr Thr Thr Lys Asn
            20                  25                  30

Thr Lys Pro Gln Cys Arg Pro Glu Asp Tyr Ala Thr Arg Leu Gln Asp
        35                  40                  45

Leu Arg Val Thr Phe His Arg Val Lys Pro Thr Leu Gln Arg Glu Asp
    50                  55                  60

Asp Tyr Ser Val Trp Leu Asp Gly Thr Val Val Lys Gly Cys Trp Gly
65                  70                  75                  80

Cys Ser Val Met Asp Trp Leu Leu Arg Arg Tyr Leu Glu Ile Val Phe
                85                  90                  95

Pro Ala Gly Asp His Val Tyr Pro Gly Leu Lys Thr Glu Leu His Ser
            100                 105                 110

Met Arg Ser Thr Leu Glu Ser Ile Tyr Lys Asp Met Arg Gln Cys Pro
        115                 120                 125

Leu Leu Gly Cys Gly Asp Lys Ser Val Ile Ser Arg Leu Ser Gln Glu
    130                 135                 140

Ala Glu Arg Lys Ser Asp Asn Gly Thr Arg Lys Gly Leu Ser Glu Leu
145                 150                 155                 160

Asp Thr Leu Phe Ser Arg Leu Glu Glu Tyr Leu His Ser Arg Lys
                165                 170                 175

<210> SEQ ID NO 12
<211> LENGTH: 197
<212> TYPE: PRT
<213> ORGANISM: Artificial
<220> FEATURE:
<223> OTHER INFORMATION: His-tagged rhcmvIL10 sequence

<400> SEQUENCE: 12

Met Arg Pro Thr Leu Leu Trp Ser Leu Leu Leu Leu Leu Gly Val Phe
1               5                   10                  15

Ala Ala Ala Ala Ala Ala Pro Pro His His His His His His Ser Asp
            20                  25                  30
```

```
Ile Glu Gly Arg Ala His Asp His Glu His Lys Glu Val Pro Ala
            35                  40                  45

Cys Asp Pro Val His Gly Asn Leu Ala Gly Ile Phe Lys Glu Leu Arg
 50                  55                  60

Ala Thr Tyr Ala Ser Ile Arg Glu Gly Leu Gln Lys Lys Asp Thr Val
 65                  70                  75                  80

Tyr Tyr Thr Ser Leu Phe Asn Asp Arg Val Leu His Glu Met Leu Ser
                 85                  90                  95

Pro Met Gly Cys Arg Val Thr Asn Glu Leu Met Glu His Tyr Leu Asp
                100                 105                 110

Gly Val Leu Pro Arg Ala Ser His Leu Asp Tyr Asp Asn Ser Thr Leu
            115                 120                 125

Asn Gly Leu His Val Phe Ala Ser Ser Met Gln Ala Leu Tyr Gln His
130                 135                 140

Met Leu Lys Cys Pro Ala Leu Ala Cys Thr Gly Lys Thr Pro Ala Trp
145                 150                 155                 160

Met Tyr Phe Leu Glu Val Glu His Lys Leu Asn Pro Trp Arg Gly Thr
                165                 170                 175

Ala Lys Ala Ala Ala Glu Ala Asp Leu Leu Leu Asn Tyr Leu Glu Thr
            180                 185                 190

Phe Leu Leu Gln Phe
            195

<210> SEQ ID NO 13
<211> LENGTH: 195
<212> TYPE: PRT
<213> ORGANISM: Artificial
<220> FEATURE:
<223> OTHER INFORMATION: His-tagged rhcmvIL10 sequence

<400> SEQUENCE: 13

Met Arg Pro Thr Leu Leu Trp Ser Leu Leu Leu Leu Gly Val Phe
 1               5                  10                  15

Ala Ala Ala Ala Ala His Asp His Glu His Lys Glu Val Pro Pro
                 20                  25                  30

Ala Cys Asp Pro Val His Gly Asn Leu Ala Gly Ile Phe Lys Glu Leu
             35                  40                  45

Arg Ala Thr Tyr Ala Ser Ile Arg Glu Gly Leu Gln Lys Lys Asp Thr
 50                  55                  60

Val Tyr Tyr Thr Ser Leu Phe Asn Asp Arg Val Leu His Glu Met Leu
 65                  70                  75                  80

Ser Pro Met Gly Cys Arg Val Thr Asn Glu Leu Met Glu His Tyr Leu
                 85                  90                  95

Asp Gly Val Leu Pro Arg Ala Ser His Leu Asp Tyr Asp Asn Ser Thr
                100                 105                 110

Leu Asn Gly Leu His Val Phe Ala Ser Ser Met Gln Ala Leu Tyr Gln
            115                 120                 125

His Met Leu Lys Cys Pro Ala Leu Ala Cys Thr Gly Lys Thr Pro Ala
130                 135                 140

Trp Met Tyr Phe Leu Glu Val Glu His Lys Leu Asn Pro Trp Arg Gly
145                 150                 155                 160

Thr Ala Lys Ala Ala Ala Glu Ala Asp Leu Leu Leu Asn Tyr Leu Glu
                165                 170                 175

Thr Phe Leu Leu Gln Phe Ser Ile Glu Gly Arg Thr Gly His His His
            180                 185                 190
```

His His His
        195

<210> SEQ ID NO 14
<211> LENGTH: 13
<212> TYPE: PRT
<213> ORGANISM: Artificial
<220> FEATURE:
<223> OTHER INFORMATION: C-terminal his-tag sequence of
      pMTA-rhcmvIL10FXH

<400> SEQUENCE: 14

Ser Ile Glu Gly Arg Thr Gly His His His His His His
1               5                   10

<210> SEQ ID NO 15
<211> LENGTH: 160
<212> TYPE: PRT
<213> ORGANISM: Macaca mulatta cytomegalovirus

<400> SEQUENCE: 15

His Asp His Glu His Lys Glu Val Pro Pro Ala Cys Asp Pro Val His
1               5                   10                  15

Gly Asn Leu Ala Gly Ile Phe Lys Glu Leu Arg Ala Thr Tyr Ala Ser
            20                  25                  30

Ile Arg Glu Gly Leu Gln Lys Lys Asp Thr Val Tyr Tyr Thr Ser Leu
        35                  40                  45

Phe Asn Asp Arg Val Leu His Glu Met Leu Ser Pro Met Gly Cys Arg
    50                  55                  60

Val Thr Asn Glu Leu Met Glu His Tyr Leu Asp Gly Val Leu Pro Arg
65                  70                  75                  80

Ala Ser His Leu Asp Tyr Asp Asn Ser Thr Leu Asn Gly Leu His Val
                85                  90                  95

Phe Ala Ser Ser Met Gln Ala Leu Tyr Gln His Met Leu Lys Cys Pro
            100                 105                 110

Ala Leu Ala Cys Thr Gly Lys Thr Pro Ala Trp Met Tyr Phe Leu Glu
        115                 120                 125

Val Glu His Lys Leu Asn Pro Trp Arg Gly Thr Ala Lys Ala Ala Ala
    130                 135                 140

Glu Ala Asp Leu Leu Leu Asn Tyr Leu Glu Thr Phe Leu Leu Gln Phe
145                 150                 155                 160

<210> SEQ ID NO 16
<211> LENGTH: 160
<212> TYPE: PRT
<213> ORGANISM: Homo sapiens

<400> SEQUENCE: 16

Ser Pro Gly Gln Gly Thr Gln Ser Glu Asn Ser Cys Thr His Phe Pro
1               5                   10                  15

Gly Asn Leu Pro Asn Met Leu Arg Asp Leu Arg Asp Ala Phe Ser Arg
            20                  25                  30

Val Lys Thr Phe Phe Gln Met Lys Asp Gln Leu Asp Asn Leu Leu Leu
        35                  40                  45

Lys Glu Ser Leu Leu Glu Asp Phe Lys Gly Tyr Leu Gly Cys Gln Ala
    50                  55                  60

Leu Ser Glu Met Ile Gln Phe Tyr Leu Glu Glu Val Met Pro Gln Ala
65                  70                  75                  80

Glu Asn Gln Asp Pro Asp Ile Lys Ala His Val Asn Ser Leu Gly Glu
            85                  90                  95

Asn Leu Lys Thr Leu Arg Leu Arg Leu Arg Arg Cys His Arg Phe Leu
            100                 105                 110

Pro Cys Glu Asn Lys Ser Lys Ala Val Glu Gln Val Lys Asn Ala Phe
            115                 120                 125

Asn Lys Leu Gln Glu Lys Gly Ile Tyr Lys Ala Met Ser Glu Phe Asp
            130                 135                 140

Ile Phe Ile Asn Tyr Ile Glu Ala Tyr Met Thr Met Lys Ile Arg Asn
145                 150                 155                 160

<210> SEQ ID NO 17
<211> LENGTH: 160
<212> TYPE: PRT
<213> ORGANISM: Macaca mulatta

<400> SEQUENCE: 17

Ser Pro Gly Gln Gly Thr Gln Ser Glu Asn Ser Cys Thr Arg Phe Pro
1               5                   10                  15

Gly Asn Leu Pro His Met Leu Arg Asp Leu Arg Asp Ala Phe Ser Arg
            20                  25                  30

Val Lys Thr Phe Phe Gln Met Lys Asp Gln Leu Asp Asn Ile Leu Leu
            35                  40                  45

Lys Glu Ser Leu Leu Glu Asp Phe Lys Gly Tyr Leu Gly Cys Gln Ala
50                  55                  60

Leu Ser Glu Met Ile Gln Phe Tyr Leu Glu Glu Val Met Pro Gln Ala
65                  70                  75                  80

Glu Asn His Asp Pro Asp Ile Lys Glu His Val Asn Ser Leu Gly Glu
            85                  90                  95

Asn Leu Lys Thr Leu Arg Leu Arg Leu Arg Arg Cys His Arg Phe Leu
            100                 105                 110

Pro Cys Glu Asn Lys Ser Lys Ala Val Glu Gln Val Lys Asn Ala Phe
            115                 120                 125

Ser Lys Leu Gln Glu Lys Gly Val Tyr Lys Ala Met Ser Glu Phe Asp
            130                 135                 140

Ile Phe Ile Asn Tyr Ile Glu Ala Tyr Met Thr Met Lys Ile Gln Asn
145                 150                 155                 160

<210> SEQ ID NO 18
<211> LENGTH: 157
<212> TYPE: PRT
<213> ORGANISM: Human herpesvirus 5

<400> SEQUENCE: 18

Ser Glu Glu Ala Lys Pro Ala Thr Thr Thr Ile Lys Asn Thr Lys
1               5                   10                  15

Pro Gln Cys Arg Pro Glu Asp Tyr Ala Thr Arg Leu Gln Asp Leu Arg
            20                  25                  30

Val Thr Phe His Arg Val Lys Pro Thr Leu Gln Arg Glu Asp Asp Tyr
            35                  40                  45

Ser Val Trp Leu Asp Gly Thr Val Val Lys Gly Cys Trp Gly Cys Ser
50                  55                  60

Val Met Asp Trp Leu Leu Arg Arg Tyr Leu Glu Ile Val Phe Pro Ala
65                  70                  75                  80

Gly Asp His Val Tyr Pro Gly Leu Lys Thr Glu Leu His Ser Met Arg
            85                  90                  95

```
Ser Thr Leu Glu Ser Ile Tyr Lys Asp Met Arg Gln Cys Pro Leu Leu
            100                 105                 110

Gly Cys Gly Asp Lys Ser Val Ile Ser Arg Leu Ser Gln Glu Ala Glu
        115                 120                 125

Arg Lys Ser Asp Asn Gly Thr Arg Lys Gly Leu Ser Glu Leu Asp Thr
    130                 135                 140

Leu Phe Ser Arg Leu Glu Glu Tyr Leu His Ser Arg Lys
145                 150                 155

<210> SEQ ID NO 19
<211> LENGTH: 27
<212> TYPE: DNA
<213> ORGANISM: Artificial
<220> FEATURE:
<223> OTHER INFORMATION: Mutagenesis primer

<400> SEQUENCE: 19
gcacggcaaa agcagcggcc gaggctg                                       27

<210> SEQ ID NO 20
<211> LENGTH: 36
<212> TYPE: DNA
<213> ORGANISM: Artificial
<220> FEATURE:
<223> OTHER INFORMATION: PCR primer

<400> SEQUENCE: 20
gctcagccgc ggcccatgac catgaacaca aagaag                             36

<210> SEQ ID NO 21
<211> LENGTH: 55
<212> TYPE: DNA
<213> ORGANISM: Artificial
<220> FEATURE:
<223> OTHER INFORMATION: PCR primer

<400> SEQUENCE: 21
cgtatcaccg gtgcggccct cgatgctgaa ctgcagcagc agcaggaacg tttcc        55
```